United States Patent
McGrath et al.

(10) Patent No.: US 9,579,346 B2
(45) Date of Patent: Feb. 28, 2017

(54) TREATMENT OF MACROPHAGE-RELATED DISORDERS

(71) Applicants: Neuraltus Pharmaceuticals, Inc., Palo Alto, CA (US); The Regents of the University of California, Oakland, CA (US)

(72) Inventors: Michael S. McGrath, Burlingame, CA (US); Arasteh Ari Azhir, Los Altos, CA (US)

(73) Assignees: The Regents of the Univerity of California, Oakland, CA (US); Neuraltus Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 14/271,054

(22) Filed: May 6, 2014

(65) Prior Publication Data

US 2015/0037320 A1 Feb. 5, 2015

Related U.S. Application Data

(63) Continuation of application No. 13/388,411, filed as application No. PCT/US2010/043150 on Jul. 23, 2010, now abandoned.

(60) Provisional application No. 61/231,989, filed on Aug. 6, 2009, provisional application No. 61/232,678, filed on Aug. 10, 2009, provisional application No. 61/238,609, filed on Aug. 31, 2009.

(51) Int. Cl.

| *A61K 33/20* | (2006.01) |
| *A61K 31/10* | (2006.01) |
| *A61K 31/185* | (2006.01) |
| *A61K 31/327* | (2006.01) |
| *A61K 33/00* | (2006.01) |
| *A61K 33/04* | (2006.01) |
| *A61K 33/16* | (2006.01) |
| *A61K 33/18* | (2006.01) |
| *A61K 33/24* | (2006.01) |
| *A61K 33/32* | (2006.01) |
| *A61K 33/38* | (2006.01) |
| *A61K 33/40* | (2006.01) |
| *A61K 45/06* | (2006.01) |
| *A61K 31/137* | (2006.01) |
| *A61K 31/7076* | (2006.01) |
| *A61K 39/395* | (2006.01) |
| *C07K 16/28* | (2006.01) |

(52) U.S. Cl.
CPC .............. *A61K 33/20* (2013.01); *A61K 31/10* (2013.01); *A61K 31/137* (2013.01); *A61K 31/185* (2013.01); *A61K 31/327* (2013.01); *A61K 31/7076* (2013.01); *A61K 33/00* (2013.01); *A61K 33/04* (2013.01); *A61K 33/16* (2013.01); *A61K 33/18* (2013.01); *A61K 33/24* (2013.01); *A61K 33/32* (2013.01); *A61K 33/38* (2013.01); *A61K 33/40* (2013.01); *A61K 39/3955* (2013.01); *A61K 45/06* (2013.01); *C07K 16/2839* (2013.01); *G01N 2333/70596* (2013.01)

(58) Field of Classification Search
CPC ...... A61K 31/10; A61K 31/327; A61K 33/00; A61K 33/04; A61K 33/16; A61K 33/18; A61K 33/20; A61K 33/24; A61K 33/32; A61K 33/38; A61K 33/40; A61K 45/06; A61K 39/3955; A61K 31/7076; C07K 16/2839; G01N 2333/70596
USPC .............................................. 424/133.1, 665
See application file for complete search history.

(56) References Cited

U.S. PATENT DOCUMENTS

| 4,507,285 | A |  | 3/1985 | Kuhne |  |
|---|---|---|---|---|---|
| 5,667,817 | A |  | 9/1997 | Kross |  |
| 5,855,922 | A |  | 1/1999 | Danner et al. |  |
| 6,086,922 | A |  | 7/2000 | Kuhne |  |
| 6,099,855 | A |  | 8/2000 | Mullerat et al. |  |
| 8,067,035 | B2 | * | 11/2011 | Boulanger et al. | ........... 424/615 |
| 8,501,244 | B2 | * | 8/2013 | Boulanger et al. | ........... 424/661 |
| 2005/0181068 | A1 |  | 8/2005 | McGrath |  |
| 2006/0159775 | A1 |  | 7/2006 | McGrath |  |
| 2007/0145328 | A1 |  | 6/2007 | Boulanger et al. |  |
| 2009/0004295 | A1 |  | 1/2009 | Kuehne et al. |  |
| 2010/0216746 | A1 |  | 8/2010 | Chong et al. |  |
| 2012/0134929 | A1 |  | 5/2012 | McGrath et al. |  |

FOREIGN PATENT DOCUMENTS

| EA | 012368 B1 | 10/2009 |
| SU | 327132 | 1/1972 |
| WO | WO 99/17787 A2 | 4/1999 |

OTHER PUBLICATIONS

European search report and opinion dated May 22, 2013 for EP Application No. 10806852.9.

(Continued)

*Primary Examiner* — Johann R Richter
*Assistant Examiner* — Robert Cabral
(74) *Attorney, Agent, or Firm* — Wilson Sonsini Goodrich & Rosati

(57) ABSTRACT

The present invention provides a method of treating a macrophage related disease comprising administering to a subject in need thereof an effective amount of an oxidative agent or an immunosuppressive agent. The present invention also provides a method of modulating macrophage accumulation or activation comprising administering to a subject in need thereof an effective amount of an oxidative agent or an immunosuppressive agent. The oxidative agent can be chlorite or a chlorite containing compound.

19 Claims, 16 Drawing Sheets

(56) References Cited

OTHER PUBLICATIONS

Hatz, et al. The tetrachlorodecaoxygen complex reverses the effect of cortisone on wound healing. Plast Reconstr Surg. Dec. 1989;84(6):953-9.
Inorganic Ventures. "Certificate of Analysis for 1000 µg/ml Chlorite Solution." 2008. 2 pgs.
International search report and written opinion dated Mar. 4, 2011 for PCT Application No. US2010/043150.
McGrath, et al. Development of WF10, a novel macrophage-regulating agent. Curr Opin Investig Drugs. 2002; 3(3):365-73.
Office action dated Nov. 7, 2013 for U.S. Appl. No. 13/388,411.
Product Insert: Data and instruction for the Use of Immunokine WF10 (TCDO) 1.v.Solution for Intravenous Infusion. OXO Chemie. Published approximately 1997.
Shahangian, et al. The reaction of chloroperoxidase with chlorite and chlorine dioxide. J Biol Chem. Jun. 25, 1981;256(12):6034-40.
Steffen, et al. Chlorate poisoning: mechanism of toxicity. Toxicology. Nov. 12, 1993;84(1-3):217-31.
Tissot, et al. Anti-inflammatory properties of a novel wound healing and immunomodulating agent, tetrachlorodecaoxygen complex (TCDO). Agents Actions. Nov. 1990;31(3-4):368-74.
Khymicheskaja encyclopedija. Bolshaja rossijskaja encyclopedija. M. 5:564 (1998) (English translation).

\* cited by examiner

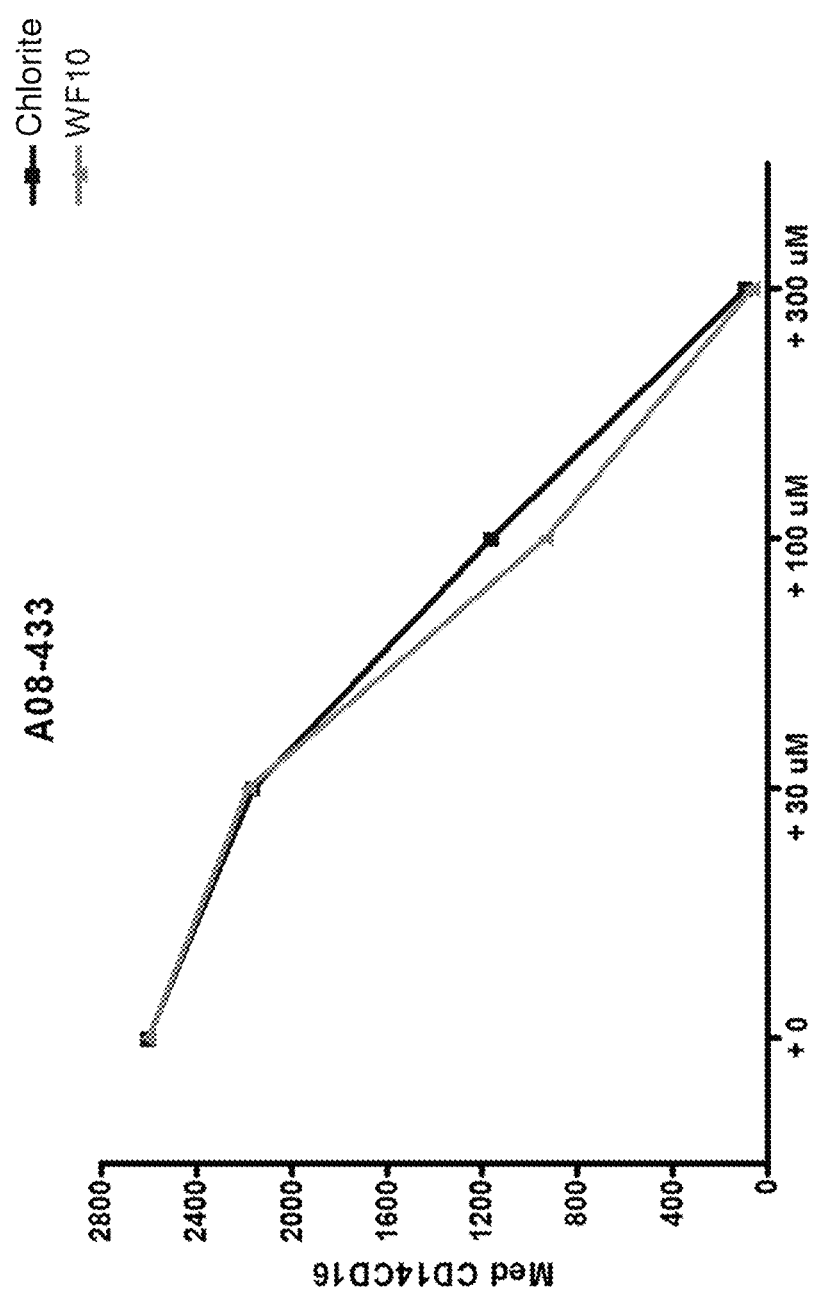

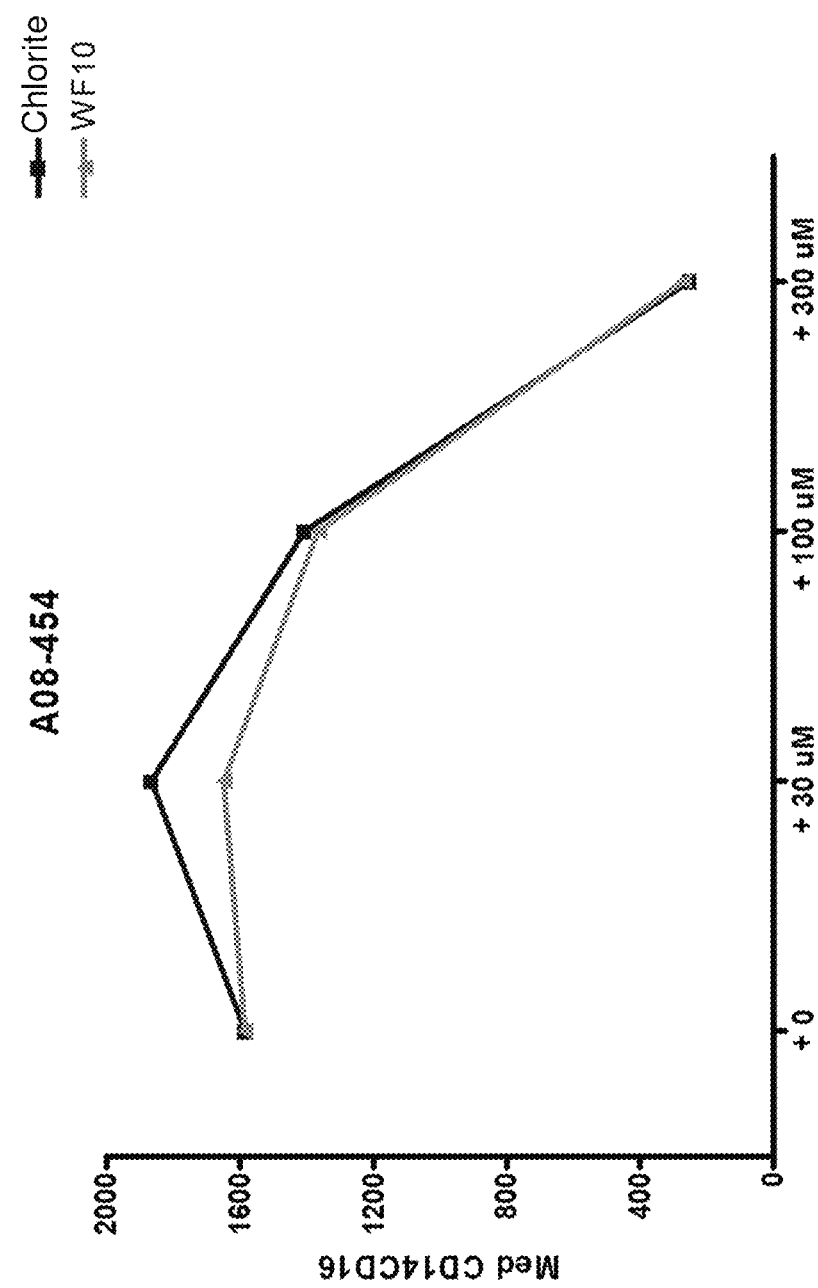

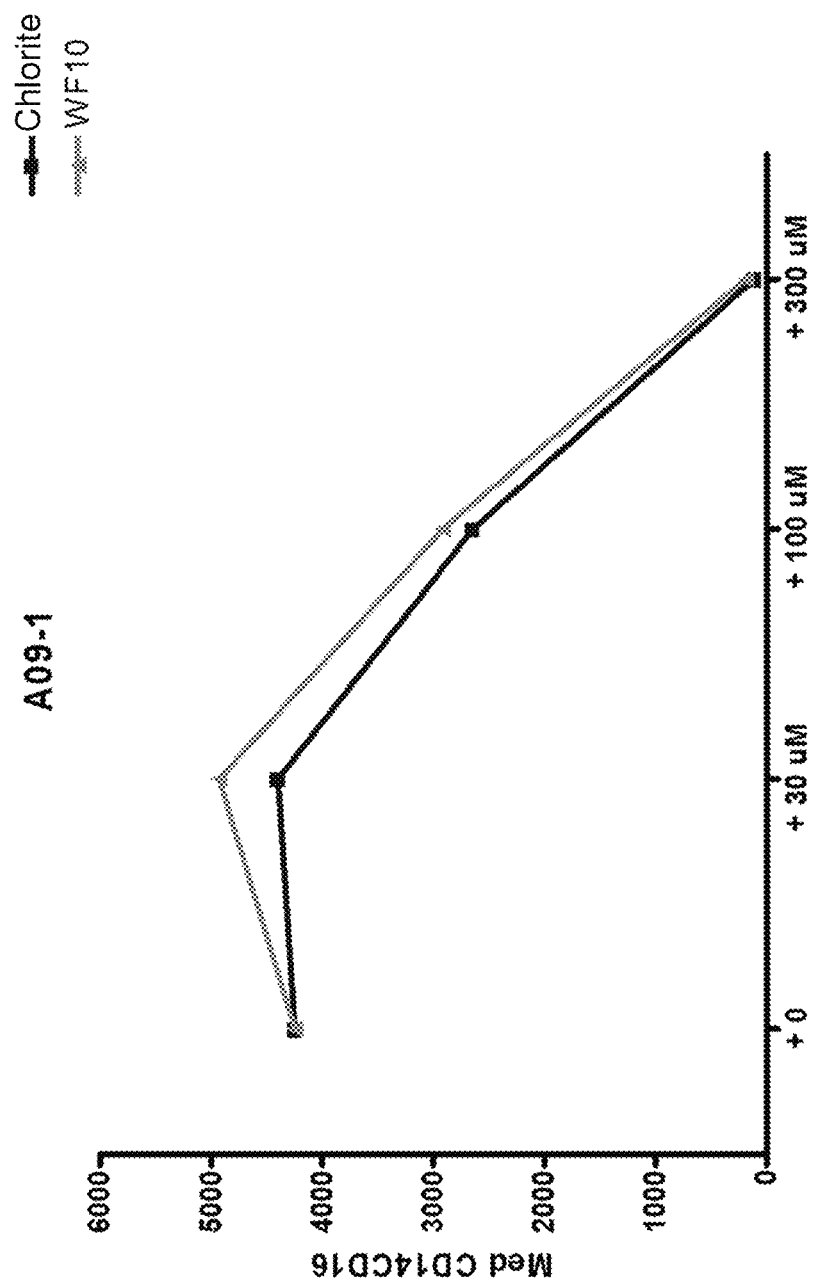

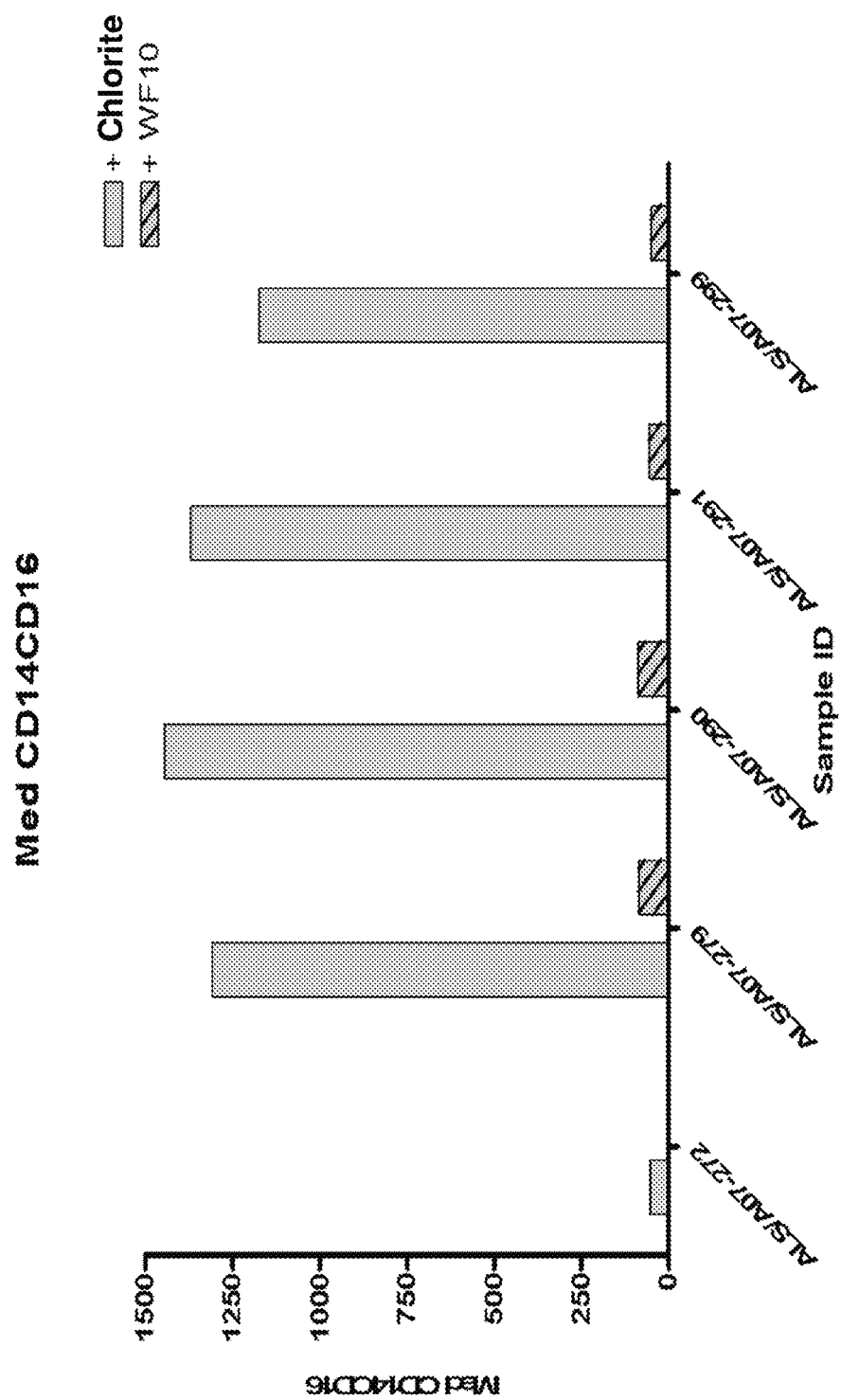

X-Ray Powder Diffraction (XRPD) of purified sodium chlorite

FIGURE 8

| Compounds (300 micromolar) | %Reduction of Med CD14CD16 | Toxicity* |
|---|---|---|
| sodium chlorite (n=4) | 75.12 ± 3.55 | No |
| N- Chlorophthalimide | 4.47 | + |
| N- Chlorosuccinimide | -34.73 | + |
| N- Chlorosaccharin | 56.05 | +/- |
| N, N- Dichlorourethane | 18.47 | +/- |
| N- Chloroacetanilide | 35.53 | + |
| 1, 3- Dichloro-5,5-dimethylhydantoin | 79.38 | No |
| Trichloroisocyanuric acid | 86.30 | +++ |
| Sodium dichloroisocyanurate | 85.54 | +++ |
| Chloramine-T hydrate | 63.31 | No |
| Halazone | 69.83 | +++ |

TREATMENT OF MACROPHAGE-RELATED DISORDERS

This application is a Continuation of application Ser. No. US 13/388,411, which is a national stage application of PCT/US2010/043150, filed Jul. 23, 2010, which claims benefit under 35 U.S.C. §119(e) to Provisional Application Nos. US 61/231,989, filed Aug. 6, 2009, US 61/232,678, filed Aug. 10, 2009, and US 61/238,609, filed Aug. 31, 2009, each of which is herein incorporated by reference in its entirety.

BACKGROUND OF THE INVENTION

Macrophages are white blood cells produced by the division of monocytes. Monocytes and macrophages are phagocytes, and play a role in innate immunity (non-specific immune defenses) as well as helping to initiate adaptive immunity (specific defense mechanisms). These cells phagocytose (engulf and then digest) cellular debris and pathogens either as stationary or as mobile cells. When activated by pathogens or by other mechanisms, macrophages stimulate and recruit lymphocytes and other immune cells to respond to the insult.

Although macrophages play a vital role in host immune defenses, activated macrophages are also involved in the progression of a number of diseases and disorders. Activated macrophages elicit massive leukocyte infiltration and flood the surrounding tissue with inflammatory mediators, pro-apoptotic factors, and matrix degrading proteases. These actions can result in inflammation that can dismantle tissues to the point of inflicting serious injury. Tissue destruction perpetrated by macrophage-induced inflammation has been associated with the development of tumors, autoimmune disorders, and other conditions.

Oxidative agents such as chlorite can return macrophages to their inactivated state. Immunosuppressant agents can mitigate macrophage activation. The present invention provides methods for the treatment of macrophage-related diseases and related conditions with oxidative agents or immunosuppressant agents.

SUMMARY OF THE INVENTION

In one aspect, the present invention provides a method of treating a macrophage related disease comprising administering to a subject in need thereof an effective amount of a pharmaceutical composition comprising an oxidative agent.

In another aspect, the present invention provides a method of treating a macrophage related disease comprising administering to a subject in need thereof an effective amount of a pharmaceutical composition comprising: chlorite; a pH adjusting agent; and a pharmaceutically acceptable excipient. In some embodiments, the pH adjusting agent comprises monosodium phosphate and/or disodium phosphate. In some embodiments, the pH of the composition is between about 7.1 and about 7.7. In some embodiments, the weight ratio of chlorite:chlorate is greater than 100:1.5.

In still another aspect, the present invention provides a method of treating a macrophage related disease comprising administering to a subject in need thereof an effective amount of a pharmaceutical composition comprising an immunomodulatory agent.

In a further aspect, the present invention provides a method of modulating macrophage accumulation or activation comprising administering to a subject in need thereof an effective amount of a pharmaceutical composition comprising an oxidative agent. A method is also provided to modulate macrophage accumulation or activation comprising administering to a subject in need thereof an effective amount of a pharmaceutical composition comprising an immunomodulatory agent. In some embodiments, the macrophage activation is enhanced. In some embodiments, the macrophage activation is reduced or inhibited.

Macrophage related diseases that are treated by the invention include, but are not limited to, cancer, autoimmune disease, macrophage activation syndrome, atherosclerosis, diabetes mellitus, Kawasaki disease, asthma, hemophagocytic lymphohistiocytosis, sarcoidosis, periodontitis, Whipple's disease, pulmonary alveolar proteinosis, macrophage related pulmonary disease, Leishmaniasis, obesity complications, hemodialysis related inflammation, microbial infection, viral infection, inflammation, and complications thereof. The cancer can be, without limitation, adrenal cortical cancer, anal cancer, aplastic anemia, bile duct cancer, bladder cancer, bone cancer, bone metastasis, central nervous system (CNS) cancers, peripheral nervous system (PNS) cancers, breast cancer, Castleman's Disease, cervical cancer, childhood Non-Hodgkin's lymphoma, colon and rectum cancer, endometrial cancer, esophagus cancer, Ewing's family of tumors (e.g., Ewing's sarcoma), eye cancer, gallbladder cancer, gastrointestinal carcinoid tumors, gastrointestinal stromal tumors, gestational trophoblastic disease, hairy cell leukemia, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, thyroid cancer, uterine cancer (e.g., uterine sarcoma), vaginal cancer, vulvar cancer, or Waldenstrom's macroglobulinemia.

Autoimmune diseases treated by the methods of the invention include, without limitation, acute disseminated encephalomyelitis, Addison's disease, alopecia areata, ankylosing spondylitis, antiphospholipid antibody syndrome, autoimmune hemolytic anemia, autoimmune hepatitis, Bullous pemphigoid, Celiac disease, Crohn's disease, dermatomyositis, diabetes mellitus type 1, Goodpasture's syndrome, Graves' disease, Guillain-Barré syndrome, Hashimoto's disease, Idiopathic thrombocytopenic purpura, Lupus erythematosus, Mixed Connective Tissue Disease, multiple sclerosis, myasthenia gravis, narcolepsy, *Pemphigus vulgaris*, Pernicious anemia, Polymyositis, Primary biliary cirrhosis, Rheumatoid arthritis, Sjögren's syndrome, Temporal arteritis, Ulcerative Colitis, Vasculitis, or Wegener's granulomatosis.

Various disease complications treated by the methods of the invention comprise one or more of retinopathy, neuropathy, foot problems, gastroparesis, skin complications, bacterial infections, fungal infections, itching, dermopathy, necrobiosis lipoidica diabeticorum, diabetic blisters, eruptive xanthomatosis, nephropathy, hypertension, coronary heart disease, stroke, rheumatic heart disease, myocardial infraction, metabolic syndrome, ischemic cardiac disease, coronary artery disease, cerebrovascular disease, vascular dementia, preeclampsia, heart disease, stroke, atherogenesis, thrombogenesis, carotid, coronary vascular disease, transplant-related complications, acute atheroma, metabolic syndrome, tobacco-related disease, liver complications, AIDS-related complications, or inflammatory neurological diseases.

In one aspect, the present invention provides a method of treating a macrophage related disease comprising administering to a subject in need thereof an effective amount of a pharmaceutical composition comprising an oxidative agent, wherein the macrophage related disease is a neurological disease. In another aspect, the present invention provides a method of treating a neurological disease comprising administering to a subject in need thereof an effective amount of a pharmaceutical composition comprising an oxidative agent. In another aspect, the present invention provides a method of treating a neurological disease comprising administering to a subject in need thereof an effective amount of a pharmaceutical composition comprising chlorite or a chlorite-containing agent, optionally in combination with another therapeutic agent or intervention used for treating the neurological disorder.

In another aspect, the present invention provides a method of treating a symptom of a neurological disease comprising administering to a subject in need thereof an effective amount of a pharmaceutical composition comprising chlorite or a chlorite-containing agent in combination with another therapeutic agent or intervention used for treating the symptom. Symptoms treated by the methods of the invention include but are not limited to motor impairment, cognitive impairment, dementia, pain, disorganization, sleep disorder, infection, depression, anxiety, pneumonia, compulsive behavior, injuries, dysphagia, constipation, incontinence, akinesia, restless legs syndrome, tremor, agitation, sensory impairment, visual impairment, smell impairment, hearing impairment, or osteoporosis.

The methods the invention can be used to treat any number of neurological diseases, disorders, or symptoms of any thereof. In some embodiments, the neurological disease is amyotrophic lateral sclerosis (ALS). For ALS, the second therapeutic agent or intervention includes but is not limited to riluzole, KNS-760704, minocycline, RNAi targeting SOD1 gene, physical therapy, insulin-like growth factor-1 (IGF1), brain-derived neurotrophic factor (BDNF), nerve growth factor (NGF) like factors, 5-hydroxytryptophan (5-HTP), tyrosine, levodopa (L-DOPA), tryptophan, cysteine, exercise, ventilatory assistance or communication assistance. For ALS, the second therapeutic agent or intervention can also comprise 2-PMPA, adenosine, anisomycin, apocynin, apomorphine, arimoclomol, aspergillin, BMP-7, carboxyfullerenes, ceftriaxone, celastrol, geldanamycin, celecoxib (Celebrex®), cyclooxygenase 2, CGP 3466B, chlorpromazine, clioquinol, clozapine, ciliary neurotrophic factor (CTNF), colchicine, colivelin, copaxone, copper chelators, lipoic acid, coenzyme Q10 (CoQ10), creatine, curcumin, cytotoxic T-lymphocyte antigen 4 antibody fusions (CTLA4-Ig), cycloheximide, cobra venom factor (CVF), cycloserine, cyclosporin, d-penicillamine, JAK3/Dapsone, Dapsone/Gusperimus/JAK3 Cocktail, Diethyldithiocarbamate DDC, desferoxamine, desipramine, α-difluoromethylornithine (DFMO), dietary restriction, dihydrotestosterone, 5,5-dimethyl-pyrroline N-oxide (DMPO), excitatory amino acid transporter 2 (EAAT2), erythro-9-[3-(2-hydroxynonyl)]adenine (EHNA), emetine, estradiol benzoate, exercise, FK-506, fluorouracil, glial cell line-derived neurotrophic factor (GDNF), decreased spinal copper levels, genistein, glutamate receptor 3 (GLUR3) antisense, hepatocyte growth factor (HGF), hNT neurons, anti-oxidant SOD1 protein, human umbilical cord blood mononuclear cells, hydroxyurea, interleukin-1beta-converting enzyme (ICE) inhibition, IGF-1 or isoforms thereof, intravenous immunoglobulin (IVIG), indomethacin, hydroquinone hydrochloride derivative of 17-AAG (IPI-504), iron porphyrin, ivermectin (22,23-dihydroavermectin B1a+22, 23-dihydroavermectin B1b), L-acetyl-carnitine, lactacystin, leflunomide, lentiviral RNAi SOD1 gene silencing, leukemia inhibitory factor (LIF), lithium, lyophilized red wine extract, magnesium supplementation, melatonin, memantine, metalloporphyrins (MnTE-Py-P (AEOL10113 and AEOL10150)), metallothioneins, metformin, methotrexate, mechano growth factor (MGF; IGF-I Ec peptide; mIGF-1 isoform), minocycline, minocycline/creatine, minocycline/riluzole/nimodipine cocktail, mithramycin, 1-methyl-4-phenyl-1,2,3,6-tetrahydropyridine (MPTP) and/or 3-nitropropionic acid (3NP), N-acetyl-L-cysteine, N-acetylcysteine, 2,3-dihydroxy-6-nitro-7-sulfamoyl-benzo[f]quinoxaline-2,3-dione (NBQX), nordihydroguaiaretic acid (NDGA), neurofilament heavy (NF-H) protein, neurofilament light (NF-L) protein, nimesulide, nitric oxide synthase inhibitors, 17 beta-estradiol, p75 neurotrophin receptor, p75 neurotrophin agonist, p75 neurotrophin antisense, parvalbumin, sodium phenyl butyrate (PBA), peripheral axotomy, phosphatidyl choline-bound Cu/Zn SOD, pioglitazone, polyamine-modified catalase, porphyrin, prednisolone, progesterone, puromycin, putrescine-modified catalase (PUT-CAT), quinacrine, R(+) pramipexole, radicicol, rasagiline, resveratrol/red wine extract, riluzole, ritonavir, anti-myostatin mAb, vascular endothelial growth factor (VEGF), RNAi targeting human SOD1 gene, rofecoxib, rolipram, alpha-amino-3-hydroxy-5-methyl-4-isoxazolepropionic acid antagonist RPR 119990, 5-hydroxytryptophan (5-HTP), sodium valproate, stem cells, sulindac, tamoxifen, propargylamine TCH346, tepoxalin, testosterone, thalidomide, trehalose, trichostatin A, trientine/ascorbate, vincristine, vitamin E/riluzole/gabapentin, Janus kinase 3 (JAK3) inhibitor such as WHI-P131, bone marrow transplant, zileuton, zinc sulfate, or a noncompetitive AMPA antagonist such as ZK 187638. The invention further contemplates combination therapy for ALS comprising administering chlorite and/or a chlorite containing agent and any appropriate combination of other agents or interventions.

In some embodiments, the neurological disease treated by the methods of the invention is Parkinson's disease (PD). For Parkinson's disease, the second therapeutic agent or intervention includes but is not limited to antioxidant, immunosuppressive calcincurin inhibitor, NOS inhibitor, sigma-1 modulator, AMPA antagonist, Ca2+ channel blocker, estrogen agonist, MAO-B inhibitor, selegiline, rasagiline, kinase inhibitor, mitochondrial modulator or enhancer, alpha synuclein modulator, glycoprotein IIb/IIIa antagonist, erythropoietin, astaxanthin, boswellia, caffeine, curcumin, E vitamins, tocotrienol, flavonoid, naringenin, huperzine, ubiquinol, levodopa (L-DOPA), levodopa-carbidopa, co-beneldopa, a slow-release levodopa mono-therapy or combination formulation, amantadine, benztropine, procyclidine, trihexyphenidyl, a COMT inhibitor, tolcapone, entacapone, a dopamine agonist, bromocriptine, pergolide, pramipexole, ropinirole, cabergoline, apomorphine, lisuride, surgery, deep brain stimulation, neurorehabilitation, or exercise. The invention further contemplates combination therapy for Parkinson's disease comprising administering chlorite and/or a chlorite containing agent and any appropriate combination of other agents or interventions.

In some embodiments, the neurological disease treated by the methods of the invention is Alzheimer's disease (AD). For Alzheimer's disease, the second therapeutic agent or intervention includes but is not limited to an acetylcholinesterase inhibitor, donepezil, rivastigmine, galantamine, THA, an NMDA receptor antagonist, memantine, vitamin E, vitamin D, progesterone, or a behavioral, emotional, cognitive, or stimulation-oriented intervention. The invention further contemplates combination therapy for Alzheimer's disease comprising administering chlorite and/or a chlorite containing agent and any appropriate combination of other agents or interventions.

In some embodiments, the oxidative agent of the invention is chlorite or a chlorite-based derivative or functional product. In some embodiments, the oxidative agent is Tetrachlorodecaoxygen (TCDO). In some embodiments, the oxidative agent is chloramine-T or a hydrate thereof or taurine chloramine. In some embodiments, the oxidative agent is WF10. In some embodiments, the oxidative agent is heme oxygenase 1 (HO-1) or a functional product thereof. In some embodiments, the oxidative agent is potassium nitrate (KNO3), hypochlorite, a hypohalite compound, fluorine (F), chlorine (Cl), bromine (Br), iodine (I), astatine (At), chlorite, chlorate, perchlorate, a halogen-containing compound, a permanganate salt, ammonium cerium(IV) nitrate, a Cerium (IV) compound, a hexavalent chromium compound, chromic acid, dichromic acid, chromium trioxide, pyridinium chlorochromate (PCC), a chromate/dichromate compounds, a peroxide, Tollens' reagent, a sulfoxide, persulfuric acid, ozone, osmium tetroxide ($OsO_4$), nitric acid, nitrous oxide ($N_2O$), or a derivative of any thereof.

In some embodiments, the immunomodulatory agent is an immunosuppressive agent. The immunomodulatory agent can also be an immunostimulator. In some embodiments, the immunomodulatory agent is a glucocorticoid, hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a cytostatic agent, an alkylating agent, nitrogen mustard (cyclophosphamide), nitrosourea, a platinum compound, an antimetabolite, a purine analog, azathioprine, mercaptopurine, mycophenolic acid, a pyrimidine synthesis inhibitor, leflunomide, teriflunomide, a folic acid analog, methotrexate, a cytotoxic antibiotic, dactinomycin, anthracyclines, mitomycin C, bleomycin, mithramycin, an antibody or fusion thereof, anti-thymocyte globulin, anti-lymphocyte globulin, an anti-IL-2 receptor antibody, an anti-CD3 antibody, OKT3 (muromonab), otelixizumab, teplizumab, visilizumab, an anti-CD4 antibody, clenoliximab, keliximab, zanolimumab, an anti-CD11a antibody, efalizumab, an anti-CD18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an CTLA4-Ig fusion protein, abatacept, belatacept, an anti-CTLA4 antibody, ipilimumab, tremelimumab, an anti-eotaxin 1 antibody, bertilimumab, an anti-α4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an immunophilin modulating agent, rapamycin, a calcincurin inhibitor, tacrolimus, ciclosporin (cyclosporin), pimecrolimus, abetimus, gusperimus, ridaforolimus, everolimus, temsirolimus, zotarolimus, a TNF inhibitor, infliximab, adalimumab, certolizumab pegol, golimumab, etanercept, thalidomide, lenalidomide, pentoxifylline, bupropion, curcumin, catechin, an IL-1 receptor antagonist, anakinra, an anti-IL-5 antibody, mepolizumab, an IgE inhibitor, omalizumab, talizumab, an IL12 inhibitor, an IL23 inhibitor, ustekinumab, an opiod, an IMPDH inhibitor, mycophenolic acid, myriocin, fingolimod, an NF-κB inhibitor, raloxifene, drotrecogin alfa, denosumab, an NF-κB signaling cascade inhibitor, disulfiram, olmesartan, dithiocarbamate, a proteasome inhibitor, bortezomib, MG132, Pro1, NPI-0052, curcumin, genistein, resveratrol, parthenolide, thalidomide, lenalidomide, flavopiridol, non-steroidal anti-inflammatory drugs (NSAIDs), arsenic trioxide, dehydroxymethylepoxyquinomycin (DHMEQ), 13C(indole-3-carbinol)/DIM(di-indolmethane) (I3C/DIM), Bay 11-7082, luteolin, cell permeable peptide SN-50, IκBα-super repressor overexpression, NFκB decoy oligodeoxynucleotide (ODN), or a derivative or analog of any thereof.

The pharmaceutical compositions of the invention can be administered intravenously. In some embodiments, the subject treated using the methods of the invention is a mammal. In some embodiments, the mammal is a human.

In some embodiments, modulating of macrophage activation or accumulation according to the invention comprises modulating one or more molecules involved in one or more cellular pathways selected from the group consisting of NFkB, toll-like receptor (TLR)-2, TLR-4, Tie-2/Ang-2, TRIF/TBK1/IRF3, NFAT, and hypoxia-induced pathways, lipopolysaccharide (LPS), prostaglandin E2 (PGE2), interferon (IFN)-α, IFN-β, IFN-γ, interleukin (IL)-1, IL-4, IL-6, sIL1Ra, IL-8, IL-10, IL-12, IL-12p40, IL-13, IP10, MHCII, TNF-α, macrophage inflammatory protein 1 alpha (MIP1-α), IFN-gamma-inducing factor (IGIF), macrophage-stimulating protein (MSP), inter-cellular adhesion molecule 1(ICAM-1), colony stimulating factor 1 (CSF-1R), L-arginine, nitric oxide signaling pathways, and macrophage migration inhibitory factor (MIF). In some embodiments, the modulating of macrophage activation with the agent has effect on one or more molecules selected from the group consisting of TLR-2, TLR-4, mkp-1, COX-2, SOCS-3, FcγR1, IFN-α, IFN-β, IL-4, IL-6, IL-1Ra, IGIF, IL-1β, MHCI, MHCII IAA, MHCII IAB, MHCII IEB, IP10, IL-10, cathepsin H, lysozyme, CathB, stk, TNF-α, IL-12p35, IL-12p40, MIP-1α, ICAM-1, INOS, mig, Cat-2, CIITA, ICSBP, CathL, CSF1R, GM-CSF, IRF1, IRF-2, c-fos, VEGF, IL-8, bFGF, CSF-1, EGF, MMP-2, MMP-7, MMP-9, MMP-12, EMAPII, endothelin 2, HIF-1, HIF-2, CXCL8, TGFβ, PGE2, and MDF.

In some embodiments, the methods of the invention further comprise administering a second therapeutic agent sequentially or simultaneously.

In the case of proliferative diseases such as cancer, the second therapeutic agent can comprise a chemotherapeutic, immunotherapeutic, or radiotherapeutic agent. Such agents can be selected from the group consisting of alkylating agents, antimetabolites, natural antineoplastic agents, hormonal antineoplastic agents, angiogenesis inhibitors, differentiating reagents, RNA inhibitors, antibodies or immunotherapeutic agents, gene therapy agents, small molecule enzymatic inhibitors, biological response modifiers, and anti-metastatic agents.

In the case of autoimmune diseases, the second therapeutic agent can comprise an immunosuppressant or anti-inflammatory agent. Such agents can be selected from the group consisting of alkylating agent, an antimetabolite, a cytotoxic antibiotic, a folic acid analog, a purine analog, an antibody, a TNF binding protein, an interferon, an opioid, a mycophenolate, a calcineurin inhibitor, or an analog thereof.

In some embodiments, the second therapeutic agent comprises a therapeutic agent for treating type II diabetes or related complications. Such agents include without limitation a biguanide, metformin, a thiazolidinedione, ciglitazone, pioglitazone, troglitazone, rosiglitazone, a dipeptidyl-peptidase-4 inhibitors, vildagliptin, sitagliptin, a glucagon-like peptide-1 ("GLP-1") receptor agonist, exanatide, a GLP-1 mimetic, a PPAR gamma agonist or partial agonist, a dual PPAR alpha-PPAR gamma agonist or partial agonist, a dual PPAR delta-PPAR gamma agonist or partial agonist, a pan PPAR agonist or partial agonist, dehydroepiandrosterone or its conjugated sulphate ester, an antiglucocorticoid, a TNF-alpha inhibitor, an alpha-glucosidase inhibitor, acarbose, miglitol, voglibose, a sulfonylurea, chlorpropamide, tolbutamide, acetohexamide, tolazamide, glyburide, gliclazide, glynase, glimepiride, glipizide, pramlintide, an insulin secretagogue, repaglinide, gliquidone, nateglinide, insulin, an insulin mimetic, a glucagon receptor antagonist, gastric inhibitory peptide ("GIP"), a GIP mimetic, ketotifen fumarate or cromolyn.

In some embodiments, the second therapeutic agent comprises a therapeutic agent used for treating a vascular disease and/or related disorders. Such agents include without limitation an endothelin receptor antagonist, bosentan, darusentan, enrasentan, tezosentan, atrasentan, ambrisentan sitaxsentan, a smooth muscle relaxant, a PDE5 inhibitor, minoxidil, an angiotensin converting enzyme (ACE) inhibitor, captopril, enalapril, lisinopril, fosinopril, perindopril, quinapril, trandolapril, benazepril, ramipril, an angiotensin II receptor blocker, irbesartan, losartan, valsartan, eprosartan, olmesartan, candesartan, telmisartan, a beta blocker, atenolol, metoprolol, nadolol, bisoprolol, pindolol, acebutolol, betaxolol, propranolol, a diuretic, thiazide, hydrochlorothiazide, furosemide, torsemide, metolazone, a calcium channel blocker, amlodipine, felodipine, nisoldipine, nifedipine, verapamil, diltiazem, an alpha receptor blocker, doxazosin, terazosin, alfuzosin, tamsulosin, a central alpha agonist, clonidine, a statin, atovastatin, fluvastatin, lovastatin, pravastatin, rosuvastatin calcium, simvastatin, nicotinic acid, an agent that stimulate PPAR alpha, a fibrate, gemfibrozil, fenofibrate, bezafibrate, ciprofibrate, a bile acid sequestrant, cholestyramine, colestipol, a cholesterol absorption inhibitor, a COX-1 inhibitor, aspirin, an NSAID, or a COX-2 inhibitor.

In some embodiments, the second therapeutic agent comprises a therapeutic agent used for treating obesity and/or related disorders. Such agents include without limitation phenylpropanolamine, phenteramine, diethylpropion, mazindol, fenfluramine, dexfenfluramine, phentiramine, a beta-3 adrenoceptor agonist agent, sibutramine, a gastrointestinal lipase inhibitor, orlistat, a leptin, a cannabinoid-1 ("CB-1") receptor antagonist, rimonabant, a PPAR delta agonist or partial agonist, a dual PPAR alpha-PPAR delta agonist or partial agonist, a dual PPAR delta-PPAR gamma agonist or partial agonist, a pan PPAR agonist or partial agonist, neuropeptide Y, enterostatin, cholecytokinin, bombesin, amylin, a histamine H3 receptor, a dopamine D2 receptor, melanocyte stimulating hormone, corticotrophin releasing factor, galanin, gamma amino butyric acid (GABA), ketotifen fumarate or cromolyn.

In some embodiments, the second therapeutic agent comprises a therapeutic agent used for treating atherosclerosis. Such agents include without limitation an antihyperlipidemic agent, a plasma HDL-raising agent, an antihypercholesterolemic agent, a cholesterol biosynthesis inhibitor, an hydroxymethylglutaryl (HMG) CoA reductase inhibitor, a statin, lovastatin, simvastatin, pravastatin, fluvastatin, and atorvastatin, an HMG-CoA synthase inhibitor, a squalene epoxidase inhibitor, a squalene synthetase inhibitor, a squalene synthase inhibitor, an acyl-coenzyme A cholesterol acyltransferase (ACAT) inhibitor, melinamide, probucol, nicotinic acid and salts thereof, niacinamide, a cholesterol absorption inhibitor, beta-sitosterol, a bile acid sequestrant anion exchange resin, cholestyramine, colestipol, a dialkylaminoalkyl derivative of a cross-linked dextran, an LDL receptor inducer, a fibrate, clofibrate, bezafibrate, fenofibrate, gemfibrizol, vitamin B6 (pyridoxine) and pharmaceutically acceptable salts thereof, vitamin B6 HCl salt, vitamin B12 (cyanocobalamin), vitamin B3 (nicotinic acid or niacinamide), an anti-oxidant vitamin, vitamin C, vitamin E, beta carotene, a beta-blocker, an angiotensin II antagonist, an angiotensin converting enzyme inhibitor, a PPAR alpha agonist or partial agonist, a PPAR delta agonist or partial agonist, a PPAR gamma agonist or partial agonist, a dual PPAR alpha-PPAR delta agonist or partial agonist, a dual PPAR alpha-PPAR gamma agonist or partial agonist, a dual PPAR delta-PPAR gamma agonist or partial agonist, a pan PPAR agonist or partial agonist, a platelet aggregation inhibitor, a fibrinogen receptor antagonists, a glycoprotein IIb/IIIa fibrinogen receptor antagonist, or aspirin.

In some embodiments, the second therapeutic agent comprises a therapeutic agent used for treating hyperlipidemia. Such agents include without limitation a statin, atorvastatin, fluvastatin, lovastatin, pravastatin, simvastatin, a CETP inhibitor, torcetrapib, a cholesterol absorption inhibitor, ezetimibe, a PPAR alpha agonist or partial agonist, a PPAR delta agonist or partial agonist, a dual PPAR alpha-PPAR delta agonist or partial agonist, a dual PPAR alpha-PPAR gamma agonist or partial agonist, a dual PPAR delta-PPAR gamma agonist or partial agonist, a pan PPAR agonist or partial agonist, a fenofibric acid derivative, gemfibrozil, clofibrate, fenofibrate, bezafibrate, a bile acid-binding resin, colestipol, cholestyramine, nicotinic acid and salts thereof, probucol, betacarotene, vitamin E, or vitamin C.

In some embodiments the invention provides a method of treating Type II diabetes or related complications comprising administering to a subject in need thereof an effective amount of a pharmaceutical composition comprising chlorite or a chlorite-containing agent.

In some embodiments the invention provides a method of treating a disease associated with migration of monocytes or activated macrophages, the method comprising administering a therapeutically-effective amount of an oxidative agent to a subject in need thereof, where the oxidative agent is selected from the group consisting of non-halogen activated-oxygen compounds, non-oxygen activated-halogen compounds, activated-halogen activated-oxygen compounds, and N-halo compounds. In some embodiments, the disease is characterized by elevated CD16 expression levels in CD14+ cells. In some embodiments, the oxidative agent is selected from sodium chlorite, 1,3-dichloro-5,5-dimethylhydantoin and chloramine-T. In some embodiments, the disease is characterized by migration of PBMCs in response to chemoattractant. In some embodiments, the oxidative agent is sodium chlorite.

In some embodiments, the invention provides a method of treating a disease associated with excess production of sCD14 and/or sCD163 by activated macrophages, the method comprising administering a therapeutically-effective amount of an oxidative agent to a subject in need thereof, where the oxidative agent is selected from the group consisting of non-halogen activated-oxygen compounds, non-oxygen activated-halogen compounds, activated-halogen activated-oxygen compounds, and N-halo compounds. In some embodiments, the oxidative agent is sodium chlorite.

In some embodiments, the method of diagnosing a macrophage related disease in a subject comprising measuring the level of a biomarker in the subject and correlating the measured level of biomarker to normal and diseased levels of said biomarker, where the biomarker is selected from CD16 expression in CD14+ cells, sCD14, sCD163, expression of chemoattractants by macrophages, and combinations thereof.

In some embodiments, the invention provides a method of determining efficacy of treatment with an oxidative agent for a macrophage related disease in a subject comprising the steps of: i) initiating treatment with an oxidative agent; ii) measuring the level of a biomarker in the subject; and iii) correlating the measured level of biomarker to normal and diseased levels of the biomarker and/or levels of biomarker in said subject prior to treatment; where the biomarker is selected from CD16 expression in CD14+ cells, sCD14, sCD163, expression of chemoattractants by macrophages, and combinations thereof. In some embodiments, oxidative treatment is sodium chlorite.

In some embodiments, the invention provides a sodium chlorite compound, where the compound is a crystalline solid of greater than 95% purity. In some embodiments, the compound is a crystalline solid of greater than 99% purity. In some embodiments, the compound has an x-ray powder diffraction pattern with peaks expressed in degrees 2θ at about 21, 30, 31, 32, 34, and 39. In some embodiments, the invention provides a pharmaceutical composition comprising one or more pharmaceutical excipients and the sodium chlorite compound. In some embodiments, the invention provides a pharmaceutical composition comprising: (a) the sodium chlorite compound; (b) a pH adjusting agent; and (c) a pharmaceutically acceptable excipient or carrier, wherein said composition is a liquid that exhibits 25% less pH drift compared to an identical composition without said pH adjusting agent. In some embodiments, the pH adjusting agent is sodium phosphate dibasic.

In another aspect, the present invention provides a kit comprising: (a) one or more unit dose forms comprising an effective amount of a pharmaceutical composition comprising an oxidative agent and/or an immunomodulatory agent; and (b) one or more of packaging and instructions for use to treat a macrophage related disease. In some embodiments, the oxidative agent is chlorite or a chlorite-based compound. In some embodiments, the unit dose form is ready for administration to a subject. In some embodiments, the unit dose form is to be diluted prior to administration to a subject.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 shows that treatment of cells from five amyotrophic lateral sclerosis (ALS) blood samples with chlorite (striped bars) causes down regulation of CD16 expression on CD14+ cells.

FIG. 8 shows the effect of various compounds on CD16 expression in CD14+cells as well as monocyte toxicity (Toxicity: Reduction of %CD14 monocytes; No: %CD14 monocytes increase or no change by compound; +/−: <5% Reduction; +: Reduction between 11-20%; ++: Reduction between 21-30%; +++: Reduction between 31-40%; ++++: Reduction between 41-50%).

DETAILED DESCRIPTION OF THE INVENTION

Figure 1C:
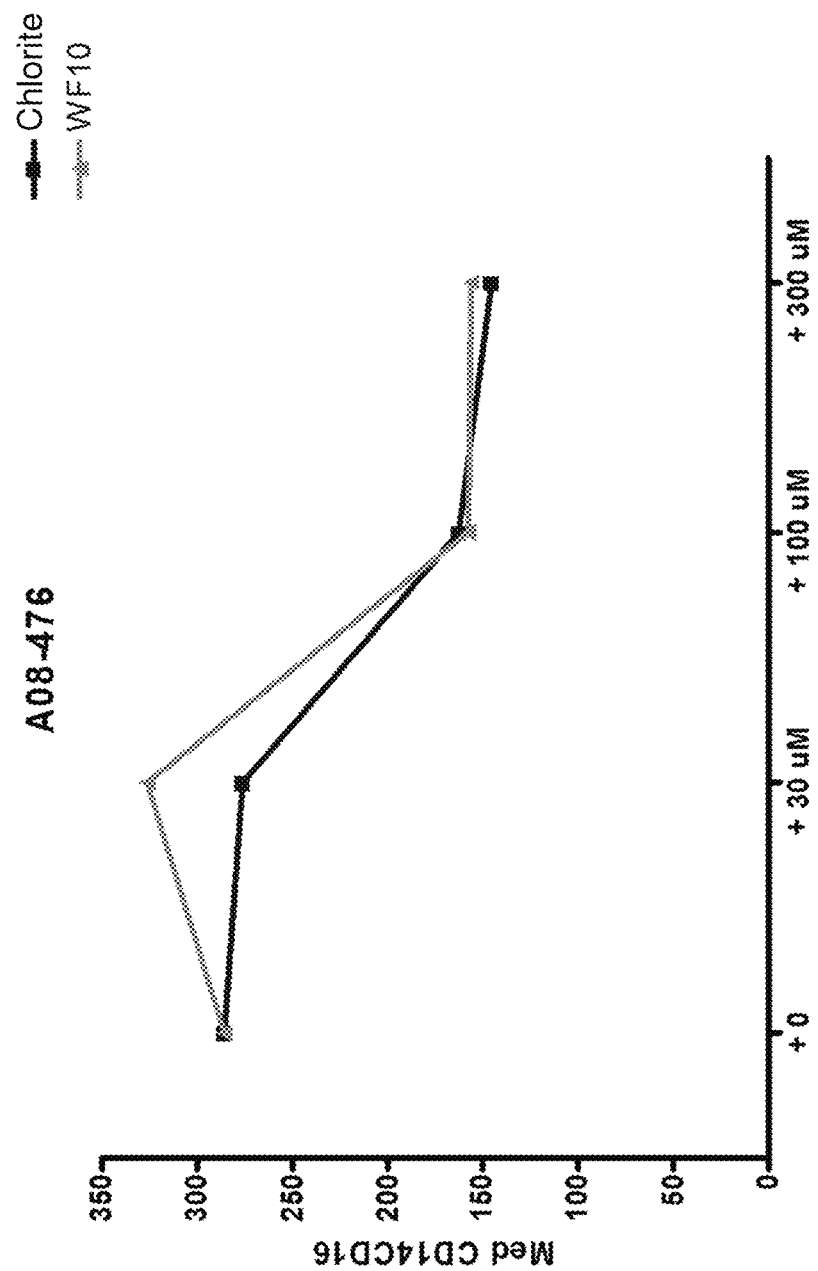
FIG. 1 shows median CD14CD16 cell surface expression levels after exposure of five samples (FIGs. 1A to 1E) of normal PBMCs to WF10 or chlorite at various concentrations for three days.

In one aspect, the present invention provides a method of treating a macrophage related diseases and conditions comprising administering to a subject in need thereof an effective amount of an oxidative agent. Macrophage related diseases and conditions include those which result directly from aberrant macrophage action, and also include any disease in which macrophages play a role, e.g., by inducing inflammation. In another aspect, the present invention provides a method of modulating macrophage accumulation or activation comprising administering to a subject in need thereof an effective amount of an oxidative agent. In some embodiments, macrophage activation is enhanced with the oxidative agent of the present invention. In other embodiments, macrophage activation is reduced or inhibited with the oxidative agent of the present invention. In still another aspect, the present invention provides a method of treating a macrophage related disease comprising administering to a subject in need thereof an effective amount of an immunomodulating agent, e.g., an immunosuppressive agent. Modulating macrophage function according to the present invention can have direct therapeutic effect, e.g., by reducing harmful inflammation. In addition, other therapeutic agents may work more effectively in the non-inflamed environment.

In some embodiments, the oxidative agent for use with the present invention comprises chlorite. In some embodiments, a chlorite formulation comprises chlorite, a buffer, e.g., monosodium phosphate buffer or disodium phosphate buffer, and a pharmaceutical excipient. In some embodiments, the oxidative agent is WF10, chloramine-T or taurine chloramine.

Immunomodulators, e.g., immunosuppressants for use with the invention include without limitation cyclophosphamide, dexamethasone, cyclosporine, azathioprine, methotrexate, FK-506 and rapamycin. Antibodies against cell surface receptors which modulate the immune response can also be used. For instance, some antibodies and soluble receptor ligands that block ligand binding to cellular receptors on B cells, T cells, NK cells, and macrophages can be used to downregulate the macrophage response directly or indirectly.

Macrophage-related diseases that can be treated by the methods of the invention include but are not limited to cancer, autoimmune diseases such as rheumatoid arthritis and multiple sclerosis, metabolic disorder, diabetes, peripheral vascular and cardiovascular disorders, infection, inflammation, and adverse effects of obesity. In some embodiments, oxidative agents or immunomodulators are used to treat a disease that is related to macrophages or monocytes. In some embodiments, the macrophage related disease is an inflammatory disease. In some embodiments, the macrophage related disease involves granuloma formation. In some embodiments, the macrophage related disease is a cancer. In some embodiments, the oxidative agent or immunomodulating agent modulates a pathway involved in macrophage activation. The macrophage activation related cellular pathways that can be modulated by the methods of the present invention include but are not limited to TLR4, CAT2, ICSBP, IFNR-I, IFNR-II, IRF1, IRF2, Raf-1, MEK1, MEK2, ERK1, ERK2, p38, MAPKK4, MAPKK6, PKC, JAK1, JAK2, STAT1, STAT3, Elk1, JNK/SAPK, AP1, Pu1, NFkB, NFAT, iNOS, USF1, ISGF3, SP1, Bcl6, ATF2, c-Jun, and COX-2. Molecules important to macrophage activation, function or effects that can be modulated, either directly or indirectly, by the methods of the present invention include but are not limited to TLR-2, TLR-4, mkp-1, COX-2, SOCS-3, FcγR1, IFN-α, IFN-β, IL-4, IL-6, IL-1Ra, IGIF, IL-1β, MHCI, MHCII IAA, MHCII TAB, MHCII IEB, IP10, IL-10, cathepsin H, lysozyme, CathB, stk, TNF-α, IL-12p35, IL-12p40, MIP-1α, ICAM-1, INOS, mig, Cat-2, CIITA, ICSBP, CathL, CSF1R, GM-CSF, IRF1, IRF-2, c-fos, VEGF, IL-8, bFGF, CSF-1, EGF, MMP-2, MMP-7, MMP-9, MMP-12, EMAPII, endothelin 2, HTF-1, HTF-2, CXCL8, TGFβ, PGE2, and MDF.

A. Oxidative Agents

In one aspect, the present invention provides a method of treating a macrophage related disease comprising administering to a subject in need thereof an effective amount of an oxidative agent. In another aspect, the present invention provides a method of modulating macrophage accumulation or activation comprising administering to a subject in need thereof an effective amount of an oxidative agent.

1. Chlorite and Other Oxidative Agents

Substances that have the ability to oxidize other substances are typically referred to as oxidative and are known as oxidizing agents, oxidants, or oxidizers, which are used interchangeably herein. An oxidizing agent (also called an oxidant, oxidizer) can be defined as either: a chemical compound that readily transfers oxygen atoms, or a substance that gains electrons in a redox chemical reaction. In both cases, the oxidizing agent becomes reduced in the process. Various common oxidizers contain oxygen (e.g., $KClO_4$) and can be considered as storage forms of oxygen. Alternatively, the term "oxidizing agent" also includes any time where formal charge is increased (losing electrons), and applies to substances that contain no oxygen, typically halogens comprising fluorine, (F); chlorine, (Cl); bromine, (Br); iodine, (I); and astatine, (At), and substances rich in these elements.

Common oxidizing or oxidative agents that can be used in the methods of the present invention include but are not limited to potassium nitrate ($KNO_3$), hypochlorite and other hypohalite compounds, iodine and other halogens, chlorite, chlorate, perchlorate, and other analogous halogen compounds, permanganate salts, ammonium cerium(IV) nitrate and related cerium(TV) compounds, hexavalent chromium compounds such as chromic and dichromic acids and chromium trioxide, pyridinium chlorochromate (PCC), and chromate/dichromate compounds; peroxide compounds, Tollens' reagent, sulfoxides, persulfuric acid, ozone, osmium tetroxide ($OsO_4$), nitric acid, and nitrous oxide ($N_2O$). In one embodiment, the oxidative agent is non-toxic to CD14 monocytes at physiologically effective concentrations.

In one aspect, the oxidative agents of the invention are compounds that readily transfer oxygen atoms and/or provide compact storage of oxygen while containing no halogens. As used herein, such compounds are referred to as non-halogen activated-oxygen compounds, and include but are not limited to potassium nitrate ($KNO_3$), permanganate salts, ammonium cerium(IV) nitrate and related cerium(IV) compounds, hexavalent chromium compounds such as chromic and dichromic acids and chromium trioxide, and chromate/dichromate compounds; peroxide compounds, Tollens' reagent, ammonium silver nitrate, sulfoxides, persulfuric acid, ozone, osmium tetroxide ($OsO_4$), nitric acid, nitrous oxide (N2O), hydrogen peroxide, organic peroxides, superoxides, and ozone.

In one aspect, the oxidative agents of the invention are compounds that contain both readily-transferrable oxygen and halogen atoms, including but not limited to hypochlorite and other hypohalite compounds, chlorite, chlorate, perchlorate and other analogous halogen compounds, and pyridinium chlorochromate (PCC). As used herein, such compounds are referred to as activated-oxygen activated-halogen compounds.

Alternatively, the oxidative agent may be a substance that contains no oxygen, typically halogens comprising fluorine, (F); chlorine, (Cl); bromine, (Br); iodine, (I); and astatine, (At). As used herein, such compounds are referred to non-oxygen activated-halogen compounds.

In one embodiment, the oxidative agent may be an N-halo compound. Such compounds include but are not limited to N-halophthalimide, N-halosuccinimide, N-halosaccharin, N,N-dihalourethane, N-haloacetanilide, 1,3-dihalo-5,5-dimethylhydantoin, trihaloisocyanuric acid, and sodium dihaloisocyanurate, where the halogen is selected from fluorine, chlorine, bromine, and iodine. Preferably, the oxidative agent may be an N-chloro compound. Such compounds include but are not limited to N-chlorophthalimide, N-chlorosuccinimide, N-chlorosaccharin, N,N-dichlorourethane, N-chloroacetanilide, 1,3-dichloro-5,5-dimethylhydantoin, trichloroisocyanuric acid, sodium dichloroisocyanurate, chloramine-T (including hydrate), and halazone (4-(N,N-dichlorosulfamoyl)benzoic acid). In one embodiment, the oxidative agent is selected from the group consisting of 1,3-dichloro-5,5-dimethylhydantoin and chloramine-T.

Many oxidative compounds have demonstrated protective and anti-inflammatory activities, likely due to induction of endogenous defense pathways. For example, metabolites of the stress induced enzyme heme oxygenase 1 (HO-1) such as carbon monoxide (CO) and biliverdin exert potent anti-inflammatory effects (Otterbein L E et al. Nat. Med. 6 (2000) 422-428). The catalytic products of HO-1 including the oxidants CO, Fe2+, and biliverdin are capable of down-regulating inflammatory reactions. Similar cell-protective properties have been described for the redox-active molecule thioredoxin (Hirota K. et al. J. Biol. Chem. 274 (1999) 27891-27897). The use of chlorite to treat various diseases and conditions is described in U.S. Pat. No. 4,725,437; U.S. Pat. No. 4,851,222; McGrath et al., Development of WF10, a novel macrophage-regulating agent, *Curr Opin Investig Drugs*, 3(3):365-73 (March 2002); U.S. Pat. No. 6,086,922; US Patent Pub. No. 2005/0181068 (Ser. No. 11/042,816), filed Jan. 24, 2005 and entitled "Chlorite in the Treatment of Neurodegenerative Disease"; and US Patent Pub. No. 2007/0145328, filed Dec. 21, 2006 and entitled "Chlorite Formulations, and Methods of Preparation and Use Thereof," all of which are incorporated herein by reference in their entirety.

In one aspect, the present invention provides for the treatment of a macrophage related disease using chlorite. The chlorite ion is $ClO_2^-$. A chlorite (compound) is a compound that contains this group, with chlorine in oxidation state +3. Chlorites are also known as salts of chlorous acid. Chlorine can assume oxidation states of −1, +1, +3, +5, or +7 within the corresponding anions $Cl^-$, $ClO^-$, $ClO_2^-$, $ClO_3^-$, or $ClO_4^-$, known commonly and respectively as chloride, hypochlorite, chlorite, chlorate, and perchlorate.

II. Tetrachlorodecaoxide (TCDO) and WF10

In some embodiments, the present invention provides methods using one or more chlorite containing agents. The source of chlorite ions for administration of chlorite according to the present invention can be provided in a variety of forms. For example, chlorite can be administered as a chlorite salt, for example, alkali metal salt, e.g. sodium chlorite, potassium chlorite, and the like, or a mixture of chlorite salts, where the chlorite salts are preferably pharmaceutically acceptable. In addition or alternatively, chlorite can be administered as a matrix of chlorite ions, e.g., described in U.S. Pat. No. 4,507,285. In one embodiment, the chlorite ions as provided in a composition having the general formula

wherein "n" can be a value of about 0.1-0.25. Such agents can have an $O_2$ band at 1562 $cm^{-1}$ in the Raman spectrum and an O—O interval of 123 pm. Production of such agents is known in the art, see e.g., U.S. Pat. No. 4,507,285.

In one embodiment, the method of treatment involves administration of an aqueous solution of a product known as "tetrachlorodecaoxygen anion complex", commonly known as TCDO. Production of TCDO is well known, see e.g., Example 1 of U.S. Pat. No. 4,507,285. In some embodiments, the chlorite containing agents that can be used in the methods of the present invention for treating diabetes or related disorders include but are not limited to chlorite salt, such as alkali metal salt, sodium chlorite, potassium chlorite, and the like, a matrix of chlorite salts, a matrix of chlorite ions, e.g., compositions having the general formula $ClO_2 \times nO_2$, where "n" can be a value or about 0.1-0.25. One example is TCDO. One of the aqueous TCDO formulations is WF10. WF10 is an aqueous formulation of the drug OXO-K993. Oxoferin is a topical formulation of the same drug and is registered and marketed as a wound healing agent in Europe and Asia. WF10 is a sterile, pyrogen-free, aqueous 10% (w/v) solution of OXO-K993 with no additional inactive ingredients and is intended for intravenous infusion. TCDO is analytically characterized as a solution containing 4.25% chlorite, 1.9% chloride, 1.5% chlorate, 0.7% sulfate, and sodium as the cation. The active principle is defined by the chlorite ion content. In one embodiment, WF10 solution contains about 63 mmol/l of chlorite.

Tetrachlorodecaoxide (TCDO) is a chlorite-containing drug used for the dressing of wounds, immunomodulation and as radiation protective agent. Due to its oxidizing properties, TCDO can destroy most pathogens although it is not regarded as antibiotic. But the main reason for its use for dressing of wounds is not its bactericidal activity. This drug is regarded as immunomodulating, that is, it acts by stimulating the immune system of the body. Tetrachlorodecaoxide combines with the heme part of hemoglobin, myoglobin and peroxidase, forming a TCDO-hemo complex. This in turn activates the macrophages and accelerates the process of phagocytosis which engulfs most of the pathogens and cell debris present on the surface of the wound, thus cleaning the wound surface and helping in the regenerative process. Tetrachlorodecaoxide is also mitogenic and chemotactic. The mitogenic impulse gives rise to two factors, MDGF (Macrophage derived growth factor) and WAF (Wound angiogenesis factor). The MDGF deposits fibroblasts and synthesizes collagen fibers, which fill the gap in the wounds, the WAF helps in the formation of new capillaries which further enhances the healing process. The chemotactic impulse acts on the myocyte (muscle cell) and causes it to contract, thereby bringing the wound edges closer and reducing the wound surface. Simultaneous influence of all these factors accelerates the wound healing with minimal scarring.

WF10 is a 1:10 dilution of tetrachlorodecaoxide (TCDO) formulated for intravenous injection. WF10 specifically targets macrophages. WF10 potentially modulates disease-related up-regulation of immune responses both in vitro and in vivo. Thus immune response is influenced in a way that inappropriate inflammatory reactions are downregulated (Arzneimittelforschung. 2001; 51(7):554-62. Schempp H, et al). WF10 is currently being studied for treatment of late-stage HIV disease, as well as recurrent prostate cancer, late post-radiation cystitis, autoimmune disease and chronic active hepatitis C disease. WF10 is approved for use in Thailand under the name IMMUNOKINE in patients with post-radiation chronic inflammatory disease including cystitis, proctitis and mucositis.

In vivo studies have investigated the effects of WF10 on monocytes, macrophages and lymphocytes, on humoral and cellular immunity, and on response to local or total body irradiation (reviewed by McGrath M S et al. *Current Opinion in Investigational Drugs* 2002 3(3)). WF10 increased the number of macrophages infiltrating a skin blister in a human wound healing model (Hansel M et al. Skin Pharmacol 1988 1:64). In rats, WF10 increased the proportion of granulocytes, peripheral blood monocytes (PBMCs) and large granular lymphocytes (LGLs), and stimulated erythropoiesis after total body X-irradiation (Ivankovic S et al. OXO Study Report 1988 March; Ivankovic S et al. Radiat Res 1988 115: 115-123). In mice, WF10 stimulated regeneration of hematopoietic stem cells receiving sublethal doses of J-irradiation (Mason K A et al. Radiat Res 1993 136: 229-235). In other studies, WF10 displayed direct antitumor effects against radiation-induced, heroical-induced and metastatic malignant and benign tumors (Kempf S R et al. International Symposium on Tissue Repair 1990 Thailand; Milas L. OXO Study Report 1991 September; Kempf S R et al. Radiat Res 1994 139: 226-231). WF10 altered proportions of T-helper and suppressor/cytotoxic cells in spleen and thymus and increased both the humoral and cellular immune responses (Gillissen G et al. OXO Study Report 1993).

Without being bound by theory, it has been suggested that WF10 causes marked inhibition of inducible genes related to T-cell proliferation and cause reproducible upregulation of inflammatory gene expression in macrophages in vitro, which is thought to contribute to the higher rate of apoptosis in activated macrophages. These data, coupled with an earlier report of WF10 inhibition of T-cell activation (McGrath M S et al. Transplant Proc. 1998 30: 4200-4202), show that WF10 causes profound changes in T-cell function through regulation of macrophage activation. The WF10 oxygen/chlorite matrix is stable until interaction with heme-associated iron, whereupon it is converted to an active chlorite molecule through a Michealis-Menten reaction and intermediate production of a reactive compound I. Chlorite is the active form of the drug thought to mediate the immunological effects in macrophages.

A dose-ranging clinical study was conducted from 1993 to 1994 in 44 HIV-positive patients with <500 CD4+ T cells/mm (Raffanti S P et al. Infection 1998 26: 201-206). The study established the maximum tolerated dose as 0.5 ml/kg/day of WF10, when administered in four 5-day cycles, with each cycle followed by 16 days of without treatment. No significant adverse events or clinical laboratory toxicity were observed at this dosage. Plasma CD8+ T-cell counts increased in a dose-dependent manner over four cycles of WF10 administration. This study demonstrated that WF10 at a dose of 0.5 ml/kg was associated with a sustained immunological response, i.e., sustained elevation of CD8+ T cell numbers, consistent with the proposed mechanism of action. Furthermore, a single-center, phase I/II study, was conducted in 1997 to evaluate safety and the effects of WF10 on the kinetics of red blood cell (RBC) survival, selective immunological markers of HIV disease, macrophage activation and viral kinetics (Herndier B et al. Keystone Symposia on Molecular and Cellular Biology. 1998). Changes in immunological parameters of cells from HIV+ patients in response to WF10 treatment are summarized in Table 1 in McGrath M S et al. *Current Opinion in Investigational Drugs* 2002 3(3), including an increase in CD3+ CD4+ cells, an increase in CD3+ CD8+ cells, an increase in CD3+ CD4+ CD38− cells, an increase in CD3+ CD8+ CD38− cells, an increase in CD3+ CD8+ CD28− cells, a decrease in CD3+ CD8+ CD28+ cells, a decrease in CD3+ CD4+ CD38+ cells, a decrease in all CD14+ cells, and a decrease in CD20+ HLR−DR+ cells. The results suggested that WF10 reduced antigen presentation while concurrently inducing phagocytosis in macrophages with impaired function. WF10 had no effect on HIV load over the course of the trial. No significant differences were detected between the WF10 and placebo group in hematological and blood chemistry values, including parameters specifically associated with hemolysis.

As appropriate, agents that provide a source of chlorite ions can be administered in a free base or free acid form, i.e., as the free compound and not as a salt. In some embodiments, the chlorite formulation contains about 150 µM chlorite.

Additionally, any pharmaceutically acceptable salt(s) of the compound(s) can also be used. Pharmaceutically acceptable salts are those salts which retain the biological activity of the free compounds and which are not biologically or otherwise undesirable. As appropriate, stereoisomers of the compounds disclosed can also be used in the invention, including diastereomers and enantiomers, as well as mixtures of stereoisomers, including but not limited to racemic mixtures. Unless stereochemistry is explicitly indicated in a structure, the structure is intended to embrace all possible stereoisomers of the compound depicted.

In some embodiments, the oxidative compound is WF10. WF10 is a chlorite-based compound. After interaction with heme proteins, the chlorite matrix of WF10 acquires oxidizing and chlorinating properties (Schempp H. et al. 1999). It has been suggested that WF10 exerts potent immunomodulatory effects most likely through generating physiologic oxidative compounds namely chloramines. Chloramines have been reported to exert cell-protective and anti-inflammatory activities (Choray M. et al. Amino Acids 23 (2002) 407-413).

Another stable oxidant that can be used in the methods of the present invention is taurine-chloramine (TauCl), which is produced by activated neutrophils in the course of inflammation and was shown to possess cell-protective as well as anti-inflammatory activities (Park E. et al. Clin. Immunol 102 (2002) 179-184). Its precursor, taurine, represents the most abundant free amino acid not incorporated into proteins in the cytosol of leukocytes. Taurine acts as a scavenger for HOCl, a microbicidal agent produced physiologically by the myeloperoxidase-hydrogen peroxide-halide system of activated neutrophils and monocytes during the oxidative burst (Cunningham C et al. Biochem J. 330 (1998) 939-945). The reaction of taurine and HOCl forms taurine-chloramine, a long-lived oxidant that is much less toxic than HOCl. TauCl itself represents a potent biologic effector molecule, which contributes to self-limitation of inflammatory processes (Marcinkiewicz J et al. J. Leuko. Biol 58 (1995) 667-674). It has been demonstrated that incubation of human peripheral mononuclear cells with WF10 leads to a rapid and stable generation of chloramines (Giese T. et al. Cellular Immunology, 229 (2004) 149-158) and TauCl represents the most relevant functional product that is formed under the influence of WF10.

In some embodiments, the present invention provides methods of modulating macrophage activation or treating a macrophage related disease comprising administering an effective amount of taurine-chloramine into a subject. TauCl possesses the ability to regulate the production of macrophage derived pro-inflammatory mediators such as NO, IL-1, TNF-alpha, and PGE2. The mechanisms involved include transcriptional as well as post-translational regulation.

Pro-oxidative substances also have a direct effect on transcriptional activities of the NFAT species of transcription factors. The nuclear translocation of NFAT requires their dephosphorylation by the calcium/calmodulin dependent serine/threonine phosphatase calcineurin. The phosphatase activity of calcineurin is redox sensitive. WF10 is able to inhibit antigen receptor driven lymphocyte proliferation. Expression of NFAT regulated genes is strongly suppressed by WF10, and the nuclear translocation of NFATc is inhibited. The WF10 associated inhibition of NFAT regulated genes in activated T cells, in concert with the induction of several monocyte associated pro-inflammatory genes, suggest activation of the innate myeloid functions concomitant with the inactivation of adaptive proliferative lymphocyte response. This approach represents a novel method of targeting redox-regulation for the treatment of inflammatory disorders. In some embodiments, the macrophage related diseases that can be treated using the methods of the present invention are inflammatory diseases.

III. Chlorite Purity and pH

Methods of formulating chlorite have been described in described in US Patent Pub. No. 20070145328, filed Dec. 21, 2006 and entitled "Chlorite Formulations, and Methods of Preparation and Use Thereof," which is incorporated herein by reference in its entirety. Such formulations are suitable for various modes of administration, including but not limited to non-topical, parenteral, systemic, or intravenous administration.

In some embodiments, the present invention makes use of chlorite formulated in aqueous solution in which the chlorite is 97-99% pure. As used herein, the "purity" of chlorite in a sample is calculated as the percent weight of chlorite salt to the total weight of the sample. In determining the purity of chlorite in a solution, the weight of the solvent (e.g., water in an aqueous solution) is not included. Purity may be evaluated using ion chromatography and an ion detector, by calibrated integration of the respective peaks; for example, chlorite, chloride, chlorate, phosphate and sulfate in the compound or formulation. For example, chlorite is commercially available as sodium chlorite, technical grade, at a purity of 80% (catalog No. 244155 Sigma-Aldrich).

Alternatively, crystalline sodium chlorite is provided in a purity greater than 95%, greater than 96%, greater than 97%, greater than 98%, greater than 99%, or greater than 99.9%. Solid pharmaceutical formulations comprising crystalline sodium chlorite in a purity greater than 95%, greater than 96%, greater than 97%, greater than 98%, greater than 99%, or greater than 99.9% in addition to one or more pharmaceutical excipients are also encompassed.

In some embodiments, the chlorite formulations for use with the present invention comprise low amounts of chlorate, sulfate or chloride. As used herein, a formulation is "substantially free" of a molecule if the molecule comprises no more than 1 part in 1000 per weight of non-solvent molecules in the formulation. In certain embodiments, the weight ratio of chlorite to chlorate is greater than 100:1.5, greater than 100:0.5, greater than 100:1, or greater than 100:0.1. In one embodiment, the composition is substantially free of chlorate. In another embodiment, the weight ratio of chlorite to chloride is greater than 100:45.5 or greater than 100:8.5. In one embodiment the composition is substantially free of chloride. In a further embodiment, the weight ratio of chlorite to sulfate is greater than 100:16.4 or greater than 100:1.6. In one embodiment the composition is substantially free of sulfate.

The pH of a chlorite formulation for use with the present invention can be adjusted to between about 7 and about 11.5. In some embodiments, the pH of a chlorite formulation is lowered to between about 7 and about 11.5 using a pH adjusting compound that does not expose the formulation to high local acidity. In some embodiments, the pH adjusting compound is any one or more of monosodium phosphate, disodium phosphate, or acetic acid.

Also described herein are methods of preparing chlorite formulations and pharmaceutical formulations, including but not limited to the chlorite formulations specifically described herein. Also described herein are kits and methods of administration of the formulations and pharmaceutical formulations described herein. Various exemplary aspects and variations of the invention are described in the "Brief Summary of the Invention," as well as elsewhere herein, including but not limited to the Examples. It is also understood that the invention includes embodiments comprising, consisting essentially of, and/or consisting of one or more elements as described herein.

In some embodiments, the invention makes use of aqueous formulations comprising chlorite. In some embodiments, the chlorite formulation comprises an aqueous solvent, and optionally one or more other solvents for chlorite. In some embodiments, the formulations comprise chlorite and an aqueous solvent for chlorite, and have a pH of about 7 to about 11.5.

Solvents or combinations of solvents for use in the formulations described herein can be determined by a variety of methods known in the art. One nonlimiting example includes (1) theoretically estimating solvent solubility parameter value(s) and choosing the one(s) that match with chlorite, using standard equations in the field; and (2) experimentally determining the saturation solubility of chlorite in the solvent(s), and (3) choosing one or more that exhibits the desired solubility, and (4) selecting a solvent or solvents that do not diminish the activity of chlorite, or that do not or only minimally react with chlorite. In some embodiments, the liquid formulations described herein comprise a plurality of solvents.

In some embodiments, the chlorite formulations comprise an aqueous solvent. In some variations, water is the principal solvent in the aqueous formulations. In some variations, water is at least about 50% by volume of the solvent component of an aqueous formulation. In some variations, water is at least about 50% by volume of the aqueous formulation. In some variations, water is any of between about 50 to about 60, between about 60 to about 70, between about 70 to about 80, between about 80 to about 90, between about 90 to about 99, at least about 50, at least about 60, at least about 70, at least about 80, at least about 90, or at least about 95, about 50, about 60, about 70, about 80, about 90, or about 95 percent by volume of the solvent component. In some variations, water is any of between about 50 to about 60, between about 60 to about 70, between about 70 to about 80, between about 80 to about 90, between about 90 to about 99, at least about 50, at least about 60, at least about 70, at least about 80, at least about 90, or at least about 95, percent by volume of the aqueous formulation. In some variations, water is at least about 95% by volume of the aqueous formulation. In some variations, water is between about 80 to about 90% by volume of the aqueous formulation. In some variations, water is between about 90 to about 99% by volume of the aqueous formulation.

The formulations may have differing concentration of chlorite. In some embodiments, the concentration of chlorite in the formulation is high, and then is diluted to a less concentrated form prior to administration. In some embodiments, a formulation described herein is diluted any of about 2.5×, about 5×, about 7.5×, about 10×, about 20×, about 25×, about 50×, about 100×, about 200×, about 250×, about 300×, about 500×, or about 1000×. In some embodiments, a formulation described herein is diluted about 2.5×, about 5×, about 10×, about 20×, about 25×, about 50×, about 100×, about 200×, about 250×, about 300×, about 500×, about 1000×; between about 2× and about 10×, between about 10× and about 50×, between about 50× and about 100×, between about 100× and about 500×, or between about 500× and about 1000×. In some embodiments, a formulation as described herein is diluted between about 2× and about 10×. In some embodiments, a formulation as described herein is diluted between about 10× and about 50×. In some embodiments, a formulation as described herein is diluted about 7.5×. In some embodiments, a formulation as described herein is diluted about 25×. In some embodiments, a formulation as described herein is diluted about 200×. In some embodiments, the concentration of chlorite in the formulations described herein is between about 1 µM and about 1.5 M. In another embodiments, the concentration of chlorite in the formulations described herein is between any of about 1 M and about 1.5 M; between about 1 µM and about 100 mM; between about between about 10 µM and about 100 mM; between about 0.1 mM and about 10 mM; between about 0.1 mM and about 500 mM; between about 0.1 mM and about 200 mM; between about 1 mM and about 100 mM; between about 0.1 mM and about 5 mM; between about 50 mM and about 100 mM; between about 55 mM and about 70 mM; between about 60 mM and about 65 mM; between about 100 mM and about 500 mM; between about 200 mM and about 400 mM; between about 300 mM and about 700 mM; about 1 mM; about 1.5 mM; about 2 mM; about 2.5 mM; about 3 mM; about 3.5 mM; about 4 mM; about 5 mM; about 10 mM; about 20 mM; about 30 mM; about 40 mM; about 50 mM; about 60 mM; about 62 mM; about 65 mM; about 70 mM; about 80 mM; about 90 mM; about 100 mM; at least about 0.1 mM; at least about 1 mM; at least about 2 mM; at least about 5 mM; at least about 10 mM; at least about 20 mM; at least about 30 mM; at least about 40 mM; at least about 50 mM; at least about 60 mM; at least about 70 mM; at least about 80 mM; at least about 90 mM; or at least about 100 mM. In some embodiments, the concentration of chlorate in the formulations described herein is between about 50 mM and about 100 mM. In some embodiments, the concentration of chlorate in the formulations described herein is between about 55 mM and about 75 mM. In some embodiments, the concentration of chlorate in the formulations described herein is between about 0.1 mM and about 10 mM. In some embodiments, the concentration of chlorate in the formulations described herein is between about 1 mM and about 5 mM.

In some embodiments, the chlorite formulation has a pH no greater than about 12.0. In some embodiments, the pH of the formulation is any of no greater than about 11.5, about 11.0, about 10.5, about 10.0, about 9.5, about 9.0, about 8.5, about 8.0, about 7.5, about 7.0, about 6.5, or about 6.0. In some embodiments, the pH of the formulation is no greater than about 11.5. In some embodiments, the pH of the formulation is no greater than about 10.5. In some embodiments, the pH of the formulation is no greater than about 8.5. In some embodiments, the pH of the formulation is no greater than about 7.5. In some embodiments, the pH of the formulation is between any one or more of about 7 and about 12; between about 7 and about 11.5; between about 7 and about 10.5; between about 7 and about 10; between about 7 and about 9.5; between about 7 and about 9.0; between about 7 and about 8.5; between about 7 and about 8.0; between about 7 and about 7.5; between about 7.5 and about 8; between about 7.5 and about 8.5; between about 7 and about 8; between about 8 and about 9; between about 7.0 and about 8.5; between about 8 and about 8.5; between about 8.5 and about 9; between about 7.1 and about 7.7; between about 7.2 and about 7.6; between about 7.3 and about 7.4; about 7.0; about 7.1; about 7.2; about 7.3; about 7.4; about 7.5; about 7.6; about 7.7; about 7.8; about 7.9; about 8.0; about 8.1; about 8.2; about 8.3; about 8.4; about 8.5; about 8.6; about 8.7; about 8.8; or about 8.9. In some embodiments, the chlorite formulation has a pH of about 7.0 to about 9.0. In some embodiments, the chlorite formulation has a pH of about 7.0 to about 8.5. In some embodiments, the chlorite formulation has a pH of about 6.0 to about 8.5. In some embodiments, the chlorite formulation has a pH of about 7.0 to about 8.0. In some embodiments, the chlorite formulation has a pH of about 7.4.

In some embodiments, the chlorite formulations have a pH as described above, and are formulated for any one or more of parenteral, systemic, or intravenous administration.

In some embodiments, the chlorite formulations have a pH as described above, and have a percentage chlorite purity as described herein.

In some embodiments, the formulations described herein have a pH as described above, and have a concentration of chlorite as described herein. In some embodiments, the aqueous formulations described herein have a pH between about 7 and about 11.5, or between about 7.0 and about 10, or between about 7.0 and about 9.0, or between about 7.0 and about 8.5, or between about 7.1 and about 7.7, and have a concentration of chlorite between about 1 and about 100 mM. In some embodiments, the aqueous formulations described herein have a pH between about 7 and about 11.5, or between about 7.0 and about 10, or between about 7.0 and about 9.0, or between about 7.0 and about 8.5, or between about 7.1 and about 7.7, and have a concentration of chlorite between about 1 and about 5 mM. In some embodiments, the aqueous formulations described herein have a pH between about 7 and about 11.5, or between about 7.0 and about 10, or between about 7.0 and about 9.0, or between about 7.0 and about 8.5, or between about 7.1 and about 7.7, and have a concentration of chlorite between about 50 and about 80 mM.

In some embodiments, the aqueous formulations described herein have a pH between about 7 and about 11.5, or between about 7.0 and about 10, or between about 7.0 and about 9.0, or between about 7.0 and about 8.5, or between about 7.1 and about 7.7, wherein the pH was adjusted with a pH adjusting agent that is any one or more of a phosphate, or acetic acid.

In some embodiments, the formulations described herein are stable with respect to one or more of pH or chlorite degradation over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In some embodiments, the formulations described herein are stable with respect to one or more of pH or chlorite degradation over a period of any of at least about 1 month. In some embodiments, the formulations are stable with respect to one or more of pH or chlorite degradation over a period of any of at least about 1 month. In some embodiments, the formulations described herein are stable with respect to one or more of pH or chlorite degradation at one or more of room temperature, refrigerated conditions, or approximately 4° C. In some embodiments, the formulations described herein are stable with respect to one or more of pH or chlorite degradation under conditions of diminished light or storage in a container that limits the amount of light to which the formulation is subjected. In some embodiments, the formulations described herein are stable with respect to one or more of pH or chlorite degradation when stored in the dark. Examples of stable pH, as used herein, means that the pH of the formulation changes by less than any of about 0.1, about 0.2, about 0.3, about 0.4, about 0.5, about 0.6, about 0.7, about 0.8, about 0.9, or about 1 relative to the pH of the formulation as initially prepared. In some embodiments, the pH of the formulation changes by less than about 0.2 relative to the pH of the formulation as initially prepared. The pH may be measured using, for example, a pH meter. Examples of stable chlorite formulations include those in which less than any of about 0.1%, less than about 0.2%, less than about 0.3%, less than about 0.4%, less than about 0.5%, less than about 0.6%, less than about 0.7%, less than about 0.8%, less than about 0.9%, less than about 1%, less than about 2%, less than about 3%, less than about 4%, less than about 5%, less than about 6%, less than about 7%, less than about 8%, less than about 9%, or less than about 10% of the chlorite degrades into a non-chlorite ion relative to the amount of chlorite present in the formulation as initially prepared. In some embodiments, less than about 2% of the chlorite degrades into a non-chlorite compound relative to the amount of chlorite present in the formulation as initially prepared. In some embodiments, less than about 0.5% of the chlorite degrades into a non-chlorite compound relative to the amount of chlorite present in the formulation as initially prepared. The presence of non-chlorite elements may be measured, for example, using gas chromatography (GC), mass spectrometry, or other methods known by those of skill in the art.

In some embodiments, the chlorite formulations described herein comprise no greater than about 5% by weight of deleterious non-chlorite elements of other commercially available formulations. In some embodiments, the chlorite formulations described herein comprise any of no greater than about 4%, about 3%, about 2%, about 1%, about 0.5%, about 0.3%, about 0.25%, about 0.2%, about 0.1%, about 0.05%, or about 0.02%, by weight of deleterious non-chlorite elements of other commercially available formulations. In some embodiments, the chlorite formulations described herein comprise any of no greater than about 4% by weight of deleterious non-chlorite elements of other commercially available formulations. In some embodiments, the chlorite formulations described herein comprise any of no greater than about 2% by weight of deleterious non-chlorite elements of other commercially available formulations. In some embodiments, the chlorite formulations described herein comprise any of no greater than about 0.5% by weight of deleterious non-chlorite elements of other commercially available formulations. In some embodiments, the chlorite formulations described herein comprise any of no greater than about 0.05% by weight of deleterious non-chlorite elements of other commercially available formulations. In some embodiments, the chlorite formulations described herein are substantially free of the deleterious non-chlorite elements of other commercially available formulations. Nonlimiting examples of methods of detection of non-chlorite components include HPLC; SPCS, for example using a Novosep A2 column with 3.6 mM Sodium Carbonate as a mobile phase, 5μ, 250×4.0 mm, flow rate 0.8 mL/min; DS-Plus Suppressor, for example using a Novosep A2 column with 3.6 mM Sodium Carbonate as a mobile phase, 5μ, 250×4.0 mm, flow rate 0.8 mL/min; an Allsep A-2 Anion column using 2.1 mM $NaHCO_3$/1.6 mM $Na_2CO_3$ as a mobile phase, 100×4.6 mm, flow rate 2.0 mL/min; an anion HC column using 2.8 mM $NaHCO_3$:2.2 mM $Na_2CO_3$ in 10% Methanol as a mobile phase, 150×4.6 mm, flow rate 1.4 mL/min; or an Allsep A-2 Anion column using 2.1 mM $NaHCO_3$/1.6 mM $Na_2CO_3$ as a mobile phase, 5μ, 100×4.6 mm, flow rate 1.0 mL/min. See, for example, the Alltech Associates, Inc. Grace Davison line of products and product information for details. In some embodiments, formulations described herein comprise no greater than about 10%, about 20%, about 30%, about 40%, about 50%, about 60%, about 70%, about 75%, about 80%, about 85%, about 90%, or about 95% of the amount of a member of the group consisting of, or alternatively any one or more of, chlorate ions and sulfate ions present in an equal weight/volume percent of chlorite formulated as WF10 or a dilution thereof. That is, in some embodiments, when a non-WF10 formulation as described herein comprises a certain percent w/v of chlorite, such formulation has no greater than about the stated percentage of the amount of one or more of the specified non-chlorite components in WF10 or a dilution thereof, wherein the WF10 or dilution thereof comprises the same percent w/v of chlorite as is found in the non-WF10 formulation with which it is being compared. In some embodiments, the formulations described herein comprise no greater than about 75% of the amount of a member of the group consisting of, or alternatively any one or more of, chlorate ions and sulfate ions present in an equal weight/volume percent of chlorite formulated as WF10. In some embodiments, the formulations described herein comprise no greater than about 85% of the amount of a member of the group consisting of, or alternatively any one or more of, chlorate ions and sulfate ions present in an equal weight/volume percent of chlorite formulated as WF10. In some embodiments, the formulations described herein comprise no greater than about 50% of the amount of a member of the group consisting of, or alternatively any one or more of, chlorate ions and sulfate ions present in an equal weight/volume percent of chlorite formulated as WF10.

It can be understood from the product insert of WF10 that WF10 reportedly includes a ratio of chlorite to chlorate of 100:35.7 (4.25% to 1.5%), a ratio of chlorite to chloride of 100:45.5 (4.25% to 1.9%) and a chlorite to sulfate ratio of 100:16.4 (4.25% to 0.7%).

Examples of deleterious non-chlorite components include non-chlorite components that cause an adverse reaction when administered to physiological systems. In some variations, a deleterious non chlorite component is associated with one or more indicia of toxicity in one or more of in vitro or in vivo assays known in the art, or are associated with one or indicia of toxicity when administered to a physiological system, including but not limited to a subject, including but not limited to a human subject. Deleterious non chlorite components include but are not limited to sulfate, chlorine dioxide, chlorate, and borate. In some embodiments, the chlorite formulations described herein are substantially free of the deleterious non-chlorite elements of WF10. In some variations, the chlorite formulations described herein are substantially free of sulfate and chlorate ions.

In some embodiments, the chlorite formulations described herein contain less than about 1.9% of chloride ions. In some embodiments, the chlorite formulation contains any of less than about 1.9%, less than about 1.8%; less than about 1.5%; less than about 1.0%; less than about 0.5%; less than about 0.3%; less than about 0.1%; less than about 0.05%; less than about 0.01%; less than about 0.001%; between about 0.001 to about 0.1%; between about 0.1 to about 0.5%; between about 0.5 to about 1.0%; between about 1.0 to about 1.5%; or between about 1.5 to about 1.8% by weight of chloride ions. In some embodiments, the chlorite formulation contains less than about 0.5% by weight of chloride ions. In some embodiments, the chlorite formulation contains less than about 0.24% by weight of chloride ions. In some embodiments, the chlorite formulation contains less than about 0.2% by weight of chloride ions. In some embodiments, the chlorite formulation contains less than about 0.1% by weight of chloride ions. In some embodiments, the chlorite formulation is substantially free of chloride ions. In some embodiments, the level of chloride ions is below the level of detection using HPLC.

In some embodiments, the chlorite formulation contains less than about 1.5% of chlorate ions. In some embodiments, the chlorite formulation contains any of less than about 1.4%, less than about 1.3%; less than about 1.0%; less than about 0.5%; less than about 0.3%; less than about 0.1%; less than about 0.01%; less than about 0.001%; between about 0.001 to about 0.1%; between about 0.001 to about 0.01%; between about 0.01 to about 0.1%; between about 0.1 to about 0.5%; between about 0.5 to about 1.0%; or between about 1.0 to about 1.4% of chlorate ions. In some embodiments, the chlorite formulation is substantially free of chlorate ions. In some embodiments, the chlorite formulation contains less than about 0.5% by weight of chlorate ions. In some variations, the chlorite formulation is substantially free of chlorate ions. In some embodiments, the chlorite formulation contains less than about 0.19% by weight of chlorate ions. In some embodiments, the chlorite formulation contains less than about 0.1% by weight of chlorate ions. In some embodiments, the level of chlorate ions is below the level of detection using HPLC.

In some embodiments, the chlorite formulation contains less than about 0.7% of sulfate ions. In some embodiments, the chlorite formulation contains any of less than about 0.65%; less than about 0.6%; less than about 0.5%; less than about 0.4%; less than about 0.3%; less than about 0.2%; less than about 0.1%; less than about 0.08%; less than about 0.07%; less than about 0.06%; less than about 0.05%; less than about 0.005%; less than about 0.0005%; between about 0.001 to about 0.1%; between about 0.01 to about 0.1%; between about 0.01 to about 0.5%; between about 0.06 to about 0.08%; or between about 0.5 to about 0.65% of sulfate ions. In some embodiments, the chlorite formulation contains between about 0.5 to about 0.65% of sulfate ions. In some embodiments, the chlorite formulation is substantially free of sulfate ions. In some embodiments, the chlorite formulation contains less than about 0.5% by weight of sulfate ions. In some embodiments, the chlorite formulation is substantially free of sulfate ions. In some embodiments, the chlorite formulation contains less than about 0.08% by weight of sulfate ions. In some embodiments, the level of sulfate ions is below the level of detection using HPLC.

In some embodiments, the chlorite formulations described herein comprise phosphate ions. In some embodiments, the chlorite formulations described herein comprise sodium ions. In some embodiments, a chlorite formulation comprises chlorite, an aqueous solvent, sodium, and phosphate ions. In some variations, the aqueous solvent consists essentially of water. In some embodiments, a chlorite formulation consists essentially of chlorite, water, sodium, and phosphate, and is substantially free of chlorate. In some embodiments, a chlorite formulation consists essentially of chlorite, water, sodium, and phosphate, and is substantially free of chlorate, and further comprises a pharmaceutically acceptable diluent. In some embodiments, sodium and phosphate are provided in whole or in part as monosodium phosphate or disodium phosphate. In some embodiments, the pharmaceutically acceptable diluent is a saline solution.

In some embodiments, the chlorite formulations described herein comprise no greater than about 10% by weight of by products or impurities present in commercially available technical grade chlorite. Nonlimiting examples of by-products or impurities present in commercially available technical grade chlorite include chlorate, sulfate, chlorine dioxide, chloride, sodium bicarbonate, and sodium carbonate. In some embodiments, the chlorite formulations described herein comprise no greater than about any of 15%, about 12%, about 10%, about 9%, about 8%, about 7%, about 6%, about 5%, about 4%, about 3%, about 2%, about 1%, about 0.5%, about 0.3%, about 0.1%, between about 0.1 to about 5%; between about 5 to about 10%; or between about 10 to about 15% by weight of one or more degradation products or impurities present in commercially available technical grade chlorite, including but not limited to one or more of chlorate or sulfate. In some embodiments, the chlorite formulations described herein comprise no greater than about 0.5% by weight of degradation products or impurities present in commercially available technical grade chlorite, including but not limited to one or more of chlorate or sulfate. In some embodiments, the chlorite formulations described herein comprise no greater than about 5% by weight of degradation products or impurities present in commercially available technical grade chlorite, including but not limited to one or more of chlorate or sulfate. In some embodiments, the chlorite formulations described herein are substantially free of the degradation products or impurities present in commercially available technical grade chlorite, including but not limited to chlorate or sulfate.

In some embodiments, the formulations described herein are less toxic to a subject than previously reported chlorite formulations at the same concentration of chlorite, when administered by at least one of the routes of administration described herein, including but not limited to by non-topical, systemic, parenteral, or intravenous administration. In some embodiments, the toxicity of a chlorite formulation is analyzed for toxicity using an in vivo or in vitro toxicity assay, including well-known toxicity assays. In some embodiments, the chlorite formulation is analyzed for toxicity using a non-specific in vitro toxicity assay.

In another variation, toxicity is measured according to various response indicia of toxicity in a subject after administration of the chlorite formulations described herein, as compared to administration of other commercially available chlorite formulations. In some variations, toxicity is measured relative to systemic administration of chlorite formulated as WF10. In another variation, toxicity is measured relative to intravenous administration of chlorite formulated as WF10 to a subject. In some variations, toxicity is measured after administration to a mammalian subject, including but not limited to a human subject. In some variations, toxicity is measured as one or more of irritation to the surface to which the chlorite formulation is exposed, including but not limited to the gastrointestinal tract, nausea, vomiting, diarrhea, abdominal pain, hemolysis, methemoglobinemia, cyanosis, anuria, coma, convulsions, liver damage, kidney damage, loss of appetite, or weight loss. In some variations, toxicity is measured as one or more of asthenia, injection site pain, headache, rhinitis, or diarrhea. See, e.g., McGrath M S, "Development of WF10, A Novel Macrophage-Regulating Agent," *Curr Opin Investig Drugs,* 3(3): 365-73 (March 2002), which is incorporated by reference in its entirety. In another variation, toxicity is measured as anemia. See, e.g., Kempf et al., "Comparative Study on the Effects of Chlorite Oxygen Reaction Product TCDO (Tetrachlorodecaoxygen) and Sodium Chlorite Solution (NaClO2) With Equimolar Chlorite Content on Bone Marrow and Peripheral Blood of BDIX Rats," *Drugs Under Experimental and Clinical Research,* 19(4):165-1 (1993). In some variations, toxicity is measured as asthenia. In some variations, toxicity is measured as injection site reaction. In some variations, toxicity is measured as injection site pain.

IV. Methods of Purifying Chlorite

Various methods can be used for purifying chlorite, e.g., to produce the formulations or pharmaceutical formulations described herein. However, the formulations and pharmaceutical formulations described herein may also be produced by other methods, and the formulations and pharmaceutical formulations described herein are not limited to those produced by the methods described herein.

In some embodiments, the purification is by subjecting a mixture comprising chlorite to conditions in which chlorite is in solution but one or more impurities are insoluble. The chlorite is separated from the insoluble impurities. In some embodiments, the chlorite is further purified by crystallization of the chlorite from the mixture, and separation of the chlorite from the remaining mixture. In some embodiments, the chlorite is purified from a mixture comprising sodium chlorite.

Generally, the chlorite ions may be from any source containing chlorite. For example, chlorite may be a chlorite salt, for example alkali metal salts, sodium chlorite, potassium chlorite, and the like, or a mixture of chlorite salts. Alternatively, the source of chlorite may be from a formulation comprising chlorite. In some embodiments, chlorite is purified from a formulation comprising TCDO or WF10. In some embodiments, chlorite is from a solution comprising sodium chlorite.

In some embodiments, impure chlorite, including but not limited to impure sodium chlorite, is dissolved in a solvent or a solvent system. In some variations, any solvent in which chlorite dissolves is used. In some embodiments, any solvent in which chlorite dissolves and with which chlorite does not react is used. In some embodiments, the solvent is distilled water. In some embodiments, the solvent is a non-organic solvent.

In some embodiments, impure sodium chlorite is between about 0.1% to about 99% per weight of the starting material. As non-limiting example of the purity of the chlorite starting material, the chlorite is between about any of 0.1% and about 5%; between about 1% and about 5%; between about 4% and about 10%; between about 1% and about 15%; between about 15% and about 25%; between about 5% and about 25%; between about 25% and about 50%; between about 50% and about 75%; between about 75% and about 85%; between about 85% to about 95%; between about 60% and about 90%; between about 95% and about 99% per weight of the starting material; at least about 50, at least about 60, at least about 70, at least about 80, at least about 90, or at least about 95% pure. If the impure chlorite is in a solvent, the percent purity is relative to the non-solvent components. In some embodiments, the chlorite is between about 75% and about 85% pure. In some embodiments, the chlorite is between about 85% and about 95% pure. In some embodiments, the chlorite is at least about 85% pure.

In some embodiments, small amounts of hydrogen peroxide are added to the dissolved chlorite. While not bound by theory, the addition of small amounts of hydrogen peroxide may reduce sodium chlorate to sodium chlorite. If desired, unreacted hydrogen peroxide may be subsequently removed. In some embodiments, hydrogen peroxide is added after the initial dissolution of chlorite step and subsequently removed by filtration, for example, by centrifugal filtration.

In some embodiments, an impure solution of chlorite is subjected to conditions wherein the chlorite remains soluble, but one or more of the impurities is no longer soluble. One such method is described in Russian Patent No. SU327132, which is hereby incorporated by reference in its entirety. In some variations, the impure solution is concentrated at an elevated temperature until one or more impurities precipitate. It is envisioned that the precipitated impurities can include but are not limited to chlorate, chloride, and sulfate. In some embodiments, the impure solution is concentrated at a temperature that is any of between about 60 to about 100° C.; between about 65 to about 75° C.; between about 60 to about 80° C.; between about 60 to about 100° C.; between about 70 to about 90° C.; at about 60° C.; at about 65° C.; at about 70° C.; at about 75° C.; or at about 80° C. In some variations, the impure solution is concentrated at a temperature that is between about 65 to about 75° C.

In some embodiments, the impure solution is concentrated using the methods described herein and under reduced pressure. A skilled artisan is familiar with a range of suitable techniques for providing reduced pressure including but not limited to the application of a vacuum during concentration.

The degree to which the chlorite solution is concentrated may be varied. In some variations, the solid to liquid phase volume ratio in the suspension is no greater than about 1 part to about 12 parts. By way of one non-limiting example, at least 50% water removal from a starting solution of chlorite has been demonstrated to result in the elimination of a significant amount of impurities, e.g., chloride and/or chlorate, while maintaining chlorite in solution. One or more impurities are thereafter separated from the chlorite. In some variations, the impurities are removed while the mixture is still subject to conditions wherein the chlorite remains soluble, but one or more of the impurities are no longer soluble. One method of removing the impurities is by filtration. If filtration is used, the temperature upon filtration may be, e.g., at an elevated temperature that is similar to the temperature at which the concentration was performed. In some variations filtration is used, and the filtration occurs shortly after concentration. The concentrated chlorite solution includes greater than 80% pure chlorite by weight. The purity of chlorite in the concentrated solution can be greater than 85% pure or greater than 90% pure by weight.

The resulting chlorite solution may optionally be again subjected to conditions wherein the chlorite remains soluble, but one or more of the impurities is no longer soluble. The conditions may be optimized to reduce the same or a different impurity as was reduced in the first purification.

In some embodiments, the chlorite is subjected to conditions wherein the chlorite is not soluble, but the impurities are soluble. In some embodiments, chlorite is purified by inducing chlorite to crystallize from a solution. In some embodiments, the chlorite is induced to crystallize from a concentrated filtrate prepared by the methods described herein. As one non-limiting example, chlorite may be induced to crystallize by cooling the chlorite solution. In some variations, chlorite is induced to crystallize by exposure of a chlorite solution to a temperature that is any of no greater than about 10° C., no greater than about 0° C., no greater than about −10° C.; no greater than about −20° C.;

no greater than about −30° C.; no greater than about −40° C.; between about −15° C. and about −35° C., between about −20° C. and about −30° C.; about 10° C.; about 0° C.; about −10° C.; about −15° C.; about −20° C.; about −25° C.; about −30° C.; about −35° C.; or about −40° C. In some embodiments, the chlorite is induced to crystallize by exposure of a chlorite solution to a temperature no greater than about −20° C. In some embodiments, the chlorite is induced to crystallize by exposure of a chlorite solution to a temperature between about −20° C. and about −30° C.

In general, the chlorite may be cooled at different rates, such as a stepwise placement into increasingly cool environments, or the chlorite formulation may be placed in a single cooling environment. The chlorite formulation may be cooled over a period of, for example, 12 to 24 hours. Longer or shorter periods may also be utilized. In some embodiments, the chlorite formulation is cooled over a period of between about 12 and about 14, about 14 and about 16, about 16 and about 18, about 18 and about 20, about 20 and about 22, or about 22 to about 24 hours.

In some embodiments, chlorite is harvested from a mixture comprising chlorite solids. The solids may be harvested by various methods known by those of skill in the art, including but not limited to by filtration. In some variations, chlorite solids are harvested from a mixture comprising chlorite that has been cooled to crystallize the chlorite solids.

In some embodiments, a mixture comprising chlorite solids is filtered as a frozen mixture comprising chlorite melts. When filtration is specified, those of skill in the art can determine an appropriate method of filtration. In some embodiments, suction filtration is used to separate chlorite solids from a mixture. The chlorite solids can be in the form of a slurry or slush. In another embodiment, centrifugal filtration is used to separate chlorite solids from a mixture. During centrifugal centrifugation, water (ice) remaining in the mixture containing chlorite solids melts and can be eliminated while the chlorite solids remain associated with a filter. In some embodiments, centrifugal filtration is performed using a 50 micron filter at 1200 rpm. In some embodiments, the filter is about 50 to about 250 microns. In some embodiments, the rpm are about 1000 to about 3600. In some embodiments, the force of gravity is used to separate the solids from the rest of the mixture. The resulting chlorite solids can be in a hydrated form.

The chlorite may optionally be recrystallized by the above or a different method. In some embodiments, the chlorite is recrystallized to give chlorite of increased purity relative to the first recrystallization.

The present invention can use mixtures comprising chlorite, wherein the chlorite is any of greater than about 70%, greater than about 80%, greater than about 85%, greater than about 90%, greater than about 95%, greater than about 99%; between about 70-80%; between about 80-90%; between about 90-99%; about 70%; about 75%; about 80%; about 85%; about 90%; about 95%; or about 99% pure. If a solvent is present, including but not limited to water, the percentage purity is relative to the non-solvent components. In some embodiments, the chlorite is between about 70-80% pure. In some embodiments, the chlorite is between about 80-90% pure.

Purified chlorite may be dissolved in an aqueous solvent to give a chlorite solution of the desired concentration or molarity. As one example, the purified chlorite may be dissolved in distilled water or a saline solution, or any solvent, mixture of solvents, or solvent system that is capable of dissolving chlorite, or a solvent that is pharmaceutically acceptable for administration in a subject. Such a solvent is readily identified by those of skill in the art. See, e.g., Remington: The Science and Practice of Pharmacy, Twentieth Edition, Lippincott Williams & Wilkins; 20th edition (Dec. 15, 2000), which is incorporated herein by reference in its entirety. In some embodiments, the solvent is water. The resulting chlorite solution can include greater than 90% pure chlorite ions by weight. In some embodiments, the purity of chlorite in the solution can be greater than 95% pure chlorite ions or greater than 99% pure chlorite ions by weight. In some embodiments, wherein the purified chlorite is dissolved in water to an approximately 1M concentration, the solution includes a pH, e.g., of about pH 8.5 to about pH 10.

Alternatively, the chlorite may be suspended in a suspending medium, including but not limited to any suspending medium that is capable of suspending chlorite, or a suspending medium that is pharmaceutically acceptable for administration in a subject. Such a suspending medium is readily identified by those of skill in the art. See, e.g., Remington, cited above.

Briefly, one method of preparing a formulation comprising chlorite as disclosed herein can be achieve through the steps of: (a) concentrating a chlorite solution at a temperature between 60° C. to about 100° C., whereby impurities precipitate from the solution, (b) removing the impurities from the concentrated solution by filtration, (c) inducing crystallization of chlorite from the concentrated solution, (d) harvesting the resulting chlorite solids by filtration, and (e) dissolving the chlorite solids in an aqueous solvent. It is envisioned that in some variations the resulting aqueous formulation of chlorite comprises a purity of at least 80% chlorite, at least 85% chlorite, at least 90% chlorite, at least 95% chlorite or at least 99% chlorite.

The chlorite may also be emulsified in an emulsification system, including but not limited to any emulsification system that is capable of emulsifying chlorite, or an emulsification system that is pharmaceutically acceptable. Such an emulsification system is readily identified by those of skill in the art. See, e.g., Remington, cited above.

(a) Good Manufacturing Practice (GMP) Formulations and Methods

The chlorite formulations for use with the present invention can be prepared under a standard relating to manufacture and quality control of pharmaceutical goods, called GMP (Good Manufacturing Practice), which has been enacted in many countries. GMP specifies, because of the importance of pharmaceutical goods which can decide one's life, quality control measures such as chemical analysis, to maintain optimum equipment and environments for manufacturing pharmaceutical goods, and to take care of all manufacturing practices including manufacture, packaging, display, and storage of pharmaceutical products and materials. GMP further refers to the Good Manufacturing Practice Regulations promulgated by the US Food and Drug Administration (FDA) under the authority of the Federal Food, Drug, and Cosmetic Act. GMP is also sometimes referred to as "cGMP". The "c" stands for "current," reminding manufacturers that they must employ technologies and systems which are up-to-date in order to comply with the regulation. For example, systems and equipment used to prevent contamination, mix-ups, and errors, which were state-of-the-art 20 years ago, may be less than adequate by current standards.

Accordingly, GMP is well known to those of skill in the art in relation to the manufacture of pharmaceutical goods.

It is envisioned that the compositions and methods described herein can be manufactured and performed under GMP or cGMP.

(b) Methods of Adjusting the pH of Formulations Sensitive to pH

Various methods can be used to adjust the pH of formulations and pharmaceutical formulations comprising chlorite. It is intended that the methods described herein can be used to produce the formulations or pharmaceutical formulations described herein for use with the present invention. However, the formulations and pharmaceutical formulations described herein may also be produced by other methods, and the formulations and pharmaceutical formulations described herein are not limited to those produced by the methods described herein.

Some compounds or formulations are sensitive to high local acidity or alkalinity, requiring proper methods to adjust the pH of such compounds or formulations. Preferred pH adjusting agent(s) or pH adjusting compound(s) are weak acids or weak bases having a pKa of about 4 to about 9, a pKa of about 5 to about 9, or a pKa of about 5 to about 8, or a pKa of about 6 to about 7.5. Examples include, but are not limited to a phosphate buffer having a pKa of about 4 to about 9 as well known in the field, for example, monobasic phosphates, or monosodium phosphate and/or disodium phosphate and lower alkanoic acids, for example, acetic acid or propionic acid. In some embodiments, the pH of a formulation sensitive to acidity is lowered to between about 7 and about 11.5 using a pH adjusting compound that does not expose the formulation to acidity, including but not limited to a high local acidity in the area around the pH adjusting compound. In some embodiments, the pH of a formulation sensitive to acidity is lowered to between about 7 and about 10 using a pH adjusting compound that does not expose the formulation to acidity, including but not limited to a high local acidity in the area around the pH adjusting compound. In some embodiments, the pH of a formulation sensitive to acidity is lowered to between about 7 and about 9.5 using a pH adjusting compound that does not expose the formulation to acidity, including but not limited to a high local acidity in the area around the pH adjusting compound. In some embodiments, the pH of a formulation sensitive to acidity is lowered to between about 7 and about 9.0 using a pH adjusting compound that does not expose the formulation to acidity, including but not limited to a high local acidity in the area around the pH adjusting compound. In some embodiments, the pH of a formulation sensitive to acidity is lowered to between about 7 and about 8.5 using a pH adjusting compound that does not expose the formulation to acidity, including but not limited to a high local acidity in the area around the pH adjusting compound. In some embodiments, the pH of a formulation sensitive to acidity is lowered to between about 7.1 and about 7.7 using a pH adjusting compound that does not expose the formulation to acidity, including but not limited to a high local acidity in the area around the pH adjusting compound.

"High local acidity," as used herein, refers to the pKa of one or more molecules local to a chlorite molecule, as opposed to the overall acidity of a solution as would be measured, for example, using a pH meter. To determine whether a pH-adjusting agent will subject chlorite to high local acidity, the pKa of the pH adjusting agent can be identified using, for example, the CRC Handbook of Chemistry and Physics (86th Edition, David R. Lide ed., CRC Press, 2005).

Lowering the pH of chlorite formulations has been challenging because many pH adjusting agents expose compounds or formulations to high acidity in the local area of the molecules of the pH-adjusting compound. In the presence of high local acidity, some amount of non-chlorite compounds are generated, e.g., chlorate and/or chlorine dioxide. See, e.g., Ullmann's Encyclopedia of Industrial Chemistry, Vol. A6, Ed. Wolfgang Gerhartz, 5th Ed. (1986), which is incorporated herein by reference in its entirety. Such degradation products may not be desired in formulations for parenteral or systemic administration to physiological systems, e.g., because they are not inactive in physiological systems. Some such degradation products result in toxicity, including but not limited to the toxicities, including but not limited to non-specific toxicity, described herein.

Unless the context makes clear, the pH of any of the formulations or pharmaceutical formulations described herein may be adjusted using the methods described herein.

In some variations, the activity of a therapeutic agent, including but not limited to chlorite, is diminished by exposure to high local acidity. "Diminished activity," as used herein, refers to an activity of a therapeutic agent that is qualitatively or quantitatively inferior to that of the therapeutic agent prior to the exposure to high local acidity. As one example, a changed activity that is qualitatively or quantitatively inferior to that of the therapeutic agent prior to the exposure to high local acidity would be a lesser efficacy of wound healing, or a lesser efficacy in treating one or more of the diseases or conditions described herein. In some variations, the changed activity is any of at least about 3%, at least about 5%, at least about 10%, at least about 15%, at least about 20%, or at least about 25% lower than the activity of the therapeutic agent prior to the exposure to high local acidity. In some variations, the changed activity is at least about 5% lower than the activity of the therapeutic agent prior to the exposure to high local acidity.

In some embodiments, the pH of a chlorite formulation is adjusted to any one or more of the pH levels described in the formulations section or elsewhere herein. In some embodiments, the pH of a chlorite formulation described between about 7 and about 11.5. In some embodiments, the method comprises lowering the pH of a formulation comprising chlorite to any of between about between about 7 and about 11; between about 7 and about 10.5; between about 7 and about 10; between about 7 and about 9.5; between about 7 and about 9; between about 7 and about 8.5; between about 7 and about 8.0; between about 7 and about 7.5; between about 7.5 and about 8; between about 7.5 and about 8.5; between about 7 and about 8; between about 7.1 and about 7.7; between about 7.2 and about 7.6; between about 7.3 and about 7.5; between about 8 and about 9; between about 8 and about 8.5; between about 8.5 and about 9; about 7.0; about 7.1; about 7.2; about 7.3; about 7.4; about 7.5; about 7.6; about 7.7; about 7.8; about 7.9; about 8.0; about 8.1; about 8.2; about 8.3; about 8.4; about 8.5; about 8.6; about 8.7; about 8.8; or about 8.9 using a pH adjusting agent that does not expose the chlorite to a high local acidity. In some embodiments, the method comprises lowering the pH of a formulation comprising chlorite to between about 7 and about 8.5. In some embodiments, the method comprises lowering the pH of a formulation comprising chlorite to between about 7 and about 8.0. In some embodiments, the method comprises lowering the pH of a formulation comprising chlorite to between about 7.1 and about 7.7. In some embodiments, the method comprises lowering the pH of a formulation comprising chlorite to about 7.4.

In one nonlimiting example, the pH of a mixture comprising chlorite is adjusted using a pH adjusting agent that does not subject the chlorite to a local pH of below 7 when exposed to the mixture comprising chlorite. In some embodiments, the pH adjusting agent is monosodium phosphate, disodium phosphate, or a mixture thereof. In some embodiments, monosodium phosphate and/or disodium phosphate is used as a solid or in solution. In some embodiments, the pH adjusting agent is acetic acid.

In some embodiments, the pH of chlorite is adjusted by adding chlorite or an aqueous mixture comprising chlorite to a solution containing buffer. In some embodiments, the pH of chlorite is adjusted by adding chlorite or an aqueous mixture comprising chlorite to a solution of a phosphate buffer.

In some variations, one or more pH-adjusting agents are used to adjust the pH of a chlorite solution or mixture, and the resulting solution or mixture is analyzed for the presence of degradation products of chlorite, including but not limited to degradation products generated by high local acidity. In some variations, pH-adjusting agents such as acetic acid, monosodium phosphate, and/or disodium phosphate are used to adjust the pH of a chlorite solution or mixture, and the resulting solution or mixture is analyzed for the presence of chlorate or chlorine dioxide.

In some embodiments, the resulting solution or mixture is analyzed for degradation products using well known analytical methods such as HPLC, mass spectrometry, etc. In some embodiments, the resulting solution or mixture is analyzed for degradation products using a toxicity assay, including well-known toxicity assays. In some embodiments, the resulting solution or mixture is analyzed for impurities using a non-specific toxicity assay.

In some embodiments, the pH of a chlorite formulation is adjusted after a chlorite purification step.

In some embodiments, the pH of a chlorite formulation is adjusted to between about 7 and about 11.5 without the generation of chlorite degradation products that are a result of high local acidity. In some embodiments, the pH of a chlorite formulation is adjusted to between about 7 and about 8.0 without the generation of chlorite degradation products that are a result of high local acidity. In some embodiments, the pH of the chlorite formulation is adjusted to any of between about 7 and about 11; between about 7 and about 10.5; between about 7 and about 10; between about 7 and about 9.5; between about 7 and about 9; between about 7 and about 8.5; between about 7 and about 8; between about 7 and about 7.5; between about 7.5 and about 8; between about 7.5 and about 8.5; between about 7 and about 8; between about 8 and about 9; between about 8 and about 8.5; or between about 8.5 and about 9 without the generation of chlorite degradation products that are a result of high local acidity.

V. Pharmaceutical Formulations

Unless the context clearly indicates otherwise, any of the formulations described herein may be used in any of the pharmaceutical formulations described herein. In a preferred embodiment, the pharmaceutical composition comprises: (a) chlorite; (b) a pH adjusting agent; and (c) a pharmaceutically acceptable excipient. In some embodiments, the pH adjusting agent comprises monosodium phosphate and/or disodium phosphate. In some embodiments, the pH of the composition is between about 7.1 and about 7.7, e.g., 7.4. The formulations can have low levels of harmful chlorate, e.g., the weight ratio of chlorite:chlorate can be greater than 100:1.5. In some embodiments, such formulations are formulated to be administered intravenously.

In some embodiments, the pharmaceutical formulations described herein are suitable for administration to a subject. By "suitable for administration to a subject" is meant that the pharmaceutical formulation, when obtained from a newly opened bottle and administered via the desired route, causes no greater than a clinically acceptable level of deleterious side effects.

In some embodiments, the formulations or pharmaceutical formulations described herein further comprise a saline solution. A saline solution, as used herein, refers to a physiologically acceptable solution with a physiologically acceptable level of sodium chloride. In some embodiments, the saline solution is isotonic.

The chlorite formulations for use with the present invention are pharmaceutically acceptable chlorite formulations comprising one or more pharmaceutically acceptable excipients. Excipients, as used herein, refer to any non-chlorite, non-water, or non-saline element of a pharmaceutical formulation. Excipients include but are not limited to carriers, adjuvants, diluents, stabilizers, wetting agents, emulsifiers, buffers, preservatives, flavorings, inactive ingredients, gel formulations, erodible and non-erodible polymers, microspheres, liposomes, etc., including combinations of the foregoing, known to skilled artisans and described further herein. In some embodiments, the percent by weight of the excipient per the total volume of the formulation or pharmaceutical formulation is no greater than any of about 10%, about 9%, about 8%, about 7%, about 6%, about 5%, about 4%, about 3%, about 2%, about 1%, about 0.5%, about 0.4%, about 0.3%, about 0.2%, about 0.1%, or about 0.05%. In some embodiments, the percent by weight of the excipient per the total volume of the formulation or pharmaceutical formulation is no greater than about 1%. In some embodiments, the percent by weight of the excipient per the total volume of the formulation or pharmaceutical formulation is no greater than about 3%.

Below is a non-limiting and non-exhaustive list of excipients that are commonly used in the pharmaceutical arts. These excipients are commonly used in various types of formulations, including those formulated for intravenous, oral, intramuscular, or parenteral administration. Given the reactivity of chlorite, it is likely that some of the excipients listed below are inappropriate for a given pharmaceutical formulation. Whether or not a particular excipient is inappropriate for a given pharmaceutical formulation may depend upon the amount of the excipient being added to the pharmaceutical formulation. Before adding one or more of any excipient, including but not limited to the excipients described herein, to a pharmaceutical formulation of chlorite, it is important to consider the reactivity of the excipient with chlorite. Some organic molecules that are commonly used as excipients react with chlorite in such a way that the excipient is changed, including but not limited to a change that results in increased toxicity of the pharmaceutical formulation prior to exposure of the excipient to chlorite. In some embodiments, the pharmaceutical formulations described herein comprise one or more pharmaceutically acceptable excipients that do not react with chlorite. Preferably, the pharmaceutical formulations described herein comprise one or more pharmaceutically acceptable excipients that do not diminish the therapeutic effect of the pharmaceutical formulation relative to prior to exposure to the excipient.

In some embodiments, the chlorite formulations described herein comprise one or more pharmaceutically acceptable excipients that do not generate one or more of the deleterious non-chlorite elements of other commercially available chlorite formulations. In some embodiments, the chlorite formulations described herein comprise an excipient, and are substantially free of one or more of the deleterious non-chlorite elements of other commercially available chlorite formulations. In some embodiments, the chlorite formulations described herein comprise an excipient, and are substantially free of one or more of the degradation products or impurities of other commercially available chlorite formulations as described herein.

In some embodiments, the chlorite formulation comprises a stabilizer. Stabilizers include but are not limited to agents that will do any of (1) improve the compatibility of excipients with a container, including a glass bottle or an encapsulating materials such as gelatin, (2) improve the stability of chlorite (e.g., prevent degradation), or (3) improve formulation stability.

Stabilizers may be selected from, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. Amide analogues of stabilizers can also be used. The chosen stabilizer may change the hydrophobicity of the formulation (e.g., oleic acid, waxes), or improve the mixing of various components in the formulation (e.g., ethanol), control the moisture level in the formula (e.g., PVP or polyvinyl pyrrolidone), control the mobility of the phase (substances with melting points higher than room temperature such as long chain fatty acids, alcohols, esters, ethers, amides etc. or mixtures thereof; waxes), and/or improve the compatibility of the formula with encapsulating materials (e.g., oleic acid or wax). Some of these stabilizers may be used as solvents/co-solvents (e.g., ethanol). Stabilizers may be present in sufficient amount to inhibit chlorite's degradation.

The formulations described herein may contain one or more of a gelling agent or a release modifying agent.

The formulations described herein may contain one or more adjuvants appropriate for the indicated route of administration. Again, prior to the addition of any excipient to the formulations described herein, the reactivity of chlorite should be considered with respect to whether the resulting pharmaceutical formulation will be appropriate for administration via the desired route of administration. Adjuvants with which the therapeutic agent may be admixed with include but are not limited to lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol. When a solubilized formulation is required the therapeutic agent may be in a solvent including but not limited to polyethylene glycol of various molecular weights, propylene glycol of various molecular weights, carboxymethyl cellulose colloidal solutions, methanol, ethanol, DMSO, corn oil, peanut oil, cottonseed oil, sesame oil, tragacanth gum, and/or various buffers. Other adjuvants and modes of administration are well known in the pharmaceutical art and may be used in the practice of the methods and formulations described herein. The carrier or diluent may include time delay material, such as glyceryl monostearate or glyceryl distearate alone or with a wax, or other materials well known in the art. The formulations for use as described herein may also include gel formulations, erodible and non-erodible polymers, microspheres, and liposomes.

Additives and diluents normally utilized in the pharmaceutical arts can optionally be added to the pharmaceutical composition and the liquid formulation. These include thickening, granulating, dispersing, flavoring, sweetening, coloring, and stabilizing agents, including pH stabilizers, other excipients, anti-oxidants (e.g., tocopherol, BHA, BHT, TBHQ, tocopherol acetate, ascorbyl palmitate, ascorbic acid propyl gallate, and the like), preservatives (e.g., parabens), and the like. Exemplary preservatives include, but are not limited to, benzylalcohol, ethylalcohol, benzalkonium chloride, phenol, chlorobutanol, and the like. Some antioxidants provide oxygen or peroxide inhibiting agents and may be used in the formulations described herein, including but not limited to, butylated hydroxytoluene, butylhydroxyanisole, propyl gallate, ascorbic acid palmitate, a-tocopherol, and the like. Thickening agents, such as lecithin, hydroxypropylcellulose, aluminum stearate, and the like, may be used if desired, for example to improve one or more qualities of the formulation, such as the texture.

In some variations, the chlorite formulations for use with the invention are sterile. Sterilization can be by any method that is compatible with chlorite. In some embodiments, sterilization is via a method that does not generate a substantial amount of a degradation product of chlorite. In some embodiments, sterilization is via a method that does not cause a structural change in chlorite. In some embodiments, the formulations described herein are sterile pharmaceutical formulations for parenteral or intravenous administration. In some embodiments, the chlorite formulations described herein are sterile filtered, for example, through a sterile 0.22 micron filter.

In some embodiments, the formulations or pharmaceutical formulations are sterile-filterable. In some embodiments, the chlorite formulations described herein are formulated for administration by one or more of the routes of administration described herein. A formulation that is "formulated for administration" by a specified route of administration, as used herein, is a formulation that does not include pharmaceutical excipients that are considered inappropriate for the route of administration by those of skill in the relevant art. As one example, a formulation that is suitable for intravenous administration would not include a toothpaste excipient or carrier intended for topical administration, where the excipient or carrier is considered inappropriate for the specified route of administration by those of skill in the relevant art.

Chlorite-containing agent in any form disclosed herein can be provided in any suitable formulation, which can be selected according to the desired route of administration as disclosed herein. In one embodiment, the formulation of the drug product comprises purified sodium chlorite which may include a certain amount of water content, buffer such as sodium phosphate dibasic, and sterile water for injection (USP) as a vehicle. In one embodiment, the amount of purified sodium chlorite is about 5.6 mg/mL (including a batch factor to reflect the water content of the batch), the amount of sodium phosphate dibasic is 0.107 mg/mL, and sterile water to bring the volume up to 1 mL. In certain embodiments, a formulation according to the invention consists essentially of purified sodium chlorite, buffer, and sterile water for injection (USP) as the vehicle. In certain embodiments, the formulated drug product is stable for up to 3 months at 25° C./60% relative humidity and/or 40° C./75% relative humidity conditions.

U.S. Pat. No. 4,725,437 describes an aqueous solution of a chemically stabilized chlorite matrix suitable for intravenous administration in a dosed amount of about $6.2 \times 10^{-6}$ mole of $ClO_2$ to $9.3 \times 10^{-5}$ mole of $ClO_2$ per kg of body weight in humans and non-human animals. The solution contains the chlorite matrix in a concentration of about 12 to 72 micromol of $ClO_2$ per ml. Further chlorite formulations are described in U.S. Pat. Nos. 4,507,825, and 4,725,437, which are herein incorporated by reference in their entireties.

In some embodiments, the present invention provides methods of treating disease such as type II diabetes or diabetes related diseases or complications comprising administering an effective amount of TCDO in a subject. Formulations of TCDO are provided in this application. In one example, the TCDO formulation is WF10. WF10 is also known as Oxoferin® and is available commercially. In another example, the chlorite formulation contains chlorite. Other formulations of TCDO or chlorite are encompassed within the scope of the present invention. Alternatively, in some embodiments TCDO and/or WF10 can be excluded in part or in whole.

Chlorite-containing compositions, such as TCDO, can be formulated for parenteral or enteral administration, generally parenteral administration. Accordingly, formulations of chlorite, or chlorite-containing agents such as TCDO and WF10, are suitable for parenteral, topical or transdermal administration, usually intravenous, intramuscular, or subcutaneous administration, and may be suitable for administration by bolus injection, sustained release (including controlled release), infusion, and the like. More details on the route of administration are disclosed herein below. In some embodiments, the administration of the chlorite containing agents is by infusion e.g., by subcutaneous or intravenous infusion, or in the form of suppositories.

VI. Administration and Dosing of Chlorite or Chlorite Containing Agents

Unless the context indicates otherwise, all of the formulations and pharmaceutical formulations described herein may be administered by any of systemic, parenteral (e.g., intramuscular, intraperitoneal, intravenous, ICV, intracisternal injection or infusion, subcutaneous injection, or implant), by inhalation spray, nebulized or aerosolized using aerosol propellants, nasal, vaginal, rectal, sublingual, urethral (e.g., urethral suppository), by infusion, intraarterial, intrathecal, intrabronchial, subcutaneous, intradermal, intravenous, intracervical, intraabdominal, intracranial, intrapulmonary, intrathoracic, intratracheal, nasal routes, oral administration that delivers the therapeutic agent systemically, drug delivery device, or by a dermal patch that delivers the therapeutic agent systemically, transdermally or transbuccally. In some variations, the formulation is formulated for other than oral or transbuccal administration.

In some variations, the formulations described herein are not administered topically.

In some embodiments, the formulations, pharmaceutical formulations, and methods of administration and treatment described herein are suitable for use in any warm- or cold-blooded animal. In some embodiments, the formulations, pharmaceutical formulations, and methods of administration and treatment described herein are suitable for use in a mammal, including in the veterinary context, including domestic pets (such as cats, dogs, rabbits, birds, horses, etc.) and agricultural animals (such as bovine, ovine, fowl, etc.). In some variations, the formulations, pharmaceutical formulations, and methods of administration and treatment described herein are suitable for use in primates, including but not limited to humans.

Chlorite formulations are generally dosed in vivo corresponding to the body weight of the subject. Due to the continuous breakdown of the active agent in the blood, the agent is normally administered at regular intervals. Those of skill in the art will readily appreciate that actual dosages and regimen will vary as a function of the agent, formulation, the severity of the symptoms, the susceptibility of the subject to treatment and/or side effects, and the like. Dosages are readily and routinely determined by those of skill in the art by a variety of means.

Exemplary doses of chlorite-containing formulations can vary between about 0.1 ml/kg to about 1.5 ml/kg, preferably about 0.5 ml/kg of body weight and at a concentration of about 40 to about 80 mmol $ClO_2^-$ per liter, usually about 60 mMol $ClO_2$ per liter, respectively. In the case of TCDO, in some embodiments, WF10 is administered intravenously to patients with diabetes or a diabetes related disease or complication at a maximum dose of approximately 0.5 ml/kg. Other suitable doses may be approximately 0.25 ml/kg.

The regimen of administration e.g. dose combined with frequency of administration will generally involve administration in an amount and at a frequency to provide a desired effect, e.g. administration of an amount effective to provide for improvement in one or more symptoms of a patient suffering from diabetes or a diabetes related disease or complication, such as a cardiovascular disease, a metabolic disease such as metabolic syndrome, and macular degeneration symptoms. For example, chlorite or a chlorite-containing agent can be administered for 2, 3, 4, 5, 6, 7, 8, 9, 10 or more consecutive days, which administration period may be reinitiated after 1, 2, 3 or more weeks following the last dose.

Chlorite according to the invention can be administered on a daily basis. In some embodiments, chlorite is administered on a daily basis at a dose of about 0.2 mg/kg/day of chlorite to about 3.3 mg/kg/day of chlorite. In some embodiments, chlorite is administered on a daily basis at a dose of about 0.2 mg/kg/day of chlorite per day, about 0.4 mg/kg/day of chlorite per day, about 0.5 mg/kg/day of chlorite, about 0.6 mg/kg/day of chlorite, about 0.7 mg/kg/day of chlorite, about 0.8 mg/kg/day of chlorite, about 0.9 mg/kg/day of chlorite, about 1.0 mg/kg/day of chlorite, about 1.1 mg/kg/day of chlorite, about 1.2 mg/kg/day of chlorite, about 1.3 mg/kg/day of chlorite, about 1.4 mg/kg/day of chlorite, about 1.5 mg/kg/day of chlorite, about 1.6 mg/kg/day of chlorite, about 1.7 mg/kg/day of chlorite, about 1.8 mg/kg/day of chlorite, about 1.9 mg/kg/day of chlorite, about 2.0 mg/kg/day of chlorite, about 2.1 mg/kg/day of chlorite, about 2.2 mg/kg/day of chlorite, about 2.3 mg/kg/day of chlorite, about 2.4 mg/kg/day of chlorite, about 2.5 mg/kg/day of chlorite, about 2.6 mg/kg/day of chlorite, about 2.7 mg/kg/day of chlorite, about 2.8 mg/kg/day of chlorite, about 2.9 mg/kg/day of chlorite, about 3.0 mg/kg/day of chlorite, about 3.1 mg/kg/day of chlorite, about 3.2 mg/kg/day of chlorite, about 3.3 mg/kg/day of chlorite, about 3.4 mg/kg/day of chlorite, or about 3.5 mg/kg/day of chlorite.

In some embodiments, the pharmaceutical composition used in the methods of the invention can be further administered in a cycle. An exemplary cycle consists of: a) a first period of time wherein the pharmaceutical composition is administered at a first dose for a first number of times; and b) a second period of time wherein the pharmaceutical composition is administered at a second dose for a second number of times. In some embodiments, the first period of time is about one week, the first number of times is about five, the second period of time is about two weeks, and the second number of times is zero. In other embodiments, the first period of time is about one week, the first number of times is about three, the second period of time is about one week, and the second number of times is zero. The first dose can be about 0.4 mg/kg/day of chlorite to about 3.3 mg/kg/day of chlorite. For example, the first dose can be about 2.1 mg/kg/day of chlorite. The cycle can be performed multiple times, e.g., about 2, 3, 4, 5, 6, 7, 8, 9, 10 or 10 or more times. In some embodiments, the cycle is performed about 2-4 times.

In some embodiments, the dosing schedule consists of periods of administration alternating with periods of non-administration. For example, chlorite might be administered in a three week cycle, comprising dosing chlorite up to 5 times in a week followed by two weeks without treatment. The cycle could be repeated as necessary to achieve the desired result. In another embodiment, chlorite is administered in a two week cycle, e.g., up to 3 times in a week followed by a week without administration. In some embodiments, a total of 2-4 cycles are performed. In an exemplary embodiment, the dosing regimen comprises administration of 2.1 mg/kg/day of chlorite for a total of 2-4 three week cycles.

B. Immunomodulating Agents

In one aspect, the present invention provides a method of treating a macrophage related disease comprising administering to a subject in need thereof an effective amount of an immunomodulating agent. In another aspect, the present invention provides a method of modulating macrophage accumulation or activation comprising administering to a subject in need thereof an effective amount of an immunomodulating agent. In some embodiments, the immunomodulating agent is an immunosuppressor and downregulates the immune response. In some embodiments, the agent has immunostimulatory effects. The immunosuppressor can act directly and/or indirectly on activated macrophage. In some embodiments, the immunosuppressor acts directly on macrophage, e.g., by inhibiting macrophage activity. In some embodiments, the immunosuppressor disrupts immune cell signaling, e.g., by interfering with the production or activity of cytokines produced by immune cells such as T-cell, B-cells or macrophage. Any desirable combination of immunmodulatory effects may be observed. In one embodiment, the present invention provides for methods of treating non-MS neuroinflammation with an immunomodulatory agent capable of blocking migration of monocytes or activated macrophages.

In some embodiments, the present invention provides for lower dosages of the immunomodulating agents than typically used, e.g., when used as monotherapy. For example, the immunomodulating agent can be used in combination with an oxidative agent, including but not limited to chlorite or a chlorite-containing agent, thereby allowing a lower dosage of the immunomodulating agent to achieve the desired therapeutic effect. In such instances, the oxidative agent potentiates the effect of the immunomodulating agent. Alternatively, the oxidative agent can be administered to ameliorate or reduce toxicity or other side effects of the immunomodulating agent, thereby allowing for a higher dosage of he immunomodulating agent than would otherwise be tolerated during monotherapy with the immunomodulating agent. For example, in certain embodiments, combination therapy with the oxidative agent allows for administration of an amount of immunomodulating agent that might otherwise result in an unacceptable level of opportunistic infections.

Immunosuppressive drugs or immunosuppressive agents inhibit or prevent activity of the immune system. Immunosuppressive therapy has a number of uses, including but not limited to preventing the rejection of transplanted organs and tissues (e.g., bone marrow, heart, kidney, liver), treating autoimmune diseases or diseases that are most likely of autoimmune origin (e.g., rheumatoid arthritis, multiple sclerosis, myasthenia gravis, systemic lupus erythematosus, Crohn's disease, pemphigus, and ulcerative colitis), and also treating some other non-autoimmune inflammatory diseases (e.g., long term allergic asthma control).

Immunosuppressants have certain side-effects and risks. For example, in some cases, the immune system is less able to resist infections and the spread of malignant cells. Other side-effects include hypertension, dyslipidemia, hyperglycemia, peptic ulcers, liver, and kidney injury. Immunosuppressive agent can also interact with and affect the metabolism and action of other therapeutic agents. In some embodiments, the present invention provides for lower dosages of the immunosuppressive agents than typically used, e.g., for transplant rejection. For example, the immunosuppressive agent can be used in combination with an oxidative agent, including but not limited to chlorite or a chlorite-containing agent, thereby allowing lower dosage of the immunosuppressant to achieve the desired therapeutic effect. In such instances, the oxidative agent potentiates the effect of the immunosuppressant.

Immunosuppressive drugs can generally be classified as glucocorticoids, cytostatics, antibodies, drugs acting on immunophilins, or other drugs.

Glucocorticoids are a class of steroid hormones that bind to and activate the glucocorticoid receptor. The activated glucocorticoid receptor complex in turn up-regulates the expression of anti-inflammatory proteins in the nucleus (a process known as transactivation) and represses the expression of pro-inflammatory proteins in the cytosol by preventing the translocation of other transcription factors from the cytosol into the nucleus (transrepression). Glucocorticoids suppress cell-mediated immunity by inhibiting genes that code for the cytokines IL-1, IL-2, IL-3, IL-4, IL-5, IL-6, IL-8, and TNF-$\gamma$. They also suppress IL-2 and IL-2 receptor production by B-cells, thereby reducing B cell clonal expansion and antibody production.

Glucocorticoids induce the synthesis of lipocortin-1 (annexin-1), leading to diminished pro-inflammatory eicosanoid production. The expression of cyclooxygenases COX-1 and COX-2 is also suppressed, further inhibiting inflammation. Glucocorticoids also stimulate the lipocortin-1 escaping to the extracellular space, where it binds to the leukocyte membrane receptors and inhibits various inflammatory events: epithelial adhesion, emigration, chemotaxis, phagocytosis, respiratory burst, and the release of various inflammatory mediators (lysosomal enzymes, cytokines, tissue plasminogen activator, chemokines, etc.) from neutrophils, macrophages, and mastocytes. Glucocorticoids downregulate the expression of Fc receptors on macrophages, thereby decreased phagocytosis of opsonised cells.

Glucocorticoids for use with the present invention include without limitation hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (doca) and aldosterone.

Cytostatics inhibit cell division. Used at lower levels that those used to treat cancer, cytostatics can affect the proliferation of immune cells, e.g., B-cells and T-cells. Alkylating agents used as immunosuppressants include nitrogen mustards (cyclophosphamide), nitrosoureas, platinum compounds, and others. Antimetabolites interfere with the synthesis of nucleic acids. These include purine synthesis inhibitors azathioprine, mercaptopurine and mycophenolic acid; pyrimidine synthesis inhibitors leflunomide and teriflunomide; and the folic acid analog methotrexate. Cytotoxic antibiotics include without limitation dactinomycin, anthracyclines, mitomycin C, bleomycin, and mithramycin.

Antibodies can also be used as immune modulators. An "antigen" is an entity to which an antibody specifically binds. The term "antibody" or "immunoglobulin" is used to include intact antibodies and binding fragments thereof. Typically, fragments compete with the intact antibody from which they were derived for specific binding to an antigen fragment including separate heavy chains, light chains Fab, Fab', F(ab')$_2$, F(ab)c, and Fv. Fragments may be produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments (See, e.g., Songsivilai and Lachmann, Clin. Exp. Immunol., 79:315-321 (1990); Kostelny et al., J. Immunol., 148:1547-53 (1992)). An antibody or fragment thereof may be labeled with a detectable marker or conjugated to a second molecule, such as a therapeutic agent (e.g., a cytotoxic agent) thereby resulting in an immunoconjugate. For example, the therapeutic agent includes, but is not limited to, an anti-tumor drug, a toxin, a radioactive agent, a cytokine, a second antibody or an enzyme. The immunoconjugate also includes an embodiment wherein the antibody of the invention is linked to an enzyme that converts a prodrug into a cytotoxic drug.

Heterologous polyclonal antibodies can affect all lymphocytes and cause general immunosuppression. Anti-thymocyte globulin and anti-lymphocyte globulin comprise horse and rabbit polyclonal antibodies against human T cells. Preparations available to the market in Atgam®, obtained from horse serum, and Thymoglobuline®, obtained from rabbit serum. Because of a high immunogenicity of heterologous polyclonal antibodies, almost all patients have an acute reaction to the treatment. Monoclonal antibodies are directed towards defined target antigens and cause fewer side-effects. Common treatments include IL-2 receptor-(CD25–) and CD3-directed antibodies. OKT3 (also called muromonab) is a murine anti-CD3 monoclonal antibody that prevents T-cell activation and proliferation by binding the T-cell receptor complex present on all differentiated T cells. It is one of the most potent immunosuppressive agents. CD3 is also targeted by the monoclonal antibodies otelixizumab, teplizumab, and visilizumab.

CD4 (cluster of differentiation 4) is a glycoprotein expressed on the surface of T helper cells, regulatory T cells, monocytes, macrophages, and dendritic cells. Antibodies against CD4 include clenoliximab, keliximab, and zanolimumab.

Efalizumab (Raptiva®) is a recombinant humanized monoclonal antibody that binds to CD11a and acts as an immunosuppressant by inhibiting white blood cell migration out of blood vessels into tissues.

Erlizumab and rovelizumab are humanized monoclonal antibodies that bind CD18. They are intended to suppress white blood cells that become overly active, e.g., during shock.

CD20 is a non-glycosylated phosphoprotein expressed on the surface of mature B-cells. Anti-CD20 antibodies include afutuzumab, ocreliximab, ofatumumab and pascolizumab. Rituximab is a chimeric monoclonal antibody against CD20, which is primarily found on the surface of B cells. Rituximab thereby destroys both normal and malignant B cells that express CD20.

Lumiliximab is a chimeric monoclonal antibody that targets against CD23 to acts as an immunomodulator.

CD40 is a costimulatory protein found on antigen presenting cells and is required for their activation. In the macrophage, the primary signal for activation is IFN-γ from Th1 type CD4 T cells. The secondary signal is CD40 ligand (CD40L or CD154) on the T cell which binds CD40 on the macrophage cell surface. As a result, the macrophage expresses more CD40 and TNF receptors on its surface which helps increase the level of activation. Activation results in the induction of potent microbicidal substances in the macrophage, including reactive oxygen species and nitric oxide, which can destroy ingested microbes. Teneliximab and Toralizumab are monoclonal antibodies against CD40. Ruplizumab is an anti-CD40L monoclonal antibody.

Aselizumab is a monoclonal antibody that binds to CD62L (L-selectin) a cell adhesion molecule found on leukocytes.

Galiximab is a chimeric monoclonal antibody that binds CD80. CD80 is found on activated B cells and monocytes and provides a costimulatory signal necessary for T cell activation and survival. It is also known as B7.1.

Gavilimomab is a mouse monoclonal antibody (also known as ABX-CBL) that binds antigen CD147 (basigin), which is expressed by many cell types, including epithelial cells, endothelial cells and leukocytes.

Belimumab is a fully human monoclonal antibody that specifically recognizes and inhibits the biological activity of B-Lymphocyte stimulator (BLyS), also known as B cell activation factor of the TNF family (BAFF). BLyS is secreted, sometimes under the influence of interferon-gamma, by a variety of cells, including monocytes and macrophages.

CTLA4 (Cytotoxic T-Lymphocyte Antigen 4) also known as CD152 (Cluster of differentiation 152) is expressed on the surface of Helper T cells and transmits an inhibitory signal to T cells. The CTLA4-Ig fusion proteins abatacept and belatacept act as immunosuppressants. In contrast, ipilimumab and tremelimumab are monoclonal antibodies that bind CTLA4 and to stimulate immune response.

Bertilimumab is a human monoclonal antibody that binds to eotaxin 1, a chemokine that selectively recruits cosinophils by inducing their chemotaxis.

Natalizumab is a humanized monoclonal antibody against the cellular adhesion molecule α4-integrin. Natalizumab is believed to reduce the ability of inflammatory immune cells to attach to and pass through the cell layers lining the intestines and blood-brain barrier. Natalizumab may be available as Tysabri®.

Tocilizumab is a humanized monoclonal antibody against IL-6R (interleukin-6 receptor). IL-6 is an interleukin that acts as both a pro-inflammatory and anti-inflammatory cytokine. It is secreted by T cells and macrophages to stimulate immune response to trauma, especially burns or other tissue damage leading to inflammation.

Lymphocyte function-associated antigen 1 (LFA-1) is found on T-cells, B-cells, macrophages and neutrophils and is involved in recruitment to the site of infection. Odulimomab is a mouse monoclonal antibody that binds LFA-1.

Interleukin-2 (IL-2) plays a role in the clone expansion and survival of activated T lymphocytes. Basiliximab (Simulect®), daclizumab (Zenapax®) and inolimomab are monoclonal antibodies that bind the IL-2a receptor's a chain (i.e., CD25), thereby preventing the IL-2 induced clonal expansion of activated lymphocytes and shortening their survival.

Zolimomab aritox is a conjugate of a murine monoclonal antibody with the A chain of the toxin ricin. It is directed against the CD5 antigen of human lymphocytes.

Siplizumab (MEDI-507) is a monoclonal antibody with a human IgG1, kappa directed to CD2. The agent has shown potent immunomodulatory effects, selectively suppressing the function of T and NK cells.

Other antibodies and fusion proteins that act as immunosuppressants include nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept and rilonacept.

Immunophilins are peptidyl-prolyl isomerases that play a role in immunoregulation and basic cellular processes involving protein folding and trafficking. Modulators of members of the immunophilin FKBP/cyclophilin/calcineurin pathway can inhibit cytokine production and activity, such as that of IL-2. Such agents include rapamycin, tacrolimus, ciclosporin, pimecrolimus, abetimus and gusperimus. The mammalian target of rapamycin (mTOR) protein, also known as FK506 binding protein 12-rapamycin associated protein 1 (FRAP1), is a serine/threonine protein kinase that regulates cell growth, cell proliferation, cell motility, cell survival, protein synthesis, and transcription. mTOR inhibitors include rapamycin (sirolimus) and related drugs, including ridaforolimus, everolimus, temsirolimus, and zotarolimus.

Other classes of immunosuppressive agents include interferons, tumor necrosis factor-alpha (TNFα or TNF) modulators, IL-1 receptor antagonists, opiods, mycophenolate and other small biological agents. Interferon-β (IFN-β) suppresses the production of Th1 cytokines and the activation of monocytes. TNF is a cytokine that promotes the inflammatory response. TNF inhibitors include monoclonal antibody such as infliximab (Remicade®), adalimumab (Humira®), certolizumab pegol (Cimzia®), and golimumab (Simponi™), or with a circulating receptor fusion protein such as etanercept (Enbrel®). Small molecule TNF inhibitors include thalidomide, lenalidomide, pentoxifylline and bupropion. Natural TNF inhibitors include curcumin and catechin.

Therapeutic agents are available to modulate other cytokines. The cytokine IL-1 also plays a role in the inflammatory response. Therapeutic agents that interfere with signal reception include the IL-1 receptor antagonist anakinra, a recombinant, non-glycosylated version of human IL-1. Mepolizumab is a humanized monoclonal antibody that recognizes interleukin-5 (IL-5) and interferes with proliferation of eosinophil granulocytes. Omalizumab is another humanized monoclonal antibody that inhibits the binding of IgE to the high-affinity IgE receptor FcεRI. Talizumab also binds IgE. Ustekinumab is a human monoclonal antibody that recognizes and inhibits Interleukin 12 and Interleukin 23, which help activate certain T-cells.

Opiods can suppress both innate and adaptive immunity. A decrease in proliferation as well as immune function has been observed in macrophages and lymphocytes. Mycophenolic acid acts as a non-competitive, selective, and reversible inhibitor of Inosine-5'-monophosphate dehydrogenase (IMPDH), which is a key enzyme in the de novo guanosine nucleotide synthesis. Unlike other human cell types, lymphocytes B and T are very dependent on this process. Myriocin is an atypic amino acid that can inhibit the proliferation of IL-2-dependent cytotoxic T cells. Fingolimod is chemically similar to the myriocin and prevents egress of lymphocytes from lymph nodes.

NF-κB (nuclear factor kappa-light-chain-enhancer of activated B cells; NFkB) is a dimeric protein complex that controls DNA transcription. NF-κB is a rapid responder to cellular stimuli such as stress, cytokines, free radicals, ultraviolet irradiation, oxidized LDL, and bacterial or viral antigens. NF-κB plays a key role in regulating the immune response to infection. Improper regulation of NF-κB has been linked to cancer, inflammatory and autoimmune diseases, septic shock, viral infection, and improper immune development. NF-κB has also been implicated in processes of synaptic plasticity and memory. NF-κB is one of the most crucial transcription factors regulating the inflammatory repertoire of macrophages, particularly their expression of proinflammatory cytokines, costimulatory molecules, and other activation markers in response to diverse environmental cues (e.g., stress signals, inflammatory cytokines, pathogens, and hypoxia).

Prior to stimuli as described above, NF-κB dimers are sequestered in the cytoplasm by a family of inhibitors, called IκBs (Inhibitor of κB), which are proteins that contain multiple ankyrin repeat sequences. Activation of the NF-κB is initiated by the signal-induced degradation of IκB proteins by the proteasome. This signal occurs primarily via activation of a kinase called the IκB kinase (IKK). With the degradation of the IκB inhibitor, the NF-κB complex can then enter the nucleus and activate the expression of specific genes that have nearby DNA-binding sites for NF-κB. The activation of these genes by NF-κB then leads to the given physiological response, for example, an inflammatory or immune response, a cell survival response, or cellular proliferation. NF-κB also activates the production of its repressor IκBα, thereby acting to inhibit its own synthesis.

Inhibitors of NF-κB can act at various steps of the NF-κB signaling cascade. Some inhibitors of NF-κB are described in U.S. Pat. No. 6,410,516. Other agents include raloxifene, an oral selective estrogen receptor modulator, and drotrecogin alfa, a recombinant form of human activated protein C that has anti-thrombotic, anti-inflammatory, and profibrinolytic properties. The monoclonal antibody denosumab indirectly inhibits NF-κB. The drugs disulfiram, olmesartan and dithiocarbamates can inhibit the NF-κB signaling cascade. Other direct or indirect inhibitors of NF-κB include but are not limited to proteasome inhibitors (e.g., bortezomib, MG132, Pro1, NPI-0052), natural small molecules (curcumin, genistein, resveratrol, parthenolide), thalidomide, lenalidomide, flavopiridol, non-steroidal anti-inflammatory drugs (NSAIDs), arsenic trioxide, dehydroxymethylepoxyquinomycin (DHMEQ), I3C(indole-3-carbinol)/DIM(di-indolmethane) (I3C/DIM), Bay 11-7082, luteolin, cell permeable peptides such as SN-50, and gene therapy such as overexpression of IκBα-super repressor and NFκB decoy oligodeoxynucleotide (ODN). See, e.g., Melisi D, Chiao P J. NF-kappa B as a target for cancer therapy. Expert Opin Ther Targets. 2007 February; 11(2):133-44; Baud V, Karin M. Is NF-kappaB a good target for cancer therapy? Hopes and pitfalls. Nat Rev Drug Discov. 2009 January; 8(1):33-40.

Immunomodulators that directly or indirectly modulate NF-κB can be used in the methods of the invention. In some embodiments, immunomodulators are used that suppress the activity of NF-κB. In some embodiments, immunomodulators are used that promote the activity of NF-κB.

Immunosuppressants that suppress the activation of macrophages, or suppress the activity of activated macrophages can be used in the methods of the invention. In some embodiments, agents that suppress the production or activity of stimulatory cytokines and other immune modulatory signals are used. In some embodiments, agents that block recruitment of immune cells are used. The methods of the invention also include the treatment of macrophage related diseases and disorders with immunomodulating agents through indirect effects on macrophages. For example, macrophage migration inhibitory factor (MIF) is a known pro-inflammatory cytokine. See U.S. Patent Publication No. 2009/0170951 ("Description of the Related Art"). Methods according to the invention include inhibitors and/or antagonists of MIF, such as N-acetyl-p-benzoquinone imine (NAPQI), (S,R)-3-(4-hydroxyphenyl)-4,5-dihydro-5-isoxazole acetic acid methyl ester (ISO-1), 2-[3-(4-hydroxyphenyl)-4,5-dihydro-isoxazol-5-yl]-3-phenyl-propanoic acid and its esters, including the methyl ester, phenylmethylsulfonyl fluoride (PMSF), Cyc-Oxi-11,2-oxo-4-phenyl-3-butynoate, AVP-13546, phenylpyruvate, 2-[(4-hydroxybenzylidene)amino]-3-(1H-indol-3-yl)propionic acid methyl ester, and anti-MIF antibodies. For addition al example, see Garai et al., Curr. Med. Chem. 2009; 16(9): 1091-114, and U.S. Pat. No. 7,662,843, each of which is hereby incorporated by reference in its entirety. In various embodiments, immunomodulators according to the invention may include inhibitors and/or antagonists of monocyte chemoattractant protein-1 (MCP-1).

Immunomodulators that directly or indirectly modulate cell adhesion can be used in the methods of the invention. In some embodiments, immunomodulators are used that suppress the expression or activity of cell adhesion proteins. In various embodiments, such cell adhesion molecules may include IgSF type molecules (N-CAM (Myelin protein zero), ICAM (1,5), VCAM-1, PE-CAM, L1-CAM), Integrins (LFA-1, Integrin alphaXbeta2, Macrophage-1 antigen, VLA-4, Glycoprotein IIb/IIIa), Cadherins (Desmoglein (DSG1, DSG2, DSG3, DSG4), Desmocollin (DSC1, DSC2, DSC3), T-cadherin, Protocadherin, CDH1, CDH2, CDH3, CDH4, CDH5, CDH6, CDH8, CDH11, CDH12, CDH15, CDH16, CDH17), Selectins (E-selectin, L-selectin, P-selectin), or other types of molecules (Carcinoembryonic antigen, CD22, CD24, CD44, CD146, CD164).

In some embodiments, the macrophage related diseases that can be treated using the methods of the present invention are inflammatory diseases.

C. Macrophage Activation

In one aspect, the present invention provides a method of modulating macrophage accumulation or activation comprising administering an effective amount of an immunomodulatory agent in combination with an oxidative agent to a subject in need thereof to treat macrophage related diseases or related conditions. The oxidative agent may include, but is not limited to, chlorite.

Macrophages are released from the bone marrow as immature monocytes, circulate in the blood stream, and can eventually migrate into tissues to undergo final differentiation into resident macrophages. Resident macrophages include Kupffer cells in the liver, alveolar macrophages in the lung, and osteoclasts in the bone. Monocytes and macrophages are phagocytes, acting in innate immunity as well as to help adaptive immunity of vertebrate animals. Their role is to phagocytose (engulf and then digest) cellular debris and pathogens either as stationary or mobile cells, and to stimulate lymphocytes and other immune cells to respond to the pathogen. They can be identified by specific expression of a number of proteins including CD14, CD11b, F4/80 (mice)/EMR1 (human), Lysozyme M, MAC-1/MAC-3 and CD68 by flow cytometry or immunohistochemical staining (Khazen W, et al. 2005 FEBS Lett. 579 (25): 5631-4). When a monocyte enters damaged tissue through the endothelium of a blood vessel (a process known as the leukocyte extravasation), it undergoes a series of changes to become a macrophage. Monocytes are attracted to a damaged site by chemical substances through chemotaxis, triggered by a range of stimuli including damaged cells, pathogens and cytokines released by macrophages already at the site. At some sites such as the testis, macrophages have been shown to populate the organ through proliferation. Unlike short-lived neutrophils, macrophages survive longer in the body up to a maximum of several months.

Macrophages perform a multitude of functions essential for tissue remodeling, inflammation, and immunity, including but not limited to phagocytosis, cytotoxicity, and secretion of a variety of cytokines, growth factors, lysozymes, proteases, complement components, coagulation factors, and prostaglandins. One important role of the macrophage is the removal of necrotic cellular debris in the lungs. Removing dead cell material is important in chronic inflammation as the early stages of inflammation are dominated by neutrophil granulocytes, which are ingested by macrophages if they come of age. The removal of necrotic tissue is to a greater extent handled by fixed macrophages, which typically stay at strategic locations such as the lungs, liver, neural tissue, bone, spleen and connective tissue, where microbial invasion or accumulation of dust is likely to occur, ingesting foreign materials such as pathogens, recruiting additional macrophages if needed. Macrophages can express paracrine functions within organs that are specific to the function of that organ. In the testis for example, macrophages have been shown to be able to interact with Leydig cells by secreting 25-hydroxycholesterol, an oxysterol that can be converted to testosterone by neighboring Leydig cells. Also, testicular macrophages may participate in creating an immune privileged environment in the testis, and in mediating infertility during inflammation of the testis. A list of different types of macrophages in tissues is shown in Table 1.

TABLE 1

| Name of cell | Location |
| --- | --- |
| Dust cells/Alveolar macrophages | pulmonary alveolus of lungs |
| Histiocytes | connective tissue |
| Kupffer cells | liver |
| Microglia | neural tissue |
| Epithelioid cells | granulomas |
| Osteoclasts | bone |
| Sinusoidal lining cells | spleen |
| Mesangial cells | kidney |

Macrophages as scavengers remove dying cells and other debris from the body. They are a type of antigen presenting cells which play a crucial role in initiating an immune response. As secretory cells, monocytes and macrophages are vital to the regulation of immune responses and the development of inflammation as they produce monokines including enzymes, complement proteins, and regulatory factors such as interleukin-1. Macrophages also carry receptors for lymphokines for lymphocyte activation important for killing microbes and tumor cells. After digesting a pathogen, a macrophage presents the antigen on a MHC class II molecule to the corresponding helper T cell. Eventually the antigen presentation results in the production of antibodies that bind to the antigens of pathogens, leading to phagocytosis or antibody-dependent cell cytotoxicity by macrophages. The antigen presentation on the surface of infected macrophages (in the context of MHC class II) in a lymph node stimulates TH1 (type 1 helper T cells) to proliferate (mainly due to IL-12 secretion from the macrophage). When a B-cell in the lymph node recognizes the same unprocessed surface antigen on the microbe with its surface bound antibody, the antigen is endocytosed and processed. The processed antigen is then presented in MHCII on the surface of the B-cell. TH1 receptor that has proliferated recognizes the antigen-MHCII complex (with co-stimulatory factors-CD40 and CD40L) and causes the B-cell to produce antibodies that help opsonisation of the antigen so that the pathogen can be better cleared by macrophages.

Macrophages provide yet another line of defense against tumor cells and somatic cells infected with fungus or parasites. Once a T cell has recognized its particular antigen on the surface of an aberrant cell, the T cell becomes an activated effector cell producing lymphokines including families of interleukins, chemokines and interferons that further stimulate and activate macrophages. These activated macrophages can then engulf and digest affected cells more efficiently. The macrophage does not generate a response specific for an antigen, but attacks the cells present in the local area in which it was activated.

Macrophages also play a role in muscle regeneration. A previous study has shown macrophage influences on muscle repair of soleus muscle on mice (Tidball J G, Wehling-Henricks M, 2007, *The Journal of Physiology* 578: 327-336). Macrophage depletion also reduces muscle growth during a growth period.

I. Classically Activated Macrophages

In one aspect, the present invention provides a method of modulating macrophage accumulation or activation comprising administering an effective amount of an oxidative agent or an immunomodulatory agent. In some embodiments, the oxidative agent is chlorite. In some embodiments, the oxidative agent is WF10. In some embodiments, the immunomodulatory agent is an immunosuppressant. In some embodiments, the oxidative or immunomodulating agent modulates the stimulation of macrophages via receptors expressed by macrophages including but not limited to interferon (IFN)-gamma receptor, CD14/LPS receptor, MHC II molecule, or interleukin receptors such as IL-4 and IL-13 receptors. In some embodiments, the oxidative or immunomodulating agent modulates the release of chemokines by macrophages. In some embodiments, the oxidative or immunomodulating agent modulates the release of pro-inflammatory cytokines such as IL-1, IL-6, and TNF-alpha, or anti-inflammatory cytokines such as IL-10 and TGF-beta by macrophages. In some embodiments, the oxidative or immunomodulating agent modulates the release of proteolytic enzymes by macrophages. In some embodiments, the oxidative or immunomodulating agent modulates the release of extracellular matrix (ECM) related molecules by macrophages.

A model of two major macrophage classes has developed (Gordon, S. (1999) Fundamental Immunology, 4th Ed., Paul, W. E., ed., Lippincott-Raven Publishers, Philadelphia, pp. 533-545; Stein, M. et al. (1992) J. Exp. Med. 176:287). Classically activated macrophages typically exhibit a Th1-like phenotype, promoting inflammation, extracellular matrix (ECM) destruction, and apoptosis, while alternatively activated macrophages typically display a Th2-like phenotype, promoting ECM construction, cell proliferation, and angiogenesis. Although both phenotypes are important components of both the innate and adaptive immune systems, the classically activated macrophage tends to elicit chronic inflammation and tissue injury whereas the alternatively activated macrophage tends to resolve inflammation and facilitate wound healing (See reviews: Duffield, J. S. (2003) Clin. Sci. 104:27; Gordon, S. (2003) Nat. Rev. Immunol. 3:23; Ma, J. et al. (2003) Cell. Mol. Life Sci. 60:2334; Mosser, D. M. (2003) J. Leukoc. Biol. 73:209).

Differentiation of classically activated macrophages requires a priming signal in the form of IFN-gamma via the IFN-gamma R (Dalton, D. K. et al. (1993) Science 259:1739; Huang, S. et al. (1993) Science 259:1742). When the primed macrophage subsequently encounters an appropriate stimulus, such as bacterial LPS, it becomes classically activated. LPS is first bound by soluble LBP and then by either soluble or membrane-bound CD14. CD14 delivers LPS to the LPS recognition complex (Janeway, C. A. & R. Medzhitov (2002) Annu. Rev. Immunol. 20:197), which consists of at least TLR410 and MD-2 (Nagai, Y. et al. (2002) Nat. Immunol. 3:667). Pathogens and pathogen components are subsequently taken up by phagocytosis (Honey, K. & A. Y. Rudensky (2003) Nat. Rev. Immunol. 3:472) and delivered to lysosomes where they are exposed to a variety of degradation enzymes including several cathepsin cysteine proteases. Suitable antigens are processed and loaded onto MHC class II molecules in late endocytic compartments and antigen/MHCII complexes as well as co-stimulatory B7 family members are presented to T cells (Harding, C. V. et al. (2003) Curr. Opin. Immunol. 15:112).

These events are followed closely by a significant change in cellular morphology and a dramatic alteration in the secretory profile of the cell. A variety of chemokines including IL-8/CXCL8, IP-10/CXCL10, MIP-1 alpha/CCL3, MIP-1 beta/CCL4, and RANTES/CCL5, are released as chemoattractants for neutrophils, immature dendritic cells, natural killer cells, and activated T cells (Luster, A. D. (2002) Curr. Opin. Immunol. 14:129). Further, several pro-inflammatory cytokines are released including IL-1 beta/IL-1F2, IL-6, and TNF-alpha/TNFSF1A. TNF-alpha also contributes to the pro-apoptotic activity of the classically activated macrophage (Boyle, J. J. et al. (2003) Arterioscler. Thromb. Vasc. Biol. 23:1553; Duffield, J. S. et al. (2001) Am. J. Pathol. 159:1397; Song, E. et al. (2000) Cell. Imunol. 204:19). TNF-alpha is accompanied by Fas Ligand/TNFSF6 secretion and NO release as a result of iNOS upregulation (Hesse, M. et al. (2001) J. Immunol. 167:6533; Thomassen, M. J. & M. S. Kavuru (2001) Int. Immunopharmacol. 1:1479; Duffield, J. S. et al. (2000) J. Immunol 164:2110; Munder, M. et al. (1998) J. Immunol 160:5347). In addition, the classically activated macrophage releases proteolytic enzymes including MMP-1, -2, -7, -9, and -12, which degrade collagen, elastin, fibronectin, and other ECM components (Chizzolini, C. et al. (2000) J. Immunol. 164:5952; Gibbs, D. F. et al. (1999) Am. J. Respir. Cell Mol. Biol. 20:1136; Gibbs, D. F. et al. (1999) Am. J. Respir. Cell Mol. Biol. 20:1145).

Although the release of these molecules is important for host defense and direction of the adaptive immune system, when uncontrolled their release can levy significant collateral damage on the microenvironment. By eliciting massive leukocyte infiltration and flooding the surrounding tissue with inflammatory mediators, pro-apoptotic factors, and matrix degrading proteases, the classically activated macrophage is capable of dismantling tissues to the point of inflicting serious injury. Tissue destruction perpetrated by chronic inflammation has been associated with the development of tumors, type 1 autoimmune diseases, and glomerulonephritis among other pathologies (Gordon, S. (2003) Nat. Rev. Immunol. 3:23; Mosser, D. M. (2003) J. Leukoc. Biol. 73:209).

In some embodiments, the methods of the present invention comprise administering an oxidative compound, e.g., chlorite, or an immunomodulating agent, e.g., an immunosuppressant, for the treatment of a macrophage related disease including but not limited to tumors, type 1 autoimmune diseases such as multiple sclerosis, glomerulonephritis, rheumatoid arthritis, diabetes, atherosclerosis, Kawasaki disease, bacteria infections, and viral infection, e.g., HIV. In some embodiments, the present invention provides a method for treating a macrophage related disease with an oxidative agent or an immunomodulatory agent by modulating IFN-gamma receptor. In some embodiments, the present invention provides a method for treating a macrophage related disease with an oxidative agent or an immunomodulatory agent by modulating LPS receptor. In some embodiments, the present invention provides a method for treating a macrophage related disease with an oxidative agent or an immunomodulatory agent by modulating MHC II antigen presentation pathway. In some embodiments, the present invention provides a method for treating a macrophage related disease with an oxidative agent or an immunomodulatory agent by modulating release of chemokines including but not limited to IL-8/CXCL8, IP-10/CXCL10, MIP-1 alpha/CCL3, MIP-1 beta/CCL4, and RANTES/CCL5. In some embodiments, the present invention provides a method for treating a macrophage related disease with an oxidative agent or an immunomodulatory agent by modulating release of pro-inflammatory cytokines including but not limited to IL-1 beta/TL-1F2, IL-6, and TNF-alpha/TNFSF1A. In some embodiments, the present invention provides a method for treating a macrophage related disease with an oxidative agent by modulating release of proteolytic enzymes including but not limited to MMP-1, -2, -7, -9, and -12.

II. Alternatively Activated Macrophages

Differentiation of alternatively activated macrophages does not require any priming. IL-4 and/or IL-13 can act as sufficient stimuli (Stein, M. et al. (1992) J. Exp. Med. 176:287; Doherty, T. M. et al. (1993) J. Immunol. 151:7151). The binding of these factors to their respective receptors is followed by fluid-phase pinocytosis of soluble antigen (Brombacher, F. (2000) BioEssays 22:646; Montaner, L. J. et al. (1999) J. Immunol. 162:4613; Conner, S. D. & S. L. Schmid (2003) Nature 422:37). Soluble antigen is then loaded onto MHC class II molecules and antigen/MHCII complexes and co-stimulatory B7 family members are subsequently displayed to T cells (Harding, C. V. et al. (2003) Curr. Opin. Immunol. 15:112).

Similar to the classically activated macrophage, the alternatively activated macrophage changes its cellular morphology and secretory pattern as a result of appropriate stimulation. Leukocytes are attracted by the macrophage via its release of chemokines including MDC/CCL22 (Andrew, D. P. et al. (1998) J. Immunol 161:5027; Imai, T. et al. (1999) Int. Immunol. 11:81), PARC/CCL18 (Kodelja, V. et al. (1998) J. Immunol. 160:1411; Goerdt, S. et al. (1999) Pathobiology 67:222) and TARC/CCL17. Inflammation is counteracted by the release of factors such as IL-1ra/IL-1F3 (Mantovani, A. et al. (2001) Trends Immunol 22:328), Ym1, Ym2, RELMa (Raes, G. et al. (2002) J. Leukoc. Biol. 71:597; Loke, P. et al. (2002) BMC Immunol. 3:7), IL-10, and TGF-beta. TGF-beta also functions indirectly to promote ECM building by inducing nearby fibroblasts to produce ECM components. The alternatively activated macrophage itself secretes the ECM components, Fibronectin and bIG-H3 (Gratchev, A. et al. (2001) Scand. J. Immunol. 53:386), the ECM cross-linking enzyme, Trans-glutaminase (Haroon, Z. A. et al. (1999) Lab. Invest. 79:1679), and Osteopontin, which is involved in cell adhesion to the ECM (Murry, C. E. et al. (1994) Am. J. Pathol. 145:1450).

In addition, alternatively activated macrophages upregulate the enzyme Arginase I, which is involved in proline as well as polyamine biosynthesis. Proline promotes ECM construction while polyamines are involved in cell proliferation (Hesse, M. et al. (2001) J. Immunol. 167:6533). Other factors secreted by the alternatively activated macrophage that promote cell proliferation include PDGF, IGF, and TGF-beta (Song, E. et al. (2000) Cell. Imunol. 204:19; Cao, B. et al. (2000) Chin. Med. J. 113:776). These factors, along with FGF basic, TGF-alpha, and VEGF, also participate in angiogenesis (Cao, B. et al. (2000) Chin. Med. J. 113:776; Sunderkötter, C. et al. (1991) Pharmac. Ther. 51:195).

The molecules secreted by the alternatively activated macrophage work toward resolution of inflammation and promotion of wound repair due to their anti-inflammatory, fibrotic, proliferative, and angiogenic activities. This macrophage is also especially efficient at combating parasitic infections such as Schistosomiasis. In addition to its beneficial activities, the alternatively activated macrophage has been implicated in several pathologies, the most prominent of which are allergy and asthma (Duffield, J. S. (2003) Clin. Sci. 104:27; Gordon, S. (2003) Nat. Rev. Immunol. 3:23).

In some embodiments, the methods of the present invention comprise administering an oxidative compound, e.g., chlorite, or an immunomodulatory agent, e.g., an immunosuppressor, for the treatment of a macrophage related disease including but not limited to allergy and asthma among other pathologies. In some embodiments, the present invention provides a method for treating a macrophage related disease with an oxidative agent or an immunomodulatory agent by modulating the IL-4 receptor. In some embodiments, the present invention provides a method for treating a macrophage related disease with an oxidative agent or an immunomodulatory agent by modulating the IL-13 receptor. In some embodiments, the present invention provides a method for treating a macrophage related disease with an oxidative agent or an immunomodulatory agent by modulating release of chemokines including but not limited to MDC/CCL22, PARC/CCL18 and TARC/CCL17. In some embodiments, the present invention provides a method for treating a macrophage related disease with an oxidative agent or an immunomodulatory agent by modulating release of factors including but not limited to IL-1ra/IL-1F3, Ym1, Ym2, RELMa, IL-10, and TGF-beta. In some embodiments, the present invention provides a method for treating a macrophage related disease with an oxidative agent or an immunomodulatory agent by modulating release of ECM related molecules including but not limited to ECM components, fibronectin and bIG-H3, ECM cross-linking enzyme, trans-glutaminase and osteopontin.

The present invention also encompasses methods of modulating macrophage accumulation or activation with an oxidative agent or an immunomodulatory agent targeting a signaling pathway including but not limited to lipopolysaccharide (LPS), toll-like receptor (TLR), prostaglandin E2 (PGE2), interferon (IFN)-α, IFN-β, IFN-γ, interleukin (IL)-1, IL-4, IL-6, sIL1Ra, IL-10, IL-12, IL-12p40, IL-13, IP10, MHC (major histocompatibility complex) Class II molecules (MHCII), TNF-α, macrophage inflammatory protein 1 alpha (MIP1-a), IFN-gamma-inducing factor (IGIF), macrophage-stimulating protein (MSP), inter-cellular adhesion molecule 1(ICAM-1), colony stimulating factor 1 (CSF-1R), L-arginine, and nitric oxide signaling pathways. The oxidative or immunomodulatory agent of the present invention may target or have an effect on any receptor, cytosolic or nuclear intermediate signaling molecule, or transcription factor involved in any one of the signaling pathways disclosed herein. Examples of important signaling molecules as part of one or more signaling pathways that can be modulated by the oxidative agent or immunomodulatory agent of the present invention include but are not limited to TLR2, TLR4, CAT2, ICSBP, IL1-R, Tie-2, TRIF/IRF3, IFNR-I, IFNR-II, IRE1, IRF2, Raf-1, MEK1, MEK2, ERK1, ERK2, p38, MAPKK4, MAPKK6, PKC, JAK1, JAK2, STAT1, STAT3, Elk1, JNK/SAPK, AP1, Pu1, NFkB, NFAT, iNOS, USF1, ISGF3, SP1, Bcl6, ATF2, c-Jun, and COX-2. Molecules important to macrophage activation or effects that can be modulated, either directly or indirectly, by the oxidative agent or immunomodulatory agent of the present invention include those that belong to transcription factors, cell surface receptors, cytokines, chemokines, cytokine or chemokine receptors, growth factors, interferons, interferon receptors, and adhesion molecules. Specifically, the oxidative or immunomodulatory agent of the present invention can modulate molecules including but not limited to TLR-2, TLR-4, mkp-1, COX-2, SOCS-3, FcγR1, IFN-a, IFN-β, IL-4, IL-6, IL-1Ra, IGIF, MHCI, MHCII IAA, MHCII IAB, MHCII IEB, IP10, IL-10, cathepsin H, lysozyme, CathB, stk, TNF-α, IL-12p35, IL-12p40, MIP-1α, ICAM-1, INOS, mig, Cat-2, CIITA, ICSBP, CathL, CSF1R, GM-CSF, IRF1, IRF-2, c-fos, VEGF, IL-8, bFGF, CSF-1, EGF, MMP-2, MMP-7, MMP-9, MMP-12, EMAPII, endothelin 2, HIF-1, HIF-2, CXCL8, TGFβ, PGE2, and/or MDF.

III. Monocytes

Monocytes are a type of white blood cell. Monocytes have two main functions in the immune system: (1) replenish resident macrophages and dendritic cells under normal states; and (2) in response to inflammation signals, monocytes can move quickly to sites of infection in the tissues and divide/differentiate into macrophages and dendritic cells to elicit an immune response. Monocytes are produced by the bone marrow from haematopoietic stem cell precursors called monoblasts. Monocytes circulate in the bloodstream for about one to three days and then typically move into tissues throughout the body. In the tissues monocytes mature into different types of macrophages at different anatomical locations. Monocytes which migrate from the bloodstream to other tissues will then differentiate into tissue resident macrophages or dendritic cells. Macrophages are responsible for protecting tissues from foreign substances but are also suspected to be the predominant cells involved in triggering atherosclerosis. They are cells that possess a large smooth nucleus, a large area of cytoplasm and many internal vesicles for processing foreign material.

There are two types of monocytes in human blood: a) the classical monocyte, which is characterized by high level expression of the CD14 cell surface receptor (CD14++ monocyte) and b) the non-classical, pro-inflammatory monocyte with low level expression of CD14 and with additional co-expression of the CD16 receptor (CD14+ CD16+ monocyte). After stimulation with microbial products the CD14+ CD16+ monocytes produce high amounts of pro-inflammatory cytokines such as tumor necrosis factor and interleukin-12.

An increase or decrease in the number of CD14+ CD16+ monocytes has been indicated in various diseases (Loems Ziegler-Heitbrock, Journal of Leukocyte Biology, Vol 81, 2007). These CD14+ CD16+ monocytes may play a role in giving rise to macrophages that contribute to the inflammation of a disease. CD14+ CD16+ monocytes are involved in many inflammatory diseases including but not limited to rheumatoid arthritis, diabetes, hemodialysis, atherosclerosis, Kawasaki disease, as well as bacteria infections and viral infections, which are disclosed in more details herein below. In some embodiments, the present invention provides a method of treating a macrophage related disease comprising administering to a subject in need thereof an effective amount of an oxidative and/or immunomodulatory agent, wherein the agent modulates or has an effect on CD14+ CD16+ monocytes.

IV. Tumor-Associated Macrophages (TAM)

In some embodiments, the present invention provides a method of modulating tumor associated macrophages comprising administering an oxidative and/or an immunomodulatory agent into a subject. Macrophages are prominent in the stromal compartment of virtually all types of malignancy. Macrophages respond to the presence of stimuli in different parts of tumors with the release of a distinct repertoire of growth factors, cytokines, chemokines, and enzymes that regulate tumor growth, angiogenesis, invasion, and/or metastasis. The distinct microenvironments where tumor-associated macrophages (TAM) act include: 1) areas of invasion where TAMs promote cancer cell motility; 2) stromal and perivascular areas where TAMs promote metastasis; and 3) avascular and perinecrotic areas where hypoxic TAMs stimulate angiogenesis (reviewed by Lewis C E et al. Cancer Res. 2006 (66) 605-612). TAMs have a phenotype that are relatively immature, characterized by low expression of the differentiation-associated macrophage antigens, carboxypeptidase M and CD51, high constitutive expression of IL-1 and IL-6, and low expression of TNF-α.

TAM infiltration correlates positively with tumor cell proliferation as measured by MIB-1 levels in breast carcinomas, Ki67 levels in endometrial carcinomas, or mitotic index in renal cell carcinoma (reviewed by Lewis C E et al. Cancer Res. 2006 (66) 605-612). Various studies have shown that TAMs express a number of factors that stimulate tumor cell proliferation and survival, including epidermal growth factor (EGF) (Goswami S. et al. Cancer Res 2005; 65; 5278-83; Lewis C E et al. Lancet 1993; 342; 148-9), platelet-derived growth factor (PDGF), TGF-h1, hepatocyte growth factor, MMP-9, and basic fibroblast growth factor (bFGF). TAMs also play an important part in regulating angiogenesis. TAMs release a number of potent proangiogenic cytokines and growth factors, such as vascular endothelial growth factor (VEGF), TNF-α, IL-8, and bFGF. Additionally, they express a broad array of angiogenesis-modulating enzymes, including MMP-2, MMP-7, MMP-9, MMP-12, and cyclooxygenase-2 (COX-2) (Sunderkotter C. et al. Pharmacol Ther 1991; 51: 195-216; Klimp A H et al. Cancer Res. 2001; 61: 7305-9). TAMs respond to tumor hypoxia by upregulating the hypoxia-inducible transcription factors HIF-1 and HIF-2. Macrophages also upregulate VEGF and other proangiogenic factors in response to hypoxia. For example, macrophages synthesize elevated levels of MMP-7 when exposed to hypoxia in vitro and in avascular areas of human tumors. A cDNA array study has identified upregulation of messages encoding more than 30 other proangiogenic genes in primary macrophages exposed to hypoxia, including CXCL8, angiopoietin, COX-2 and other factors (White J R, et al. Genomics 2004; 83: 1-8).

TAMs have also been implicated in the regulation of metastasis. High numbers of TAMs in primary tumors have been correlated with early establishment of metastases in a number of tumor types (Hanada T et al. Int J. Urol 2000; 7: 263-9). TAMs play roles in both the release of metastatic cells from the primary tumor as well as the establishment of secondary tumors at distant sites.

TAMs also play a role in tumor immunosuppression. Unlike macrophages from healthy tissues, which are capable of presenting tumor-associated antigens, lysing tumor cells, and stimulating the antitumor functions of T cells and NK cells, TAMs in the tumor microenvironment lack these activities, leaving the host without the ability to mount an effective antitumor immune response. A number of studies have shown that tumor-derived molecules, like cytokines, growth factors, chemotactic molecules, and proteases, influence TAM functions (Elgert K D et al. J Leukoc Biol 1998; 64: 275-90). For example, tumor cells secrete proteins that can inhibit the cytotoxic activity of TAMs, e.g., IL-4, IL-6, IL-10, MDF, TGF-h1 and PGE 2 (Ben-Baruch, Scmin Cancer Biol 2005). Moreover, TGF-hl, IL-10, and PGE 2 may suppress the expression of MHC class II molecules by macrophages in the tumor microenvironment as well as distant sites like the spleen and peritoneum. This effect may limit the ability of TAMs to present tumor-associated antigens to T cells effectively in these areas. Another important aspect of TAM involvement in antitumor immune mechanisms is the ability of these cells to release immunostimulatory cytokines. For example, macrophage expression of IL-12, a cytokine known to stimulate both the proliferation and cytotoxicity of T cells and NK cells, is markedly suppressed in tumors, possibly by exposure to IL-10, PGE 2, and TGF-h1 (Mitsuhashi M. et al. J Leuko Biol 2004; 76: 322-23). Hypoxia in the tumor microenvironment is likely to contribute suppressing the antitumor activity of TAMs as it stimulates the release of the potent immunosuppressive factors PGE 2 and IL-10. They act on TAMs to reduce their cytotoxicity activity toward tumor cells. Hypoxia also inhibits the ability of macrophages to phagocytose dead or dying cells and present antigens to T cells. One mechanism by which this may be achieved is by reduced surface expression of CD80, a costimulatory molecule needed for the full activation of T-cell responses to antigenic peptides.

Many signaling pathways are important to TAM functions. Exemplary signaling pathways regulating TAM function include but are not limited to NFkB pathway, TLR pathways, specifically TLR/IL-1R signaling, TLR2 and TLR4 signaling, the Tie-2/Ang-2 pathway, the TRIF/TBK1/IRF3 pathway, and hypoxia-induced pathways. NFkB is one of the most crucial transcription factors regulating the inflammatory repertoire of macrophages, particularly their expression of proinflammatory cytokines, costimulatory molecules, and other activation markers in response to diverse environmental cues (e.g., stress signals, inflammatory cytokines, pathogens, and hypoxia). TLR/IL-1R signaling is an important upstream component of NFkB activation in macrophages. In inflammation-induced cancers, activation of TLR/IL-1R on stromal macrophages may be triggered by: 1) direct interaction with bacteria at sites of chronic infection (e.g., enteric bacteria in colitis-associated colon cancer or *H. pylori* in gastric cancer) (Karin M et al. Cell 2006 124: 823-835); or 2) interaction with tumor-cell-derived proinflammatory cytokines like IL-1; and/or 3) recognition of components of necrotic tumor cell debris like HMGB1 (high mobility group box 1) or S100 (reviewed by Biswas S K et al. J. Immunol. 2008 180: 2011-2017). TLR4 activation on human lung cancer cells promotes production of the immunosuppressive cytokine TGF-β and the proangiogenic factors VEGF and CXCL8 as well as conferring resistance to TNF-α-induced apoptosis and tumor cell survival (He W et al. Mol. Immunol 2007 44: 2850-2859). A preferential role of TLR2 activation in triggering an M2 (immunosuppressive)-like cytokine profile (IL-12 low, IL-10 high) in dendritic cells and macrophages through ERK/MAPK phosphorylation has been reported (Dillon S et al. J Immunol 2004 172: 4733-4743).

Tie-2-expressing monocytes (TEM) exist in human and murine tumors (De Palma et al 2005 Cancer Cell 8: 211-226). Endothelial cells as well as tumor cells are known to up-regulate Ang-2, a ligand for Tie-2 in tumors. It has been suggested that tumor-derived Ang-2 may facilitate the recruitment of Tic-2 monocytes/macrophages into tumors (Murdoch C et al. J Immunol. 178: 7405-7411). Importantly, Ang-2 also significantly inhibits the release of proinflammatory cytokines like TNF-α and IL-12 by Tie-2 monocytes in vitro (Biswas S K et al. J. Immunol. 2008 180: 2011-2017), an effect more pronounced in hypoxia. These findings suggest that the Ang-2/Tie-2 axis may represent another potential mechanism for dampening the antiangiogenic phenotype and prompting the immunosuppressive phenotype of TAM, especially in hypoxic areas of tumors.

Preferential activation of the TRIF-dependent IRF3/STAT1 pathway (where TRIF is TLR/IL-1R domain-containing adaptor inducing IFN-β, TBK is TANK-binding kinase, and IRF is IFN regulatory factor) has been demonstrated in TAM in murine fibrosarcoma (Biswas S et al. Blood 107: 2112-2122). This was evident from the constitutive activation of STAT1 and the up-regulation of type I IFN-inducible genes including CCL5, CXCL9, and CXCL10 in the TAM under basal and LPS-activated conditions (Biswas S K et al. J. Immunol 2008 180: 2011-2017). IL-10 transcription has also been shown to be regulated by the TRIF/IRF3 pathway via TRAF3 and type I IFNs (Chang E Y et al. J Immunol 178: 6705-6709). Taken together, TRIF pathway members such as TBK1 and IRF3 may play a role in mediating the effects of TAM and may represent a potential therapeutic target.

As mentioned hereinabove, hypoxia has profound effects on macrophage functions including their migration into tumors and patterns of gene expression, especially those encoding proangiogenic cytokines and enzymes. Hypoxia induces gene expression in these cells through up-regulation of the transcription factors hypoxia-inducible factors (HIF) 1 and 2 (HIF-1 and HIF-2). Macrophages up-regulate both HIFs and subsequently a wide array of HIF target genes in hypoxic/necrotic areas of human tumors (Murdoch C et al. 2005 Int J Cancer, 117: 701-708). Most importantly, hypoxia is a potent inducer of both VEGF and MMP7 in TAM, both of which are known to support tumor angiogenesis, invasion, and metastasis. In addition, hypoxia up-regulates the expression of M2 macrophage markers like IL-10, arginase, and PGE 2. It also modulates expression of proinflammatory genes like TNF-α, IL-1, migration inhibitory factor (MIF), CCL3, and COX2.

In some embodiments, the present invention provides a method of treating cancer comprising administering an oxidative agent or an immunomodulatory agent. In some embodiments, macrophage activation or function is modulated by the oxidative or immunomodulatory agent of the present invention such that the antitumor activity is enhanced. In some embodiments, the oxidative agent of the present invention modulates one or more pathways involved in macrophage activation or function, wherein the pathways include but are not limited to the NFkB pathway, TLR pathway, Tie-2/Ang-2 pathway, TRIF/TBK1/IRF3 pathway, hypoxia-induced pathway and any pathway involving any molecule disclosed herein.

D. Methods of Treatment of Disease

The present invention provides methods for the treatment of a variety of diseases and disorders using an oxidative agent, including but not limited to chlorite or chlorite-containing agents, alone or in combination with another agent effective in treating the disease. The present invention also provides methods for the treatment of a variety of diseases and disorders using an immunomodulatory agent, including but not limited to immunosuppressive agents, alone or in combination with another agent effective in treating the disease.

In some embodiments, an oxidative agent and an immunomodulatory agent are used together for combination therapy. By combination therapy is meant the simultaneous administration of an immunomodulator and an oxidative agent in the same formulation or in separate formulations, or the administration of an immunomodulator and an oxidative agent at separate times. In one aspect, the present invention provides for a method of treating a disease that responds to an immunomodulator by administering to a subject in need thereof an immunomodulator in combination with an oxidative agent. In an alternative embodiment, the present invention provides for a method of ameliorating the side effects of immunomodulator therapy, the method comprising administering an oxidative agent to a subject experiencing or at risk of experiencing side effects from immunomodulator therapy.

Unless the context indicates otherwise, all of the formulations and pharmaceutical formulations described herein may be used in the methods of treatment provided by the invention. As used herein and as well understood in the art, examples of treatment include obtaining beneficial or desired results, including clinical results. Non-limiting examples of beneficial or desired clinical results include one or more of alleviation or amelioration of one or more symptoms, diminishment of extent of a condition, including a disease, stabilized (i.e., not worsening) state of a condition, including diseases, preventing spread of disease, delay or slowing of condition, including disease, progression, amelioration or palliation of the condition, including disease, state, and remission (whether partial or total), whether detectable or undetectable. In some variations, oxidative and/or immunomodulatory agents as described herein are used to achieve one or more of treating, preventing, delaying the onset of, or causing the regression of the diseases or conditions described herein.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis can include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition. Treating or treatment of a disease or condition with oxidative and/or immunomodulatory agents includes: (1) preventing or reducing the risk of developing the disease, i.e., causing the clinical symptoms of the disease not to develop in a subject that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms. In some embodiments, treatment may be understood to not include prevention. The term "modulate" can refer to the treating, prevention, suppression, enhancement or induction of a function or condition. For example, compounds can modulate macrophage activation by enhancing macrophage activation or inhibiting macrophage activation. In some embodiments, the term "modulate" may be understood to not include prevention of a function or condition.

A "subject" or "patient" includes humans and non-human mammals. Examples of subject or patients include, but are not limited to mice, rats, hamsters, guinea pigs, pigs, rabbits, cats, dogs, goats, sheep, cows, and humans. The term "mammal" includes, without limitation, humans, domestic animals (e.g., dogs or cats), farm animals (cows, horses, or pigs), and laboratory animals (mice, rats, hamsters, guinea pigs, pigs, rabbits, dogs, or monkeys).

The terms "disease" and "disorder" are used interchangeably herein. In general, a therapeutically effective amount of a formulation is administered to a subject. An "effective amount," which is also referred to herein as a "therapeutically effective amount," of a therapeutic agent for administration as described herein is that amount of the therapeutic agent that provides the therapeutic effect sought when administered to the subject. A therapeutically effective amount may be achieved in a single administration or after multiple administrations. The achieving of different therapeutic effects may require different effective amounts of therapeutic agent. For example, the therapeutically effective amount of a therapeutic agent used for preventing a disease or condition may be different from the therapeutically effective amount used for treating, inhibiting, delaying the onset of, or causing the regression of the disease or condition. In addition, the therapeutically effective amount may depend on the age, weight, the bioavailability of the compound, the severity of the disease or condition, and other health conditions of the subject as is well know to those versed in the disease or condition being addressed. Thus, the therapeutically effective amount may not be the same in every subject to which the therapeutic agent is administered. In some embodiments, the therapeutically effective amount of an oxidative or immunomodulatory agent of the invention is reduced by combination therapy with another oxidative or immunomodulatory agent, or other therapy or intervention.

To determine whether a level of therapeutic agent is a "therapeutically effective amount" to treat the diseases or conditions described herein, the chlorite formulations may be administered in appropriate animal models for the diseases or conditions of interest, and the effects may be observed to determine whether the treatment was effective in the animal model. The appropriate level for a different subject, including but not limited to a human subject, may be estimated using methods known by those of skill in the art.

Effective dosages may be estimated initially from in vitro assays. For example, an initial dosage for use in animals may be formulated to achieve a circulating blood or serum concentration of active compound that is at or above an IC50 of the particular compound as measured in an in vitro assay. Calculating dosages to achieve such circulating blood or serum concentrations, taking into account the bioavailability of the particular active agent, is well within the capabilities of skilled artisans. For guidance, the reader is referred to Fingl & Woodbury, "General Principles," In: *Goodman and Gilman's The Pharmaceutical Basis of Therapeutics*, Chapter 1, pp. 1-46, latest edition, Pergamagon Press, which is hereby incorporated by reference in its entirety, and the references cited therein.

The oxidative agent or immunomodulatory agent of the present invention can be administered alone or as part of a combination therapy, e.g., administered in combination with or adjunctive to other therapies or interventions for treating the diseases or conditions described herein. Administration of the oxidative agent or immunomodulatory agent may be prior to, subsequent to, or concurrent with one or more other treatments, including but not limited to treatments using other active agents or non-pharmaceutical therapies such as radiotherapy. In some variations the oxidative agent, e.g., chlorite, or immunomodulatory agent are used in accordance with their standard or common dosages, as specified in the prescribing information accompanying other commercially available chlorite formulations. See, e.g., the prescribing information in the 2005 Edition of The Physician's Desk Reference, the disclosures of which are incorporated herein by reference.

Combination therapy includes administration of a single pharmaceutical dosage formulation that contains an oxidative agent, e.g., chlorite as described herein, and/or an immunomodulatory agent, e.g., an immunosuppressive agent, and one or more additional active agents, as well as administration of an oxidative agent and each active agent in its own separate pharmaceutical dosage formulation. In a non-limiting example, chlorite and a DPP-IV inhibitor can be administered to a subject having Type II diabetes together in a single dosage composition, or each agent can be administered in separate dosage formulations. Where separate dosage formulations are used, oxidative agents, immunomodulatory agents, and/or one or more additional active agents can be administered at essentially the same time (i.e., concurrently), or at separately staggered times (i.e., sequentially). Combination therapy is understood to include all these regimens.

One of skill in the art will appreciate that the effective amount may be adjusted when therapeutic agents are used in combination with the oxidative or immunomodulatory agents of the present invention. In a non-limiting example, a chlorite composition provided by the present invention may be used in combination with a DPP4 inhibitor, e.g., sitagliptin. When such combinations are used, the dose of one or more of the agents may be reduced to a level below the level required for a desired efficacy when the one or more agents are used alone.

The term "diagnosing" refers to determining the presence or absence of a particular disease or condition. Additionally, the term refers to determining the level or severity of a particular disease or condition, as well as monitoring of the disease or condition to determine its response to a particular therapeutic regimen.

In one aspect, the present invention provides a method of treating a macrophage related disease comprising administering to a subject in need thereof an effective amount of a pharmaceutical composition comprising an oxidative agent, e.g., chlorite or a chlorite-containing agent, or an immunomodulatory agent, e.g., an immunosuppressant. In some embodiments, the chlorite composition further comprises a pH adjusting agent and a pharmaceutically acceptable excipient. In another aspect, the present invention provides a method of treating a macrophage related disease comprising administering to a subject in need thereof an effective amount of an oxidative and/or immunomodulatory agent. In some embodiments, an oxidative agent and an immunomodulatory agent are used together for combination therapy.

In the present invention, the term "macrophage related diseases" encompasses diseases related to monocytes as well.

Due to their role in phagocytosis, macrophages are involved in many diseases of the immune system. For example, they participate in the formation of granulomas, which are inflammatory lesions that are caused by a large number of diseases. Some disorders of ineffective phagocytosis and macrophage function have been described. Macrophages are the predominant cells involved in creating the progressive plaque lesions of atherosclerosis (Lucas A D, Greaves D R *Expert Rev Mol Med* 3 (25): 1-18). Macrophages also play a role in human immunodeficiency virus (HIV) infection. Similar to T cells, macrophages can be infected with HIV, and become a reservoir of ongoing virus replication throughout the body. Furthermore, macrophages are believed to help cancer cells proliferate as well. They are attracted to oxygen-starved (hypoxic) tumor cells and promote chronic inflammation. Inflammatory compounds such as tumor necrosis factor (TNF) released by the macrophage activates the gene switch nuclear factor-kappa B. NF-kB then enters the nucleus of a tumor cell and turns on production of anti-apoptotic proteins that prevent apoptosis and promote cell proliferation and inflammation (Gary Stix 2007 *Scientific American:* 46-49). Several non-limiting examples of macrophage related diseases are described below.

Diseases related to macrophage presence or function are encompassed within the scope of the methods of the present invention. In one embodiment, macrophage related diseases are diseases characterized by activated macrophages. The macrophages may be chronically activated or acutely activated, or both. While not wishing to be bound by theory, treatments according to certain embodiments of the invention may interfere with the activation of monocytes to macrophages, or may increase deactivation of macrophages, or both.

Macrophage related diseases that can be treated or prevented by the methods of the present invention include but are not limited to cancer, autoimmune diseases such as multiple sclerosis and rheumatoid arthritis, macrophage activation syndrome, atherosclerosis, diabetes mellitus, Kawasaki disease, asthma, hemophagocytic lymphohistiocytosis, sarcoidosis, periodontitis, Whipple's disease, pulmonary alveolar proteinosis, macrophage related pulmonary disease, Leishmaniasis, obesity complications, hemodialysis related inflammation, microbial infection, retroviral infection such as HIV infection, and inflammation. In addition, for many of the diseases, although macrophages may not be the primary trigger of the disease, their involvement is evident in the disease related complications or secondary manifestations. Such macrophage related complications can be treated or prevented by the methods of the present invention. For example, macrophages contribute to neurological signs in acquired immunodeficiency syndrome (AIDS) and non-AIDS-related diseases. Other examples of complications that may involve macrophages and can be treated with the subject methods include but are not limited to transplant-related complications, acute atheroma complication, metabolic syndrome, hypertension, obesity, diabetic complications (nephropathy, neuropathy and retinopathy), complications of the tobacco-related disease, liver complications, inflammatory neurological diseases, and a variety of other disorders. In one embodiment, the diseases to be treated exclude neurodegenerative diseases. In one embodiment, the diseases to be treated are limited to diseases of the organs of the thorax. Alternatively, the diseases to be treated involve the peripheral nervous system.

In one embodiment, the diseases to be treated according to the invention are related to or can be identified by elevated levels of soluble CD14 (sCD14) in plasma. Such diseases may include hemodialysis patients, periodontitis, chronic heart failure, pulmonary tuberculosis, oral lichen planus and burning mouth syndrome, inflammatory bowel disease, carrageenan-primed endotoxin shock mouse model, sepsis, inactive Crohn's Disease, brucellosis, severe acute pancreatitis, atopic syndrome including atopic conditions in children, aortic stiffness, chronic Hepatitis B and C, transplant-related conditions including lung transplant patients, multiple organ dysfunction syndrome, Non-Hodgkin's lymphoma, systemic lupus erythematosus, status asthmaticus, Lyme Disease, arthritis such as rheumatoid arthritis, Kawasaki Disease, acute respiratory distress syndrome, scleroderma, acute plasmodium falciparum malaria, and sarcoidoisis. In one embodiment, the diseases to be treated according to the invention are related to or can be identified by elevated levels of soluble CD14 (sCD14) in plasma which can be attributed to a pathogen. Such diseases may include periodontitis, pulmonary tuberculosis, oral lichen planus and burning mouth syndrome, carrageenan-primed endotoxin shock mouse model, sepsis, brucellosis, chronic Hepatitis B and C, Lyme Disease, pathogen-induced Kawasaki Disease, and acute plasmodium falciparum malaria. In one embodiment, the diseases to be treated according to the invention are related to or can be identified by elevated levels of soluble CD14 (sCD14) in plasma where the diseases do not directly involve the central nervous system. Alternately, the disease to be treated may have an unknown etiology, such as arthrities, asthma, scleroderma, inflammatory bowel disease, systemic lupus erythematosus, and atopic syndrome.

In one embodiment, the diseases to be treated according to the invention are related to or can be identified by elevated levels of soluble CD163 (sCD163) in plasma. Such diseases may include inflammatory disorders and sepsis, Type 2 diabetes, acute malaria, bacteraemia, acute liver failure, fulminant hepatic failure, multiple sclerosis, Macrophage Activation Syndrome, pneumoniae bacteremia, coeliac disease, Hepatitis C and B, coronary atherosclerosis, reactive hemophagocytic syndrome, Gaucher's Disease, myeloid leukaemia, and rheumatoid arthritis. In one embodiment, the diseases to be treated according to the invention are related to or can be identified by elevated levels of soluble CD163 (sCD163) in plasma which can be attributed to a pathogen. Such diseases may include sepsis, acute malaria, bacteraemia, pneumoniae bacteremia, and Hepatitis C and B, Alternately, the disease to be treated may have an unknown etiology, or a non-pathogenic etiology.

In one embodiment, the diseases to be treated according to the invention are related to or can be identified by elevated levels of more than one biomarker in plasma. For example, levels of sCD14 and sCD163 may both be measured and correlated. In certain embodiments, treatment according to the invention reduces the elevated levels of biomarker, such as sCD14 and/or sCD163.

In one preferred embodiment, the disease to be treated shows upregulation of differentiation of monocytes to activated macrophages, where treatment according to the invention reduces such upregulation. The reduction in upregulation may in some embodiments occur before upregulation, or alternatively, by downregulation after the fact, or both. In one embodiment, macrophage deactivation is characterized by levels of expression of CD16 in monocytes or macrophages, for example, median CD16 expression levels in CD14+ cells. A preferred oxidative agent according to this embodiment is an N-halo compound such as 1,3-dichloro-5,5-dimethylhydantoin or chloramine T, alone or in combination with an immunomodulatory agent such as natalizumab (Tysabri®), fingolimod, or cladribine. In one embodiment, the disease to be treated is multiple sclerosis or Crohn's disease.

Diseases to be treated according to the invention include but are not limited to the following diseases.

I. Metabolic and Vascular Disorders

In some embodiments, the methods of the present invention comprise administration of oxidative agent and/or immunomodulatory agent in combination with other therapeutic agents and/or interventions that are commonly used for the treatment of diabetes and related disorders. In such embodiments, combination therapy can be used for modulating (preventing the onset of the symptoms or complications associated with) diabetes, or treating, preventing or reducing the risk of developing, diabetes and its related symptoms, complications, and disorders. In non-limiting examples, an oxidative agent and/or immunomodulatory agent can be used in combination with, for example, biguanides (such as metformin); thiazolidinediones (such as ciglitazone, pioglitazone, troglitazone, and rosiglitazone); dipeptidyl-peptidase-4 ("DPP-IV") inhibitors (such as vildagliptin, sitagliptin, saxagliptin, linagliptin and alogliptin); glucagonlike peptide-1 ("GLP-1") receptor agonists (such as exanatide) or GLP-1 mimetics; PPAR gamma agonists or partial agonists; dual PPAR alpha, PPAR gamma agonists or partial agonists; dual PPAR delta, PPAR gamma agonists or partial agonists; pan PPAR agonists or partial agonists; dehydroepiandrosterone (also referred to as DHEA or its conjugated sulphate ester, DHEA-$SO_4$); antiglucocorticoids; TNF-alpha inhibitors; alpha-glucosidase inhibitors (such as acarbose, miglitol, and voglibose); sulfonylureas (such as chlorpropamide, tolbutamide, acetohexamide, tolazamide, glyburide, gliclazide, glynase, glimepiride, and glipizide); pramlintide (a synthetic analog of the human hormone amylin); other insulin secretogogues (such as repaglinide, gliquidone, and nateglinide); insulin (or insulin mimetics); glucagon receptor antagonists; gastric inhibitory peptide ("GIP"); or GIP mimetics.

In some embodiments, the methods of the present invention comprise administration of an oxidative agent and/or immunomodulatory agent in combination with other therapeutic agents and/or interventions that are commonly used for the treatment of complications of macrophage related diseases. Such agents include but are not limited to agents used to treat vascular disease, including but not limited to endothelin receptor antagonists commonly used for the treatment of hypertension and other endothelial dysfunction-related disorders, such as bosentan, darusentan, enrasentan, tezosentan, atrasentan, ambrisentan sitaxsentan; smooth muscle relaxants such as PDE5 inhibitors (indirect-acting) and minoxidil (direct-acting); angiotensin converting enzyme (ACE) inhibitors such as captopril, enalapril, lisinopril, fosinopril, perindopril, quinapril, trandolapril, benazepril, ramipril; angiotensin II receptor blockers such as irbesartan, losartan, valsartan, eprosartan, olmesartan, candesartan, telmisartan; beta blockers such as atenolol, metoprolol, nadolol, bisoprolol, pindolol, acebutolol, betaxolol, propranolol; diuretics such as thiazide, hydrochlorothiazide, furosemide, torsemide, metolazone; calcium channel blockers such as amlodipine, felodipine, nisoldipine, nifedipine, verapamil, diltiazem; alpha receptor blockers doxazosin, terazosin, alfuzosin, tamsulosin; and central alpha agonists such as clonidine. Such agents include but are not limited to agents used to treat hyperlipidemia, including but not limited to agents that lower LDL such as statins (atovastatin, fluvastatin, lovastatin, pravastatin, rosuvastatin calcium, simvastatin) and nicotinic acid, agents that stimulate PPAR alpha such as fibrates, gemfibrozil, fenofibrate, bezafibrate, ciprofibrate, agents that bind and prevent readsorption of bile acids and reduce cholesterol levels such as bile acid sequestrants, cholestyramine and colestipol, and cholesterol absorption inhibitors. Such agents include those that reduce risk of heart attack, including COX-1 inhibitors including aspirin and non-steroidal anti-inflammatory drugs (NSAIDs), or COX-2 inhibitors. Such agents include but are not limited to agents used to treat microbial infections, including antibiotics, antiviral and antifungal. Such agents include but are not limited to agents used to treat inflammation, including various immunosuppressants, for example glucocorticoids, non-glucocorticoid steroids, cytostatics, antibodies, and drugs acting on immunophilins. Examples of immunosuppressants that can be used in combination with the oxidative agents of the present invention for treatment of autoimmune diseases and various inflammatory diseases include but are not limited to a cytostatic, such as an alkylating agent, an antimetabolite, or a cytotoxic antibiotic, a folic acid analog such as methotrexate, or a purine analog such as azathioprine and mercaptopurine, an antibody, a TNF binding protein, methotrexate, azathioprine, mercaptopurine, an interferon, an opioid, or mycophenolate, a calcineurin inhibitor such as cyclosporin, tacrolimus, sirolimus, or an analog of any thereof.

In some embodiments, the methods of the present invention comprise administration of an oxidative agent and/or immunomodulatory agent in combination with other therapeutic agents and/or interventions that are used for the treatment of obesity or obesity-related disorders. In some embodiments, the methods comprise administration of the oxidative and/or immunomodulatory agent in combination with, e.g., phenylpropanolamine, phenteramine; diethylpropion; mazindol; fenfluramine; dexfenfluramine; phentiramine, beta-3 adrenoceptor agonist agents; sibutramine; gastrointestinal lipase inhibitors (such as orlistat); and leptins. Other agents used in treating obesity or obesity-related disorders wherein the compounds of the present invention can be effectively used in combination with, e.g., cannabinoid-1 ("CB-1") receptor antagonists (such as rimonabant); PPAR delta agonists or partial agonists; dual PPAR alpha, PPAR delta agonists or partial agonists; dual PPAR delta, PPAR gamma agonists or partial agonists; pan PPAR agonists or partial agonists; neuropeptide Y; enterostatin; cholecytokinin; bombesin; amylin; histamine H3 receptors; dopamine D2 receptors; melanocyte stimulating hormone; corticotrophin releasing factor; galanin; and gamma amino butyric acid (GABA).

In some embodiments, the methods of the present invention comprise administration of an oxidative agent and/or immunomodulatory agent in combination with other therapeutic agents and/or interventions that are used for the treatment of hyperlipidemia and related complications, e.g., statins (such as atorvastatin, fluvastatin, lovastatin, pravastatin, and simvastatin), CETP inhibitors (such as torcetrapib); a cholesterol absorption inhibitor (such as ezetimibe); PPAR alpha agonists or partial agonists; PPAR delta agonists or partial agonists; dual PPAR alpha, PPAR delta agonists or partial agonists; dual PPAR alpha, PPAR gamma agonists or partial agonists; dual PPAR delta, PPAR gamma agonists or partial agonists; pan PPAR agonists or partial agonists; fenofibric acid derivatives (such as gemfibrozil, clofibrate, fenofibrate, and bezafibrate); bile acid-binding resins (such as colestipol or cholestyramine); nicotinic acid; probucol; betacarotene; vitamin E; or vitamin C.

In some embodiments, the methods of the present invention comprise administration of an oxidative agent and/or immunomodulatory agent in combination with other therapeutic agents and/or interventions that are used for the treatment of atherosclerosis. In some embodiments, the methods comprise administration of the oxidative and/or immunomodulatory agent in combination with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin); an HMG-CoA synthase inhibitor; a squalene epoxidase inhibitor; or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as beta-sitosterol; a bile acid sequestrant anion exchange resin, such as cholestyramine, colestipol or dialkylaminoalkyl derivatives of a cross-linked dextran; an LDL receptor inducer; fibrates, such as clofibrate, bezafibrate, fenofibrate, and gemfibrizol; vitamin B6 (also known as pyridoxine) and the pharmaceutically acceptable salts thereof, such as the HCl salt; vitamin B12 (also known as cyanocobalamin); vitamin B3 (also known as nicotinic acid and niacinamide); anti-oxidant vitamins, such as vitamin C and E and beta carotene; a beta-blocker; an angiotensin II antagonist; an angiotensin converting enzyme inhibitor; PPAR alpha agonists or partial agonists; PPAR delta agonists or partial agonists; PPAR gamma agonists or partial agonists; dual PPAR alpha, PPAR delta agonists or partial agonists; dual PPAR alpha, PPAR gamma agonists or partial agonists; dual PPAR delta, PPAR gamma agonists or partial agonists; pan PPAR agonists or partial agonists; and a platelet aggregation inhibitor, such as fibrinogen receptor antagonists (i.e., glycoprotein IIb/IIIa fibrinogen receptor antagonists) and aspirin. The oxidative agent, e.g., chlorite, or immunomodulatory agent, e.g., immunosuppressor, can be administered in combination with more than one additional active agent, e.g., a combination of chlorite with an HMG-CoA reductase inhibitor (e.g., atorvastatin, fluvastatin, lovastatin, pravastatin, and simvastatin) and aspirin, or in combination with an HMG-CoA reductase inhibitor and a blocker.

In some embodiments, the methods of the present invention comprise administration of an oxidative agent and/or immunomodulatory agent in combination with other therapeutic agents and/or interventions that are used for the treatment of hyperlipidemia. In some embodiments, the methods comprise administration of the oxidative and/or immunomodulatory agent combination with one or more of the following active agents for modulating hyperlipidemia (treating hyperlipidemia and its related complications) including but not limited to statins (such as atorvastatin, fluvastatin, lovastatin, pravastatin, and simvastatin), CETP inhibitors (such as torcetrapib); a cholesterol absorption inhibitor (such as ezetimibe); PPAR alpha agonists or partial agonists; PPAR delta agonists or partial agonists; dual PPAR alpha, PPAR delta agonists or partial agonists; dual PPAR alpha, PPAR gamma agonists or partial agonists; dual PPAR delta, PPAR gamma agonists or partial agonists; pan PPAR agonists or partial agonists; fenofibric acid derivatives (such as gemfibrozil, clofibrate, fenofibrate, and bezafibrate); bile acid-binding resins (such as colestipol or cholestyramine); nicotinic acid; probucol; betacarotene; vitamin E; or vitamin C.

Additionally, the methods of the present invention comprise administration of an oxidative agent and/or immunomodulatory agent in combination with a therapeutically effective amount of one or more active agents selected from the group consisting of: an antihyperlipidemic agent; a plasma HDL-raising agent; an antihypercholesterolemic agent, such as a cholesterol biosynthesis inhibitor, for example, an HMG-CoA reductase inhibitor; an HMG-CoA synthase inhibitor; a squalene epoxidase inhibitor, or a squalene synthetase inhibitor (also known as squalene synthase inhibitor); an acyl-coenzyme A cholesterol acyltransferase inhibitor; probucol; nicotinic acid and the salts thereof; CETP inhibitors such as torcetrapib; a cholesterol absorption inhibitor such as ezetimibe; PPAR alpha agonists or partial agonists; PPAR delta agonists or partial agonists; dual PPAR alpha, PPAR delta agonists or partial agonists; dual PPAR alpha, PPAR gamma agonists or partial agonists; dual PPAR delta, PPAR gamma agonists or partial agonists; pan PPAR agonists or partial agonists; niacinamide; a cholesterol absorption inhibitor; a bile acid sequestrant anion exchange resin; a LDL receptor inducer; clofibrate, fenofibrate, and gemfibrozil; vitamin B6 and the pharmaceutically acceptable salts thereof; vitamin B12; an anti-oxidant vitamin; a beta-blocker; an angiotensin II antagonist; an angiotensin converting enzyme inhibitor; a platelet aggregation inhibitor; a fibrinogen receptor antagonist; aspirin; phentiramines, beta-3 adrenergic receptor agonists; sulfonylureas, biguanides, alpha-glucosidase inhibitors, other insulin secretogogues, and insulin.

In some embodiments, the present invention provides a method to administer an oxidative agent and/or immunomodulatory agent in combination with one or more other therapeutic agents and/or interventions used for the treatment of metabolic syndrome (or treating metabolic syndrome and its related symptoms, complications and disorders), wherein the compounds of the present invention can be effectively used in combination with, for example, the active agents discussed above for modulating or treating diabetes, obesity, hyperlipidemia, atherosclerosis, and/or their respective related symptoms, complications and disorders.

In a further embodiment, the present invention provides a method to administer an oxidative agent and/or immunomodulatory agent in combination with halofenic acid, an ester of halofenic acid, or another prodrug of halofenic acid, preferably with (−)-(4-chlorophenyl)-(3-trifluoromethylphenoxy)-acetic acid 2-acetylaminoethyl ester (metaglidasen).

In some embodiments, the present invention provides a method that comprises administering an oxidative agent and/or immunomodulatory agent in combination with one or more allergy drugs for the treatment of diabetes and obesity. Two common over-the-counter allergy medications are effective in reducing complications of both obesity and Type 2 diabetes in mice. The medications, ketotifen fumarate and cromolyn, stabilize a population of inflammatory immune cells called mast cells in people suffering from asthma or allergy. Theses anti-allergy or asthma drugs may have therapeutic effects for the treatment of macrophage related diseases including but not limited to diabetes and obesity in humans. Researchers have also found that a regulatory T cell also acts as a liaison between the metabolic and immune systems-in this case, controlling inflammation in fat tissue. Fat tissue from obese and insulin-resistant mice and people is marked by a dramatic absence of regulatory T cells or Tregs, in dramatic contrast to an already reported overabundance in fat tissue of inflammatory macrophages (Calisha, "Common allergy drug reduces obesity and diabetes in mice", *FierceBiotech* July 2009). Although obese and diabetic fat tissue was full of inflammatory macrophages and nearly absent of Tregs, normal-weight fat tissue was the diametric opposite. It is possible that the inflammation caused by macrophages results in insulin resistance. It is further likely that Tregs keep the macrophages in check in normal fat tissue, thus preventing inflammation.

II. Macrophage-Activation Syndrome

In some embodiments, the present invention provides a method of treating a macrophage-activation syndrome comprising administering an effective amount of an oxidative agent, including but not limited to chlorite, chlorite containing agents, or derivatives thereof. In some embodiments, the present invention provides a method of treating a macrophage-activation syndrome comprising administering an effective amount of an immunomodulatory agent, including but not limited to immunosuppressants. In some embodiments, an oxidative agent and an immunomodulatory agent are used together for combination therapy to treat macrophage-activation syndrome.

Macrophage-activation syndrome (MAS) is a severe, potentially life-threatening, complication of several chronic rheumatic diseases of childhood. It occurs most commonly with systemic-onset juvenile idiopathic arthritis (SoJIA), which is also known as Still's disease. In addition, MAS has been described in association with diseases including but not limited to systemic lupus erythematosus (SLE), Kawasaki disease, and adult-onset Still's disease. It is thought to be closely related and pathophysiologically very similar to reactive (secondary) hemophagocytic lymphohistiocytosis (HLH). The hallmark clinical and laboratory features include high fever, hepatosplenomegaly, lymphadenopathy, pancytopenia, liver dysfunction, disseminated intravascular coagulation, hypofibrinogenemia, hyperferritinemia, and hypertriglyceridemia. Despite marked systemic inflammation, the erythrocyte sedimentation rate (ESR) is paradoxically depressed, caused by low fibrinogen levels. A bone marrow biopsy or aspirate usually shows hemophagocytosis. There is uncontrolled activation and proliferation of macrophages and T lymphocytes, with a marked increase in circulating cytokines, such as IFN-gamma, and granulocyte-macrophage colony-stimulating factor (GM-CSF). In many cases of MAS, decreased natural killer cell (NK-cell) function is observed. Most commonly used treatments include high-dose glucocorticoids, and cyclosporine. In refractory cases treatment regimens are used similar to that in HLH (Pinto L, et al. J Assoc Physicians India. 2007 55:185-7).

III. Autoimmune Diseases

In some embodiments, the present invention provides a method of treating a macrophage related disease comprising administering an effective amount of an oxidative agent, including but not limited to chlorite, chlorite containing agents, or derivatives thereof, wherein the macrophage related disease is an autoimmune disease. In some embodiments, the present invention provides a method of treating a macrophage related disease comprising administering an effective amount of an immunomodulatory agent, including but not limited to immunosuppressants, wherein the macrophage related disease is an autoimmune disease. In some embodiments, an oxidative agent and an immunomodulatory agent are used together for combination therapy to treat autoimmune diseases.

Autoimmunity is the failure of an organism to recognize its own constituent parts as self, which allows an immune response against its own cells and tissues. Diseases that results from such aberrant immune response can be considered autoimmune diseases. Prominent examples include Coeliac disease, diabetes mellitus type 1 (IDDM), systemic lupus erythematosus (SLE), Sjögren's syndrome, Churg-Strauss Syndrome, Hashimoto's thyroiditis, Graves' disease, idiopathic thrombocytopenic purpura, and rheumatoid arthritis (RA). The treatment of autoimmune diseases is typically immunosuppressive, anti-inflammatory, or palliative. Hormone levels have been shown to affect the severity of some autoimmune diseases such as multiple sclerosis. Other causes may include the presence of fetal cells in the maternal bloodstream, i.e., microchimerism, and infections with some viruses and bacteria. The autoimmune diseases that can be treated with the methods of the present invention include but are not limited to acute disseminated encephalomyelitis, Addison's disease, alopecia areata, ankylosing spondylitis, antiphospholipid antibody syndrome, autoimmune hemolytic anemia, autoimmune hepatitis, Bullous pemphigoid, Coeliac disease, Crohns disease, dermatomyositis, diabetes mellitus type 1, Goodpasture's syndrome, Graves' disease, Guillain-Barré syndrome, Hashimoto's disease, Idiopathic thrombocytopenic purpura, Lupus erythematosus, Mixed Connective Tissue Disease, multiple sclerosis, myasthenia gravis, narcolepsy, Pemphigus vulgaris, Pernicious anemia, Polymyositis, Primary biliary cirrhosis, Rheumatoid arthritis, Sjögren's syndrome, Temporal arteritis, Ulcerative Colitis, Vasculitis, and Wegener's granulomatosis.

IV. Multiple Sclerosis

In some embodiments, the present invention provides a method of treating multiple sclerosis comprising administering an effective amount of an oxidative agent, including but not limited to chlorite, chlorite containing agents, or derivatives thereof. In some embodiments, the present invention provides a method of treating multiple sclerosis comprising administering an effective amount of an immunomodulatory agent, including but not limited to immunosuppressants. In some embodiments, an oxidative agent and an immunomodulatory agent are used together for combination therapy to treat multiple sclerosis.

Multiple sclerosis (MS) is an autoimmune disease in which a body's immune response attacks the central nervous system, leading to demyelination (Compston A, Coles A 2002 Lancet 359 (9313):1221-31). MS affects the ability of nerve cells in the brain and spinal cord to communicate with each other. Nerve cells communicate by sending electrical signals called action potentials down axons, which are wrapped in myelin. In MS, the body's own immune system destroys oligodendrocytes, the cells responsible for creating and maintaining the myelin sheath, which helps the neurons carry electrical signals. MS results in a thinning or complete loss of myelin, and, as the disease advances, the cutting (transection) of the neuron's extensions or axons. When the myelin is lost, a neuron can no longer effectively conduct electrical signals. The name multiple sclerosis refers to scars in the white matter of the brain and spinal cord, which is mainly composed of myelin. Almost any neurological symptom can appear with the disease, and often progresses to physical and cognitive disability and neuropsychiatric disorder.

Apart from demyelination, inflammation is the other pathological hallmark of MS. According to a strictly immunological explanation of MS, the inflammatory process is caused by T cells. In MS, T cells gain entry into the brain via the blood-brain barrier. The blood-brain barrier is normally not permeable to these types of cells, unless triggered by infection or a virus, which decreases the integrity of the tight junctions forming the barrier. When the blood-brain barrier regains its integrity, usually after infection or virus has cleared, the T cells are trapped inside the brain. The T cells recognize myelin as foreign and attack it as if it were an invading virus. This triggers inflammatory processes, stimulating other immune cells and the production of soluble factors including cytokines and antibodies. Leaks form in the blood-brain barrier, which in turn cause a number of other damaging effects such as swelling, activation of macrophages, and more activation of cytokines and other destructive proteins. Macrophages are present within active plaques of MS patients (L. Steinman, A molecular trio in relapse and remission in multiple sclerosis, Nature Reviews Immunology 9, 440-447 (2009)). Immunohistochemistry with macrophage markers shows that in the pathogenesis of experimental autoimmune encephalomyetitis, which is a mouse disease model of multiple sclerosis, different populations of macrophages (i.e., perivascular cells, microglia and infiltrating blood-borne macrophages) are present in the central nervous system (Bauer J, et al. The Histochemical Journal 28:83-97, 1996).

Administration of high doses of intravenous corticosteroids, such as methylprednisolone, has been the standard therapy for acute relapses of MS. Several studies have shown that treatment with interferons during an initial attack can decrease the chance that a patient will develop MS. These results support the use of interferon after a first clinical demyelinating event and indicate that there may be modest beneficial effects of immediate treatment compared with delayed initiation of treatment (Jacobs L D, et al. (2000). N Engl J Med 343 (13): 898-904). Several disease-modifying treatments have been approved by regulatory agencies of different countries. Interferon formulations including those of interferon beta-1a (Avonex®, which is injected weekly; Rebif®, injected three times a week; and CinnoVex™, a biosimilar/biogeneric), and interferon beta-1b (Betaseron® in the U.S. and Betaferon® in Europe and Japan, injected every other day). Another M S medication is glatiramer acetate (Copaxone®), injected daily, a mixture of polypeptides which may protect myelin proteins by substituting itself as the target of immune system attack (Ziemssen T, Schrempf W (2007). Int. Rev. Neurobiol. 79: 537-70). Still another approved MS medication, mitoxantrone, is an immunosuppressant also used in cancer chemotherapy. Finally, natalizumab is a humanized monoclonal antibody against the cellular adhesion molecule α4-integrin and is believed to reduce the ability of inflammatory immune cells to attach to and pass through the cell layers lining the intestines and blood-brain barrier.

In some embodiments, the present invention provides a method of treating multiple sclerosis by modulating macrophage activation with an oxidative agent, including but not limited to chlorite and chlorite-containing agents. In some embodiments, the present invention provides a method of treating multiple sclerosis by modulating macrophage activation with an immunomodulatory agent. In some embodiments, the macrophage activation is reduced or inhibited.

V. Rheumatoid Arthritis

In some embodiments, the present invention provides a method of treating rheumatoid arthritis comprising administering an effective amount of an oxidative agent including but not limited to chlorite, a chlorite containing agent, or a derivative or any thereof. In some embodiments, the present invention provides a method of treating rheumatoid arthritis comprising administering an effective amount of an immunomodulatory agent, e.g., an immunosuppressant. In some embodiments, an oxidative agent and an immunomodulatory agent are used together for combination therapy to treat rheumatoid arthritis.

Rheumatoid arthritis (RA) is a chronic, systemic inflammatory disorder that may affect many tissues and organs, but principally attacks the joints producing an inflammatory synovitis that often progresses to destruction of the articular cartilage and ankylosis of the joints. Rheumatoid arthritis can also produce diffuse inflammation in the lungs, pericardium, pleura, and sclera, and also nodular lesions, most common in subcutaneous tissue under the skin. Although the cause of rheumatoid arthritis is unknown, autoimmunity plays a pivotal role in its chronicity and progression. The rheumatoid nodule, which is often subcutaneous, is the feature most characteristic of rheumatoid arthritis. The nodule has a central area of fibrinoid necrosis that may be fissured and which corresponds to the fibrin-rich necrotic material found in and around an affected synovial space. Surrounding the necrosis is a layer of palisading macrophages and fibroblasts, corresponding to the intimal layer in synovium and a cuff of connective tissue containing clusters of lymphocytes and plasma cells, corresponding to the subintimal zone in synovitis.

RA is an autoimmune disease. Once the abnormal immune response has become established, plasma cells derived from B lymphocytes produce rheumatoid factors and ACPA of the IgG and IgM classes in large quantities. These are not deposited in the way that they are in systemic lupus. Rather, they appear to activate macrophages through Fc receptor and perhaps complement binding. This can contribute to inflammation of the synovium, in terms of edema, vasodilation and infiltration by activated T-cells (mainly CD4 in nodular aggregates and CD8 in diffuse infiltrates). Synovial macrophages and dendritic cells further function as antigen presenting cells by expressing MHC class II molecules, leading to an established local immune reaction in the tissue. The disease progresses in concert with formation of granulation tissue at the edges of the synovial lining (pannus) with extensive angiogenesis and production of enzymes that cause tissue damage. Modern pharmacological treatments of RA target these mediators. Once the inflammatory reaction is established, the synovium thickens, the cartilage and the underlying bone begins to disintegrate and evidence of joint destruction accrues. Pharmacological treatment of RA can be divided into disease-modifying antirheumatic drugs (DMARDs), anti-inflammatory agents and analgesics (Vital E, Emery P (2005) Am Pam Physician 72 (6): 1002, 1004). Traditional small molecular mass drugs include chemically synthesized DMARDs such as azathioprine, ciclosporin (cyclosporine A), D-penicillamine, gold salts, hydroxychloroquine, leflunomide, methotrexate (MTX), minocycline, and sulfasalazine (SSZ). Biological agents (biologics) are produced through genetic engineering, and include but are not limited to tumor necrosis factor alpha (TNFα) blockers—etanercept (Enbrel®), infliximab (Remicade®), adalimumab (Humira®); Interleukin 1 (IL-1) blockers—anakinra (Kineret®); monoclonal antibodies against B cells—rituximab (Rituxan®); T cell costimulation blocker—abatacept (Orencia®); and Interleukin 6 (1L-6) blockers—tocilizumab (an anti-IL-6 receptor antibody) (Ro-Actemra, Actemra™). Anti-inflammatory agents include but are not limited to glucocorticoids and non-steroidal anti-inflammatory drug (NSAIDs). Analgesics include but are not limited to paracetamol (acetaminophen in US and Canada); opiates, diproqualone, and lidocaine topical. Other therapies for RA include but are not limited to weight loss, occupational therapy, podiatry, physiotherapy, immunoadsorption therapy, joint injections, and special tools to improve hard movements.

The abundance and activation of macrophages in the inflamed synovial membrane/pannus significantly correlates with the severity of rheumatoid arthritis (RA). Although unlikely to be the 'initiators' of RA, macrophages possess widespread pro-inflammatory, destructive, and remodeling capabilities that can critically contribute to acute and chronic disease. Also, activation of the monocytic lineage is not locally restricted, but extends to systemic parts of the mononuclear phagocyte system (Kinne R W et al, Arthritis Res. 2000; 2(3):189-202). A rise in the presence of CD14+ CD16+ monocytes has been shown in active RA (Kawanaka N, et al, Arthritis Rheum 46, 2578-2586). Macrophages in synovial fluid also express CD16 and so do macrophages in the synovial membrane-lining layer (Wahl S M, J Immunol 1992, 148, 485-490; Iwahashi M, et al, Arthritis Rheum 2004, 50, 1457-1467). Thus, selective counteraction of macrophage activation remains an efficacious approach to diminish local and systemic inflammation, as well as to prevent irreversible joint damage.

In some embodiments, the present invention provides a method of treating rheumatoid arthritis by modulating macrophage activation with an oxidative agent, including but not limited to chlorite and chlorite-containing agents. In some embodiments, the present invention provides a method of treating rheumatoid arthritis by modulating macrophage activation with an immunomodulatory agent, including but not limited to immunosuppressants. In some embodiments, the macrophage activation is reduced or inhibited.

VI. Atherosclerosis

In some embodiments, the present invention provides a method of treating atherosclerosis comprising administering an effective amount of an oxidative agent, including but not limited to chlorite, chlorite-containing agents or derivatives thereof. In some embodiments, the present invention provides a method of treating atherosclerosis comprising administering an effective amount of an immunomodulatory agent, including but not limited to immunosuppressants. In some embodiments, an oxidative agent and an immunomodulatory agent are used together for combination therapy to treat atherosclerosis.

Atherosclerosis is the condition in which an artery wall thickens as the result of a build-up of fatty materials such as cholesterol. It is a syndrome affecting arterial blood vessels, a chronic inflammatory response in the walls of arteries, in large part due to the accumulation of macrophage white blood cells and promoted by low density (especially small particle) lipoproteins (plasma proteins that carry cholesterol and triglycerides) without adequate removal of fats and cholesterol from the macrophages by functional high density lipoproteins (HDL). It is caused by the formation of multiple plaques within the arteries (Maton, et al. (1993). *Human Biology and Health*. Englewood Cliffs, N.J., USA: Prentice Hall). The atheromatous plaque is divided into three distinct components: the atheroma, which is the nodular accumulation at the center of large plaques, composed of macrophages nearest the lumen of the artery; underlying areas of cholesterol crystals; and calcification at the outer base of older/more advanced lesions.

The first step of atherogenesis is the development of fatty streaks, which are small sub-endothelial deposits of monocyte-derived macrophages. The primary documented driver of this process is oxidized lipoprotein particles within the wall, beneath the endothelial cells, though upper normal or elevated concentrations of blood glucose also plays a major role and not all factors are fully understood. Fatty streaks may appear and disappear. Low Density Lipoprotein particles in blood plasma, when they invade the endothelium and become oxidized, create a risk for cardiovascular disease. A complex set of biochemical reactions regulates the oxidation of LDL, chiefly stimulated by presence of enzymes, e.g., Lp-LpA2 and free radicals in the endothelium or blood vessel lining.

The initial damage to the blood vessel wall results in an inflammatory response. Monocytes enter the artery wall from the bloodstream, with platelets adhering to the area of insult. This may be promoted by redox signaling induction of factors such as VCAM-1, which recruit circulating monocytes. The monocytes differentiate macrophages, which ingest oxidized LDL, slowly turning into large "foam cells"—so-described because of their changed appearance resulting from the numerous internal cytoplasmic vesicles and resulting high lipid content. Foam cells eventually die, and further propagate the inflammatory process. There is also smooth muscle proliferation and migration from tunica media to intima responding to cytokines secreted by damaged endothelial cells. This would cause the formation of a fibrous capsule covering the fatty streak.

In terms of treatment for atherosclerosis, in general, the group of medications referred to as statins has been the most popular and are widely prescribed for treating atherosclerosis. The statins, and some other medications, have been shown to have antioxidant effects, possibly part of their basis for some of their therapeutic success in reducing cardiac events. Combinations of statins, niacin, intestinal cholesterol absorption-inhibiting supplements (ezetimibe and others, and to a much lesser extent fibrates) have been the most successful in changing common but sub-optimal lipoprotein patterns and group outcomes. Diet and dietary supplements are also used to help treat atherosclerosis. For example, vitamin C acts as an antioxidant in vessels and inhibits inflammatory process (Böhm F, et al. (2007) *Atherosclerosis* 190 (2): 408-15). Patients at risk for atherosclerosis-related diseases are increasingly being treated prophylactically with low-dose aspirin and a statin.

The actions of macrophages drive atherosclerotic plaque progression Immunomodulation of atherosclerosis is the term for techniques which modulate immune system function in order to suppress this macrophage action (Jan Nilsson; et al (2005) *Arteriosclerosis, Thrombosis, and Vascular Biology* 5: 18-28). In some embodiments, the present invention provides a method of treating atherosclerosis by modulating macrophage accumulation or activation with an oxidative agent, including but not limited to chlorite and chlorite-containing agents. In some embodiments, the present invention provides a method of treating atherosclerosis by modulating macrophage accumulation or activation with an immunomodulatory agent, including but not limited to immunosuppressants. In some embodiments, the macrophage activation is reduced or inhibited.

VII. Stroke and Spinal Cord Pathology

In some embodiments, the present invention provides methods for treatment of stroke, post-stroke brain damage or spinal cord pathology with an oxidative agent, including but not limited to chlorite and chlorite-containing agents. In some embodiments, the present invention provides methods for treatment of stroke, post-stroke brain damage or spinal cord pathology with an immunomodulatory agent, including but not limited to immunosuppressants. In some embodiments, an oxidative agent and an immunomodulatory agent are used together for combination therapy to treat stroke, post-stroke brain damage or spinal cord pathology.

A stroke is the rapidly developing loss of brain function(s) due to disturbance in the blood supply to the brain due to ischemia (lack of blood supply) caused by thrombosis, embolism or hemorrhage. Certain classes of immune cells flood the brain soon after a stroke, causing inflammation and more neurological damage. Mice deficient in these immune cells may suffer far less brain damage after a stroke compared to normal mice. While the initial damage from a stroke cannot be prevented, drugs can be used to limit secondary damage caused by immune cells that rush to the site of the infarction, or stroke. The initial damage happens immediately after a stroke, it cannot be efficiently blocked because it is very rapid. But after this neural damage, macrophages and T-cells are recruited and this inflammation induces the growth of the infarction. This secondary damage can be blocked by suppressing the inflammation. In mice with induced stroke, it has been observed that the subsequent recruitment of immune cells caused inflammation and more damage. One of the first cytokines found expressed within the brain was interleukin-23 (IL-23). IL-23 activates other immune cells including T-cells and macrophages, which then attack the brain. Mice genetically engineered to be deficient in IL-23 suffered the least brain damage. IL-23 operates immediately after stroke or one day later. Thus the sooner the intervention to block IL-23, the more protective it is for the brain.

Most patients suffering from stroke come to hospital within a day after a stroke. A therapeutic method could prevent further the expansion of infarction by modulating macrophages and their infiltration to the inflammatory or injury site.

In some embodiments, the present invention provides methods for treatment of stroke with an oxidative agent, including but not limited to chlorite and chlorite-containing agents. In some embodiments, the present invention provides methods for treatment of stroke with an immunomodulatory agent, including but not limited to immunosuppressants. In some embodiments, the treatment is administered in combination with blockers of IL-23, e.g., ustekinumab, an anti-IL-23 antibody. In some embodiments, the oxidative or immunosuppressive agent of the present invention can be used to treat other inflammatory diseases, for example, inflammatory bowel disease.

VIII. Diabetes Mellitus

In some embodiments, the present invention provides methods for treatment of Diabetes mellitus (diabetes) with an oxidative agent, including but not limited to chlorite and chlorite-containing agents. For example, in one aspect, the present invention provides a method of treating Type 11 diabetes comprising administering to a subject in need thereof an effective amount of a pharmaceutical composition comprising: a) chlorite, b) a pH adjusting agent, and c) a pharmaceutically acceptable excipient. In some embodiments, the present invention provides a method of treating diabetic complications comprising administering to a subject in need thereof an effective amount of a pharmaceutical composition comprising: a) chlorite, b) a pH adjusting agent, and c) a pharmaceutically acceptable excipient. In some embodiments, the present invention provides methods for treatment of Diabetes mellitus (diabetes) and/or diabetic complications with an immunosuppressive agent, including but not limited to immunosuppressants. In some embodiments, an oxidative agent and an immunomodulatory agent are used together for combination therapy to treat Diabetes mellitus.

Diabetes mellitus, or diabetes, refers to a disease or condition that is generally characterized by metabolic defects in production and utilization of glucose that result in the failure to maintain appropriate blood sugar levels in the body. The result of these defects is elevated blood glucose, referred to as "hyperglycemia." Other types of disorders of glucose homeostasis include impaired glucose tolerance, which is a metabolic stage intermediate between normal glucose homeostasis and diabetes, and gestational diabetes mellitus, which is glucose intolerance in pregnancy in women without previous diabetic history.

Diabetes is a metabolic syndrome, which refers to a cluster of metabolic abnormalities including obesity, insulin resistance, glucose intolerance, diabetes, hypertension and dyslipidemia. These abnormalities are known to be associated with an increased risk of vascular events.

Diabetes can be divided into two clinical syndromes, Type I and Type II diabetes mellitus. According to the American Diabetes Association, about 8% of the U.S. population has diabetes and the numbers are rising. See www.diabetes.org/diabetes-statistics/prevalence.jsp. About 90% of these cases are Type II diabetes.

Type I diabetes, or insulin-dependent diabetes mellitus, is a chronic autoimmune disease characterized by the extensive loss of beta cells in the pancreatic islets of Langerhans, which produce insulin. As these cells are progressively destroyed, the amount of secreted insulin decreases, eventually leading to hyperglycemia (abnormally high level of glucose in the blood) when the amount secreted drops below the level required for euglycemia (normal blood glucose level).

Type II diabetes, or non-insulin-dependent diabetes mellitus, develops when muscle, fat and liver cells fail to respond normally to insulin. This failure to respond (called insulin resistance) may be due to reduced numbers of insulin receptors on these cells, or a dysfunction of signaling pathways within the cells, or both. The beta cells initially compensate for this insulin resistance by increasing their insulin output. Over time, these cells become unable to produce enough insulin to maintain normal glucose levels, indicating progression to Type II diabetes.

The fasting hyperglycemia that characterizes Type II diabetes occurs as a consequence of the combined lesions of insulin resistance and beta cell dysfunction. The beta cell defect has two components: the first component, an elevation of basal insulin release (occurring in the presence of low, non-stimulatory glucose concentrations), is observed in obese, insulin-resistant pre-diabetic stages as well as in Type II diabetes. The second component is a failure to increase insulin release above the already elevated basal output in response to a hyperglycemic challenge. This lesion is absent in pre-diabetes and appears to define the transition from normo-glycemic insulin-resistant states to frank diabetes.

Insulin resistance includes the diminished ability of insulin to exert its biological action across a broad range of concentrations producing less than the expected biologic effect (see, e.g., Reaven G M, J. Basic & Clin. Phys. & Pharm. 9:387-406 and Flie J, Ann Rev. Med. (1983) 34:145-60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, impaired glucose tolerance, gestational diabetes, metabolic syndrome, hypertension, obesity, atherosclerosis and a variety of other disorders. Eventually, the insulin resistant individuals can progress to a point where a diabetic state is reached.

Symptoms of diabetes, include, but are not limited to, polyuria, polydipsia, and polyphagia. "Polyuria" refers to the passage of a large volume of urine during a given period; "polydipsia" refers to chronic, excessive thirst; and "polyphagia" refers to excessive eating. Other symptoms of diabetes include, e.g., increased susceptibility to certain infections (especially fungal and staphylococcal infections), nausea, and ketoacidosis (enhanced production of ketone bodies in the blood).

Diabetic complications include, but are not limited to, microvascular complications and macrovascular complications. Microvascular complications are those complications that generally result in small blood vessel damage. These complications include, e.g., retinopathy (the impairment or loss of vision due to blood vessel damage in the eyes); neuropathy (nerve damage and foot problems due to blood vessel damage to the nervous system); gastroparesis (impaired ability of the stomach to empty contents due to nerve damage, e.g., to the vagus nerve); skin complications (bacterial infections, fungal infections, itching, dermopathy, necrobiosis lipoidica diabeticorum, diabetic blisters, and eruptive xanthomatosis); and nephropathy (kidney disease due to blood vessel damage in the kidneys) and other renal disorders. Macrovascular complications are those complications that generally result from large blood vessel damage. These complications include, e.g., cardiovascular disease and peripheral vascular disease.

Cardiovascular disease refers to diseases of blood vessels of the heart. See, e.g., Kaplan R M, et al., "Cardiovascular diseases" in Health and Human Behavior, pp. 206-242 (McGraw-Hill, New York 1993). Cardiovascular disease is generally one of several forms, including, e.g., hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles. Cardiovascular disorders include, but are not limited to, hypertension, myocardial infraction, metabolic syndrome, ischemic cardiac disease, coronary artery disease, cerebrovascular disease, vascular dementia, preeclampsia, heart disease, stroke, atherogenesis, thrombogenesis, atheroscleorsis, inflammatory disease or peripheral, carotid, or coronary vascular disease.

Other conditions related to diabetes include metabolic syndrome, hyperlipidemia, obesity, and adverse effects thereof.

The guidelines for diagnosis of Type II diabetes and related conditions, e.g., impaired glucose tolerance and gestational diabetes, have been outlined by the American Diabetes Association (see, e.g., The Expert Committee on the Diagnosis and Classification of Diabetes Mellitus, Diabetes Care, (1999) Vol 2 (Suppl 1):S5-19).

There is currently no cure for Type II diabetes. Conventional treatments are limited, and focus on attempting to control blood glucose levels in order to minimize or delay complications. Type II diabetics can suffer from both hypoglycemia and hyperglycemia. Hypoglycemia is also called insulin reaction. Signs of hypoglycemia include shakiness, dizziness, sweating, hunger, headache, pale skin, sudden moodiness or behavior changes, clumsiness or jerkiness, difficulty paying attention, tingling in the mouth, or in some cases seizure. Immediate care comprises sugar intake, e.g., in the form of sugar pills, candy, or direct injection of glucagon. Signs and symptoms of hyperglycemia include high blood glucose, high levels of sugar in the urine, frequent urination, and increased thirst. Failure to treat hyperglycemia can lead to ketoacidosis, or diabetic coma. Ketoacidosis occurs when the body does not have enough insulin and to use glucose as fuel, and instead breaks down fat to provide energy. The latter process produces ketones as a by-product, which builds up in the body and can result in coma or death.

Diabetes control involves diligent glucose monitoring and some Type II diabetics require insulin. Insulin is broken down during digestion and is administered through injections, insulin pumps, through the skin, or inhaled. Several other classes of therapeutic agents are also available. Conventional oral medications sold today in the United States belong to one of five classes of drugs: sulfonylureas, meglitinides, biguanides, thiazolidinediones, DPP4 inhibitors and alpha-glucosidase inhibitors. These treatments can act as sensitizers to reduce insulin resistance, e.g., metformin or thiazolidinediones ("TZDs"), or can act as secretagogues to enhance insulin secretion from beta cells, e.g., sulphonylureas or meglitinides.

Sulphonylureas stimulate beta cells to produce more insulin. They have the side effect of hypoglycemia since they cause insulin secretion independent of circulating glucose levels. First generation sulphoylureas include chlorpropamide, which is still in use, and tolbutamide, acetohexamide and tolazamide. The second generation sulfonylureas are used in smaller doses than the first-generation drugs. These include glipizide, glyburide, gliclazide and glimepiride.

Meglitinides, e.g., repaglinide and nateglinide, also stimulate beta cells to release insulin. They can be taken before meals to boost insulin response to food. Like sulfonylureas, they can have the side effect of hypoglycemia. They can also lead to weight gain.

Biguanides include the first-line treatment metformin. Biguanides lower blood glucose levels primarily by reducing the amount of glucose produced by the liver. They may also make muscle tissue more amenable to glucose uptake. Side effects of metformin include diarrhea. Other biguanides include phenformin and buformin, both of which were withdrawn over lactic acidosis risk.

Similar to biguanides, thiazolidinediones help insulin work better in the muscle and fat and also reduce glucose production in the liver. Thiazolidinediones activate PPARs (peroxisome proliferator-activated receptors), specifically PPARγ, leading to a number of effects including lowering insulin resistance. Approved members include troglitazone, rosiglitazone and pioglitazone, although troglitazone was pulled from the market for causing drug-induced hepatitis. Other TZDs include MCC-555, rivoglitazone, and ciglitazon. In some patients, TZDs cause water retention which may lead to edema and heart failure. A related class of drugs with potential to treat symptoms of metabolic disease includes "dual," "balanced" or "pan" PPAR agonists. These include aleglitazar, muraglitazar and tesaglitazar.

Sitagliptin, sold by Merck under the trade name Januvia™, is the first approved drug of a class of compounds that inhibit dipeptidyl peptidase IV (DPP4). These drugs can increase blood levels of incretin hormones, which can further increase insulin secretion, reduce glucagon secretion and have other less well characterized effects. However, sitagliptin and other DPP4 inhibitors may also influence the tissue levels of other hormones and peptides, and the long-term consequences of this broader effect have not been fully investigated. In addition to sitagliptin, a number of DPP4 inhibitors have been developed, including vildagliptin, saxagliptin, linagliptin and alogliptin.

Alpha-glucosidase inhibitors include acarbose, meglitol and voglibose. These drugs do not directly effect insulin secretion of sensitivity. Rather, they inhibit the breakdown of starches and some sugars, thereby helping to maintain lower blood glucose levels after a meal. They are taken with a meal. Side effects include gas, diarrhea and weight gain.

Two other injectable drugs have been approved for Type II diabetes. The first, pramlintide, is a synthetic form of the hormone amylin. Amylin is secreted from beta cells along with insulin, and interacts with insulin to help maintain blood glucose levels. The second approved drug, exanatide, is an agonist of the incretin glucagon-like peptide-1 (GLP-1). Incretins are a group of hormones that increase insulin secretion in response to food intake. Incretins include GLP-1 and gastric inhibitory peptide ("GIP"). GLP-1 stimulates insulin secretion but is rapidly degraded by DPP4. Exanatide stimulates insulin secretion only in the presence of high glucose, but is not orally available and must be injected. Similar drugs in development include liraglutide, a GLP-1 analog, albiglutide, and taspoglatide.

The above drugs are often taken in combination. For example, metformin and a sulfonylurea may be used together.

Despite the currently available treatments, the incidence of diabetes is rising and has reached epidemic proportions. There is a continued need for improved treatments. In some embodiments, the present invention provides methods for treatment of diabetes using an oxidative agent, including but not limited to chlorite and chlorite-containing agents. In some embodiments, the present invention provides methods for treatment of diabetes using an immunomodulatory agent, including but not limited to immunosuppressants.

IX. Kawasaki Disease

In some embodiments, the present invention provides a method of treating Kawasaki disease comprising administering an effective amount of an oxidative agent, including but not limited to chlorite and chlorite-containing agents. In some embodiments, the present invention provides a method of treating Kawasaki disease comprising administering an effective amount of an immunomodulatory agent, including but not limited to immunosuppressive agent. In some embodiments, an oxidative agent and an immunomodulatory agent are used together for combination therapy to treat Kawasaki disease.

Kawasaki disease (also known as lymph node syndrome, mucocutancous node disease, infantile polyarteritis and Kawasaki syndrome) is an inflammation (vasculitis) of the middle-sized arteries. It affects many organs, including the skin, mucous membranes, lymph nodes, and blood vessel walls, but the most serious effect is on the heart where it can cause severe aneurysmal dilations. There is often a pre-existing viral infection that may play some role in pathogenesis. The conjunctival and oral mucosa, along with the epidermis (skin), become erythmatous (red and inflamed). Edema is often seen in the hands and feet and the cervical lymph nodes are often enlarged.

Like other autoimmune diseases, the cause of Kawasaki disease is presumably the interaction of genetic and environmental factors, possibly including an infection. The specific cause is unknown, but current theories center primarily on immunological causes for the disease. An association has been identified with a SNP in the ITPKC gene, which codes an enzyme that negatively regulates T-cell activation (Onouchi Y, Gunji T, Burns J C, et al. 2008 *Nat. Genet.* 40 (1): 35-42). The HLA-B51 serotype has been found to be associated with endemic instances of the disease.

Intravenous immunoglobulin (IVIG) is the standard treatment for Kawasaki disease (Oates-Whitehead R M, et al. (2003) *Cochrane Database Syst Rev* (4)) and is administered in high doses with marked improvement usually noted within 24 hours. Salicylate therapy, particularly aspirin, remains an important part of the treatment but salicylates alone are not as effective as Intravenous immunoglobulin. Corticosteroids have also been used, especially when other treatments fail or symptoms recur.

In the acute phase of the Kawasaki disease, an expansion of the CD14+ CD16+ monocytes has been described (Nakatani K, et al., 1999 Clin. Exp. Immunol, 117, 418-422). In some embodiments, the present invention provides a method of treating Kawasaki disease by modulating macrophage accumulation or activation with an oxidative agent, including but not limited to chlorite and chlorite-containing agents. In some embodiments, the present invention provides a method of treating Kawasaki disease by modulating macrophage accumulation or activation with an immunomodulatory agent, including but not limited to immunosuppressive agent. In some embodiments, the macrophage activation is reduced or inhibited.

X. Asthma

In some embodiments, the present invention provides a method of treating asthma comprising administering an effective amount of an oxidative agent, including but not limited to chlorite and chlorite-containing agents. In some embodiments, the present invention provides a method of treating asthma comprising administering an effective amount of an immunomodulatory agent, including but not limited to immunosuppressive agent. In some embodiments, an oxidative agent and an immunomodulatory agent are used together for combination therapy to treat asthma.

Asthma is a chronic inflammation of the lungs in which the airways (bronchi) are reversibly narrowed. During attacks (exacerbations), the smooth muscle cells in the bronchi constrict, and the airways become inflamed and swollen. Attacks can be prevented by avoiding triggering factors and by drug treatment. Drugs are used for acute attacks, commonly inhaled β2-agonists. In more serious cases, drugs are used for long-term prevention, starting with inhaled corticosteroids, and then long-acting β2-agonists if necessary. Leukotriene antagonists are less effective than corticosteroids but have no side effects. Monoclonal antibodies such as mepolizumab and omalizumab are sometimes effective. Prognosis is good with treatment. Symptomatic control of episodes of wheezing and shortness of breath is generally achieved with fast-acting bronchodilators. Relievers include but are not limited to short-acting, selective beta$_2$-adrenoceptor agonists, such as salbutamol, levalbuterol, terbutaline and bitolterol. Older, less selective adrenergic agonists, such as inhaled epinephrine and ephedrine tablets, have also been used. Anticholinergic medications, such as ipratropium bromide may be used instead. Inhaled glucocorticoids are usually considered preventive medications while oral glucocorticoids are often used to supplement treatment of a severe attack. Long-acting bronchodilators (LABD) are similar in structure to short-acting selective beta$_2$-adrenoceptor agonists, but have much longer side chains resulting in a 12-hour effect, and are used to give a smoothed symptomatic relief. Currently available long-acting beta$_2$-adrenoceptor agonists include salmeterol, formoterol, bambuterol, and sustained-release oral albuterol. Combinations of inhaled steroids and long-acting bronchodilators are becoming more widespread; the most common combination currently in use is fluticasone/salmeterol. Another combination is budesonide/formoterol which is commercially known as Symbicort.

Expansion of the CD14+ CD16+ monocytes has been shown in asthma (Rivier A et al, Clin. Exp. Immunol, 100, 314-318). The alveolar macrophage is the predominant immune effector cell resident in the alveolar spaces and conducting airways, and it is responsible for activating inflammatory responses sufficient to eliminate the interlopers (Hocking, W., and D. Golde. 1979. *N. Engl. J. Med.* 301:580-587, 639-644). Alveolar macrophage may exert anti-asthmatic effects (see *American Journal of Respiratory Cell and Molecular Biology*. Vol. 31, pp. 3-7, 2004).

In some embodiments, the present invention provides a method of treating asthma by modulating macrophage accumulation or activation with an oxidative agent, including but not limited to chlorite and chlorite-containing agents. In some embodiments, the present invention provides a method of treating asthma by modulating macrophage accumulation or activation with an immunomodulatory agent. In one example, the macrophage is alveolar macrophage. In some embodiments, the alveolar macrophages are activated for the treatment of asthma.

XI. Hemophagocytic Lymphohistiocytosis

In some embodiments, the present invention provides a method of treating hemophagocytic lymphohistiocytosis comprising administering an effective amount of an oxidative agent, including but not limited to chlorite and chlorite-containing agents. In some embodiments, the present invention provides a method of treating hemophagocytic lymphohistiocytosis comprising administering an effective amount of an immunomodulatory agent, including but not limited to immunosuppressive agents. In some embodiments, an oxidative agent and an immunomodulatory agent are used together for combination therapy to treat hemophagocytic lymphohistiocytosis.

Hemophagocytic lymphohistiocytosis, abbreviated HLH and also known as hemophagocytic syndrome, is an uncommon hematologic disorder that, typically, clinically manifests as fever, splenomegaly and jaundice, with laboratory findings of lymphocytosis and histiocytosis, and has the pathologic finding of hemophagocytosis. HLH can arise in a number of settings and is thought to arise from T-cell dysregulation. HLH comprises familial (primary) hemophagocytic lymphohistiocytosis (FHL) and secondary HLH (SHLH). FHL, an autosomal recessive disorder, is associated with defective triggering of apoptosis and reduced cytotoxic activity, resulting in a widespread accumulation of T lymphocytes and activated macrophages. HLH also shows expansions of CD14+ CD16+ monocytes (Emminger W et al, Eur J. Immunol. 31, 1716-1719). In terms of treatment, etoposide, cyclosporin, and methotrexate are among the medications that have been proposed (Henter J I, et al. 2002 *Blood* 100 (7): 2367-2373). Use of the CHOP protocol has been described.

In some embodiments, the present invention provides a method of treating hemophagocytic lymphohistiocytosis by modulating macrophage accumulation or activation with an oxidative agent, including but not limited to chlorite and chlorite-containing agents. In some embodiments, the present invention provides a method of treating hemophagocytic lymphohistiocytosis by modulating macrophage accumulation or activation with an immunomodulatory agent, including but not limited to immunosuppressive agents. In some embodiments, the macrophage activation is reduced or inhibited.

XII. Sarcoidosis

In some embodiments, the present invention provides a method of treating sarcoidosis comprising administering an effective amount of an oxidative agent, including but not limited to chlorite and chlorite-containing agents. In some embodiments, the present invention provides a method of treating sarcoidosis comprising administering an effective amount of an immunomodulatory agent, including but not limited to immunosuppressive agents. In some embodiments, an oxidative agent and an immunomodulatory agent are used together for combination therapy to treat sarcoidosis.

Sarcoidosis, also called sarcoid or Besnier-Boeck disease, is a multisystem disorder characterized by non-caseating granulomas (small inflammatory nodules). Virtually any organ can be affected; however, granulomas most often appear in the lungs or the lymph nodes. Sarcoidosis has a paradoxical effect on inflammatory processes; it is characterized by increased macrophage and CD4 helper T-cell activation resulting in accelerated inflammation, however, immune responses to antigen challenges such as tuberculin are suppressed. This paradoxic state of simultaneous hyper- and hypo-activity is suggestive of a state of anergy. The anergy may also be responsible for the increased risk of infections and cancer. It appears that regulatory T-lymphocytes in the periphery of sarcoid granulomas suppress IL-2 secretion which is hypothesized to cause the state of anergy by preventing antigen-specific memory responses (Kettritz R, et al. 2006 *Nephrol. Dial. Transplant.* 21 (10): 2690-4). While it is widely believed that TNF-alpha plays an important role in the formation of granulomas it was observed that sarcoidosis can be triggered by treatment with the TNF-alpha antagonist etanercept (Verschueren K, et al. 2007 *Clin. Rheumatol.* 26 (11): 1969-71).

Sarcoidosis frequently causes a dysregulation of vitamin D production with an increase in extrarenal production (Barbour G L, et al. *N Engl J Med* 1981 305:440-43). Specifically, macrophages inside the granulomas convert vitamin D to its active form, resulting in elevated levels of the hormone 1,25-dihydroxyvitamin D and symptoms of hypervitaminosis D that may include fatigue, lack of strength or energy, irritability, metallic taste, temporary memory loss or cognitive problems. Hypercalcemia (high calcium levels) and its symptoms may be the result of excessive conversion of vitamin D to its active form by epithelioid macrophages.

In some embodiments, the present invention provides a method of treating sarcoidosis by modulating macrophage accumulation or activation with an oxidative agent, including but not limited to chlorite and chlorite-containing agents. In some embodiments, the present invention provides a method of treating sarcoidosis by modulating macrophage accumulation or activation with an immunomodulatory agent, including but not limited to immunosuppressive agents. In some embodiments, the macrophage activation is reduced or inhibited.

XIII. Periodontitis

In some embodiments, the macrophage related disease that can be treated with the method of the present invention is periodontitis. Periodontitis typically refers to a number of inflammatory diseases affecting the periodontium—that is, the tissues that surround and support the teeth. Periodontitis involves progressive loss of the alveolar bone around the teeth, and if left untreated, can lead to the loosening and subsequent loss of teeth. In periodontitis, overgrowth of Gram-negative bacteria and access of lipopolysaccharide (LPS) to circulation may activate macrophages leading to foam cell formation. Macrophages are the important immune cells that are prominent at inflammatory periodontal sites. It has been shown that the infected/inflamed area in periodontitis is associated with macrophage activation via increased serum LPS concentration (Pussinen, P J et al. Arteriosclerosis, Thrombosis, and Vascular Biology 2004; 24:2174-2180). Furthermore, an expansion of CD14+ CD16+ monocytes has been observed in periodontitis (Nagasawa T, et al. *J. Periodontal Res.* 39, 72-78).

In some embodiments, the present invention provides a method of treating periodontitis by modulating macrophage accumulation or activation with an oxidative agent, including but not limited to chlorite and chlorite-containing agents. In some embodiments, the present invention provides a method of treating periodontitis by modulating macrophage accumulation or activation with an immunomodulatory agent, including but not limited to immunosuppressive agents. In some embodiments, the macrophage activation is reduced or inhibited. In some embodiments, an oxidative agent and an immunomodulatory agent are used together for combination therapy to treat periodontitis.

XIV. Whipple's Disease (WD)

In some embodiments, the present invention provides a method of treating Whipple's disease comprising administering an effective amount of an oxidative agent, including but not limited to chlorite or a chlorite-containing compound, or a derivative of any thereof. In some embodiments, the present invention provides a method of treating Whipple's disease comprising administering an effective amount of an immunomodulatory agent, including but not limited to an immunosuppressive agent. In some embodiments, an oxidative agent and an immunomodulatory agent are used together for combination therapy to treat Whipple's disease.

Whipple's disease is a rare, systemic infectious disease caused by the bacterium *Tropheryma whipplei* (Puéchal X (2002). *Joint Bone Spine* 69 (2): 133-40). Diagnosis is made by intestinal biopsy, which reveals presence of the organism as Periodic acid-Schiff (PAS)-positive macrophage inclusions. Intestinal macrophages can induce an effective innate response and they restrict inflammation via anergy. During WD, the small intestinal mucosa of most patients is characterized by a loss of microvilli and the infiltration of large foamy macrophages, which are filled with PAS-positive material. These macrophages contained numerous intracytoplasmic PAS-positive granules. A model has been proposed that *T. whipplei* organisms are engulfed by resident intestinal macrophages, which then shift toward the M2/alternatively activated phenotype. They produce high levels of CCL18, IL-10, and TYRO binding protein (DAP12), which may attract other macrophages and naive T cells and orient the local immune response toward a Th2 response. Newly recruited macrophages engulf bacteria and produce IL-16 and IL-1β and undergo apoptosis. *T. whipplei* infection can then spread gradually (Desnues B. et al. Clin Vaccine Immunol. 2006 February; 13(2): 170-178).

In some embodiments, the present invention provides a method of treating Whipple's disease by modulating macrophage activation with an oxidative agent, including but not limited to chlorite and chlorite-containing agents. In some embodiments, the present invention provides a method of treating Whipple's disease by modulating macrophage activation with an immunomodulatory agent, including but not limited to immunosuppressive agents. In some embodiments, the macrophage is intestinal macrophage.

XV. Pulmonary Alveolar Proteinosis

In some embodiments, the present invention provides a method of treating pulmonary alveolar proteinosis comprising administering an effective amount of an oxidative agent, including but not limited to chlorite and chlorite-containing agents. In some embodiments, the present invention provides a method of treating pulmonary alveolar proteinosis comprising administering an effective amount of an immunomodulatory agent, including but not limited to immunosuppressive agents. In some embodiments, an oxidative agent and an immunomodulatory agent are used together for combination therapy to treat pulmonary alveolar proteinosis.

Pulmonary alveolar proteinosis (PAP) is a rare lung disease in which abnormal accumulation of surfactant occurs within the alveoli, interfering with gas exchange. PAP can occur in a primary form or secondarily in the settings of malignancy (especially in myeloid leukemia), pulmonary infection, or environmental exposure to dusts or chemicals. Lung macrophages obtained by segmental lavage from patients with pulmonary alveolar proteinosis have been shown to exhibit morphologic abnormalities including excessive lipid accumulation and giant secondary lysosome formation. These cells survive poorly in tissue culture, show impaired chemotactic activity, and have decreased adhesiveness to glass. They phagocytize normally but have substantially decreased capacity to kill ingested *Candida pseudotropicalis*. Previous studies suggest that the lung macrophage in alveolar proteinosis is a defective cell as a consequence of an abnormal pulmonary environment (Golde D W et al. *Annals of Internal Medicine* 1976 85:304-309).

In some embodiments, the present invention provides a method of treating pulmonary alveolar proteinosis by modulating macrophage activation with an oxidative agent, including but not limited to chlorite and chlorite-containing agents. In some embodiments, the present invention provides a method of treating pulmonary alveolar proteinosis comprising administering an effective amount of an immunomodulatory agent, including but not limited to immunosuppressive agents.

XVI. Macrophage-Related Pulmonary Diseases

In some embodiments, the present invention provides a method of treating macrophage-related pulmonary diseases comprising administering an effective amount of an oxidative agent, including but not limited to chlorite and chlorite-containing agents. In some embodiments, the present invention provides a method of treating macrophage-related pulmonary diseases comprising administering an effective amount of an immunomodulatory agent, including but not limited to immunosuppressive agents. In some embodiments, an oxidative agent and an immunomodulatory agent are used together for combination therapy to treat macrophage-related pulmonary diseases.

Macrophage-related pulmonary diseases are a heterogeneous group of disorders characterized by macrophage accumulation or activation. These conditions include without limitation smoking-related interstitial lung diseases, metabolic disorders such as Niemann-Pick or Gaucher's disease, and rare primary lung tumors. High-resolution computed tomography abnormalities include pulmonary ground-glass opacification secondary to infiltration by macrophages, centrilobular nodules or interlobular septal thickening reflecting peribronchiolar or septal macrophage accumulation, respectively, emphysema caused by macrophage dysfunction, and honeycombing following macrophage-related lung matrix remodeling.

Niemann-Pick disease, also known as sphingomyelin lipidosis, comprises a group of disorders characterized by foam cell infiltration of the reticuloendothelial system. In the classic infantile type A variant, a missense mutation causes complete deficiency of sphingomyelinase. Sphingomyelin is a component of cell membrane including the organellar membrane and so the enzyme deficiency blocks degradation of lipid, resulting in the accumulation of sphingomyclin within lysosomes in the macrophage-monocyte phagocyte system. Histology demonstrates lipid laden macrophages in the marrow, as well as "sea-blue histiocytes" on pathology. Numerous small vacuoles of relatively uniform size are created, imparting a foamness to the cytoplasm. Foam cells in Niemann-Pick become engorged with sphingomyelin and, to a lesser extent, other membrane lipids including cholesterol. Niemann-Pick is typically caused by inactivation of the enzyme sphingomyelinase in Type A and B disease, with 27-fold more residual enzyme activity in Type B. Mutations in the sphingomyelin phosphodiesterase 1, acid lysosomal (acid sphingomyelinase), also known as SMPD1 gene, cause Niemann-Pick disease types A and B, and mutations in NPC1 and NPC2 cause Niemann-Pick disease, type C (NPC). NPC1 gene encodes a putative integral membrane protein containing sequence motifs consistent with a role in intracellular transport of cholesterol to post-lysosomal destinations.

Gaucher's disease is one of the most common lysosomal storage diseases. It is caused by a hereditary deficiency of the enzyme glucocerebrosidase (also known as acid β-glucosidase). The enzyme acts on a fatty substance glucocerebroside (also known as glucosylceramide, GlcCer). Glucocerebrosidase normally catalyzes the hydrolysis of glucocerebroside to glucose and ceramide. When the enzyme is defective, glucocerebroside accumulates, particularly in cells of the mononuclear cell lineage, e.g., macrophages. Fatty material can collect in the spleen, liver, kidneys, lungs, brain and bone marrow. The macrophages that clear these cells are unable to eliminate the waste product, which accumulates in fibrils, and turn into Gaucher cells, which appear on light microscopy to resemble crumpled-up paper. Diagnosis can be implied by biochemical abnormalities such as high alkaline phosphatase, angiotensin-converting enzyme (ACE) and immunoglobulin levels, or by cell analysis showing "crinkled paper" cytoplasm and glycolipid-laden macrophages.

In some embodiments, the present invention provides a method of treating macrophage-related pulmonary diseases, including but not limited to Niemann-Pick disease and Gaucher's disease, by modulating macrophage accumulation or activation with an oxidative agent, including but not limited to chlorite and chlorite-containing agents. In some embodiments, the present invention provides a method of treating macrophage-related pulmonary diseases, including but not limited to Niemann-Pick disease and Gaucher's disease, by modulating macrophage accumulation or activation with an immunomodulatory agent, including but not limited to immunosuppressive agents.

XVII. Leishmaniasis

In some embodiments, the present invention provides a method of treating Leishmaniasis by modulating macrophage activation or function with an oxidative agent, including but not limited to chlorite and chlorite-containing agents. In some embodiments, the present invention provides a method of treating Leishmaniasis by modulating macrophage activation or function with an immunomodulatory agent, including but not limited to immunosuppressive agents. In some embodiments, an oxidative agent and an immunomodulatory agent are used together for combination therapy to treat Leishmaniasis.

Leishmaniasis is a disease caused by protozoan parasites that belong to the genus *Leishmania*. Most forms of the disease are transmissible only from animals (zoonosis), but some can be spread between humans. Leishmaniasis is transmitted by the bite of female phlebotomine sandflies. The sandflies inject the infective stage, metacyclic promastigotes, during blood meals. Metacyclic promastigotes that reach the puncture wound are phagocytized by macrophages and transform into amastigotes. Amastigotes multiply in infected cells and affect different tissues, depending in part on which *Leishmania* species is involved. These differing tissue specificities cause the differing clinical manifestations of the various forms of leishmaniasis. Sandflies become infected during blood meals on an infected host when they ingest macrophages infected with amastigotes. In the sandfly's midgut, the parasites differentiate into promastigotes, which multiply, differentiate into metacyclic promastigotes and migrate to the proboscis. Amastigotes are seen with monocytes or, less commonly in neutrophil in peripheral blood and in macrophages in aspirates. In terms of treatment, one study has reported that the intracellular growth of *Leishmania* parasites was controlled by nelfinavir and ritonavir in a human monocyte cell line and also in human primary monocyte-derived macrophages (Trudel N. et al. (2008) *Journal of Infectious Diseases* 198 (9): 1292-1299).

In some embodiments, the present invention provides a method of treating Leishmaniasis by modulating macrophage activation or function with an oxidative agent, including but not limited to chlorite and chlorite-containing agents. In some embodiments, the present invention provides a method of treating Leishmaniasis by modulating macrophage activation or function with an immunomodulatory agent, including but not limited to immunosuppressive agents.

XVIII. Obesity

In some embodiments, the present invention provides a method of treating obesity-related complications comprising administering an effective amount of an oxidative agent to modulate macrophage accumulation or activation. The oxidative agents include but are not limited to chlorite and chlorite-containing compounds. In some embodiments, the present invention provides a method of treating obesity-related complications comprising administering an effective amount of an immunomodulatory agent to modulate macrophage accumulation or activation. In some embodiments, an oxidative agent and an immunomodulatory agent are used together for combination therapy to treat obesity-related complications.

Obesity alters adipose tissue metabolic and endocrine function and leads to an increased release of fatty acids, hormones, and proinflammatory molecules that contribute to obesity associated complications. It has been demonstrated that obesity is associated with increased macrophage infiltration into adipose tissue and these adipose tissue macrophages participate in inflammatory pathways that are activated in adipose tissues of obese individuals. (Stuart P. Weisberg et al. *Clin. Invest.* 112(12): 1796-1808).

XIX. Hemodialysis

In some embodiments, the present invention provides a method of treating or preventing post-hemodialysis inflammation comprising administering an effective amount of an oxidative agent to modulate macrophage accumulation or activation. The oxidative agents include but are not limited to chlorite and chlorite-containing compounds. In some embodiments, the present invention provides a method of treating or preventing post-hemodialysis inflammation comprising administering an effective amount of an immunomodulatory agent to modulate macrophage accumulation or activation. In some embodiments, an oxidative agent and an immunomodulatory agent are used together for combination therapy to treat post-hemodialysis inflammation.

Hemodialysis and extracorporal cardiopulmonary bypass systems are based on direct contact of patient blood with artificial membranes to allow for clearance of toxic metabolites and for gas exchange, respectively. Exposure of leukocytes to such membrane can induce an inflammatory response with increased cytokine production. An increased number of CD14+ CD16+ monocytes in hemodialysis patients have been observed (Saionji K, 2001 *Acta Haematol* 105, 21-26). Adhesion of such monocytes to the membrane and cytokine release by these monocytes may contribute to the post-hemodialysis inflammatory syndrome (Caglar K, et al. *Kidney Int.* 62, 1408-1416). In some embodiments, the oxidative agent, including but not limited to chlorite and chlorite-containing agents, is administered to a subject to treat or prevent hemodialysis related inflammations by modulating macrophage adhesion and activation. In some embodiments, the immunomodulatory agent, including but not limited to immunosuppressive agents, is administered to a subject to treat or prevent hemodialysis related inflammations by modulating macrophage adhesion and activation.

XX. Microbial Infection

In some embodiments, the present invention provides a method of treating microbial infection comprising administering an effective amount of an oxidative agent to modulate macrophage activation. In some embodiments, the present invention provides a method of treating microbial infection comprising administering an effective amount of an immunomodulatory agent to modulate macrophage activation. In some embodiments, an oxidative agent and an immunomodulatory agent are used together for combination therapy to treat microbial infection.

Macrophages are the resident immune cells of the lung, sensing bacteria and initiating subsequent host responses. Following phagocytosis, macrophages recruit activated inflammatory cells to the site of infection, as well as processing and presenting bacterial antigens, thereby linking innate and adaptive immunity Macrophages play an important part in the host defense against infection because they are capable of phagocytosing pathogens and their Fey receptors recognize antibody-coated bacteria. Natural killer cell activation also primes macrophages to clear bacterial infection. Furthermore, pronounced increases of CD14+ CD16+ monocytes have been observed in patients with a variety of bacterial infections including bacterial sepsis, bacteremia, neonatal sepsis, erysipelas, a skin infection, and hemolytic uremic syndrome.

In some embodiments, the present invention provides a method of treating microbial infection by modulating macrophage activation or function with an oxidative agent, including but not limited to chlorite and chlorite-containing agents. In some embodiments, the present invention provides a method of treating microbial infection by modulating macrophage activation or function with an immunomodulatory agent, including but not limited to immunosuppressive agents.

XXI. HIV Infection

In some embodiments, the present invention provides a method of treating HIV infection comprising administering an effective amount of an oxidative agent, including but not limited to chlorite and chlorite-containing agents, to modulate macrophage activation. In some embodiments, the present invention provides a method of treating HIV infection comprising administering an effective amount of an immunomodulatory agent, including but not limited to immunosuppressive agents, to modulate macrophage activation. In some embodiments, an oxidative agent and an immunomodulatory agent are used together for combination therapy to treat HIV infection.

Many viruses have been shown to modulate emerging immune responses by infecting monocyte-macrophages. For example, monocytes have been demonstrated to be productively infected by human immunodeficiency virus (HIV) in vivo (Lambotte O, et al. J. Acquir. Immune Defic. Syndr. 23, 114-119). The innate immune functions of monocyte-macrophages, such as recruitment, differentiation and chemokine secretion or activation of adaptive responses through cytokine secretion, may alter the capacity of HIV-1 to infect and replicate in macrophages. In addition to the central role of macrophages in contributing to the immunopathology leading to AIDS, macrophage infection in the CNS is directly associated with viral-induced neuropathology. HIV-infected macrophages induce a pro-inflammatory response when interacting with endothelial cells (Pereira, C. F., et al. (2000) J. Leukoc. Biol. 68, 423-428) and induce apoptosis in bystander astrocytes (Aquaro, S., et al. (2000) J. Leukoc. Biol. 68, 429-435).

Results from clinical and non-clinical studies suggest that the chlorite-containing agent WF10 may strengthen the patient's native immunity against a variety of opportunistic infections and malignancies, and inhibit the adverse effects of inflammatory cytokines, which are stimulated as a result of HIV infection. See McGrath et al., Development of WF10, a novel macrophage-regulating agent, *Curr Opin Investig Drugs,* 3(3):365-73 (March 2002). Despite stable antiretroviral therapy, patients with late-stage HIV infection are less likely to respond to new antiretroviral drugs and, thus, have few other treatment options. These patients progress with diseases that are normally controlled by proper macrophage function, e.g., opportunistic infections such as cytomegalovirus (CMV) and Epstein-Barr virus (EBV). A small, double-blind, placebo-controlled trial has indicated the potential clinical benefit of WF10 on HIV infection. The rate of OIs and hospitalizations was significantly lower in the WF10 group than in the placebo group and long-term follow-up suggested a survival benefit to WF10-treated patients with HIV infection.

Regulation of macrophage function with oxidative agents may provide a treatment option that is not dependent upon inhibition of virus replication. Administered in conjunction with HAART, oxidative agents, including but not limited to chlorite or chlorite-containing agents, can enhance treatment effectiveness in the management of HIV disease by restoring immune function through regulation of macrophage function to downregulate inappropriate T-cell activation. Immunomodulatory agents can be used to provide similar effects. In some embodiments, oxidative and immunomodulatory agents are used together to enhance treatment effectiveness in HIV. On the basis of the balanced macrophage activation model of human disease, over time, such oxidative agents could partially restore normal macrophage function to even advanced AIDS patients. Clinical manifestations of poor macrophage function, such as pneumocystis pneumonia and mycobacterial infections normally cleared by phagocytosis should decrease, normal macrophage activation of appropriate T-cell function, although limited, may prevent recurrence of viral diseases (such as EBV lymphoma or CMV retinitis), and anti-inflammatory activity may decrease the frequency of AIDS-related dementia and wasting syndrome. Considering that macrophages are longlived cells with defined long-term baseline functional characteristics, oxidative agent-mediated re-establishment of normal baseline function may persist long after the actual period of drug administration.

In some embodiments, an oxidative agent, including but not limited to chlorite or chlorite-containing agents, is administered in a subject to treat microbial infections including bacterial infections and viral infections by modulating macrophage activation or function. In some embodiments, an immunomodulatory agent, including immunostimulating and immunosuppressive agents, is administered in a subject to treat microbial infections including bacterial infections and viral infections by modulating macrophage activation or function. In some embodiments, the viral infection comprises HIV. In some embodiments, the macrophage activation is enhanced. In some embodiments, the macrophage activation is inhibited.

XXII. Cancer

In some embodiments, the present invention provides a method of treating cancer comprising administering an effective amount of an oxidative agent, including but not limited to chlorite or chlorite-containing agents, to modulate macrophage activation. In some embodiments, the present invention provides a method of treating cancer comprising administering an effective amount of an immunomodulatory agent to modulate macrophage activation. In some embodiments, an oxidative agent and an immunomodulatory agent are used together for combination therapy to treat cancer.

Cancer (malignant neoplasm) is a class of diseases in which a group of cells display uncontrolled growth, invasion, and sometimes metastasis to other locations in the body via lymph or blood. These three malignant properties of cancers differentiate them from benign tumors, which are self-limited, and do not invade or metastasize.

The role of macrophages in tumor growth and development is complex and multifaceted. Although there is limited evidence that tumor-associated macrophages (TAMs) can be directly tumoricidal and stimulate the anti-tumor activity of T cells, there is contrasting evidence that tumor cells are able to block or evade the activity of TAMs at the tumor site. In some cases, tumor-derived molecules even redirect TAM activities to promote tumor survival and growth. Evidence has emerged for a symbiotic relationship between tumor cells and TAMs, in which tumor cells attract TAMs and sustain their survival, with TAMs then responding to microenvironmental factors in tumors such as hypoxia by producing important mitogens as well as various growth factors and enzymes that stimulate tumor angiogenesis.

Macrophages are generally not tumoricidal for tumor cells unless activated, for example, by antibodies or classic macrophages stimulants such as IFN-γ or lipopolysaccharide LPS. Once activated, direct cytotoxicity is exerted towards tumor cells, or indirect cytotoxicity is exerted via the secretion of factors that stimulate the anti-tumor functions of other cell types. Direct cytotoxicity can be further divided into macrophage-mediated tumor cytotoxicity and antibody-dependent cellular cytotoxicity. IFN-γ produced by T cells and NK cells induces macrophages to release reactive oxygen and nitrogen species that have anti-tumor effects. On the other hand, TAM may also have pro-tumor effects. For example, TAM-derived cytokines may stimulate tumor cells to produce angiogenin, resulting in tumor angiogenesis (Bingle L, et al. Journal of Pathology, 2002 196, 254-265). Moreover, TAM accumulation in hypoxic tumor areas has important implications. Human macrophages have been shown to respond to environmental hypoxia with an increased release of VEGF, which is a key component of the angiogenic process in a variety of human tumors (Ferrara N.

Tumor Angiogenesis, Oxford University Press: Oxford, 1997 185-199; Lewis J S et al. J Leukoc Biol 1999 66:889-900).

Given that tumor cells attract macrophages and sustain their survival and TAMs produce a myriad of factors to promote tumor growth and angiogenesis, activated or genetically modified macrophages may be used to restrain tumor growth. Moreover, macrophage products such as cytokines with anti-tumor effects may have utility in the treatment of cancer. In some embodiments, an oxidative agent such as chlorite is administered to a subject to treat cancer by modulating macrophage activation or function. In some embodiments, an immunomodulatory agent is administered to a subject to treat cancer by modulating macrophage activation or function.

The types of cancer that can be treated using the methods of the present invention include but are not limited to adrenal cortical cancer, anal cancer, aplastic anemia, bile duct cancer, bladder cancer, bone cancer, bone metastasis, central nervous system (CNS) cancers, peripheral nervous system (PNS) cancers, breast cancer, Castleman's Disease, cervical cancer, childhood Non-Hodgkin's lymphoma, colon and rectum cancer, endometrial cancer, esophagus cancer, Ewing's family of tumors (e.g., Ewing's sarcoma), eye cancer, gallbladder cancer, gastrointestinal carcinoid tumors, gastrointestinal stromal tumors, gestational trophoblastic disease, hairy cell leukemia, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, thyroid cancer, uterine cancer (e.g., uterine sarcoma), vaginal cancer, vulvar cancer, and Waldenstrom's macroglobulinemia.

In some embodiments, the cancer comprises Acute Lymphoblastic Leukemia. In other embodiments, the cancer comprises Acute Myeloid Leukemia. In other embodiments, the cancer comprises Adrenocortical Carcinoma. In other embodiments, the cancer comprises an AIDS-Related Cancer. In other embodiments, the cancer comprises AIDS-Related Lymphoma. In other embodiments, the cancer comprises Anal Cancer. In other embodiments, the cancer comprises Appendix Cancer. In other embodiments, the cancer comprises Childhood Cerebellar Astrocytoma. In other embodiments, the cancer comprises Childhood Cerebral Astrocytoma. In other embodiments, the cancer comprises a Central Nervous System Atypical Teratoid/Rhabdoid Tumor. In other embodiments, the cancer comprises Basal Cell Carcinoma, or other Skin Cancer(Nonmelanoma). In other embodiments, the cancer comprises Extrahepatic Bile Duct Cancer. In other embodiments, the cancer comprises Bladder Cancer. In other embodiments, the cancer comprises Bone Cancer, such as Osteosarcoma or Malignant Fibrous Histiocytoma. In other embodiments, the cancer comprises Brain Stem Glioma. In other embodiments, the cancer comprises an Adult Brain Tumor. In other embodiments, the cancer comprises Brain Tumor, Central Nervous System Atypical Teratoid/Rhabdoid Tumor, Childhood. In other embodiments, the cancer comprises a Brain Tumor comprising Cerebral Astrocytoma/Malignant Glioma. In other embodiments, the cancer comprises a Craniopharyngioma Brain Tumor. In other embodiments, the cancer comprises a Ependymoblastoma Brain Tumor. In other embodiments, the cancer comprises a Ependymoma Brain Tumor. In other embodiments, the cancer comprises a Medulloblastoma Brain Tumor. In other embodiments, the cancer comprises a Medulloepithelioma Brain Tumor. In other embodiments, the cancer comprises Brain Tumors including Pineal Parenchymal Tumors of Intermediate Differentiation. In other embodiments, the cancer comprises Brain Tumors including Supratentorial Primitive Neuroectodermal Tumors and Pineoblastoma. In other embodiments, the cancer comprises a Brain Tumor including Visual Pathway and Hypothalamic Glioma. In other embodiments, the cancer comprises Brain and Spinal Cord Tumors. In other embodiments, the cancer comprises Breast Cancer. In other embodiments, the cancer comprises Bronchial Tumors. In other embodiments, the cancer comprises Burkitt Lymphoma. In other embodiments, the cancer comprises Carcinoid Tumor. In other embodiments, the cancer comprises Gastrointestinal Carcinoid Tumor. In other embodiments, the cancer comprises Carcinoma of Unknown Primary Origin. In other embodiments, the cancer comprises Central Nervous System Atypical Teratoid/Rhabdoid Tumor. In other embodiments, the cancer comprises Central Nervous System Embryonal Tumors. In other embodiments, the cancer comprises Primary Central Nervous System Lymphoma. In other embodiments, the cancer comprises Cerebellar Astrocytoma. In other embodiments, the cancer comprises Cerebral Astrocytoma/Malignant Glioma. In other embodiments, the cancer comprises Cervical Cancer. In other embodiments, the cancer comprises Childhood Cancers. In other embodiments, the cancer comprises Chordoma. In other embodiments, the cancer comprises Chronic Lymphocytic Leukemia. In other embodiments, the cancer comprises Chronic Myelogenous Leukemia. In other embodiments, the cancer comprises Chronic Myeloproliferative Disorders. In other embodiments, the cancer comprises Colon Cancer. In other embodiments, the cancer comprises Colorectal Cancer. In other embodiments, the cancer comprises Craniopharyngioma. In other embodiments, the cancer comprises Cutaneous T-Cell Lymphoma, including Mycosis Fungoides and Sézary Syndrome. In other embodiments, the cancer comprises Central Nervous System Embryonal Tumors. In other embodiments, the cancer comprises Endometrial Cancer. In other embodiments, the cancer comprises Ependymoblastoma. In other embodiments, the cancer comprises Ependymoma. In other embodiments, the cancer comprises Esophageal Cancer. In other embodiments, the cancer comprises the Ewing Family of Tumors. In other embodiments, the cancer comprises Extracranial Germ Cell Tumor. In other embodiments, the cancer comprises Extragonadal Germ Cell Tumor. In other embodiments, the cancer comprises Extrahepatic Bile Duct Cancer. In other embodiments, the cancer comprises Intraocular Melanoma Eye Cancer. In other embodiments, the cancer comprises Retinoblastoma Eye Cancer. In other embodiments, the cancer comprises Gallbladder Cancer. In other embodiments, the cancer comprises Gastric (Stomach) Cancer. In other embodiments, the cancer comprises Gastrointestinal Carcinoid Tumor. In other embodiments, the cancer comprises Gastrointestinal Stromal Tumor (GIST). In other embodiments, the cancer comprises Gastrointestinal Stromal Cell Tumor. In other embodiments, the cancer comprises Extracranial Germ Cell Tumor. in other embodiments, the cancer comprises Extragonadal Germ Cell Tumor. In other embodiments, the cancer comprises Ovarian Germ Cell Tumor. In other embodiments, the cancer comprises Gestational Trophoblastic Tumor. In other embodiments, the cancer comprises Glioma. In other embodiments, the cancer comprises Brain Stem Glioma. In other embodiments, the cancer comprises Cerebral Astrocytoma Glioma. In other embodiments, the cancer comprises Visual Pathway or Hypothalamic Glioma. In other embodiments, the cancer comprises Hairy Cell Leukemia. In other embodiments, the cancer comprises Head and Neck Cancer. In other embodiments, the cancer comprises Hepatocellular (Liver) Cancer. In other embodiments, the cancer comprises Hodgkin Lymphoma. In other embodiments, the cancer comprises Hypopharyngeal Cancer. In other embodiments, the cancer comprises Intraocular Melanoma. In other embodiments, the cancer comprises Islet Cell Tumors (Endocrine Pancreas). In other embodiments, the cancer comprises Kaposi Sarcoma. In other embodiments, the cancer comprises Kidney (Renal Cell) Cancer. In other embodiments, the cancer comprises Laryngeal Cancer. In other embodiments, the cancer comprises Acute Lymphoblastic Leukemia. In other embodiments, the cancer comprises Acute Myeloid Leukemia. In other embodiments, the cancer comprises Chronic Lymphocytic Leukemia. In other embodiments, the cancer comprises Chronic Myelogenous Leukemia. In other embodiments, the cancer comprises Hairy Cell Leukemia. In other embodiments, the cancer comprises Lip Cancer. In other embodiments, the cancer comprises Oral Cavity Cancer. In other embodiments, the cancer comprises Primary Liver Cancer. In other embodiments, the cancer comprises Non-Small Cell Lung Cancer. In other embodiments, the cancer comprises Small Cell Lung Cancer. In other embodiments, the cancer comprises AIDS-Related Lymphoma. In other embodiments, the cancer comprises Burkitt Lymphoma. In other embodiments, the cancer comprises Cutaneous T-Cell Lymphoma. In other embodiments, the cancer comprises Mycosis Fungoides and Sézary Syndrome. In other embodiments, the cancer comprises Hodgkin Lymphoma. In other embodiments, the cancer comprises Non-Hodgkin Lymphoma. In other embodiments, the cancer comprises Primary Central Nervous System Lymphoma. In other embodiments, the cancer comprises Waldenström Macroglobulinemia. In other embodiments, the cancer comprises Malignant Fibrous Histiocytoma of Bone or Osteosarcoma. In other embodiments, the cancer comprises Medulloepithelioma. In other embodiments, the cancer comprises Melanoma. In other embodiments, the cancer comprises Intraocular (Eye) Melanoma. In other embodiments, the cancer comprises Merkel Cell Carcinoma. In other embodiments, the cancer comprises Mesothelioma. In other embodiments, the cancer comprises Metastatic Squamous Neck Cancer with Occult Primary. In other embodiments, the cancer comprises Mouth Cancer. In other embodiments, the cancer comprises Multiple Endocrine Neoplasia Syndrome. In other embodiments, the cancer comprises Multiple Myeloma/Plasma Cell Neoplasm. In other embodiments, the cancer comprises Mycosis Fungoides. In other embodiments, the cancer comprises Myelodysplastic Syndromes. In other embodiments, the cancer comprises Myelodysplastic or Myeloproliferative Diseases. In other embodiments, the cancer comprises Chronic Myelogenous Leukemia. In other embodiments, the cancer comprises Acute Myeloid Leukemia. In other embodiments, the cancer comprises Multiple Myeloma. In other embodiments, the cancer comprises Chronic Myeloproliferative Disorders. In other embodiments, the cancer comprises Nasal Cavity or Paranasal Sinus Cancer. In other embodiments, the cancer comprises Nasopharyngcal Cancer. In other embodiments, the cancer comprises Nasopharyngeal Cancer. In other embodiments, the cancer comprises Neuroblastoma. In other embodiments, the cancer comprises Non-Hodgkin Lymphoma. In other embodiments, the cancer comprises Non-Small Cell Lung Cancer. In other embodiments, the cancer comprises Oral Cancer. In other embodiments, the cancer comprises Oral Cavity Cancer. In other embodiments, the cancer comprises Oropharyngeal Cancer. In other embodiments, the cancer comprises Ostcosarcoma. In other embodiments, the cancer comprises Malignant Fibrous Histiocytoma of Bone. In other embodiments, the cancer comprises Ovarian Cancer. In other embodiments, the cancer comprises Ovarian Epithelial Cancer. In other embodiments, the cancer comprises Ovarian Germ Cell Tumor. In other embodiments, the cancer comprises Ovarian Low Malignant Potential Tumor. In other embodiments, the cancer comprises Pancreatic Cancer. In other embodiments, the cancer comprises Islet Cell Tumor Pancreatic Cancer. In other embodiments, the cancer comprises Papillomatosis. In other embodiments, the cancer comprises Paranasal Sinus Cancer. In other embodiments, the cancer comprises Nasal Cavity Cancer. In other embodiments, the cancer comprises Parathyroid Cancer. In other embodiments, the cancer comprises Penile Cancer. In other embodiments, the cancer comprises Pharyngeal Cancer. In other embodiments, the cancer comprises Pheochromocytoma. In other embodiments, the cancer comprises Pineal Parenchymal Tumors of Intermediate Differentiation. In other embodiments, the cancer comprises Pineoblastoma or Supratentorial Primitive Neuroectodermal Tumors. In other embodiments, the cancer comprises Pituitary Tumor. In other embodiments, the cancer comprises Plasma Cell Neoplasm/Multiple Myeloma. In other embodiments, the cancer comprises Pleuropulmonary Blastoma. In other embodiments, the cancer comprises Primary Central Nervous System Lymphoma. In other embodiments, the cancer comprises Prostate Cancer. In other embodiments, the cancer comprises Rectal Cancer. In other embodiments, the cancer comprises Renal Cell (Kidney) Cancer. In other embodiments, the cancer comprises Renal Pelvis and Ureter, Transitional Cell Cancer. In other embodiments, the cancer comprises Respiratory Tract Carcinoma Involving the NUT Gene on Chromosome 15. In other embodiments, the cancer comprises Retinoblastoma. In other embodiments, the cancer comprises Rhabdomyosarcoma. In other embodiments, the cancer comprises Salivary Gland Cancer. In other embodiments, the cancer comprises Sarcoma of the Ewing Family of Tumors. In other embodiments, the cancer comprises Kaposi Sarcoma. In other embodiments, the cancer comprises Soft Tissue Sarcoma. In other embodiments, the cancer comprises Uterine Sarcoma. In other embodiments, the cancer comprises Sezary Syndrome. In other embodiments, the cancer comprises Nonmelanoma Skin Cancer. In other embodiments, the cancer comprises Melanoma Skin Cancer. In other embodiments, the cancer comprises Merkel Cell Skin Carcinoma. In other embodiments, the cancer comprises Small Cell Lung Cancer. In other embodiments, the cancer comprises Small Intestine Cancer. In other embodiments, the cancer comprises Squamous Cell Carcinoma, e.g., Nonmelanoma Skin Cancer. In other embodiments, the cancer comprises Metastatic Squamous Neck Cancer with Occult Primary. In other embodiments, the cancer comprises Stomach (Gastric) Cancer. In other embodiments, the cancer comprises Supratentorial Primitive Neuroectodermal Tumors. In other embodiments, the cancer comprises Cutaneous T-Cell Lymphoma, e.g., Mycosis Fungoides and Sézary Syndrome. In other embodiments, the cancer comprises Testicular Cancer. In other embodiments, the cancer comprises Throat Cancer. In other embodiments, the cancer comprises Thymoma or Thymic Carcinoma. In other embodiments, the cancer comprises Thyroid Cancer. In other embodiments, the cancer comprises Transitional Cell Cancer of the Renal Pelvis and Ureter. In other embodiments, the cancer comprises Gestational Trophoblastic Tumor. In other embodiments, the cancer comprises a Carcinoma of Unknown Primary Site. In other embodiments, the cancer comprises an Unusual Cancer of Childhood. In other embodiments, the cancer comprises Ureter and Renal Pelvis Transitional Cell Cancer. In other embodiments, the cancer comprises Urethral Cancer. In other embodiments, the cancer comprises Endometrial Uterine Cancer. In other embodiments, the cancer comprises Uterine Sarcoma. In other embodiments, the cancer comprises Vaginal Cancer. In other embodiments, the cancer comprises Visual Pathway and Hypothalamic Glioma. In other embodiments, the cancer comprises Vulvar Cancer. In other embodiments, the cancer comprises Waldenström Macroglobulinemia. In other embodiments, the cancer comprises Wilms Tumor. In other embodiments, the cancer comprises Women's Cancers.

In some embodiments, the present invention provides a method of treating cancer comprising administering an effective amount of an oxidative agent, including but not limited to chlorite or chlorite-containing agents. In some embodiments, the present invention provides a method of treating cancer comprising administering an effective amount of an immunomodulatory agent, including but not limited to immunosuppressive agents. The oxidative agent or immunomodulatory agent of the invention can be used in combination with another anti-cancer therapy, including but not limited to chemotherapy, surgery, radiation therapy (e.g., X ray), gene therapy, immunotherapy, DNA therapy, adjuvant therapy, neoadjuvant therapy, viral therapy, RNA therapy, and nanotherapy.

(a) Breast Cancer

In one embodiment, the present invention provides a method of treating breast cancer comprising administering an effective amount of an oxidative agent to modulate macrophage activation. In one embodiment, the present invention provides a method of treating breast cancer comprising administering an effective amount of an immunomodulatory agent to modulate macrophage activation. In some embodiments, an oxidative agent and an immunomodulatory agent are used together for combination therapy to treat breast cancer.

Macrophages may play an important role in breast cancer development. Research performed with an MMTV-PyMT mouse model of mammary carcinogenesis has revealed a tumor-promoting role for TH2-CD4 T effector cells, suggesting the immune system modulates the early onset of cancer development in specific organs, and confirmed epidemiological studies showing that increased macrophage presence correlates with higher tumor grade and decreased survival (Rochman S. et al. BMC Proceedings 2009, 3(Suppl 5):I1). Eliminating the T effector cells did not regulate primary disease, and also made it more likely that the cancer would metastasize to the lung, behavior that appeared to be regulated by macrophages.

In one embodiment, the present invention provides a method of treating breast cancer comprising administering an effective amount of an oxidative agent, including but not limited to chlorite or chlorite-containing agents. In one embodiment, the present invention provides a method of treating breast cancer comprising administering an effective amount of an immunomodulatory agent, e.g., to modulate the activity of macrophages. The oxidative agent or immunomodulatory agent of the invention can be used in combination with a second anti-breast cancer therapy including but not limited to chemotherapy, surgery, radiation therapy (e.g., X ray), gene therapy, immunotherapy, DNA therapy, adjuvant therapy, neoadjuvant therapy, viral therapy, RNA therapy, and nanotherapy.

(b) Anti-Hyperproliferative Agents

In some embodiments, the present invention provides a method that comprises administering an oxidative agent and/or immunomodulatory agent in combination with one or more other therapeutic agents and/or interventions used for the treatment of cancer or a hyperproliferative disease. The therapeutic agents that can be used in combination with oxidative agent of the present invention for the treatment of cancer or a hyperproliferative disease include but are not limited to the following categories.

(i) Antineoplastic Chemotherapeutic agents

Suitable antineoplastic anti-tumor agents that can be used in the present invention include, but are not limited to, alkylating agents, antimetabolites, natural antineoplastic agents, hormonal antineoplastic agents, angiogenesis inhibitors, differentiating reagents, RNA inhibitors, antibodies or immunotherapeutic agents, gene therapy agents, small molecule enzymatic inhibitors, biological response modifiers, and anti-metastatic agents.

(ii) Alkylating Agents

Alkylating agents are known to act through the alkylation of macromolecules such as the DNA of cancer cells, and are usually strong electrophiles. This activity can disrupt DNA synthesis and cell division. Examples of alkylating reagents suitable for use herein include nitrogen mustards and their analogues and derivatives including, cyclophosphamide, ifosfamide, chlorambucil, estramustine, mechlorethamine hydrochloride, melphalan, and uracil mustard. Other examples of alkylating agents include alkyl sulfonates (e.g., busulfan), nitrosoureas (e.g., carmustine, lomustine, and streptozocin), triazenes (e.g., dacarbazine and temozolomide), ethylenimines/methylmelamines (e.g., altretamine and thiotepa), and methylhydrazine derivatives (e.g., procarbazine). Included in the alkylating agent group are the alkylating-like platinum-containing drugs comprising carboplatin, cisplatin, and oxaliplatin.

(iii) Antimetabolites

Antimetabolic antineoplastic agents structurally resemble natural metabolites, and are involved in normal metabolic processes of cancer cells such as the synthesis of nucleic acids and proteins. They differ enough from the natural metabolites so that they interfere with the metabolic processes of cancer cells. Suitable antimetabolic antineoplastic agents that can be used in the present invention can be classified according to the metabolic process they affect, and can include, but are not limited to, analogues and derivatives of folic acid, pyrimidines, purines, and cytidine. Members of the folic acid group of agents suitable for use herein include, but are not limited to, methotrexate (amethopterin), pemetrexed and their analogues and derivatives. Pyrimidine agents suitable for use herein include, but are not limited to, cytarabine, floxuridine, fluorouracil (5-fluorouracil), capecitabine, gemcitabine, and their analogues and derivatives. Purine agents suitable for use herein include, but are not limited to, mercaptopurine (6-mercaptopurine), pentostatin, thioguanine, cladribine, and their analogues and derivatives. Cytidine agents suitable for use herein include, but are not limited to, cytarabine (cytosine arabinodside), azacitidine (5-azacytidine) and their analogues and derivatives.

(iv) Natural Antineoplastic Agents

Natural antineoplastic agents comprise antimitotic agents, antibiotic antineoplastic agents, camptothecin analogues, and enzymes. Antimitotic agents suitable for use herein include, but are not limited to, vinca alkaloids like vinblastine, vincristine, vindesine, vinorelbine, and their analogues and derivatives. They are derived from the Madagascar periwinkle plant and are usually cell cycle-specific for the M phase, binding to tubulin in the microtubules of cancer cells. Other antimitotic agents suitable for use herein are the podophyllotoxins, which include, but are not limited to etoposide, teniposide, and their analogues and derivatives. These reagents predominantly target the G2 and late S phase of the cell cycle.

Also included among the natural antineoplastic agents are the antibiotic antineoplastic agents. Antibiotic antineoplastic agents are antimicrobial drugs that have anti-tumor properties usually through interacting with cancer cell DNA. Antibiotic antineoplastic agents suitable for use herein include, but are not limited to, belomycin, dactinomycin, doxorubicin, idarubicin, epirubicin, mitomycin, mitoxantrone, pentostatin, plicamycin, and their analogues and derivatives.

The natural antineoplastic agent classification also includes camptothecin analogues and derivatives which are suitable for use herein and include camptothecin, topotecan, and irinotecan. These agents act primarily by targeting the nuclear enzyme topoisomerase I. Another subclass under the natural antineoplastic agents is the enzyme, L-asparaginase and its variants. L-asparaginase acts by depriving some cancer cells of L-asparagine by catalyzing the hydrolysis of circulating asparagine to aspartic acid and ammonia.

(v) Hormonal Antineoplastic Agents

Hormonal antineoplastic agents act predominantly on hormone-dependent cancer cells associated with prostate tissue, breast tissue, endometrial tissue, ovarian tissue, lymphoma, and leukemia. Such tissues may be responsive to and dependent upon such classes of agents as glucocorticoids, progestins, estrogens, and androgens. Both analogues and derivatives that are agonists or antagonists are suitable for use in the present invention to treat tumors. Examples of glucocorticoid agonists/antagonists suitable for use herein are dexamethasone, cortisol, corticosterone, prednisone, mifepristone (RU486), their analogues and derivatives. The progestin agonist/antagonist subclass of agents suitable for use herein includes, but is not limited to, hydroxyprogesterone, medroxyprogesterone, megestrol acetate, mifepristone (RU486), ZK98299, their analogues and derivatives. Examples from the estrogen agonist/antagonist subclass of agents suitable for use herein include, but are not limited to, estrogen, tamoxifen, toremifene, RU58668, SR16234, ZD164384, ZK191703, fulvestrant, their analogues and derivatives. Examples of aromatase inhibitors suitable for use herein, which inhibit estrogen production, include, but are not limited to, androstenedione, formestane, exemestane, aminoglutethimide, anastrozole, letrozole, their analogues and derivatives. Examples from the androgen agonist/antagonist subclass of agents suitable for use herein include, but are not limited to, testosterone, dihydrotestosterone, fluoxymesterone, testolactone, testosterone enanthate, testosterone propionate, gonadotropin-releasing hormone agonists/antagonists (e.g., leuprolide, goserelin, triptorelin, buserelin), diethylstilbestrol, abarelix, cyproterone, flutamide, nilutamide, bicalutamide, their analogues and derivatives.

(vi) Angiogenesis Inhibitors

Angiogenesis inhibitors work by inhibiting the vascularization of tumors. Angiogenesis inhibitors encompass a wide variety of agents including small molecule agents, antibody agents, and agents that target RNA function. Examples of angiogenesis inhibitors suitable for use herein include, but are not limited to, ranibizumab, bevacizumab, SU11248, PTK787, ZK222584, CEP-7055, angiozyme, dalteparin, thalidomide, suramin, CC-5013, combretastatin A4 Phosphate, LY317615, soy isoflavones, AE-941, interferon alpha, PTK787/ZK 222584, ZD6474, EMD 121974, ZD6474, BAY 543-9006, celecoxib, halofuginone hydrobromide, bevacizumab, their analogues, variants, or derivatives.

(vii) Differentiating Agents

Differentiating agents inhibit tumor growth through mechanisms that induce cancer cells to differentiate. One such subclass of these agents suitable for use herein includes, but is not limited to, vitamin A analogues or retinoids, and peroxisome proliferator-activated receptor agonists (PPARs). Retinoids suitable for use herein include, but are not limited to, vitamin A, vitamin A aldehyde (retinal), retinoic acid, fenretinide, 9-cis-retinoid acid, 13-cis-retinoid acid, all-trans-retinoic acid, isotretinoin, tretinoin, retinyl palmitate, their analogues and derivatives. Agonists of PPARs suitable for use herein include, but are not limited to, troglitazone, ciglitazone, tesaglitazar, their analogues and derivatives.

(viii) Antibodies/Immunotherapeutic Agents

Antibody agents bind targets selectively expressed in cancer cells and can either utilize a conjugate to kill the cell associated with the target, or elicit the body's immune response to destroy the cancer cells. Immunotherapeutic agents can either be comprised of polyclonal or monoclonal antibodies. The antibodies may be comprised of non-human animal (e.g., mouse) and human components, or be comprised of entirely human components ("humanized antibodies"). Examples of monoclonal immunotherapeutic agents suitable for use herein include, but are not limited to, rituximab, tosibtumomab, ibritumomab which target the CD-20 protein. Other examples suitable for use herein include trastuzumab, edrecolomab, bevacizumab, cetuximab, carcinoembryonic antigen antibodies, gemtuzumab, alemtuzumab, mapatumumab, panitumumab, EMD 72000, TheraCIM hR3, 2C4, HGS-TR2J, and HGS-ETR2.

(ix) Gene Therapy Agents

Gene therapy agents insert copies of genes into a specific set of a patient's cells, and can target both cancer and non-cancer cells. The goal of gene therapy can be to replace altered genes with functional genes, to stimulate a patient's immune response to cancer, to make cancer cells more sensitive to chemotherapy, to place "suicide" genes into cancer cells, or to inhibit angiogenesis. Genes may be delivered to target cells using viruses, liposomes, or other carriers or vectors. This may be done by injecting the gene-carrier composition into the patient directly, or ex vivo, with infected cells being introduced back into a patient. Such compositions are suitable for use in the present invention.

(x) Nanotherapy

Nanometer-sized particles have novel optical, electronic, and structural properties that are not available from either individual molecules or bulk solids. When linked with tumor-targeting moieties, such as tumor-specific ligands or monoclonal antibodies, these nanoparticles can be used to target cancer-specific receptors, tumor antigens (biomarkers), and tumor vasculatures with high affinity and precision. The formulation and manufacturing process for cancer nanotherapy is disclosed in U.S. Pat. No. 7,179,484, filed Nov. 6, 2003 and entitled "Protein-stabilized liposomal formulations of pharmaceutical agents," and article M. N. Khalid, P. Simard, D. Hoarau, A. Dragomir, J. Leroux, Long Circulating Poly(Ethylene Glycol)Decorated Lipid Nanocapsules Deliver Docetaxel to Solid Tumors, *Pharmaceutical Research,* 23(4), 2006, all of which are herein incorporated by reference in their entireties.

(xi) RNA Therapy

RNA including but not limited to siRNA, shRNA, microRNA may be used to modulate gene expression and treat cancers. Double stranded oligonucleotides are formed by the assembly of two distinct oligonucleotide sequences where the oligonucleotide sequence of one strand is complementary to the oligonucleotide sequence of the second strand; such double stranded oligonucleotides are generally assembled from two separate oligonucleotides (e.g., siRNA), or from a single molecule that folds on itself to form a double stranded structure (e.g., shRNA or short hairpin RNA). These double stranded oligonucleotides known in the art all have a common feature in that each strand of the duplex has a distinct nucleotide sequence, wherein only one nucleotide sequence region (guide sequence or the antisense sequence) has complementarity to a target nucleic acid sequence and the other strand (sense sequence) comprises nucleotide sequence that is homologous to the target nucleic acid sequence.

MicroRNAs (miRNA) are single-stranded RNA molecules, typically of about 21-23 nucleotides in length, which regulate gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression.

Certain RNA inhibiting agents may be utilized to inhibit the expression or translation of messenger RNA ("mRNA") that is associated with a cancer phenotype. Examples of such agents suitable for use herein include, but are not limited to, short interfering RNA ("siRNA"), ribozymes, and antisense oligonucleotides. Specific examples of RNA inhibiting agents suitable for use herein include, but are not limited to, Cand5, Sirna-027, fomivirsen, and angiozyme.

(xii) Small Molecule Enzymatic Inhibitors

Certain small molecule therapeutic agents are able to target the tyrosine kinase enzymatic activity or downstream signal transduction signals of certain cell receptors such as epidermal growth factor receptor ("EGFR") or vascular endothelial growth factor receptor ("VEGFR"). Such targeting by small molecule therapeutics can result in anti-cancer effects. Examples of such agents suitable for use herein include, but are not limited to, imatinib, gefitinib, erlotinib, lapatinib, canertinib, ZD6474, sorafenib (BAY 43-9006), ERB-569, and their analogues and derivatives.

(xiii) Biological Response Modifiers

Certain protein or small molecule agents can be used in anti-cancer therapy through either direct anti-tumor effects or through indirect effects. Examples of direct-acting agents suitable for use herein include, but are not limited to, differentiating reagents such as retinoids and retinoid derivatives. Indirect-acting agents suitable for use herein include, but are not limited to, agents that modify or enhance the immune or other systems such as interferons, interleukins, hematopoietic growth factors (e.g., erythropoietin), and antibodies (monoclonal and polyclonal).

(xiv) Anti-Metastatic Agents

The process whereby cancer cells spread from the site of the original tumor to other locations around the body is termed cancer metastasis. Certain agents have anti-metastatic properties, designed to inhibit the spread of cancer cells. Examples of such agents suitable for use herein include, but are not limited to, marimastat, bevacizumab, trastuzumab, rituximab, erlotinib, MMI-166, GRN163L, hunter-killer peptides, tissue inhibitors of metalloproteinases (TIMPs), their analogues, derivatives and variants.

(xv) Chemopreventative Agents

Certain pharmaceutical agents can be used to prevent initial occurrences of cancer, or to prevent recurrence or metastasis. Examples of chemopreventative agents suitable for use herein include, but are not limited to, tamoxifen, raloxifene, tibolone, bisphosphonate, ibandronate, estrogen receptor modulators, aromatase inhibitors (letrozole, anastrozole), luteinizing hormone-releasing hormone agonists, goserelin, vitamin A, retinal, retinoic acid, fenretinide, 9-cis-retinoid acid, 13-cis-retinoid acid, all-trans-retinoic acid, isotretinoin, tretinoid, vitamin B6, vitamin B12, vitamin C, vitamin D, vitamin E, cyclooxygenase inhibitors, non-steroidal anti-inflammatory drugs (NSAIDs), aspirin, ibuprofen, celecoxib, polyphenols, polyphenol E, green tea extract, folic acid, glucaric acid, interferon-alpha, anethole dithiolethione, zinc, pyridoxine, finasteride, doxazosin, selenium, indole-3-carbinal, alpha-difluoromethylornithine, carotenoids, beta-carotene, lycopene, antioxidants, coenzyme Q10, flavonoids, quercetin, curcumin, catechins, epigallocatechin gallate, N-acetylcysteine, indole-3-carbinol, inositol hexaphosphate, isoflavones, glucanic acid, rosemary, soy, saw palmetto, and calcium. Cancer vaccines are an additional example of chemopreventative agents suitable for use in the present invention. These can be created through immunizing a patient with all or part of a cancer cell type that is targeted by the vaccination process.

(xvi) Side-Effect Limiting Agents

Treatment of macrophage related diseases such as cancer with oxidative or immunomodulatory agents alone or in combination with other therapeutic compounds such as antineoplastic agents may be accompanied by administration of pharmaceutical agents that can alleviate the side effects produced by the antineoplastic agents. Such agents suitable for use herein include, but are not limited to, anti-emetics, anti-mucositis agents, pain management agents, infection control agents, and anti-anemia/anti-thrombocytopenia agents. Examples of anti-emetics suitable for use herein include, but are not limited to, 5-hydroxytryptamine 3 receptor antagonists, metoclopramide, steroids, lorazepam, ondansetron, cannabinoids, their analogues and derivatives. Examples of anti-mucositis agents suitable for use herein include, but are not limited to, palifermin (keratinocyte growth factor), glucagon-like peptide-2, teduglutide, L-glutamine, amifostin, and fibroblast growth factor 20. Examples of pain management agents suitable for use herein include, but are not limited to, opioids, opiates, and non-steroidal anti-inflammatory compounds. Examples of agents used for control of infection suitable for use herein include, but are not limited to, antibacterials such as aminoglycosides, penicillins, cephalosporins, tetracyclines, clindamycin, lincomycin, macrolides, vancomycin, carbapenems, monobactams, fluoroquinolones, sulfonamides, nitrofurantoins, their analogues and derivatives. Examples of agents that can treat anemia or thrombocytopenia associated with chemotherapy suitable for use herein include, but are not limited to, erythropoietin and thrombopoietin.

XXIII. Neurological Diseases

In one embodiment, the present invention provides a method of a neurological disease, such as amyotrophic lateral sclerosis (ALS), Parkinson's disease and Alzheimer's disease, comprising administering to a subject in need thereof an effective amount of a chlorite-containing agent and optionally another therapy for treating the disease. In some embodiments, the chlorite containing agent is TCDO. In one example, the chlorite formulation is WF10.

In one embodiment, the present invention provides a method of treatment of neurological disease characterized by neuroinflammation. Such diseases may include amyotrophic lateral sclerosis (ALS), Parkinson's disease and Alzheimer's disease. Multiple sclerosis (MS) may be excluded. In one embodiment, agents capable of blocking migration as discussed herein such as natalizumab (Tysabri®), fingolimod, or cladribine are used for the treatment of non-MS neuroinflammation. Agents blocking epithelial adhesion and/or chemotaxis as discussed herein are also provided for treatment of non-MS neuroinflammation.

(a) Amyotrophic Lateral Sclerosis (ALS)

In some embodiments, the present invention provides methods for treatment of amyotrophic lateral sclerosis (ALS) comprising administering to a subject in need thereof an effective amount of an oxidative agent (for example, chlorite or a chlorite-containing agent, chloramine-T and hydrates thereof, and/or 1,3-dichloro-5,5-dimethylhydantoin) alone or in combination with another agent used for treating the disease. The complications related to ALS that can be treated with the methods of the present invention include but are not limited to breathing problems, pain, respiratory failure, eating disorders, malnutrition, dehydration, choking, pneumonia, and dementia such as frontotemporal dementia.

Amyotrophic lateral sclerosis is a form of motor neuron disease. ALS, commonly referred to as Lou Gehrig's Disease, or sometimes as Maladie de Charcot, is a progressive, fatal, neurodegenerative disease caused by the degeneration of motor neurons, the nerve cells in the central nervous system that control voluntary muscle movement. The disorder causes muscle weakness and atrophy throughout the body neurodegeneration of the motor neurons in the brain (upper motor neurons) and spinal cord (lower motor neurons). As a result, the neurons cease sending messages to muscles. Unable to function, the muscles gradually weaken, develop fasciculations because of denervation, and eventually atrophy. The patient may ultimately lose the ability to initiate and control all voluntary movement. They can also have difficulty breathing. However, bladder and bowel sphincters and the muscles responsible for eye movement are usually spared. Cognitive function is generally unaffected by ALS except in certain situations such as when ALS is associated with frontotemporal dementia (Phukan J, Pender N P, Hardiman O 2007 *Lancet Neurol* 6 (11): 994-1003). Sensory nerves and the autonomic nervous system, which controls functions such as sweating, generally remain functional.

ALS affects people worldwide of all ages, ethnicity and social classes. The onset of ALS has been linked to several factors, including: a virus; exposure to neurotoxins or heavy metals; DNA defects; immune system abnormalities; occupational factors such as military service and elite sports; and enzyme abnormalities. Surgeries involving the spinal cord have also been thought to play a role in the onset of ALS due to the disruption of nerve fibers. There is a known hereditary factor in familial ALS (FALS); however, there is no known hereditary component in the 90-95% cases diagnosed as sporadic ALS. An inherited genetic defect on chromosome 21 is associated with approximately 20% of familial cases of ALS (Conwit, Robin A. (December 2006). *Journal of the Neurological Sciences* 251 (1-2): 1-2; Al-Chalabi, Ammar; P. Nigel Leigh (August 2000). *Current Opinion in Neurology* 13 (4): 397-405). This mutation is believed to be autosomal dominant. The children of those diagnosed with familial ALS have a higher risk factor for developing the disease; however, those who have close family members diagnosed with sporadic ALS have no greater a risk factor than the general population. Dietary intake of polyunsaturated fatty acids (PUFA) has been shown in several studies to decrease the risk of developing ALS (Veldink J H, et al. April 2007, *J. Neurol. Neurosurg. Psychiatr.* 78 (4): 367-71).

The cause of ALS is not known, however, mutations in the gene that produces the Cu/Zn superoxide dismutase (SOD1) enzyme are associated with some cases (approximately 20%) of familial ALS. This enzyme is an antioxidant that protects the body from damage caused by superoxide, a toxic free radical. Free radicals can accumulate and cause damage to DNA and proteins within cells. Studies involving transgenic mice have yielded several theories about the role of SOD1 in mutant SOD1 familial amyotrophic lateral sclerosis. Mice lacking the SOD1 gene entirely do not customarily develop ALS, although they do exhibit an acceleration of age-related muscle atrophy (sarcopenia) and a shortened lifespan. This indicates that the toxic properties of the mutant SOD1 are a result of a gain in function rather than a loss of normal function. In addition, aggregation of proteins has been found to be a common pathological feature of both familial and sporadic ALS. In mutant SOD1 mice, aggregates (misfolded protein accumulations) of mutant SOD1 were found only in diseased tissues, and greater amounts were detected during motor neuron degeneration (Furukawa Y, et al. 2006 *Proc Natl Acad Sci USA* 103 (18): 7148-53). It is speculated that aggregate accumulation of mutant SOD1 plays a role in disrupting cellular functions by damaging mitochondria, proteasomes, protein folding chaperones, or other proteins (Boillée S, et al. 2006 *Neuron* 52 (1): 39-59). Other factors that may be associated with ALS include but are not limited to glutamate.

There is no cure for ALS. Riluzole is currently the only U.S. Food and Drug Administration (FDA) approved drug for ALS and targets glutamate transporters. Riluzole is marketed by Sanofi-Aventis S. A. with the brand name Rilutek®. Riluzole is believed to reduce damage to motor neurons by decreasing the release of glutamate via activation of glutamate transporters. In addition, the drug offers a wide array of other neuroprotective effects, by means of sodium and calcium channel blockades (Hubert J P, Delumeau J C, Glowinski J, Prémont J, Doble A. (1994). *Br. J. Pharmacol.* 113 (1): 261-267), inhibition of protein kinase C, and the promotion of NMDA (N-methyl d-aspartate) receptor antagonism (Noh K M, Hwang J Y, Shin H C, Koh J Y. (2000). A Novel Neuroprotective Mechanism of Riluzole: Direct Inhibition of Protein Kinase C. *Neurobiol Dis.* 7 (4): 375-383; Beal M F, Lang A E, Ludolph A C. (2005). *Neurodegenerative Diseases: Neurobiology, Pathogenesis and Therapeutics.* Cambridge: Cambridge University Press. p. p. 775). Clinical trials with ALS patients showed that riluzole lengthens survival by several months, and may have a greater survival benefit for those with a bulbar onset. The drug also extends the time before a patient needs ventilation support. Riluzole does not reverse the damage already done to motor neurons, and patients taking the drug must be monitored for liver damage and other possible side effects.

A small, open-label study recently suggested that the drug lithium which traditionally is used for the treatment of bipolar affective disorder may slow progression in both animal models and the human form of ALS (Fornai F, Longone P, Cafaro L, et al. (2008). *Proc. Natl. Acad. Sci. U.S.A.* 105: 2052).

The antibiotic ceftriaxone has demonstrated an unexpected effect on glutamate and appears to be a beneficial treatment for ALS in animal models. Ceftriaxone sodium is marketed by Hoffman-La Roche under the trade name Rocephin®. Ceftriaxone is currently being tested in clinical trials.

Other drugs are undergoing development for ALS. For example, KNS-760704 is under clinical investigation in ALS patients. It is the enantiomer of pramipexole, which is approved for the treatment of Parkinson's disease and restless legs syndrome (Abramova N A et al. J Neurosci Res. 2002 Feb. 15; 67(4):494-500). However, KNS-760704, which has been manufactured to a high degree of enantiomeric purity and which is essentially inactive at dopamine receptors, is not dose limited by the potent dopaminergic properies of pramipexole (Gribkoff V and Bozik M. CNS Neurosci Ther. 2008 Fall;14(3):215-26). The potential utility of KNS-760704 in ALS is being advanced in clinical studies by Knopp Neurosciences Inc. of Pittsburgh, Pa. The tetracycline antibiotic minocycline is also under investigation for the treatment of ALS among other neurological disorders. RNAi has been used in lab rats to shut off specific genes that lead to ALS. RNAi gene silencing technology has been used to target the mutant SOD1 gene (Xia X, Zhou H, Huang Y, Xu Z (September 2006). *Neurobiol Dis.* 23 (3): 578-86). The mutant SOD1 gene is responsible for causing ALS in a subset of the 10% of all ALS patients who suffer from the familial, or genetic, form of the disease.

The orally-administered drug arimoclomol is currently in clinical evaluation as a therapeutic treatment for ALS. Arimoclomol has been shown to extend life in an animal model of ALS. Kalmar B, et al. Late stage treatment with arimoclomol delays disease progression and prevents protein aggregation in the SOD1 mouse model of ALS. *J. Neurochem.* 107:339-50 (2008).

Insulin-like growth factor 1 has also been studied as treatment for ALS. IPLEX, which is a recombinant IGF-1 with Binding Protein 3(IGF1BP3), has been issued to be used in a clinical trial for ALS patients in Italy. Furthermore, methylcobalamin is being studied in Japan and preliminary results show it significantly lengthens survival time of ALS patients (Izumi Y, Kaji R (October 2007). *Brain Nerve* 59 (10): 1141-7).

Other treatments for ALS are designed to relieve symptoms and improve the quality of life for patients. Physicians can prescribe medications to help reduce fatigue, ease muscle cramps, control spasticity, and reduce excess saliva and phlegm. Drugs also are available to help patients with pain, depression, sleep disturbances, dysphagia, and constipation. Physical therapy and special equipment such as assistive technology can enhance patient independence and safety throughout the course of ALS. Gentle, low-impact aerobic exercise such as walking, swimming, and stationary bicycling can strengthen unaffected muscles, improve cardiovascular health, and help patients fight fatigue and depression. Range of motion and stretching exercises can help prevent painful spasticity and shortening (contracture) of muscles. ALS patients who have difficulty speaking may benefit from working with a speech-language pathologist. As ALS progresses, speech-language pathologists can recommend the use of augmentative and alternative communication such as voice amplifiers, speech-generating devices (or voice output communication devices) and/or low tech communication techniques such as alphabet boards or yes/no signals. These methods and devices help patients communicate when they can no longer speak or produce vocal sounds. When the muscles that assist in breathing weaken, use of nocturnal ventilatory assistance (intermittent positive pressure ventilation (IPPV) or bilevel positive airway pressure (BIPAP)) may be used to aid breathing during sleep. Such devices artificially inflate the patient's lungs from various external sources that are applied directly to the face or body. When muscles are no longer able to maintain oxygen and carbon dioxide levels, these devices may be used full-time. Patients may eventually consider forms of mechanical ventilation (respirators) in which a machine inflates and deflates the lungs. To be effective, this may require a tube that passes from the nose or mouth to the trachea and for long-term use, an operation such as a tracheostomy, in which a plastic breathing tube is inserted directly in the patient's windpipe through an opening in the neck. In addition, both animal and human research suggest calorie restriction (CR) may be contraindicated for those with ALS. Research on a transgenic mouse model of ALS demonstrates that CR may hasten the onset of death in ALS (Hamadeh M J, et al. (February 2005). *Muscle Nerve* 31 (2): 214-20). It has also been found that in the ALS mouse model, CR "accelerates the clinical course" of the disease and had no benefits (Pedersen W A, Mattson M P (June 1999). *Brain Res.* 833 (1): 117-20), suggesting that a calorically dense diet may slow ALS, a ketogenic diet in the ALS mouse model has been shown to slow the progress of disease (Zhao Z, Lange D J, Voustianiouk A, et al. (2006). *BMC Neurosci* 7: 29).

Potential therapeutic agents for ALS compounds include immune modulators, complement and major histocompatibility complex (MHC) inhibitors, protective agents for myelination and synaptic connections, cellular stress agents, inhibitors of protein expression, and neurotrophins. The present invention provides methods of enhancing the efficacy of such agents by treating a patient in need thereof with the agent in combination with chlorite or a chlorite-containing agent.

In some embodiments, chlorite or a chlorite-containing agents of the present invention are used in combination with immune modulators for treatment of ALS. The immune response is believed to play a role in the pathogenesis of ALS. In some cases, immune factors may mitigate disease but in other cases exacerbate the disease. Immune modulatory agents that provide treatment can be used in combination with chlorite or a chlorite-containing agent. The complement cascade may be upregulated in ALS patients. In some embodiments, modulators of the complement cascade and major histocompatibility complex (MHC) inhibitors can be used for treatment of ALS in combination with chlorite or a chlorite-containing agent.

In some embodiments, chlorite or a chlorite-containing agent of the present invention are used in combination with protective agents for myelination and synaptic connections for treatment of ALS. Motor unit dysfunction in ALS may begin at the axon and at synaptic connections. Agents and interventions that protect the myelin sheath, remyelination, and synaptic remodeling can have beneficial effects in ALS patients.

In some embodiments, chlorite or a chlorite-containing agent of the present invention are used in combination with cellular stress agents for treatment of ALS. Motor neurons in ALS may be less capable of responding to stress caused by over-activity, oxidative damage, misfolded proteins or other insults, when compared to normal cells. Therapeutic agents that reduce stress or bolster the vulnerable cells' natural stress response mechanisms can have beneficial effect in ALS patients.

In some embodiments, chlorite or a chlorite-containing agent of the present invention are used in combination with inhibitors of protein expression for treatment of ALS. For example, inhibitors of expression of genes that are known or suspected to produce or exacerbate the ALS disease state can be used to treat ALS. In a non-limiting example, RNAi can be used to downregulate the expression of ALS genes including mutant SOD and TDP-43.

Chlorite or a chlorite-containing oxidative agent disclosed herein can be used in combination with agents that are associated with nerve regrowth for treatment of ALS. Factors that promote the survival of neurons are referred to as neurotrophic factors. Neurotrophic factors are secreted by target tissue and act by preventing the associated neuron from initiating programmed cell death, and induce differentiation of progenitor cells to form neurons. Neurotrophins are a family of secreted proteins that induce the survival, development and function of neurons. Neurotrophins include nerve growth factor (NGF), brain-derived neurotrophic factor (BDNF), neurotrophin-3 (NT-3), neurotrophin-4 (NT-4) and novel neurotrophin-1 (NNT1). Insulin-like growth factor-1 (IGF1) acts on a wide variety of cell types to regulate cell growth and development, especially in nerve cells. In some embodiments of the present invention, chlorite or a chlorite-containing agent of the present invention are used in combination with neurotrophic factors and other factors that stimulate nerve cell survival and differentiation to treat ALS. Such factors can be delivered in various ways, e.g., via viral or gene therapy or intraperitoneal injection. In some embodiments of the present invention, chlorite or a chlorite-containing agent of the present invention are used in combination with agents that stimulate the activity or production of neurotrophic factors and other factors that stimulate nerve cell survival and differentiation to treat ALS.

In some embodiments, chlorite or a chlorite-containing agent of the present invention are used in combination with molecules that affect neurotransmitter levels for treatment of ALS. Examples of such molecules include but are not limited to 5-hydroxytryptophan (5-HTP), tyrosine, levodopa (L-DOPA), tryptophan, and cysteine.

Potential therapeutic agents for ALS are commonly tested in ALS animal models, including the human Cu/Zn superoxide dismutase (hSOD1) G93A transgene ALS mouse model (hSOD1-G93A mouse), which exhibits high velocity of disease progression and short lifespan. A comprehensive archive of ALS animal studies is available at the web site of the ALS Therapy Development Institute (ALSTDI). In some embodiments, chlorite or chlorite-containing agents are used to treat ALS patients in combination with therapeutic agents or interventions that have been tested in animal models, including but not limited to 2-PMPA, adenosine, anisomycin, apocynin, apomorphine, arimoclomol, aspergillin, BMP-7, carboxyfullerenes, ceftriaxone, celastrol, geldanamycin, celecoxib (Celebrex®), cyclooxygenase 2, CGP 3466B, chlorpromazine, clioquinol, clozapine, ciliary neurotrophic factor (CTNF), colchicine, colivelin, copaxone, copper chelators, lipoic acid, coenzyme Q10 (CoQ10), creatine, curcumin, cytotoxic T-lymphocyte antigen 4 antibody fusions (CTLA4-Ig), cycloheximide, cobra venom factor (CVF), cycloserine, cyclosporin, d-penicillamine, JAK3/Dapsone, Dapsone/Gusperimus/JAK3 Cocktail, Diethyldithiocarbamate DDC, desferoxamine, desipramine, a-difluoromethylornithine (DFMO), dietary restriction, dihydrotestosterone, 5,5-dimethyl-pyrroline N-oxide (DMPO), excitatory amino acid transporter 2 (EAAT2), erythro-9-[3-(2-hydroxynonyl)]adenine (EHNA), emetine, estradiol benzoate, exercise, FK-506, fluorouracil, glial cell line-derived neurotrophic factor (GDNF), decreased spinal copper levels, genistein, glutamate receptor 3 (GLUR3) antisense, hepatocyte growth factor (HGF), hNT neurons, anti-oxidant SOD1 protein, human umbilical cord blood mononuclear cells, hydroxyurea, interleukin-1beta-converting enzyme (ICE) inhibition, IGF-1 or isoforms thereof, intravenous immunoglobulin (IVIG), indomethacin, hydroquinone hydrochloride derivative of 17-AAG (IPI-504), iron porphyrin, ivermectin (22,23-dihydroavermectin B1a+22, 23-dihydroavermectin B1b), L-acetyl-carnitine, lactacystin, leflunomide, lentiviral RNAi SOD1 gene silencing, leukemia inhibitory factor (LIF), lithium, lyophilized red wine extract, magnesium supplementation, melatonin, memantine, metalloporphyrins (MnTE-Py-P (AEOL10113 and AEOL10150)), metallothioneins, metformin, methotrexate, mechano growth factor (MGF; IGF-I Ec peptide; mIGF-1 isoform), minocycline, minocycline/creatine, minocycline/riluzole/nimodipine cocktail, mithramycin, 1-methyl-4-phenyl-1,2,3,6-tetrahydropyridine (MPTP) and/or 3-nitropropionic acid (3NP), N-acetyl-L-cysteine, N-acetylcysteine, 2,3-dihydroxy-6-nitro-7-sulfamoyl-benzo[1]quinoxaline-2,3-dione (NBQX), nordihydroguaiaretic acid (NDGA), neurofilament heavy (NF-H) protein, neurofilament light (NF-L) protein, nimesulide, nitric oxide synthase inhibitors, 17 beta-estradiol, p75 neurotrophin receptor, p75 neurotrophin agonist, p75 neurotrophin antisense, parvalbumin, sodium phenyl butyrate (PBA), peripheral axotomy, phosphatidyl choline-bound Cu/Zn SOD, pioglitazone, polyamine-modified catalase, porphyrin, prednisolone, progesterone, puromycin, putrescine-modified catalase (PUTCAT), quinacrine, R(+) pramipexole, radicicol, rasagiline, resveratrol/red wine extract, riluzole, ritonavir, anti-myostatin mAb, vascular endothelial growth factor (VEGF), RNAi targeting human SOD1 gene, rofecoxib, rolipram, alpha-amino-3-hydroxy-5-methyl-4-isoxazolepropionic acid antagonist RPR 119990, 5-hydroxytryptophan (5-HTP), sodium valproate, stem cells, sulindac, tamoxifen, propargylamine TCH346, tepoxalin, testosterone, thalidomide, trehalose, trichostatin A, trientine/ascorbate, vincristine, vitamin E/riluzole/gabapentin, Janus kinase 3 (JAK3) inhibitor such as WHI-P131, bone marrow transplant, zileuton, zinc sulfate, or noncompetitive AMPA antagonist such as ZK 187638. In some embodiments, these agents have a beneficial effect in animal models of ALS and human ALS patients. In some embodiments, these agents have a beneficial effect in animal models of ALS but have attenuated or no effect in human ALS patients. indeed, there are many therapeutic agents that show activity in animal models but have reduced activity, or no beneficial activity, when administered to human patients. Without being bound by any theory, it is believed that therapeutic agents that address neuronal function (e.g., riluzole and agents that act on glutamate receptors or facilitate mitochondria repair) and neuronal regrowth (e.g., IGF1) would be more effective if the diseased inflammatory environment is at least partially resolved. Thus, many of the ALS treatments that show activity in animal models (e.g., the hSOD1-G93A mouse) but have failed in humans will be more effective for treating ALS after the inflammatory environment has been treated, e.g., in combination with chlorite or a chlorite-containing agent of the present invention. Thus, chlorite and chlorite-containing agents can be used to "rescue" drugs and other therapies or interventions.

Similarly, some of the above agents or interventions have shown a beneficial effect during in vitro studies but have attenuated or no effect in animal models of ALS or in human ALS patients. In some embodiments, such agents are efficacious in vivo when used in combination with chlorite or a chlorite-containing agent.

The methods of the invention provide administering chlorite or a chlorite-containing agent in combination with one or more other therapeutic agents or interventions that are being developed to treat ALS or are promising for treating ALS. In some embodiments, chlorite or a chlorite-containing agent is administered in combination with therapeutic agents during preclinical and/or clinical development of such agents. In some embodiments, these therapeutic agents have shown therapeutic benefit during in vitro or in vivo studies. In some embodiments, these agents are known to treat other diseases, and have an activity or benefit that is suspected to be useful in the ALS setting. In a non-limiting example, neuroprotective or anti-inflammatory agents, e.g., agents known to be useful for other diseases or disorders, may be suspected to also have a beneficial effect in ALS patients. Such promising agents can be administered in combination with chlorite or a chlorite-containing agent to further enhance their beneficial effect. A number of potential points of therapeutic intervention have been identified for treatment of ALS. ALS targets include those related to apoptosis, axon growth/transport, cell cycle, cell replacement, excitotoxicity, functional intervention, inflammation, oxidative stress and transcription. Targets further include trophic factors, biomarkers, proteins, mitochondria, and muscle factors. In some embodiments, the invention provides methods to treat ALS in a subject in need thereof comprising administration of chlorite or a chlorite-containing agent in combination with another agent that acts upon one or more ALS targets.

In some embodiments, the target for ALS treatment is a 5-HT receptor. Non-limiting examples of target related treatments include Buspirone. In some embodiments, the target for ALS treatment is a 5-LOX Inhibitor. Non-limiting examples of target related treatments include GPI-20359. In some embodiments, the target for ALS treatment is an ACE inhibitor. Non-limiting examples of target related treatments include Ramipril and Teveten. In some embodiments, the target for ALS treatment is an ADA inhibitor. Non-limiting examples of target related treatments include EHNA. In some embodiments, the target for ALS treatment is an Adenosine receptor. Non-limiting examples of target related treatments include CGS21680. In some embodiments, the target for ALS treatment is an adhesion molecule. Non-limiting examples of target related treatments include natalizumab (Tysabri®), Efomycine M, LGD5552, Lovenox or purified phenolic glycolipid (PGL). In some embodiments, the target for ALS treatment is an Adjunct Therapy. Non-limiting examples of target related treatments include BMS-387032, Cereport or Nicotine. In some embodiments, the target for ALS treatment is an Aggregate or Prion. Non-limiting examples of target related treatments include 2-amino-4,7-dimethyl-benzothiazol-6-ol, 2-methoxyestradiol, Apan, Chlorpromazine, CPHPC, Cyclodextrin, Fibrillex, Guanidine hydrochloride, Heparin, hSOD1, MG-132, Piroxicam, Porphyrin, Promethazine, Protoporphyrin, Y-27632, or Melatonin. In some embodiments, the target for ALS treatment is an AIDS drug. Non-limiting examples of target related treatments include Indinavir, or Kaletra® (ritonavir+lopinavir). In some embodiments, the target for ALS treatment is an AKT Inhibitor. Non-limiting examples of target related treatments include KP372-1, LY294002, Perifosine, Tricirbine, or Wortmannin. In some embodiments, the target for ALS treatment is an Alternate cellular energy source. Non-limiting examples of target related treatments include ATP or Trehalose. In some embodiments, the target for ALS treatment is an AMPA Receptor. Non-limiting examples of target related treatments include GLUR3 antisense, GYKI-47261, NBQX, RPR 119990, RPR117824, Temocapril, ZK 187638, or Ivermectin. In some embodiments, the target for ALS treatment is an Anti-FAS. Non-limiting examples of target related treatments include Antisense vs FAS, MFL3 or R-125224. In some embodiments, the target for ALS treatment is an Anti-Microtubule. Non-limiting examples of target related treatments include Liposome-Based Taxol or Taxol. In some embodiments, the target for ALS treatment is an anticholinesterase. Non-limiting examples of target related treatments include neostigmine or physostigmine. In some embodiments, the target for ALS treatment is an Anticoagulant. Non-limiting examples of target related treatments include Desmoteplase or Enoxaparin. In some embodiments, the target for ALS treatment is an antioxidant. Non-limiting examples of target related treatments include glutathione, Glutathione peroxidase, N-acetyl-L-cysteine, procysteine, PUT-CAT, TR500, Underexpression of MnSOD, Melatonin or hSOD1. In some embodiments, the target for ALS treatment is an Antiviral agent. Non-limiting examples of target related treatments include IFN-beta, Pleconaril or tilorone. In some embodiments, the target for ALS treatment is apoptosis. Non-limiting examples of target related treatments include Bcl-2. In some embodiments, the target for ALS treatment is Astrocyte/Microglial replacement. Non-limiting examples of target related treatments include Cord Blood cells, Cord Blood ICV or Diflunisal. In some embodiments, the target for ALS treatment is an Astrocytes/Microglia. Non-limiting examples of target related treatments include Alpha GPE, Aminoadipic acid, Anti-PS receptor neutralizing antibody, Campath, IL-4PE38, Interferon gamma, Melatonin, Mycophenolate Mofetil, RI273, Tetrathiomolybdate, tissue plasminogen activator antisense, Tranilast or Neuroserpin. In some embodiments, the target for ALS treatment is Autophagy. Non-limiting examples of target related treatments include 3-methyladenine or Rapamycin. In some embodiments, the target for ALS treatment is Axonal regeneration. Non-limiting examples of target related treatments include Chondroitinase ABC, NEP1-40, NgR(310)ecto-Fc or inosine. In some embodiments, the target for ALS treatment is Axonal transport. Non-limiting examples of target related treatments include Brimonidine or EHNA. In some embodiments, the target for ALS treatment is a Bax Inhibitor. Non-limiting examples of target related treatments include Bax antisense, BIP, hTERT, Humanin, XIAP or colivelin. In some embodiments, the target for ALS treatment is a Bcl inducer. Non-limiting examples of target related treatments include ginsenoside Rb1 and Rg1, or Genasense. In some embodiments, the target for ALS treatment is a calcium channel blocker. Non-limiting examples of target related treatments include nimodipine or verapamil. In some embodiments, the target for ALS treatment is a Calpain Inhibitor. Non-limiting examples of target related treatments include E64, Neurodur, PD150606, SJA6017 or calpeptin. In some embodiments, the target for ALS treatment is a Caspase Inhibitor. Non-limiting examples of target related treatments include ESPA-1002, IDN-6556, M826, Q-VD-OPH, zVAD-FMK or variants thereof or VX-740. In some embodiments, the target for ALS treatment is a CDK inhibitor. Non-limiting examples of target related treatments include Alsterpaullone, aragusterol A, AT7519, AT9311, Butryrolactone, CDC25 Inhibitor, CGP60474, CINK-4, CYC202, E7389, fascaplysin, Indirubin, Ken Kosik compounds 2 or 3, kenpaullone, KN-93, Olomoucine, PD 0183812, Roscovitine, indolo[6,7-a]pyrrolo[3,4-c]carbazoles, SQ-67563, Staurosporine, TNP-470 or UCN-01. In some embodiments, the target for ALS treatment is Cell Adhesion. Non-limiting examples of target related treatments include KDI tripeptide. In some embodiments, the target for ALS treatment is Cell Therapy. Non-limiting examples of target related treatments include Immune modulation therapy, Neurol stem cells, Stem cells in ALS Rat or BM-NSC. In some embodiments, the target for ALS treatment is a Ceramide. Non-limiting examples of target related treatments include Cycloserine, D-Cycloserine or ISP-1. In some embodiments, the target for ALS treatment is a Chaperone Inducer or Co-inducer. Non-limiting examples of target related treatments include celastrol, curcumin, radicicol. In some embodiments, the target for ALS treatment is a chelator. Non-limiting examples of target related treatments include clioquinol, D-penicillamine or trientine/ascorbate. In some embodiments, the target for ALS treatment is a Chemokine receptor antagonist. Non-limiting examples of target related treatments include AMD-3100, BX471, MLN1202, SCH-D, TAK-779 or vMIPII. In some embodiments, the target for ALS treatment is a Complement inhibitor. Non-limiting examples of target related treatments include CVF. In some embodiments, the target for ALS treatment is a copper chelator. Non-limiting examples of target related treatments include penicillamine. In some embodiments, the target for ALS treatment is Corticosteroid. Non-limiting examples of target related treatments include Adrenalectomy. In some embodiments, the target for ALS treatment is a COX inhibitor. Non-limiting examples of target related treatments include sulindac. In some embodiments, the target for ALS treatment is a selective COX-2 Inhibitor. Non-limiting examples of target related treatments include valdecoxib (Bextra®), celecoxib (Celebrex®), nimesulide, rofecoxib or SC-236. In some embodiments, the target for ALS treatment is a COX/LOX inhibitor. Non-limiting examples of target related treatments include licofelone or tepoxalin. In some embodiments, the target for ALS treatment is Cross Linking. Non-limiting examples of target related treatments include ALT-711. In some embodiments, the target for ALS treatment is a CXCR3 Antagonist. In some embodiments, the target for ALS treatment is a Cysteine Protease Inhibitor. Non-limiting examples of target related treatments include CA-074, CRA-3316 or Cystatin C. In some embodiments, the target for ALS treatment is a Cytochrome Enyme Inducer. Non-limiting examples of target related treatments include Isoniazid. In some embodiments, the target for ALS treatment is a Cytokine. In some embodiments, the target for ALS treatment is a Cytokine Inhibitor. Non-limiting examples of target related treatments include CP-SOCS3, etanercept (Enbrel®), adalimumab (Humira®), infliximab (Remicade®), LMP-420 or naltrexone. In some embodiments, the target for ALS treatment is a DNA intercalator. Non-limiting examples of target related treatments include Cyclophosphamide, Mithramycin, Mitomycin C or Quinacrine. In some embodiments, the target for ALS treatment is DNA synthesis. Non-limiting examples of target related treatments include MB7133, Procarbazine, Raltitrexed or Leucovorin. In some embodiments, the target for ALS treatment is Dopamine. Non-limiting examples of target related treatments include Apomorphine. In some embodiments, the target for ALS treatment is a dopamine agonist. Non-limiting examples of target related treatments include bromocriptine. In some embodiments, the target for ALS treatment is E2F-1/Sp1. Non-limiting examples of target related treatments include E2F Decoy, microgonotropen, Mitoxantrone Liposome or Tallimustine—Distamycin. In some embodiments, the target for ALS treatment is EAAT2. Non-limiting examples of target related treatments include Ceftriaxone, Sodium Valproate or ONO-2506. In some embodiments, the target for ALS treatment is ER stress. Non-limiting examples of target related treatments include salubrinal or IPI-504. In some embodiments, the target for ALS treatment is Estrogen. Non-limiting examples of target related treatments include estrone quinol, Genistein, raloxifene or Tamoxifen. In some embodiments, the target for ALS treatment is excitotoxicity. Non-limiting examples of target related treatments include dextromethorphan, L-threonine, lamotrigine, levodopa or topiramate. In some embodiments, the target for ALS treatment is a Farnesyl transferase (FTase) inhibitor. Non-limiting examples of target related treatments include BMS-214662 or tipifarnib. In some embodiments, the target for ALS treatment is a GAPDH Inhibitor. Non-limiting examples of target related treatments include Pentalenolactone or TCH-346. In some embodiments, the target for ALS treatment is Gene Therapy. Non-limiting examples of target related treatments include CT GalNAc transferase or rabies G (RabG) protein pseudotyped lentiviral vector EIAV.LacZ. In some embodiments, the target for ALS treatment is a glucocorticoid receptor agonist or Dexamethasone. In some embodiments, the target for ALS treatment is Glutamate release. Non-limiting examples of target related treatments include Riluzole. In some embodiments, the target for ALS treatment is a Growth Factor. Non-limiting examples of target related treatments include Agrin, Aranesp, CEPO, Epoetin Beta, Erythropoietin, HF0299, MGF, MMP-9 and stem cells, oprelvekin (Neumega®), RI624, thrombospindin or RK35. In some embodiments, the target for ALS treatment is a GSK3beta inhibitor. In some embodiments, the target for ALS treatment is a HAT inhibitor. Non-limiting examples of target related treatments include garcinol. In some embodiments, the target for ALS treatment is a HDAC activator. Non-limiting examples of target related treatments include Resveratrol or other red wine extract. In some embodiments, the target for ALS treatment is a HDAC inhibitor. Non-limiting examples of target related treatments include FK228, Flavin analog DPD, MNTF, MS-27-275, PBA, Pivanex, PXD101, SAHA (Suberoylanilide hydroxamine), Scriptaid, Trichostatin A or Sodium Valproate. In some embodiments, the target for ALS treatment is a Heat Shock Protein. Non-limiting examples of target related treatments include arimoclomol. In some embodiments, the target for ALS treatment is a Heat Shock Protein Inhibitor/Activator. Non-limiting examples of target related treatments include 17 DMAG or IPI-504. In some embodiments, the target for ALS treatment is a HIF-1 Inducer. Non-limiting examples of target related treatments include Cobalt. In some embodiments, the target for ALS treatment is a HIV Protease inhibitor. Non-limiting examples of target related treatments include amprenavir, fosamprenavir, nelfinavir, nelfinavir/ritonavir or saquinavir. In some embodiments, the target for ALS treatment is Hypoxia. Non-limiting examples of target related treatments include Blood Substitute. In some embodiments, the target for ALS treatment is an IL-1 inhibition. In some embodiments, the target for ALS treatment is Immune Regulation. Non-limiting examples of target related treatments include Alzhemed, Ambrotose, Anthrax lethal factor, Anti-IL15 Antibody, Anti-TNF antibody, Brefeldin A, CAMPATH-1H, CD45 antibody, Copaxone, Dapsone, Dapsone—Gusperimus—JAK3 Cocktail, Dapsone—Gusperimus Combo, Dapsone ICV, Desipramine, DFMO—Chlorpromazine, DFMO—JAK3-Ritonavir, DFMO-Ritonavir-Chlorpromazine, DHM2EQ, Early Pregnancy Factor, Fludarabine, GMDP, Granzyme inhibitor, IL-10, IL-10 Gene Therapy, Imiquimod, Immunokine, inosiplex, interferon alpha, isoprinosine, levamisole, Luteolin, Mac 1 SAP, Mycotoxins, NK 1.1, Omeprazole, Prednisolone, rFAS-ligand, RS-1178, Squalestatin, Suramin, total lymphoid irradiation, IP10 or sCR1, Cyclosporin, Lipitor or methylprednisolone. In some embodiments, the target for ALS treatment is inflammation. Non-limiting examples of target related treatments include bovine brain gangliosides, gangliosides, VX 148 or Sanglifehrin A. In some embodiments, the target for ALS treatment is an ion channel inhibitor. Non-limiting examples of target related treatments include amantadine and guanidine. In some embodiments, the target for ALS treatment is a JAK/STAT. Non-limiting examples of target related treatments include leflunomide or WHI-P131. In some embodiments, the target for ALS treatment is a JNK Inhibitor. Non-limiting examples of target related treatments include CC-105, Colostrinin, AS601245 or SP600125. In some embodiments, the target for ALS treatment is a Kinase Inhibitor. Non-limiting examples of target related treatments include PKC412, GW5074 or Y-27632. In some embodiments, the target for ALS treatment is kinase upregulation. Non-limiting examples of target related treatments include forskolin. In some embodiments, the target for ALS treatment is a PARP inhibitor. Non-limiting examples of target related treatments include GPI15427 & 16539, inosine or PJ-34. In some embodiments, the target for ALS treatment is a phosphodiesterase inhibitor. Non-limiting examples of target related treatments include Ariflo, MEM1414, Roflumilast, Rolipram, SelCID-3, Viagra or EHNA. In some embodiments, the target for ALS treatment is a Polo-like Kinase Inhibitor. Non-limiting examples of target related treatments include HMN-214. In some embodiments, the target for ALS treatment is a Polyamine analog. Non-limiting examples of target related treatments include Tetramines. In some embodiments, the target for ALS treatment is a Polyamine inhibitor. Non-limiting examples of target related treatments include mitoguazone or Xyloside. In some embodiments, the target for ALS treatment is a potassium channel blocker. Non-limiting examples of target related treatments include 3,4-diaminopyridine. In some embodiments, the target for ALS treatment is a Protease Inhibitor. In some embodiments, the target for ALS treatment is a Proteasome. Non-limiting examples of target related treatments include Aclacinomycin A, Alpha-methylomuralide, Aspergillin, CBZ-GPFL-CHO, CVT-634, Dantrolene, Dihydroeponemycin, Epoxomicin, ICV Ritonavir, IDE Antibody, Lactacystin, Lovastatin, p27 E3, Rasagiline, Ritonavir, Simvastatin, Torbafylline or Velcade. In some embodiments, the target for ALS treatment is a Protein Kinase C inhibitor. Non-limiting examples of target related treatments include ISSI-3521, LY-333531, PEP005 or Propofol. In some embodiments, the target for ALS treatment is a Protein Synthesis Inhibitor. Non-limiting examples of target related treatments include Hygromycin B, linezolid (Zyvox®) or anisomycin. In some embodiments, the target for ALS treatment is Protein Transport. Non-limiting examples of target related treatments include 17-beta-Estradiol. In some embodiments, the target for ALS treatment is REDOX. Non-limiting examples of target related treatments include AGIX-4207, Ebselen, pyrroloquinoline quinone or Resveratrol/red wine extract. In some embodiments, the target for ALS treatment is a Ribonucleotide reductase inhibitor. Non-limiting examples of target related treatments include Desferoxamine, Hydroxyurea or Trimidox. In some embodiments, the target for ALS treatment is a RNA synthesis inhibitor. In some embodiments, the target for ALS treatment is a Serine Protease. In some embodiments, the target for ALS treatment is a serine/threonine kinase inhibitor. Non-limiting examples of target related treatments include VX 680. In some embodiments, the target for ALS treatment is SOD1. Non-limiting examples of target related treatments include DDC or Temozolamide. In some embodiments, the target for ALS treatment is a SOD1 Inhibitor. Non-limiting examples of target related treatments include Dietary copper deficiency (with Clioquinol), Estradiol Benzoate, Histidine or Norethindrone. In some embodiments, the target for ALS treatment is a stem cell. Non-limiting examples of target related treatments include Human umbilical cord blood. In some embodiments, the target for ALS treatment is a TACE inhibitor (TNF-a). Non-limiting examples of target related treatments include TMI-1. In some embodiments, the target for ALS treatment is a TGF beta inhibitor. Non-limiting examples of target related treatments include AP12009, inhibitors of E3 ubiquitin ligases or Pirfenidone. In some embodiments, the target for ALS treatment is a TNF-Alpha. Non-limiting examples of target related treatments include Bupropion, Gemfibrozil, Pirfenidone, Sepsis Vaccine or Thalidomide. In some embodiments, the target for ALS treatment is a Topoisomerase I inhibitor. Non-limiting examples of target related treatments include ARQ501, Liposome Encapsulated SN38, Rebeccamycin Derivative or SN38. In some embodiments, the target for ALS treatment is a Trophic Factor. Non-limiting examples of target related treatments include AAV-GDNF, Basic fibroblast growth factor, BDNF, BMP-7, cardiotrophin-1, CNTF, GDNF, adenovirus-mediated GDNF, GDNF AAV, growth hormone, HGF, Lantus, leukemia inhibitory factor (LIF), neurophilin ligands, NF-H or NF-L overexpression, Olmesartan, p75NTR Antagonist, rHCNTF, Thymic, thyrotropin, TRH or Xaliproden hydrochloride. In some embodiments, the target for ALS treatment is a Tyrosine kinase inhibitor. Non-limiting examples of target related treatments include GLEEVEC® (imatinib mesylate) or IRESSA® (gefitinib). In some embodiments, the target for ALS treatment is Ubiquitin inhibition. Non-limiting examples of target related treatments include Leu-Ala or UCHL1. In some embodiments, the target for ALS treatment is a miscellaneous target. Non-limiting examples of related treatments include Cisplatin, Deprenyl or Nelfinavir/Combivir. In some embodiments, the target for ALS treatment is Zinc Finger Transcription Disruption. Non-limiting examples of target related treatments include DTBA.

In some embodiments, the present invention provides methods for treatment of amyotrophic lateral sclerosis (ALS) comprising administering to a subject in need thereof chlorite or a chlorite-containing agent in combination with another therapy. In some embodiments, the present invention provides methods for treatment of amyotrophic lateral sclerosis (ALS) comprising administering to a subject in need thereof chlorite or a chlorite-containing agent in combination with any one or more of the drugs disclosed hereinabove. In some embodiments, chlorite or a chlorite containing agent of the present invention is used in combination with riluzole. In some embodiments, chlorite or a chlorite containing agent of the present invention is used in combination with KNS-760704. In some embodiments, chlorite or a chlorite containing agent of the present invention is used in combination with minocycline. In some embodiments, chlorite or a chlorite containing agent of the present invention is used in combination with RNAi targeting SOD1 gene. In some embodiments, chlorite or a chlorite containing agent of the present invention is used in combination with insulin-like growth factor 1 for the treatment of ALS.

(b) Parkinson's Disease (PD)

In some embodiments, the present invention provides methods for treatment of Parkinson's disease or Parkinson's-like disease comprising administering to a subject in need thereof an effective amount of chlorite or a chlorite-containing agent. The complications related to Parkinson's disease that can be treated with the methods of the present invention include but are not limited to motor impairment, severe tremor, injury related to motor impairment, pain, dysphagia, constipation, bladder control and urinary incontinence, speech problems, depression, compulsive behavior, cognitive impairment, dementia, muscle rigidity (akinesia), hallucination, visual problems, sleep disorders, restless legs syndrome, leg cramps, impaired sexuality, worsened sense of smell, and osteoporosis.

Parkinson's disease (PD) is a progressive degenerative disease of the central and peripheral nervous systems. The risk of developing Parkinson's disease increases with age, and afflicted individuals are usually adults over 40. Parkinson's disease occurs in all parts of the world, and affects more than one million individuals in the United States alone. There are several other conditions that have the features of Parkinson's disease and are referred to as Parkinson's-like diseases. Parkinson's and Parkinson's-like diseases can be characterized by tremor, hypokinesia, rigidity, and postural instability.

The underlying causes of Parkinson's disease and Parkinson's-like diseases are numerous, and diagnosis can be complex. Parkinson's disease or Parkinson's-like disease is characterized by degeneration of dopaminergic neurons of the substantia nigra. The substantia nigra is a portion of the lower brain or brain stem that helps control voluntary movements. The shortage of dopamine in the brain caused by the loss of these neurons may cause the observable disease symptoms.

Parkinson's disease is a chronic disorder that requires broad-based management including but not limited to patient and family education, support group services, general wellness maintenance, physiotherapy, exercise, and nutrition. Medications or surgical intervention can provide relief from the symptoms. Medications for Parkinson's disease include but are not limited to levodopa (L-3,4-dihydroxyphenylalanine; L-DOPA), catechol-O-methyl transferase (COMT) inhibitors, dopamine agonists, monoamine oxidase B (MAO-B) inhibitors, surgery and deep brain stimulation, and neurorehabilitation.

The most widely used form of treatment is L-DOPA in various forms. L-DOPA is transformed into dopamine in the dopaminergic neurons by L-aromatic amino acid decarboxylase (often known by its former name dopa-decarboxylase). However, only 1-5% of L-DOPA enters the dopaminergic neurons. The remaining L-DOPA is often metabolised to dopamine elsewhere, causing a wide variety of side effects. Due to feedback inhibition, L-DOPA results in a reduction in the endogenous formation of L-DOPA, and so eventually becomes counterproductive. Carbidopa and benserazide are dopa decarboxylase inhibitors. They help to prevent the metabolism of L-DOPA before it reaches the dopaminergic neurons and are generally given as combination preparations of carbidopa/levodopa (co-careldopa) (e.g., Sinemet®, Parcopa®) and benserazide/levodopa (co-beneldopa) (e.g., Madopar®). There are also controlled release versions of Sinemet® and Madopar® that spread out the effect of the L-DOPA. Duodopa® is a combination of levodopa and carbidopa, dispersed as a viscous gel. Using a patient-operated portable pump, the drug is continuously delivered via a tube directly into the upper small intestine, where it is rapidly absorbed. Medications combining carbidopa, levodopa and entacapone are also used (Stalevo®). The use of amantadine (Symmetrel®), benztropine (Cogentin®), procyclidine (Kemadrin®), or trihexyphenidyl (Artane®) with levodopa-carbidopa can enhance the anti-Parkinson's effects of levodopa.

COMT inhibitors can be used for treating PD. Tolcapone inhibits the COMT enzyme, thereby prolonging the effects of L-DOPA, and so has been used to complement L-DOPA. However, due to its possible side effects such as liver failure, it is limited in its availability. A similar drug, entacapone has not been shown to cause significant alterations of liver function and maintains adequate inhibition of COMT over time (Gelb D, Oliver E, Gilman S (1999) *Arch Neurol* 56 (1): 33-9).

The dopamine agonists bromocriptine, pergolide, pramipexole, ropinirole, cabergoline, apomorphine, and lisuride are moderately effective for treating PD. These have their own side effects including those listed above in addition to somnolence, hallucinations and/or insomnia. Several forms of dopamine agonism have been linked with a markedly increased risk of problem gambling. Dopamine agonists initially act by stimulating some of the dopamine receptors. However, they cause the dopamine receptors to become progressively less sensitive, thereby eventually increasing the symptoms.

MAO-B inhibitors such as selegiline and rasagiline reduce the symptoms by inhibiting monoamine oxidase-B (MAO-B), thereby inhibiting the breakdown of dopamine secreted by the dopaminergic neurons. Metabolites of selegiline include levoamphetamine and levomethamphetamine. This might result in side effects such as insomnia A potential side effect of selegiline in conjunction with L-DOPA is stomatitis, an inflammation of the mucous lining of any of the structures in the mouth.

In addition to medication, deep brain stimulation is presently the most used surgical means of treatment, but other surgical therapies that have shown promise include surgical lesion of the subthalamic nucleus and of the internal segment of the globus pallidus, a procedure known as pallidotomy (Guridi J, Obeso J A (2001) *Brain* 124 (Pt 1): 5-19; Fukuda M, Kameyama S, Yoshino M, Tanaka R, Narabayashi H (2000) *Stereotactic and functional neurosurgery* 74 (1): 11-20). Regular physical exercise and/or therapy can be beneficial to the patient for maintaining and improving mobility, flexibility, strength, gait speed, and quality of life; and speech therapy may improve voice and speech function.

In some embodiments, chlorite or a chlorite-containing agent of the present invention can be used in combination with levodopa, COMT inhibitors, dopamine agonists, MAO-B inhibitors, surgery, deep brain stimulation, or neurorehabilitation for the treatment of Parkinson's disease or Parkinson's-like diseases.

In some embodiments, the methods of the present invention comprise administration of chlorite or a chlorite-containing compound in combination with other therapeutic agents and/or interventions that are used for the treatment of Parkinson's disease and related complications. In some embodiments, chlorite or a chlorite-containing agent of the present invention can be used in combination with a neuroprotective agent or therapy for treating Parkinson's disease. The neuroprotective agent or therapy can be exercise, antioxidants, immunosuppressive calcineurin inhibitors, nitric oxide synthase (NOS) inhibitors, sigma-1 modulators, AMPA antagonists, $Ca^{2+}$ channel blockers, estrogen agonists, MAO-B inhibitors, kinase inhibitors, mitochondrial modulators or enhancers, alpha synuclein modulators, glycoprotein antagonists, erythropoietin, astaxanthin, boswellia, caffeine, curcumin, E vitamins, tocotrienols, flavonoids, naringenin, huperzine, or ubiquinol. In one embodiment, chlorite or a chlorite-containing agent of the present invention is used in combination with levodopa. In another embodiment, chlorite or a chlorite-containing agent of the present invention is used in combination with a COMT inhibitor such as tolcapone and entacapone. In another embodiment, chlorite or a chlorite-containing agent of the present invention is used in combination with a dopamine agonist including but not limited to bromocriptine, pergolide, pramipexole, ropinirole, cabergoline, apomorphine, and lisuride. In another embodiment, chlorite or a chlorite-containing agent of the present invention is used in combination with a MAO inhibitor including but not limited to selegiline and rasagiline. In yet another embodiment, chlorite or a chlorite-containing agent of the present invention is used in combination with deep brain stimulation and/or neurorehabilitation such as physical exercise or therapy.

(c) Alzheimer's Disease (AD)

In some embodiments, the present invention provides methods for treatment of Alzheimer's disease comprising administering to a subject in need thereof an effective amount of chlorite or a chlorite-containing agent. The complications related to Alzheimer's disease that can be treated with the methods of the present invention include but are not limited to memory loss, sleeplessness, agitation, disorganization, wandering, anxiety, depression, cognition disintegration, personality disintegration, cognitive impairment, infections, severe urinary tract infections, slow surgical recovery, chronic brain failure, anosmia, Hirano body, pneumonia, and injuries from falls and other motor impairment.

Alzheimer's disease (AD), also called Alzheimer disease, Senile Dementia of the Alzheimer Type (SDAT) or simply Alzheimer's, is the most common form of dementia. Generally it is diagnosed in people over 65 years of age, although the less-prevalent early-onset Alzheimer's can occur much earlier. Although each sufferer experiences Alzheimer's in a unique way, there are many common symptoms. The earliest observable symptoms are often mistakenly thought to be 'age-related' concerns, or manifestations of stress. In the early stages, the most commonly recognized symptom is memory loss, such as difficulty in remembering recently learned facts. When a doctor or physician has been notified, and AD is suspected, the diagnosis is usually confirmed with behavioral assessments and cognitive tests, often followed by a brain scan if available. As the disease advances, symptoms include confusion, irritability and aggression, mood swings, language breakdown, long-term memory loss, and the general withdrawal of the sufferer as their senses decline (Waldemar G, Dubois B, Emre M, et al. (January 2007). *Eur J Neurol* 14 (1): e1-26). Gradually, bodily functions are lost, ultimately leading to death. Individual prognosis is difficult to assess, as the duration of the disease varies. AD develops for an indeterminate period of time before becoming fully apparent, and it can progress undiagnosed for years.

Research indicates that the disease is associated with plaques and tangles in the brain (Tiraboschi P, Hansen L A, Thal L J, Corey-Bloom J (June 2004). *Neurology* 62 (11): 1984-9). The disease course is divided into four stages, with a progressive pattern of cognitive and functional impairment: pre-dementia, early dementia, moderate dementia, and advanced dementia Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus. Both amyloid plaques and neurofibrillary tangles are clearly visible by microscopy in brains of those afflicted by AD.

Alzheimer's disease has been identified as a protein misfolding disease (protcopathy), caused by accumulation of abnormally folded A-beta and tau proteins in the brain (Hashimoto M, Rockenstein E, Crews L, Masliah E (2003) *Neuromolecular Med.* 4 (1-2): 21-36). Plaques are made up of small peptides, 39-43 amino acids in length, called beta-amyloid (also written as A-beta or Aβ). Beta-amyloid is a fragment from a larger protein called amyloid precursor protein (APP), a transmembrane protein that penetrates through the neuron's membrane. APP is critical to neuron growth, survival and post-injury repair (Priller C, et al. 2006 *J. Neurosci.* 26 (27): 7212-21). In Alzheimer's disease, an unknown process causes APP to be divided into smaller fragments by enzymes through proteolysis (Hooper N M (April 2005) *Biochem. Soc. Trans.* 33 (Pt 2): 335-8). One of these fragments gives rise to fibrils of beta-amyloid, which form clumps that deposit outside neurons in dense formations known as senile plaques (Ohnishi S, Takano K (March 2004) *Cell. Mol. Life Sci.* 61 (5): 511-24). AD is also considered a tauopathy due to abnormal aggregation of the tau protein. Every neuron has a cytoskeleton, an internal support structure partly made up of structures called microtubules. Tau protein stabilizes the microtubules when phosphorylated, and is therefore called a microtubule-associated protein. In AD, tau undergoes chemical changes, becoming hyperphosphorylated; it then begins to pair with other threads, creating neurofibrillary tangles and disintegrating the neuron's transport system (Hernandez F, Avila J September 2007 *Cell. Mol. Life Sci.* 64 (17): 2219-33).

It is not known exactly how disturbances of production and aggregation of the beta amyloid peptide gives rise to the pathology of AD. The amyloid hypothesis traditionally points to the accumulation of beta amyloid peptides as the central event triggering neuron degeneration. Accumulation of aggregated amyloid fibrils, which are believed to be the toxic form of the protein responsible for disrupting the cell's calcium ion homeostasis, induces apoptosis (Yankncr B A, Duffy L K, Kirschner D A (October 1990) *Science (journal)* 250 (4978): 279-82). It is also known that Aβ selectively builds up in the mitochondria in the cells of Alzheimer's-affected brains, and it also inhibits certain enzyme functions and the utilization of glucose by neurons (Chen X, Yan S D (December 2006) *IUBMB Life* 58 (12): 686-94). Various inflammatory processes and cytokines may also have a role in the pathology of Alzheimer's disease. Inflammation is a general marker of tissue damage in any disease, and may be either secondary to tissue damage in AD or a marker of an immunological response (Greig N H, Mattson M P, Perry T, et al. (December 2004) *Ann. N. Y. Acad. Sci.* 1035: 290-315).

Four medications are currently approved by regulatory agencies such as the U.S. Food and Drug Administration (FDA) and the European Medicines Agency (EMEA) to treat the cognitive manifestations of AD: three are acetylcholinesterase inhibitors and the other is memantine, an N-methyl-D-aspartic acid (NMDA) receptor antagonist. Reduction in the activity of the cholinergic neurons is a well-known feature of Alzheimer's disease (Geula C, Mesulam M M (1995). *Alzheimer Dis Assoc Disord* 9 Suppl 2: 23-28). Acetylcholinesterase inhibitors are employed to reduce the rate at which acetylcholine (ACh) is broken down, thereby increasing the concentration of ACh in the brain and combating the loss of ACh caused by the death of cholinergic neurons (Stahl S M (2000). *J Clin Psychiatry* 61 (11): 813-814). Examples of the cholinesterase inhibitors approved for the management of AD symptoms include donepezil, galantamine, and rivastigmine. There is evidence for the efficacy of these medications in mild to moderate Alzheimer's disease, and some evidence for their use in the advanced stage (Birks J, Harvey R J (2006). *Cochrane Database Syst Rev* (1): CD001190). Only donepezil is approved for treatment of advanced AD dementia. The common side effects associated with cholinesterase inhibitors include nausea and vomiting, muscle cramps, decreased heart rate (bradycardia), decreased appetite and weight, and increased gastric acid production.

Donepezil, a cholinesterase inhibitor, is the most widely used drug for Alzheimer's disease. Donepezil hydrochloride is marketed by Eisai Inc. and Pfizer Inc. under the brand name Aricept®. It helps increase the levels of acetylcholine. In Alzheimer's disease there is a deficiency in acetlycholine in some areas of the brain, which accounts for some of the symptoms of the disease. Donepezil works by slowing down the breakdown of acetylcholine. Donepezil is the only treatment approved by the FDA for all stages of Alzheimer's disease: mild, moderate, and severe. Donepezil does not cure Alzheimer's, but studies have shown that in some patients it can improve mental function, which includes effects on memory and daily living.

Rivastigmine tartrate by Novartis Pharmaceutical Corporation is branded as Exelon® and Exelon® Patch. Galantamine hydrobromide is branded as Razadyne® and Razadyne® ER by Ortho-McNeil-Janssen Pharmaceuticals, Inc. These drugs also work by inhibiting the breakdown of acetylcholine. They are most effective when given in the earlier stages of Alzheimer's disease. They also have side effects similar to donepezil.

Tacrine, a reversible cholinesterase inhibitor, also works by slowing the breakdown of acetylcholine. Tacrine hydrochloride is sold by Sciele Pharma, Inc. as Cognex®. Side effects of the drug include nausea, vomiting, diarrhea, abdominal pain, skin rash, and indigestion.

Memantine is a noncompetitive NMDA receptor antagonist first used as an anti-influenza agent. Memantine hydrochloride is marketed under the brands Axura® and Akatinol® by Merz Pharmaceuticals, Namenda® by Forest Pharmaceuticals, Inc., Ebixa® and Abixa® by H. Lundbeck A/S and Memox® by Unipharm Ltd. It acts on the glutamatergic system by blocking NMDA receptors and inhibiting their overstimulation by glutamate (Lipton S A (2006) *Nat Rev Drug Discov* 5 (2): 160-170). Memantine has been shown to be moderately efficacious in the treatment of moderate to severe Alzheimer's disease. Memantine may have increased benefit when used in combination with donepezil, rivastigmine, galantamine, or THA. Side effects of memantine include tiredness, dizziness, confusion, and headache.

Antipsychotic drugs are modestly useful in reducing aggression and psychosis in Alzheimer's patients with behavioral problems, but are associated with serious adverse effects, such as cerebrovascular events, movement difficulties or cognitive decline, that do not permit their routine use (Ballard C, et al. 2009 *Lancet Neurology* 8: 151).

In addition to these medicines, the American Academy of Neurology has stated that vitamin E supplements (alpha-tocopherol) likely delay the time to clinical worsening in patients with Alzheimer's disease.

Glutamate is a useful excitatory neurotransmitter of the nervous system, although excessive amounts in the brain can lead to cell death through a process called excitotoxicity which consists of the overstimulation of glutamate receptors. Excitotoxicity occurs not only in Alzheimer's disease, but also in other neurological diseases such as Parkinson's disease and multiple sclerosis. Progesterone and vitamin D may afford neuroprotection against excitotoxicity.

Psychosocial interventions are used as an adjunct to pharmaceutical treatment for AD and can be classified within behavior-, emotion-, cognition- or stimulation-oriented approaches. Behavioral interventions attempt to identify and reduce the antecedents and consequences of problem behaviors. This approach has not shown success in improving overall functioning, but can help to reduce some specific problem behaviors, such as incontinence. Emotion-oriented interventions for treating AD include but are not limited to reminiscence therapy, validation therapy, supportive psychotherapy, sensory integration, also called snoezelen, and simulated presence therapy. Reminiscence therapy (RT) involves the discussion of past experiences individually or in group, many times with the aid of photographs, household items, music and sound recordings, or other familiar items from the past. Although there are few quality studies on the effectiveness of RT, it may be beneficial for cognition and mood. Simulated presence therapy (SPT) is based on attachment theories and involves playing a recording with voices of the closest relatives of the person with Alzheimer's disease. There is preliminary evidence indicating that SPT may reduce anxiety and challenging behaviors. Finally, validation therapy is based on acceptance of the reality and personal truth of another's experience, while sensory integration is based on exercises aimed to stimulate senses. The aim of cognition-oriented treatments, which include reality orientation and cognitive retraining, is the reduction of cognitive deficits. Reality orientation consists in the presentation of information about time, place or person in order to ease the understanding of the person about its surroundings and his or her place in them. On the other hand cognitive retraining tries to improve impaired capacities by exercitation of mental abilities. Stimulation-oriented treatments include art, music and pet therapies, exercise, and any other kind of recreational activities. Stimulation has modest support for improving behavior, mood, and, to a lesser extent, function.

In some embodiments, the methods of the present invention comprise administration of chlorite or a chlorite-containing compound in combination with other therapeutic agents and/or interventions that are used for the treatment of Alzheimer's disease and related complications. In one embodiment, chlorite or a chlorite-containing compound of the present invention is used in combination with an acetylcholinesterase inhibitor such as donepezil, rivastigmine, galantamine, or THA. In another embodiment, chlorite or a chlorite-containing compound of the present invention is used in combination with an NMDA receptor antagonist such as memantine. In another embodiment, chlorite or a chlorite-containing compound of the present invention is used in combination with vitamin E, progesterone or vitamin D. In other embodiments, chlorite or a chlorite-containing compound of the present invention is used in combination with one or more psychosocial interventions including behavior, emotion, cognition, and stimulation-oriented therapies.

E. Methods of Diagnosis

According to an embodiment of the invention, all of the formulations and pharmaceutical formulations described herein may be used in methods of diagnosis of disease or disorders. Methods of diagnosis may be combined with methods of treatment. In some embodiments, methods of diagnosis and treatment may be integrated. For example, in some embodiments, methods of diagnosis may be used to evaluate the efficacy of treatment and/or whether additional iterations of treatment are necessary. In some embodiments, methods of treatment may be interspersed with methods of diagnosis based on biomarkers to evaluate the stage of the disease.

According to an embodiment of the invention, a macrophage-related disease is diagnosed by measuring elevated levels of one or more biomarkers such as OPN, sCD14, and/or sCD163 in a subject. For example, the plasma levels of sCD14 and/or sCD163 are measured and then correlated against the normal plasma levels to make or confirm a diagnosis of disease. Similarly, responsiveness to treatment with an oxidative agent or with an immunomodulator in combination with an oxidative agent is evaluated by measuring reduced levels of one or more biomarkers, such as OPN, sCD14, and/or sCD163 following treatment with an oxidative agent or with an immunomodulator in combination with an oxidative agent. According to certain embodiments, elevated levels of OPN, sCD14, and/or sCD163 indicate pathology, and reduction of the levels of the biomarkers are an indication of efficacy of the treatment with an oxidative agent or with an immunomodulator in combination with an oxidative agent. In certain embodiments, in vitro treatment with an oxidative agent is performed on a sample from a subject to determine if the subject's disease will be responsive to treatment with an oxidative agent. In certain embodiments, one or more bioassays are performed after treatment with the oxidative agent to measure levels of biomarker to determine in vivo efficacy. In various embodiments, the biomarkers of interest are sCD14 and/or sCD163.

Methods of diagnosis according to the invention may be used individually or in combination with other methods of diagnosis. For example, there is no single test used to make an ALS diagnosis. An ALS diagnosis is typically based on a person's symptoms, such as spasticity and muscle weakness. Tests used to rule out other diseases before making an accurate ALS diagnosis include but are not limited to electromyography (EMG), nerve conduction velocity (NCV), magnetic resonance imaging (MRT), blood and urine tests, and muscle biopsy. Electromyography (EMG) is a test that uses a special recording technique that detects electrical activity in muscles. As muscles contract, they emit a weak electrical signal that can be detected, amplified, and tracked, providing information about how well the muscles are working. These responses are abnormal in cases of ALS. Another common test measures nerve conduction velocity (NCV). Specific abnormalities in the NCV results may suggest that the patient has a form of peripheral neuropathy (damage to peripheral nerves) or myopathy (muscle disease) rather than ALS. MRI is a noninvasive procedure that uses a magnetic field and radio waves to take detailed images of the brain and spinal cord. MRI scans can reveal evidence of other problems that may be causing the symptoms, such as a spinal cord tumor, a herniated disk in the neck, syringomyelia (a cyst in the spinal cord), or cervical spondylosis (arthritis of the neck). Blood tests may be used to detect the presence of heavy metals such as lead in the blood. Laboratory tests may detect abnormal proteins or hormone levels associated with other neurological diseases. A lumbar puncture or spinal tap may be performed to analyze the cerebrospinal fluid for genetic abnormalities (e.g., viral, autoimmune, neurotoxic). In order to make a definitive ALS diagnosis, a physician will investigate the patient's full medical history and conduct a neurological exam. The examination can be performed at regular intervals to assess whether possible symptoms of ALS are getting progressively worse.

In some embodiments, ALS is diagnosed by measuring chemokine production of macrophages from a subject being screened for ALS. For example, ALS may be diagnosed by measuring levels of sCD14 and/or sCD163 in a subject and comparing the measured levels to the levels in non-ALS subjects. In various embodiments, efficacy of ALS treatment may be diagnosed or monitored by measuring levels of sCD14 and/or sCD163 in a subject and comparing such levels to normal or to the subject's previous levels. In some embodiments, the ALS diagnosis may be based on median CD16 expression levels in CD14+ cells before treatment (i.e., diagnosis) or in conjunction with treatment (i.e., monitoring efficacy of treatment). In various embodiments, treatment may be with an oxidative agent such as sodium chlorite, chloramine-T (including the hydrate), and/or 1,3-dichloro-5,5-dimethylhydantoin.

In some embodiments, the subjects that are treated with the methods of the present invention are subjects who experience one or more of the symptoms including but not limited to muscle weakness, atrophy of muscles, hyperreflexia, and spasticity. In some embodiments, the subjects that can be treated with the methods of the present invention are patients who have been diagnosed with ALS based on EMG, NCV, MRI, blood or urine tests, or muscle biopsy. In some embodiments, methods of diagnosis and/or treatment are directed to biomarkers for ALS, including, for example, ubiquitin, TAR DNA-binding protein (TARDBP, TDP-43), Nogo-A, or SOD1. See, for example, Pradat et al., Mol. Diagn. Ther., 2009:13(2):115-25, hereby incorporated by reference.

In terms of diagnosis for Parkinson's disease (PD), there is no specific test or marker for PD. Typically, the diagnosis is based on medical history and neurological examination conducted by interviewing and observing the patient in person, which may include using the Unified Parkinson's Disease Rating Scale. A radiotracer for SPECT scanning machines called DaTSCAN is specialized for diagnosing dopamine loss characteristic of Parkinson's disease. The disease can be difficult to diagnose accurately, especially in its early stages due to symptom overlap with other causes of Parkinsonism. Physicians may need to observe the person for some time until it is apparent that the symptoms are consistently present. CT and MRI brain scans of people with PD are normal and therefore, not useful for diagnosis. However, doctors may sometimes request brain scans or laboratory tests in order to evaluate for other diseases that may produce signs of Parkinsonism.

To diagnose PD, the physician will perform a standard neurological examination, involving various simple tests of reactions, reflexes, and movements. Diagnosis of PD generally depends on the presence of at least two of the three major signs: tremor at rest, rigidity, and bradykinesia, as well as the absence of a secondary cause, such as antipsychotic medications or multiple small strokes in the regions of the brain controlling movement. Patients tend to be most aware of tremor and bradykinesia, and less so of rigidity.

Bradykinesia is tested by determining how quickly the person can tap the finger and thumb together, or tap the foot up and down. Tremor is determined by simple inspection. The physician assesses rigidity by moving the neck, upper limbs, and lower limbs while the patient relaxes, feeling for resistance to movement. Postural instability is tested with the "pull test," in which the examiner stands behind the patient and asks the patient to maintain their balance when pulled backwards. The examiner pulls back briskly to assess the patient's ability to recover, being careful to prevent the patient from falling. The examination also involves recording a careful medical history, especially for exposure to medications that can block dopamine function in the brain.

In some embodiments, the subjects that can be treated with the methods of the present invention are patients who experience one or more of the symptoms including but not limited to tremor of hands, arms, legs, jaw and face, stiffness or rigidity of the arms, legs and trunk, slowness of movement, poor balance and coordination, and postural instability. In some embodiments, the subjects that can be treated with the methods of the present invention are patients who have been diagnosed with Parkinson's disease by a physician. In some embodiments, the subjects that can be treated with the methods of the present invention are patients who have not been diagnosed with Parkinson's disease but are experiencing symptoms of PD.

There is currently no single test that accurately diagnoses Alzheimer's disease. Diagnosing Alzheimer's involves several types of evaluations. Evaluations commonly performed for diagnosis of Alzheimer's disease include but are not limited to: medical history which comprises an interview or questionnaire to identify past medical problems, difficulties in daily activities and prescription drug use, among other things. The doctor may wish to speak to a close family member to supplement information. Physical examination can include evaluation of hearing and sight, as well as blood pressure and pulse readings. Standard laboratory tests may include blood and urine tests designed to help eliminate other possible conditions. These will measure things like blood count, thyroid and liver function, and levels of glucose and other blood-based indicators of illness. A depression screening is also typically conducted. In some cases, a small sample of spinal fluid may be collected for testing. Neuropsychological testing can be performed in which doctors use a variety of tools to assess memory, problem-solving, attention, vision-motor coordination and abstract thinking, such as performing simple mental calculations. The goal is to better characterize the types of cognitive symptoms present, which might provide clues to the underlying cause. Brain-imaging scan which is a "structural" brain scan such as CT or MRI is recommended to rule out brain tumors or blood clots in the brain as the reason for symptoms. Other brain-imaging techniques might be able to identify telltale signs of early Alzheimer's reliably enough to be used as diagnostic tools.

In some embodiments, the subjects that are treated with the methods of the present invention are patients who experience one or more of the symptoms of Alzheimer's disease including but not limited to disturbances in short-term memory, problems with attention and spatial orientation, changes in personality, language difficulties and unexplained mood swings. In some embodiments, the subjects that are treated with the methods of the present invention have been diagnosed with Alzheimer's disease based on one or more diagnostic tests, including but not limited to those tests disclosed herein. In some embodiments, the subjects that are treated with the methods of the present invention are patients who have not been diagnosed with Alzheimer's disease but are experiencing symptoms of Alzheimer's disease. In some embodiments, the subjects that are treated with the methods of the present invention have been diagnosed with Stage 1 (mild) Alzheimer's disease. In some embodiments, the subjects that are treated with the methods of the present invention have been diagnosed with Stage 2 (moderate) Alzheimer's disease. In some embodiments, the subjects that are treated with the methods of the present invention have been diagnosed with Stage 3 (severe) Alzheimer's disease.

F. Kits and Articles of Manufacture

Unless the context makes otherwise clear, all of the formulations and pharmaceutical formulations described herein may be used in the kits described herein. In some embodiments, the kits are intended for administration of an oxidative agent, including without limitation a chlorite or a chlorite-containing agent, or pharmaceutical formulations comprising such oxidative agents. In some embodiments, the kits are intended for administration of an immunomodulatory agent, including without limitation an immunosuppressive agent, or pharmaceutical formulations comprising such immunomodulatory agents. The kits may include a unit dosage amount of the agents or formulations as described herein. In some variations, the kits comprise suitable packaging. In some variations, the kits comprise instructions for use of the oxidative and/or immunomodulatory agent. In a non-limiting example, the kit may contain instructions for using chlorite formulations to treat macrophage related disorders. Accordingly, the kits may be used for any of the treatment methods described herein, and in some embodiments contain suitable instructions for practicing any of the treatment methods described herein. In some embodiments, the kits are used to treat any one or more of the diseases or conditions described herein. Kits may also comprise an aid to administration of the oxidative or immunomodulatory agent formulation, such as an inhaler, spray dispenser (e.g., nasal spray), syringe for injection or pressure pack for capsules, tablets, or suppositories.

The chlorite formulations described herein may be assembled in the form of kits. In some variations the kit provides the chlorite and reagents to prepare an aqueous chlorite formulation for administration. In some embodiments, the formulations in the kits of the invention comprise chlorite-containing agents, non-chlorite oxidative agents, or immunosuppressive agents. In some variations the formulation is an aqueous solution. In some variations the formulation is a sterile solution. In some variations, a kit provides a pharmaceutically acceptable diluent, either already mixed with the formulations or formulations described herein or provided in a separate container from the formulations or pharmaceutical formulations described herein. In some variations, the diluent is a saline solution. In some variations, the composition comprises a dry (such as lyophilized) composition that can be reconstituted or dissolved to form the formulations or pharmaceutical formulations described herein. When the formulation is in a dry form, the kit may comprise one or more of a pharmaceutically acceptable solvent, diluent, and a pH adjusting agent, either separately from or as part of the diluent. In some variations, a kit or article of manufacture comprises a dry form of the active agent, e.g., chlorite, a pharmaceutically acceptable solvent, and pH adjusting agent. In some variations the pH adjusting agent is incorporated into the solvent. In some variations, a kit or article of manufacture comprises the active agent in dry form and a pharmaceutically acceptable diluent. In some variations the pH adjusting agent is incorporated into the diluent. In some variations, the formulations or pharmaceutical formulations described herein are sterile, reconstituted formulations. In some variations, the formulations or pharmaceutical formulations described herein are sterile, reconstituted formulations in unit dosage form. In some variations, the formulations or pharmaceutical formulations described herein are sterile, reconstituted formulations in unit dosage form in suitable packaging.

The kit may contain a device for administration or for dispensing the compositions, including, but not limited to one or more syringes, pipettes, transdermal patches, or inhalants.

The kit may include other therapeutic compounds or formulations for use in conjunction with the formulations described herein. These compounds may be provided in a separate form, or mixed with the oxidative and/or immunomodulatory agent formulations or pharmaceutical formulations described herein. As a non-limiting example, a kit may comprise a chlorite formulation and a formulation for metformin. When the therapeutic agent is contained in a different formulation than the oxidative and/or immunomodulatory agent of the present invention, they can be administered sequentially or substantially simultaneously.

In some variations the kit includes instructions for preparation and administration of the formulation. In some variations the kit includes instructions as to side effects of the formulation. in another variation the kit optionally includes any other relevant information. The instructions may be in any suitable format, including, but not limited to, printed matter, videotape, computer readable disk, or optical disc. The instructions may be located inside the housing or outside the housing, and may be printed on the interior or exterior of any surface forming the housing that renders the instructions legible.

Described herein are kits for treating an individual who suffers from or is susceptible to a macrophage related disease treatable by the oxidative agent, for example, chlorite formulations described herein, comprising a container comprising a unit dosage amount of a chlorite formulation as described herein, and instructions for use. Further described herein are kits for treating an individual who suffers from or is susceptible to a macrophage related disease treatable by immunomodulatory agents, for example, immunosuppressants, comprising a container comprising a unit dosage amount of the agent and instructions for use. The container may be any of those known in the art and appropriate for storage and delivery of oral, intravenous, systemic, parenteral, rectal, urethral, transdermal, or inhalation formulations.

Kits may also be provided that contain sufficient dosages of the oxidative agent formulation to provide effective treatment for an individual for an extended period, including but not limited to any of about a week, about 2 weeks, about 3 weeks, about 4 weeks, about 6 weeks or about 8 weeks or more.

Also provided herein are articles of manufacture comprising the formulations or pharmaceutical formulations described herein, or unit dosage forms in suitable packaging, including but not limited to vials or vessels, including but not limited to scaled vials or vessels and sterile scaled vials or vessels. Non-limiting examples of suitable packaging for the formulations and pharmaceutical formulations described herein are known in the art, and include, for example, any of vials (such as sealed vials), vessels (such as sealed vessels), ampules, bottles, jars, flexible packaging (e.g., sealed Mylar or plastic bags), and the like. Such packaging may optionally limit the amount of light to which the formulation is exposed. These articles of manufacture may further be sterilized and/or sealed.

The invention is further illustrated by the following non-limiting examples.

EXAMPLES

Example 1

Purification of Chlorite

This procedure was performed in diminished light, e.g., with overhead lights off, and out of direct sunlight.

Sodium Chlorite (80 wt %, Sigma-Aldrich lot #09911CD) was dissolved in 1000 mL of distilled water. The flask was mounted to a rotary evaporator, and the bath temperature set to 70° C. Vacuum was applied, and increased until the water began to distill over in a controlled manner. The vacuum was applied until the mixture put down a load of solids, and 550 mL of water had distilled over. Using a coarse sintered glass funnel, the solids were removed by suction filtration of the hot solution. These solids were mostly sodium chloride.

The filtrate was stored at −25° C. for a period of time sufficient to precipitate the chlorite (approximately 24 hours). The entire mixture froze solid. The frozen mixture was broken up and centrifugally filtered while cold. Purified sodium chlorite was collected as the frozen solid melted. The centrifuge had a 12-inch stainless steel basket, 50 micron polypropylene bag, and was run at 2000 rpm. HPLC analysis using an ion-separating column and ion detector showed 99.04% purity. The material is presumed to be a mixture of hydrate and non-hydrate.

Example 2

Purification of Chlorite

The method described in Example 1 was performed, but using coarse sintered glass suction filtration rather than centrifugal filtration for the cold filtration. After the first filtration, chlorite purity after the first crystallization was 91.9%. The crystallization step was repeated a second time. After the second recrystallization/suction filtration, the chlorite was 99.5% pure.

In one method, a suspension of $NaClO_2$ (technical grade, 80% purity) is triturated with water at 17-25° C., the suspension is stored at −25° C. to −5° C., and the cold mixture is filtered. The series of steps is repeated until the sodium chlorite assay shows ≥99.0% area under the curve the ion chromatography.

Figure 5:
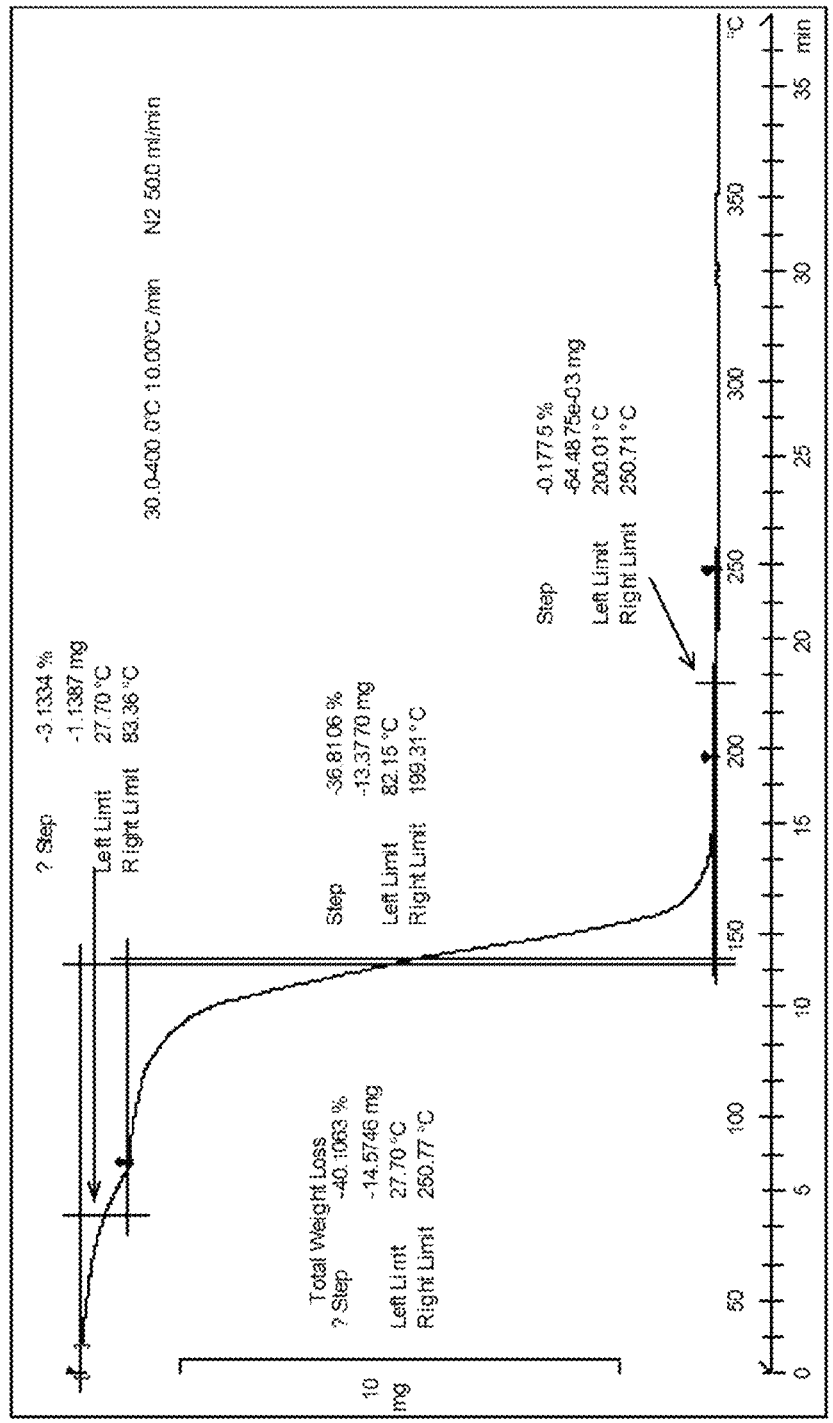
FIG. 5 shows a Thermo-Gravimetric Analysis (TGA) of a sample of sodium chlorite purified according to the invention. The thermogram shows the loss of a total of 40.0% weight from ambient temperature to about 160° C.
Figure 6:
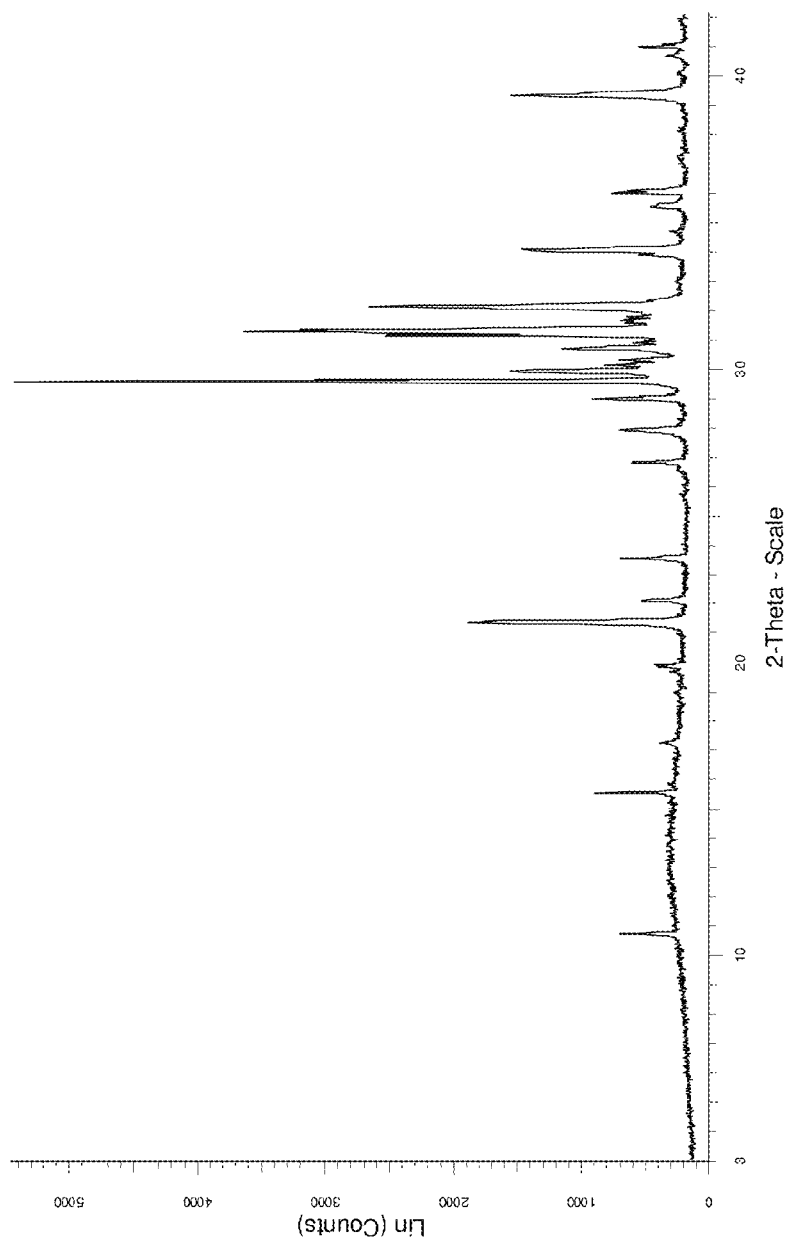
FIG. 6 shows an X-ray powder diffraction (XRPD) pattern for a sample of sodium chlorite purified according to the invention. The XRPD pattern indicates that the material is crystalline.
Figure 7:
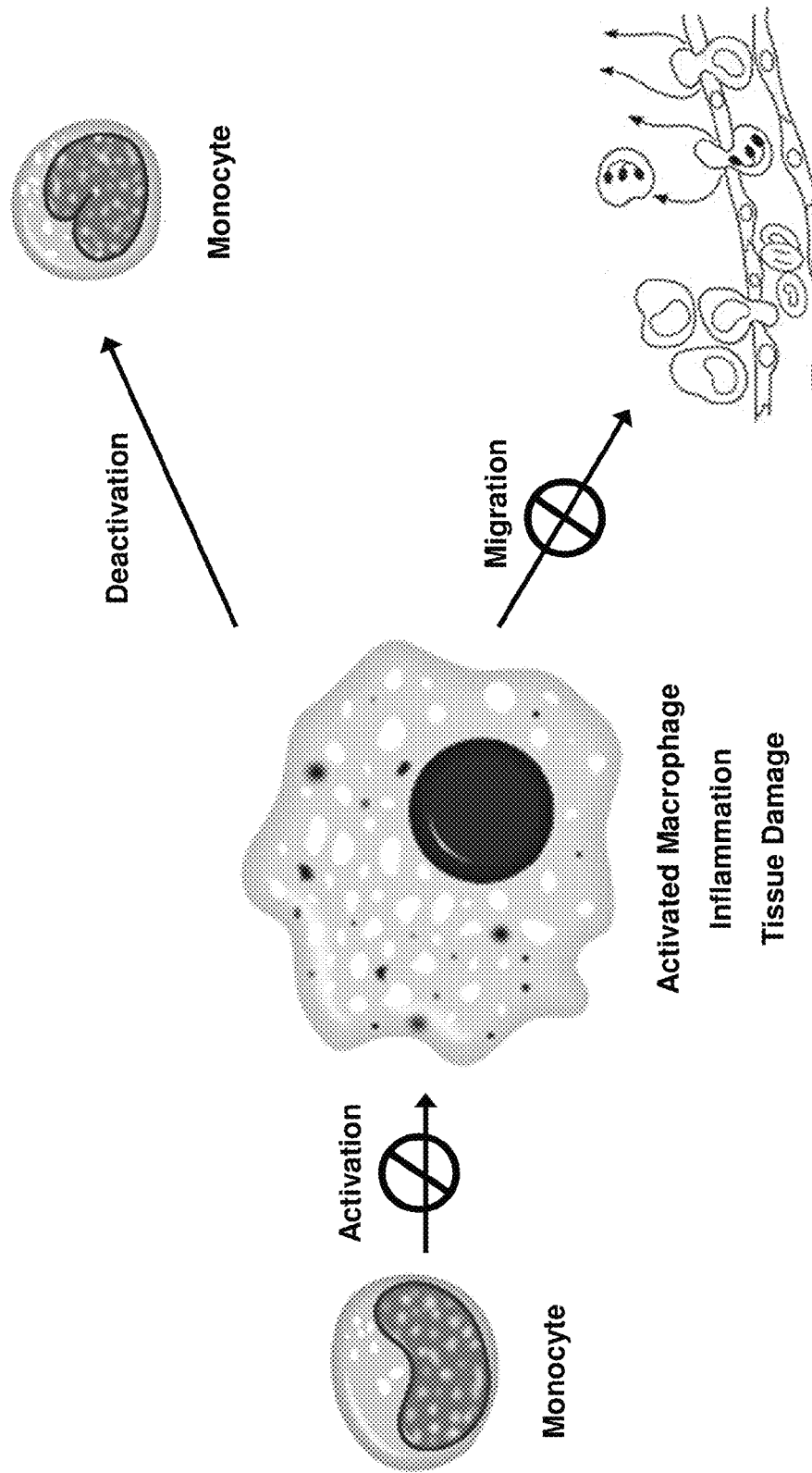
FIG. 7 shows various pathways for modulating macrophage related disorders.

FIG. 5 shows a Thermo-Gravimetric Analysis (TGA) of a sample of sodium chlorite purified according to the invention. The thermogram shows the loss of a total of 40.0% weight from ambient temperature to about 160° C. FIG. 6 shows an X-ray powder diffraction (XRPD) pattern for a sample of sodium chlorite purified according to the invention. The XRPD pattern indicates that the material is crystalline.

Example 3

Adjustment of Chlorite Formulation pH

To prepare a chlorite formulation at a lower pH, sodium chlorite purified by the method of Example 2 was dissolved in distilled water and stirred using a magnetic stirrer. A calibrated pH probe was put in the solution. Small amounts of monosodium phosphate monohydrate were added, until the pH reached and stabilized at 7.62. In the event of the pH drifting lower than the target pH, the pH can be adjusted back with 0.1 N NaOH.

This solution was sampled, and assayed for sodium chlorite content by HPLC. Column: Novosep A-2 Alltech 250×4 mm; eluant: 3.6 mM sodium carbonate. Rate: 0.8 mL/min. Detected with a suppressed Alltech 650 conductivity detector. Quantitation was performed by standard iodimetry. See Inorganic Syntheses, section under Chlorine (IV) Oxide; Sodium Chlorite analysis, p. 156. The concentration was determined to be 1.36 M. To prepare a 4.25 wt % solution (0.47 M), 200 mL were diluted to 580 mL.

Example 4

Treatment of a Macrophage Related Disease-Multiple Sclerosis

Experimental Autoimmune Encephalomyelitis (EAE) is a disease that is given to laboratory animals that produces symptoms similar to those of multiple sclerosis (MS) in humans. It is mostly used in mice and rats, but can also be produced in monkeys, rabbits and guinea pigs.

Female C57BL/6, mice 5-8 weeks old are immunized subcutaneously with 200 µg of $MOG_{35\text{-}55}$ peptide emulsified in CFA supplemented with 5 mg/ml of *Mycobacterium tuberculosis*. The mice receive intraperitoneal injections with 250 ng pertussis toxin (Sigma-Aldrich, St. Louis, Mo., USA) at the time of immunization and 48 hours later. After 7 days, the mice receive an identical booster immunization with MOG/CFA without pertussis toxin. Clinical disease of EAE usually commences between day 16 and day 20 after immunization.

Macrophages are important effector cells involved in the pathogenesis of demyelination in multiple sclerosis. These EAE mice will be administered chlorite to reduce or inhibit macrophage activation and thereby ameliorating the disease. The mice will be treated in two ways: 1) short term—i.e., just long enough to observe the desired change in macrophage phenotype—which may require only one or two injections of chlorite; and 2) longer term monitor disease progression. Setting up the model, treating the mice, and monitoring CNS lesions and neurological degeneration are straightforward to those of skill in the art.

The mice are scored four times per week as follows: 0, no detectable signs of EAE; 0.5, limp distal tail; 1, complete limp tail; 1.5, limp tail and hind limb weakness; 2, unilateral partial hind limb paralysis; 2.5, bilateral partial hind limb paralysis; 3, complete bilateral hind limb paralysis; 3.5, complete hind limb paralysis and unilateral forelimb paralysis; 4, total paralysis of both forelimbs and hind limbs; 5, death. Mice scoring greater than 4 but less than 5 are euthanized.

The results will suggest that chlorite is effective in treating EAE in mice.

Example 5

Evaluation of Oxidative Drugs for Immune Regulating Activity In Vitro and in Vivo A panel of in vitro tests shows activities of drug in dose dependent manner duplicating in vitro activities of reference drug that has in vivo activities. The goal of this example is to duplicate the in vivo regulatory activities of WF10 chlorite. Examplary in vivo regulatory activities of WF10 chlorite include but are not limited to regulation of monocyte HLA-DR expression, regulation of TNF-α RNA expression, and restoration of macrophage phagocytic function in vivo. Oxidative drugs are tested as compared to WF10. One way of evaluating oxidative drugs for equivalency is to test them in dose ranging studies for effects on monocyte cell surface antigen expression and effects on secretory molecules.

In Vitro Drug Study: Treatment of PBMC (Peripheral Blood Mononuclear Cells) with Chlorite or WF10

The purpose of this study is to assess the effect of chlorite and WF10 (a chlorite-based compound) on primary cultures of peripheral blood mononuclear cells (PBMC) and compare the differences between chlorite and WF10. The procedure is performed in a biological safety cabinet using standard aseptic techniques and universal precautions for handling human blood samples well known to one skilled in the art.

PBMCs are cultured in RPMI-1640 medium with 2.0 g/L Glucose, 0.3 g/L L-glutamine, and 2.0 g/L $NaHCO_3$ containing 10% fetal bovine serum and 11 g/L sodium pyruvate. Peripheral blood mononuclear cells (PBMC) are isolated from Heparinized Blood and collected in BD Vacutainer Blood Collection Tubes with sodium heparin according to standard techniques known in the art and the manufacturer's protocols. PBMC concentration is adjusted to $1\times10^6$ cells/mL in the culture media for chlorite/WF10 treatment.

In terms of the treatment of PBMC with chlorite or WF10, PBMCs are isolated and cell density is adjusted to $1\times10^6$ cells/mL in the culture media. PBMC suspensions ($1\times10^6$ cells/mL) are transferred to polypropylene tubes: <2 mL cell suspensions are transferred into 12×75 mm polypropylene tubes; >3 mL cell suspensions are transferred to 50 mL polypropylene tubes. For dose response experiments, 1 tube of PBMCs is treated for each dose of chlorite or WF10, and each dose is assayed with triplicate culture tubes. Chlorite and WF10 are prepared as shown in the tables below: chlorite/WF10 diluted solutions are prepared immediately before use.

| Chlorite Stock concentration = 57 mM, stored in the dark at 4° C. | | | | |
|---|---|---|---|---|
| Initial concentration (µM) | | Intermediate concentration (µM) | | Final concentration (µM) |
| 57000 | 1:9.5 (210.5 µL of chlorite stock + 1789.5 µL media) | 6000 | 1:10 (100 µL of 6000 µM chlorite solution + 900 µL of cell suspension) | 600 |

-continued

Chlorite
Stock concentration = 57 mM, stored in the dark at 4° C.

| Initial concentration (μM) | | Intermediate concentration (μM) | | Final concentration (μM) |
|---|---|---|---|---|
| 6000 | 1:2 (1000 μL of 6000 μM chlorite solution + 1000 μL media) | 3000 | 1:10 (100 μL of 3000 μM chlorite solution + 900 μL of cell suspension) | 300 |
| 3000 | 1:3 (700 μL of 3000 μM chlorite solution + 1400 μL media) | 1000 | 1:10 (100 μL of 1000 μM chlorite solution + 900 μL of cell suspension) | 100 |
| 3000 | 1:10 (100 μL of 3000 μM chlorite solution + 900 μL media) | 300 | 1:10 (100 μL of 300 μM chlorite solution + 900 μL of cell suspension) | 30 |
| 1000 | 1:10 (100 μL of 1000 μM chlorite solution + 900 μL media) | 100 | 1:10 (100 μL of 100 nM chlorite solution + 900 μL of cell suspension) | 10 |

WF10
Stock concentration = 62 mM, stored in the dark at 4° C.

| Initial concentration (μM) | | Intermediate concentration (μM) | | Final concentration (μM) |
|---|---|---|---|---|
| 62000 | 1:10.333 (241.9uL of WF10 stock + 2258.1 μL media) | 6000 | 1:10 (100 μL of 6000 μM WF10 solution + 900 μL of cell suspension) | 600 |
| 6000 | 1:2 (1000 μL of 6000 μM WF10 solution + 1000 μL media) | 3000 | 1:10 (100 μL of 3000 μM WF10 solution + 900 μL of cell suspension) | 300 |
| 3000 | 1:3 (700 μL of 3000 μM WF10 solution + 1400 μL media) | 1000 | 1:10 (100 μL of 1000 μM WF10 solution + 900 μL of cell suspension) | 100 |
| 3000 | 1:10 (100 μL of 3000 μM WF10 solution + 900 μL media) | 300 | 1:10 (100 μL of 300 μM WF10 solution + 900 μL of cell suspension) | 30 |
| 1000 | 1:10 (100 μL of 1000 μM WF10 solution + 900 μL media) | 100 | 1:10 (100 μL of 100 μM WF10 solution + 900 μL of cell suspension) | 10 |

Varying doses of chlorite or WF10 are added to each tube of PBMC suspensions and mixed gently by slowly pipeting up and down a few times. For the control tube containing no drug, the same volume of blank media is added instead. Cell suspensions are incubated in a humidified incubator at 37° C. with a 5% $CO_2$ atmosphere for 3 days. On day 3, PBMCs are centrifuged at 1520RPM (300×g) for 10 minutes at 25° C. and cell culture supernatants are collected and stored at −80° C. for cytokine assays. Cell pellets are washed once by PBS($Mg^{+2}/Ca^{+2}$ Free) for immunophenotype flow cytometric analysis.

Immunophenotype flow cytometry assay: Flow cytometry is a standard technique for assaying immunophenotype and it is well known to one of ordinary skill in the art. Briefly, PBMCs treated as described hereinabove are resuspended in PBS ($Mg^{+2}/Ca^{+2}$ Free) to make the final concentration ~0.5-1×10$^6$ cells/mL, and aliquoted at 100 μl cell suspendsion into 12×75 mm polystyrene tube. PBMCs are stained with CD16-PE and CD14-PerCP for 20 minutes in the dark at room temperature. Negative controls consist of aliquots stained with isotype IgG-PE and IgG-PerCP (all staining are performed per manufacturer's specifications). The stained PBMCs are washed by adding 2 mL of PBS($Mg^{+2}/Ca^{+2}$ Free), and then centrifuged at 1520RPM (300×g) for 10 minutes at 25° C. Cells are fixed by add 0.5 mL of fixative solution (1% paraformaldehyde/$NaN_3$/PBS). Fluorescent emission is measured using FACSCAN flow cytometor (Becton-Dickinson).

For the culture supernatant quantitative cytokine assay, some of the PBMC culture supernatants are sent out to a commercial laboratory, AssayGate, Inc, Ijamsville M D, USA, for cytokine quantitative analysis. Other quantitative cytokine assays are performed with commercially available ELISA kits according to the manufacturer's instructions.

FIGS. 1-4 illustrate examples testing two different formulations of chlorite or WF10. Chlorite and WF10 regulate cell surface and secreted antigens of monocytes in vitro. Cell surface antigen CD16 was measured on CD14+ cells, i.e., monocytes, for both normal peripheral blood mononuclear cells (PBMC) and ALS. For measuring secreted molecules, normal PBMC culture supernatants were collected and measured three days after exposure to the oxidative drug in various concentrations. Levels of secreted molecules such as osteopontin, MMP-9, TNF-α, IL-6, IL-8, and MCP-1 were measured. All results were normalized to chlorite concentration.

Figure 1E:
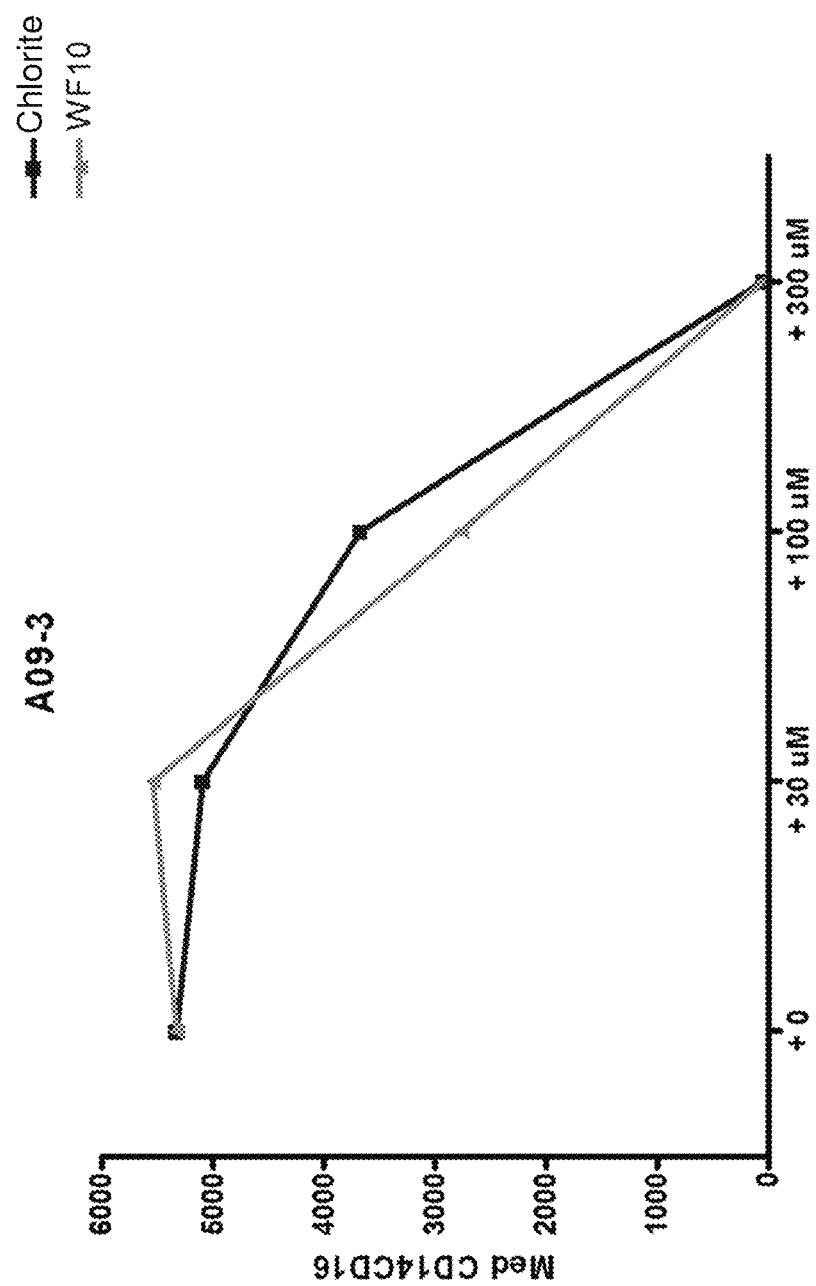

FIG. 1 shows median CD16 expression levels on CD14+ cells after exposure of five samples of normal PBMCs to WF10 (triangle) or chlorite (square) at various concentrations for three days. As the concentration of WF10 or chlorite increased, the levels of CD14CD16 on PBMCs in all five samples were decreased. FIG. 2 shows that treatment of five ALS blood samples with a chlorite formulation containing 150 μM chlorite caused down-regulation of CD16 surface expression on CD14+ cells, i.e., monocytes. Cell surface expression of a molecule can be measured by a variety of techniques known in the art, for example, flow cytometry.

Figure 3:
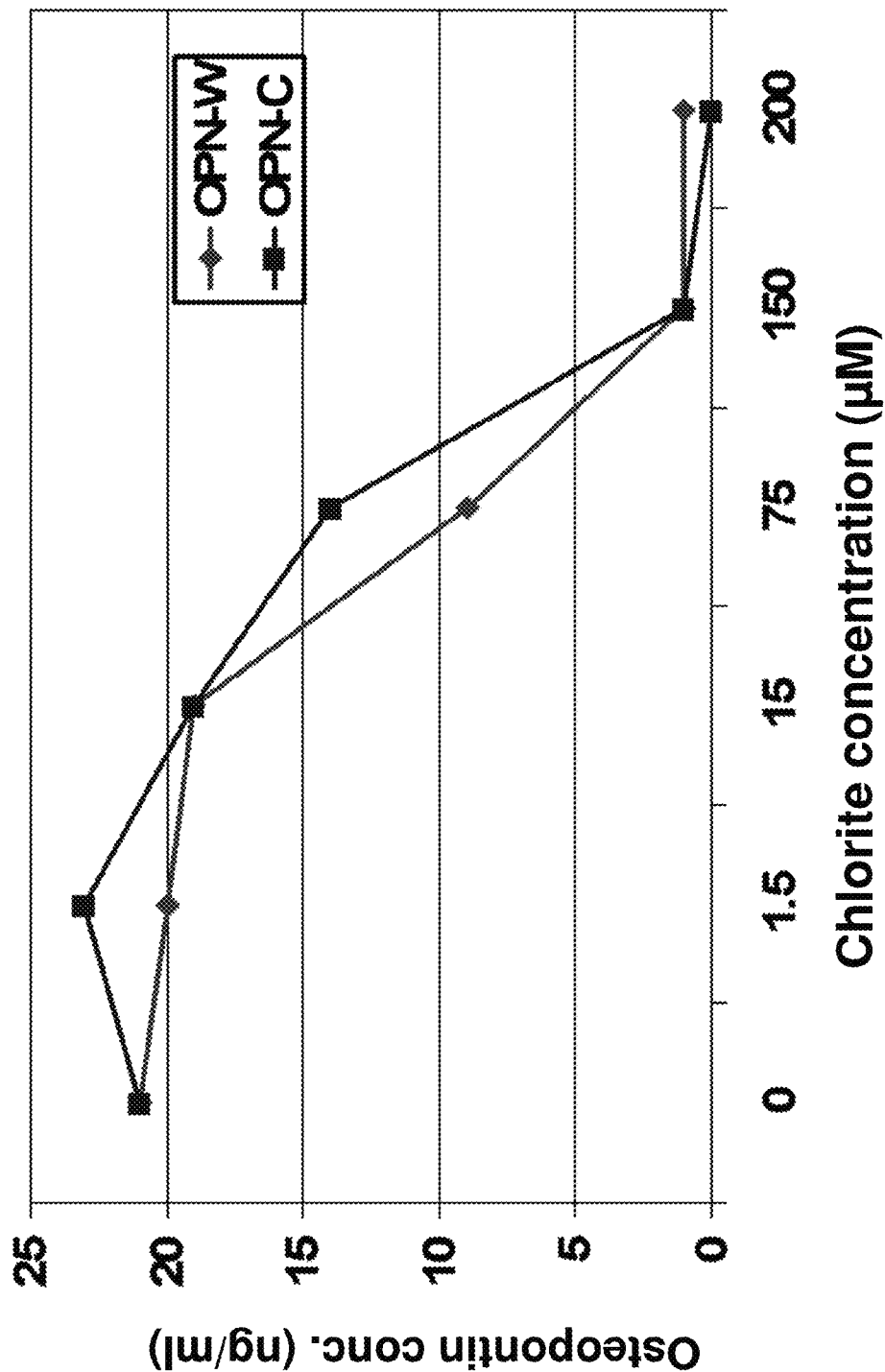
FIG. 3 shows osteopontin secretion by monocytes regulated by chlorite. WF10 (OPN-W) and chlorite (OPN-C) inhibit osteopontin secretion by monocytes to a similar extent.

Chlorite also regulates the secretion of molecules by monocytes. Monocytes were exposed to chlorite or WF10 at various concentrations for three days. Culture supernatants were collected and the levels of secreted molecules in the supernatants were measured by enzyme-linked immunosorbent assay (ELISA), which is well known to one of ordinary skill in the art. An example of such secreted molecule is osteopontin, which is a macrophage chemotactic protein. As FIG. 3 shows, osteopontin secretion by monocytes was down-regulated by both WF10 (OPN-W) and chlorite (OPN-C) to a similar extent as increasing concentrations of chlorite inhibited osteopontin secretion, suggesting an effect of chlorite on macrophage activation and accumulation.

Figure 4:
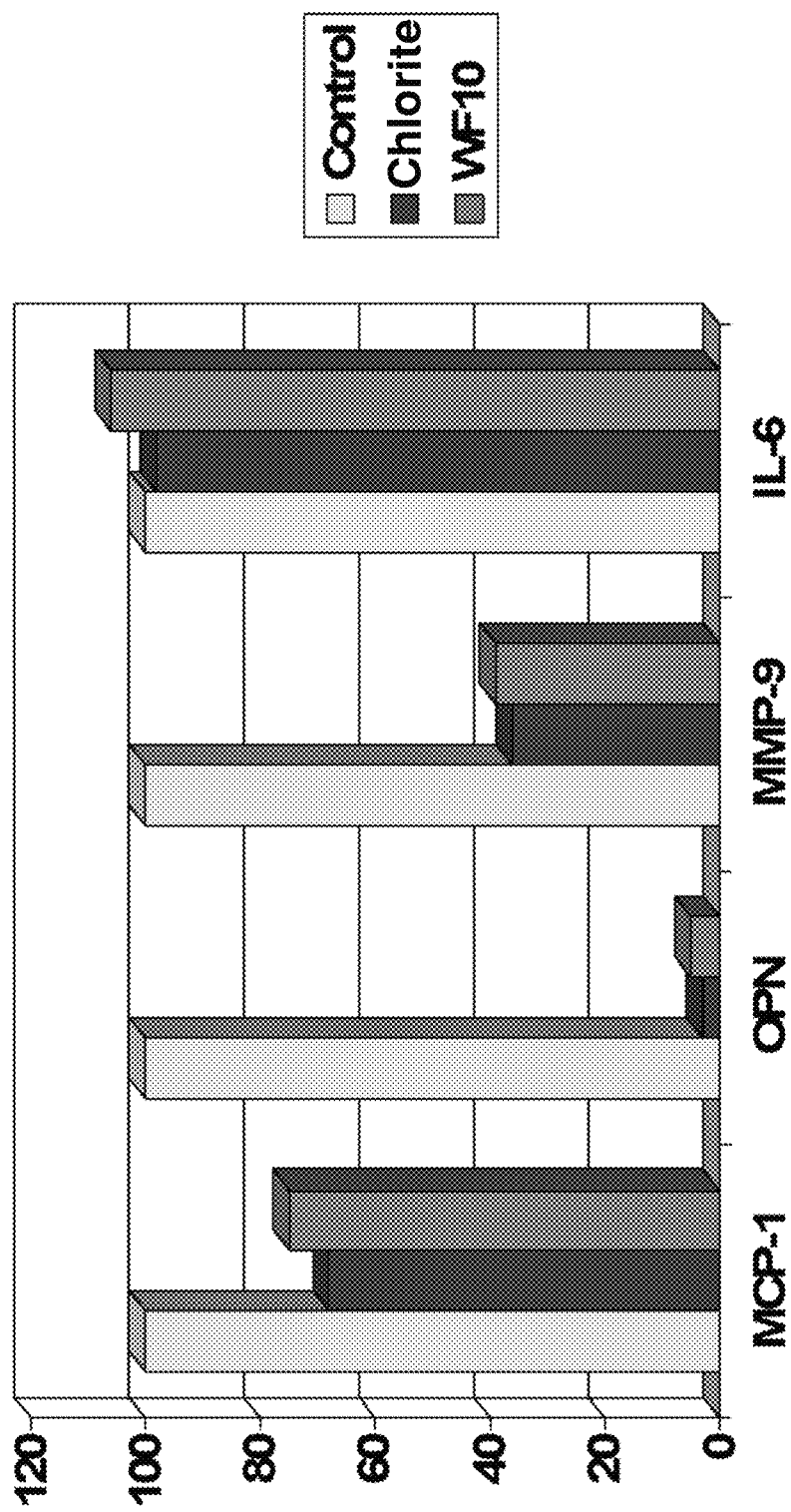
FIG. 4 shows cytokine secretion by ALS peripheral blood mononuclear cells (PBMCs) regulated by chlorite. Both WF10 and chlorite inhibit MCP-1, osteopontin (OPN), and MMP-9 secretion by PBMCs from amyotrophic lateral sclerosis (ALS) blood to a similar extent. WF10 and chlorite do not have a significant effect on IL-6 secretion by ALS PBMCs as compared to the control.
Figure 12:
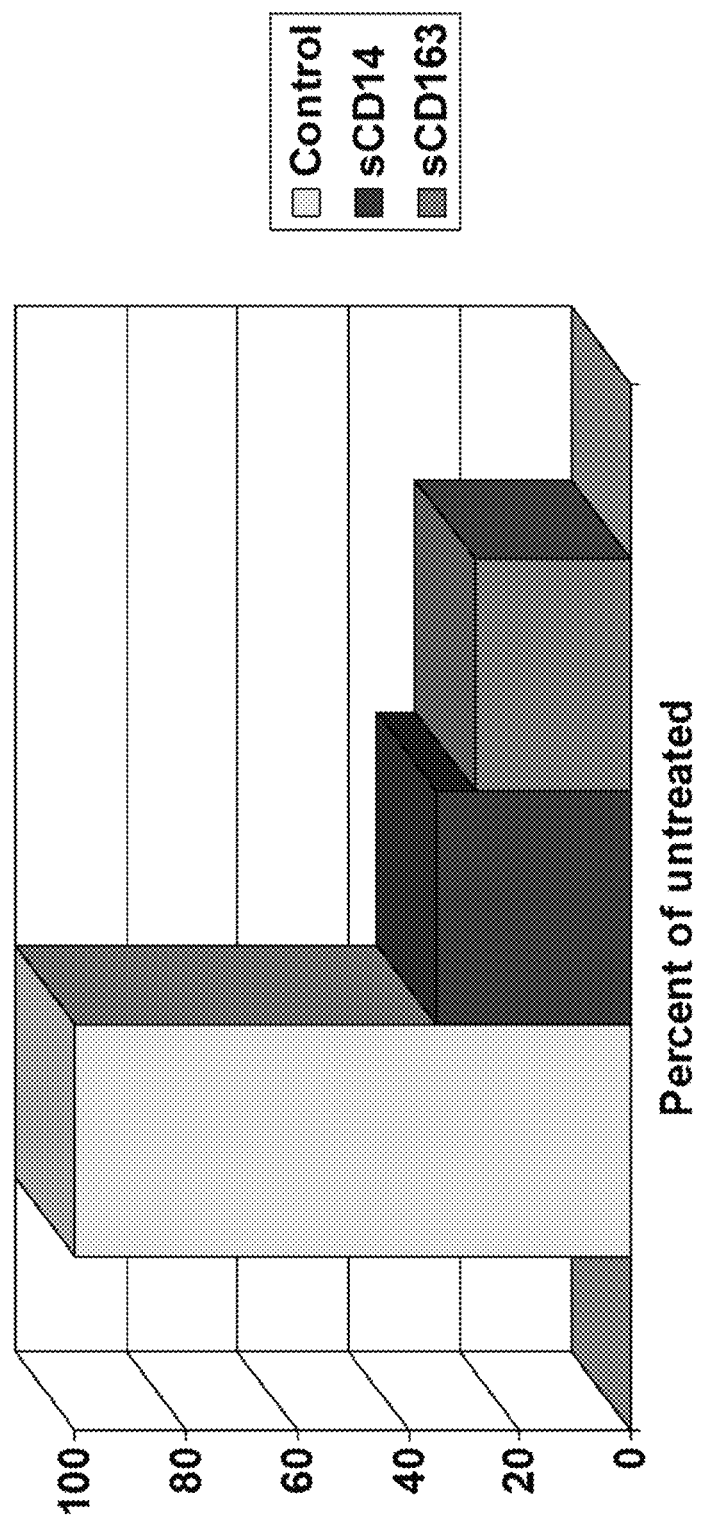
FIG. 12 shows the effect of sodium chlorite on ALS patient monocytes in blocking production of sCD14 and sCD163.

Cytokine secretion by PMBCs upon exposure to chlorite was also measured. PBMCs from ALS blood samples were exposed to chlorite or WF10 for three days. Supernatants were harvested and levels of cytokines including monocyte chemotactic protein-1 (MCP-1), OPN, matrix metallopeptidase 9 (MMP-9), and IL-6 were determined by ELISA. As shown in FIG. 4, chlorite downregulated the secretion of MCP-1, OPN, and MMP-9, while it did not have significant effect on IL-6 secretion as compared to the control. Chlorite and WF10 had similar effects on the cytokine secretion by PBMCs from ALS blood samples. As shown in FIG. 12, ALS PBMCs were treated with 300 micromolar sodium chlorite for 3 days, and supernatant mean levels of sCD14 and sCD163 were determined by ELISA (n=13), which showed that chlorite downregulated the secretion of sCD14 and sCD163.

CD14 cells typically require C16+ differentiation state to migrate from blood into tissues. FIG. 8 shows the effect of sodium chlorite (n=4) and various additional compounds at 300 micromolar concentration on CD16 expression in CD14+ cells as well as monocyte toxicity. Experimental conditions were generally as described above. Sodium chlorite and N-chloro compounds decreased CD16 expression. Toxicity data showed the reduction in % CD14 monocytes according to the following qualitative scale: "No" was an increase or no change in % CD14 monocytes following treatment with the compound; +/− was less than 5% reduction; + was reduction between 11-20%; ++ was reduction between 21-30%; +++ was reduction between 31-40%; and ++++ was reduction between 41-50%.

As shown, chlorite affected both cell surface antigen expression and cytokine secretion by monocytes.

Example 6

Treatment of Type II Diabetes

Obese mice develop insulin resistance and glucose intolerance equivalent to Type II diabetes. After being placed on a high fat/high caloric diet, the mice experience an inflammatory immune response in the visceral adipose tissue (VAT). Without being bound by theory, the inflammatory response may be a causative agent of the disease because the inflammatory response and the disease can be reversed for at least several months by brief systemic treatment with an anti-CD3 (anti-T cell) antibody. The immune cell content in human visceral fat of obese patients appears very similar to that seen in obese mice. Inflammatory macrophages appear in the VAT of obese diabetic mice and these cells appear to revert to non-inflammatory macrophages after anti-CD3 antibody treatment, suggesting that the effect of anti-CD3 antibody treatment may be at least partially mediated through the change in macrophages.

The diet induced obese (DIO) mouse model is an excellent model of Type II diabetes. To create the model, normal mice, e.g., C57Black/6, are put on a high fat/high calorie diet. DIO mice will be administered chlorite to reverse their macrophage phenotype and the disease. The mice will be treated in two ways: 1) short term—i.e., just long enough to observe the desired change in macrophage phenotype—which may require only one or two injections of chlorite; and 2) longer term monitor disease progression. Setting up the model, treating the mice, and monitoring glucose tolerance and insulin sensitivity are straightforward to those of skill in the art. VAT will be assessed for cellular analysis using flow cytometry.

Example 7

Treatment of ALS

Laboratory models of amyotrophic lateral sclerosis (ALS) can help understand the basic process of the disease, with an eye towards developing new therapies for ALS. The mainstay of animal model for ALS has been a mouse that bears the mutated human gene associated with familial ALS. Mutation of the SOD 1 gene can produce many aspects of ALS. The mouse bearing the human gene for mutant SOD1 was the first lab model clearly linked to ALS based on a known cause of the disease. But other models are now available or being designed. A newer rodent model, an ALS rat, also is engineered to express human mutant SOD 1. The rat is larger and surgery is easier for applications such as stem cell transplants and other approaches that require injections into the spinal cord. The worm, fish and the fly models of ALS will be valuable as tools as they may offer a basic and simple biology. Cell based tests that reflect the disease process in ALS can rapidly report on the potential of new molecules to serve as therapeutics.

Animal models of ALS provide an opportunity to study this incurable and fatal human disease both clinically and pathologically (Pioro E P, Mitsumoto H Clin Neurosci. 1995-1996; 3(6):375-85). Four natural disease models have been most extensively studied, including three mouse models: motor neuron degeneration (Mnd), progressive motor neuronopathy (pmn), wobbler, and one canine model: hereditary canine spinal muscular atrophy (HCSMA). The wobbler mouse has been the most extensively studied of these models with analyses of clinical, pathological (perikaryon, axon, muscle), and biochemical features. Experimentally induced ALS animal models have allowed controlled testing of various neurotoxic, viral and immune-mediated mechanisms. Molecular techniques have recently generated mouse models in which genes relevant to the human disease or motor neuron biology have been manipulated. The most clinically relevant of these is a transgenic mouse overexpressing the mutated SOD 1 gene of FALS patients, which has already provided significant insights into mechanisms of motor neuron degeneration in this disease. Because no single animal model perfectly reflects all the clinical and pathological characteristics of ALS, study of selected features from the most relevant models will contribute to a better understanding of the pathogenesis and/or etiology of this disease.

The transgenic mouse overexpressing the mutated SOD1 gene of FALS patients is an excellent model of ALS. Such ALS mice bearing the mutant human SOD1 gene will be administered chlorite to reverse their macrophage phenotype and the disease. The mice will be treated in two ways: 1) short term—i.e., just long enough to observe the desired change in macrophage phenotype—which may require only one or two injections of chlorite; and 2) longer term monitor disease progression. Setting up the model, treating the mice, and monitoring neurological signs including motor activities and disease-associated behavioral changes are straightforward to those of skill in the art. VAT will be assessed for cellular analysis using techniques such as flow cytometry.

Example 8

Blood Monocyte Migration

Figure 9:
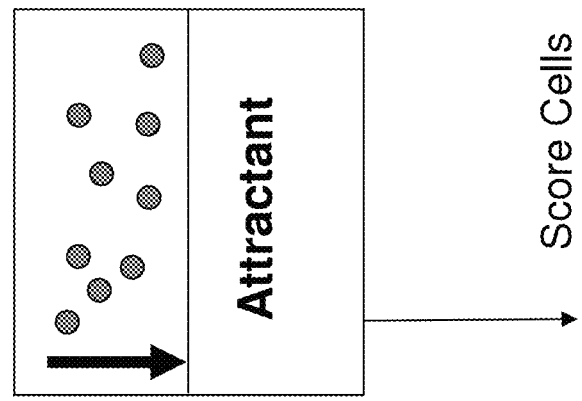
FIGS. 9, 10, and 11 show the experimental design for Example 8, the effect of ALS patient macrophage supernatant on blood monocyte migration, and the effect of sodium chlorite on blood monocyte migration ("Score Cells" in FIG. 9 means: After 4 hours score the cells that are captured by the membrane normalized to no chemoattractant background).
Figure 10:
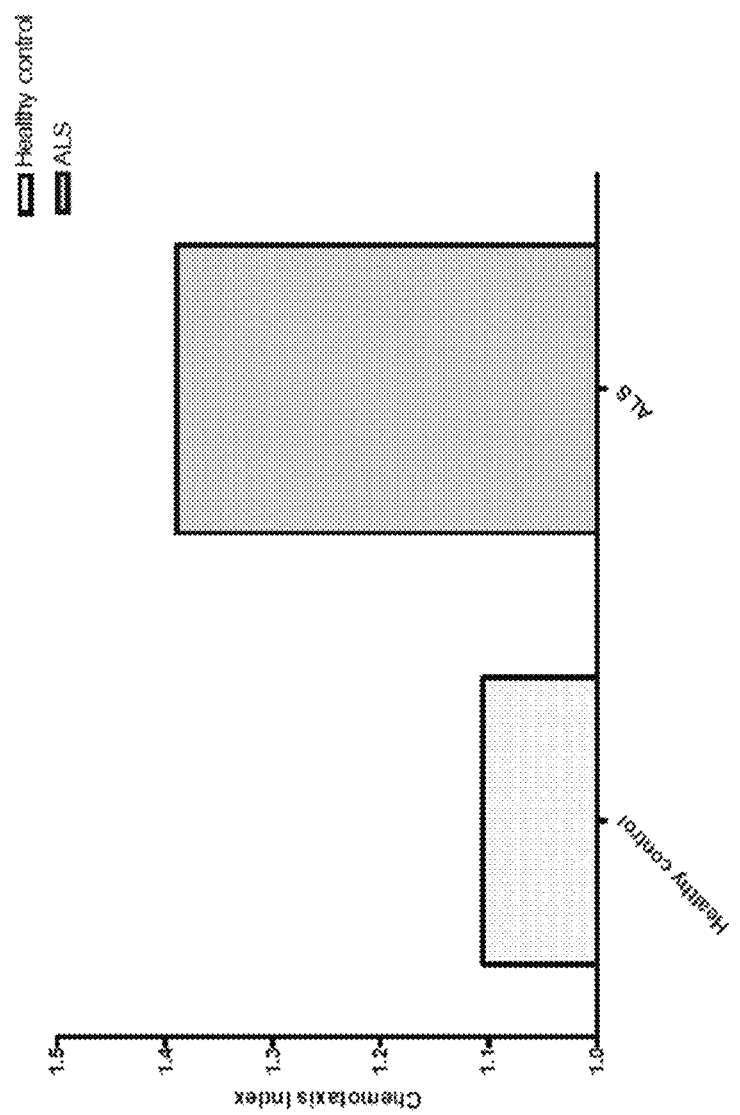
Figure 11:
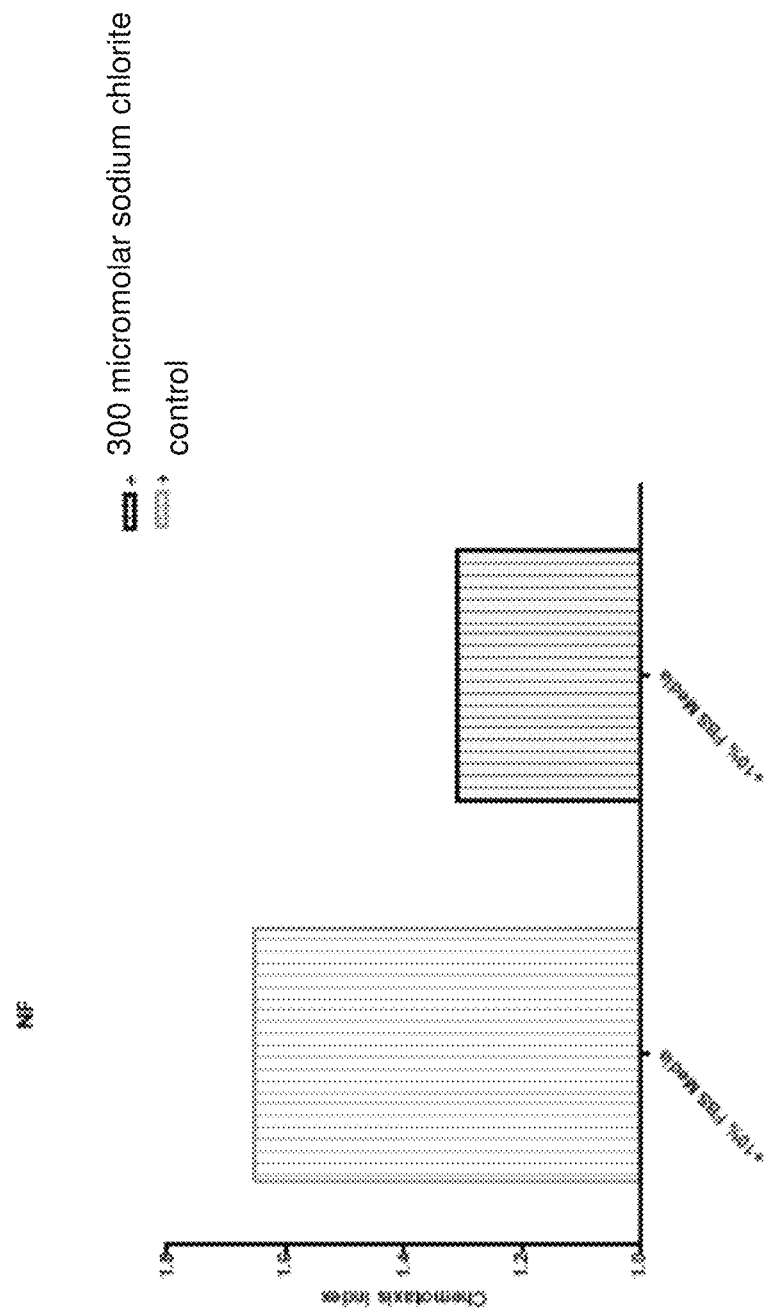

Two chamber migration studies were performed with chemoattractant in the lower chamber and normal PBMCs in the upper chamber (represented as circles), separated by a membrane, as shown in FIG. 9. After four hours, the cells captured by the membrane were normalized to a background score where no chemoattractant was present in the lower chamber to yield a chemotaxis index. FIG. 10 shows the results of normal macrophage culture supernatant (a 10× dilution of 3-day supernatant) as chemoattractant in the left bar compared with ALS patient macrophage culture supernatant (a 10× dilution of 3-day supernatant) as the chemoattractant. The results show that ALS macrophages make chemokines that attract PBMCs. FIG. 11 shows the results of adding 300 micromolar sodium chlorite (4 hours) to PBMCs versus untreated PBMCs. Untreated PBMCs migrated towards 10% FBS (fetal bovine serum containing chemokines) at a greater chemotaxis index than sodium chlorite treated PBMCs (right bar of FIG. 11). The results show that sodium chlorite treatment of normal PBMCs blocked the migration response to chemoattractants.

While preferred embodiments of the present invention have been shown and described herein, it will be clear to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A sodium chlorite compound, wherein said compound is a crystalline solid of greater than 95% purity; wherein said compound has an x-ray powder diffraction pattern with peaks expressed in degrees 2θ at about 21, 30, 32, 34, and 39; and wherein said compound has an x-ray powder diffraction (XRPD) pattern as shown in FIG. 6.

2. A compound of claim 1, wherein said compound is a crystalline solid of greater than 99% purity.

3. A compound of claim 1, wherein said compound is a crystalline solid of greater than 99.9% purity.

4. The compound of claim 1, wherein said compound is substantially free of chlorate.

5. The compound of claim 1, wherein said compound is substantially free of sulfate.

6. A pharmaceutical composition comprising:
   a) the compound of claim 1;
   b) a pH adjusting agent; and
   c) a pharmaceutically acceptable excipient or carrier;
   wherein said composition is a liquid that exhibits 25% less pH drift compared to an identical composition without said pH adjusting agent.

7. The composition of claim 6, wherein said pH adjusting agent is sodium phosphate dibasic.

8. The composition of claim 6, wherein said compound is substantially free of chlorate.

9. The composition of claim 6, wherein said compound is substantially free of sulfate.

10. A solid pharmaceutical composition comprising:
    a) the compound of claim 1; and
    b) a pharmaceutically acceptable excipient or carrier.

11. The composition of claim 10, wherein said compound is substantially free of chlorate.

12. The composition of claim 10, wherein said compound is substantially free of sulfate.

13. A method of treating a disease associated with migration of monocytes or activated macrophages, said method comprising administering a therapeutically-effective amount of the compound of claim 1.

14. The method of claim 13, wherein said disease is characterized by elevated CD16 expression levels in CD14+ cells.

15. The method of claim 13, wherein said disease is characterized by migration of PBMCs in response to a chemoattractant.

16. A method of treating a disease associated with excess activation of monocytes to activated macrophages, said method comprising administering a therapeutically-effective amount of the compound of claim 1.

17. The method of claim 16, wherein said disease is associated with excess CD14CD16 expression.

18. The method of claim 16, wherein said disease is a neurodegenerative disease selected from the group consisting of amyotrophic lateral sclerosis (ALS), Parkinson's Disease (PD), Alzheimer's Disease (AD), and complications thereof.

19. A method of treating Type II diabetes or related complications comprising administering to a subject in need thereof an effective amount of the compound of claim 1.

* * * * *